US009914921B2

(12) United States Patent
Yue et al.

(10) Patent No.: US 9,914,921 B2
(45) Date of Patent: Mar. 13, 2018

(54) SECRETED PROTEINS

(71) Applicant: INCYTE CORPORATION, Palo Alto, CA (US)

(72) Inventors: Henry Yue, Sunnyvale, CA (US); Monique G. Yao, Los Altos, CA (US); Ameena R. Gandhi, San Francisco, CA (US); Mariah R. Baughn, San Diego, CA (US); Anita Swarnakar, San Francisco, CA (US); Narinder Walia, Freemont, CA (US); Madhusudan M. Sanjanwala, Los Altos, CA (US); Michael Thorton, San Francisco, CA (US); Vicki S. Kaulback, Brentwood, CA (US); Yan Lu, Mountain View, CA (US); Kimberly J. Gietzen, San Diego, CA (US); Neil Burford, Durham, CT (US); Li Ding, Creve Coeur, MO (US); April J. A. Hafalia, Pacifica, CA (US); Y. Tom Tang, San Jose, CA (US); Olga Bandman, Mountain View, CA (US); Bridget A. Warren, Carlsbad, CA (US); Cynthia D. Honchell, San Carlos, CA (US); Dyung Aina M. Lu, San Jose, CA (US); Kavitha Thangaveln, Santa Clara, CA (US); Sally Lee, San Jose, CA (US); Yuming Xu, Mountain View, CA (US); Junming Yang, Saratoga, CA (US); Preeti G. Lal, Burlingame, CA (US); Bao M. Tran, Santa Clara, CA (US); Craig H. Ison, San Jose, CA (US); Brendan M. Duggan, San Diego, CA (US); Stephanie Kareht, San Jose, CA (US)

(73) Assignee: INCYTE CORPORATION, Palo Alto, CA (US)

(*) Notice: Subject to any disclaimer, the term of this patent is extended or adjusted under 35 U.S.C. 154(b) by 0 days.

(21) Appl. No.: 15/389,968

(22) Filed: Dec. 23, 2016

(65) Prior Publication Data
US 2017/0166888 A1    Jun. 15, 2017

Related U.S. Application Data

(62) Division of application No. 14/480,328, filed on Sep. 8, 2014, now Pat. No. 9,567,383, which is a division of application No. 14/048,277, filed on Oct. 8, 2013, now Pat. No. 8,889,833, which is a division of application No. 12/585,371, filed on Sep. 14, 2009, now Pat. No. 8,569,445, which is a division of application No. 11/378,616, filed on Mar. 20, 2006, now Pat. No. 7,608,704, which is a division of application No. 10/416,314, filed as application No. PCT/US01/47420 on Nov. 8, 2001, now abandoned.

(60) Provisional application No. 60/247,505, filed on Nov. 8, 2000, provisional application No. 60/247,642, filed on Nov. 9, 2000, provisional application No. 60/249,824, filed on Nov. 16, 2000, provisional application No. 60/252,824, filed on Nov. 21, 2000, provisional application No. 60/254,305, filed on Dec. 8, 2000, provisional application No. 60/256,448, filed on Dec. 18, 2000.

(51) Int. Cl.
*G01N 33/50* (2006.01)
*C12N 15/10* (2006.01)
*C07K 16/18* (2006.01)

(52) U.S. Cl.
CPC .......... *C12N 15/1055* (2013.01); *C07K 16/18* (2013.01); *G01N 33/5023* (2013.01); *C07K 2317/24* (2013.01); *C07K 2317/54* (2013.01); *C07K 2317/55* (2013.01); *C07K 2317/622* (2013.01); *C07K 2317/75* (2013.01); *C07K 2317/76* (2013.01)

(58) Field of Classification Search
CPC .... A61K 38/00; A61K 38/1709; A61K 45/06; A61K 48/00; C07K 14/47; C07K 14/4702; C07K 14/705; C07K 14/78; C07K 16/18; C07K 16/28; C07H 21/04
See application file for complete search history.

(56) References Cited

U.S. PATENT DOCUMENTS

| 5,175,383 A | 12/1992 | Leder et al. |
| 5,270,163 A | 12/1993 | Gold et al. |
| 5,474,796 A | 12/1995 | Brennan |
| 5,530,101 A | 6/1996 | Queen et al. |
| 5,605,662 A | 2/1997 | Heller et al. |

(Continued)

FOREIGN PATENT DOCUMENTS

| WO | WO 84/03564 | 12/1984 |
| WO | WO 95/251116 | 9/1995 |

(Continued)

OTHER PUBLICATIONS

Adam, M.A. and A.D. Miller, "Identification of a signal in a murine retrovirus that is sufficient for packaging of nonretroviral RNA into virions," (1988) *J. Virol.* 62:3802-3806.

(Continued)

*Primary Examiner* — Padmavathi Baskar
(74) *Attorney, Agent, or Firm* — Foley & Lardner LLP

(57) ABSTRACT

The invention provides human secreted proteins (SECP) and polynucleotides which identify and encode SECP. The invention also provides expression vectors, host cells, antibodies, agonists, and antagonists. The invention also provides methods for diagnosing, treating, or preventing disorders associated with aberrant expression of SECP.

9 Claims, No Drawings

(56) References Cited

U.S. PATENT DOCUMENTS

| | | | |
|---|---|---|---|
| 5,686,242 | A | 11/1997 | Bruice et al. |
| 5,707,618 | A | 1/1998 | Armentano et al. |
| 5,767,337 | A | 6/1998 | Roses et al. |
| 5,804,413 | A | 9/1998 | DeLuca |
| 5,807,522 | A | 9/1998 | Brown et al. |
| 5,837,458 | A | 11/1998 | Minshull et al. |
| 5,840,484 | A | 11/1998 | Seilhamer et al. |
| 5,888,762 | A | 3/1999 | Bandman et al. |
| 5,910,434 | A | 6/1999 | Rigg et al. |
| 5,932,435 | A | 8/1999 | Atkins et al. |
| 5,997,848 | A | 12/1999 | Patton et al. |
| 6,022,691 | A | 2/2000 | Bruice et al. |
| 6,057,101 | A | 5/2000 | Nandabalan et al. |
| 6,261,791 | B1 | 7/2001 | Reiter et al. |
| 6,627,414 | B2 | 9/2003 | Billing-Medel et al. |
| 7,608,704 | B2 | 10/2009 | Yue et al. |

FOREIGN PATENT DOCUMENTS

| | | |
|---|---|---|
| WO | WO 95/35505 | 12/1995 |
| WO | WO 99/60020 | 11/1999 |
| WO | WO 00/05586 | 2/2000 |
| WO | WO 00/09551 | 2/2000 |
| WO | WO 00/09552 | 2/2000 |
| WO | WO 01/90354 | 11/2001 |

OTHER PUBLICATIONS

Altschul, S.F. et al., "Basic local alignment search tool," (1990) *J. Mol. Biol.* 215:403-410.

Altschul, et al., "Gapped BLAST and PSI-BLAST: A New Generation of Protein Database Search Programs," *Nucl. Acids Research*, vol. 25, No. 17, pp. 3389-3402 (1997).

U.S. Appl. No. 60/247,505, filed Nov. 8, 2000, Incyte Corproation.
U.S. Appl. No. 60/247,612, filed Nov. 9, 2000, Incyte Corproation.
U.S. Appl. No. 60/249,824, filed Nov. 16, 2000, Incyte Corproation.
U.S. Appl. No. 60/252,824, filed Nov. 21, 2000, Incyte Corproation.
U.S. Appl. No. 60/254,305, filed Dec. 8, 2000, Incyte Corproation.
U.S. Appl. No. 60/256,448, filed Dec. 18, 2000, Incyte Corproation.

Anderson, N.L. and J. Seilhamer, "A Comparison of Selected mRNA and Protein Abundances in Human Liver," (1997) *Electrophoresis* 18:533-537.

Antinozzi, P.A. et al., "Metabolic engineering with recombinant adenoviruses," (1999) *Annu. Rev. Nutr.* 19:511-544.

Armentano, D. et al., "Effect of internal viral sequences on the utility of retroviral vectors," (1987) *J. Virol.* 61:1647-1650.

Arndt, G.M. et al., "A rapid genetic screening system for identifying gene-specific suppression constructs for use in human cells," (2000) *Nucleic Acids Res.* 28:E15.

Baltimore, D., "Intracellular Immunization," (1988) *Nature* 335:395-396.

Bauer, G. et al., "Inhibition of Human Immunodeficiency Virus-1 (HIV-1) Replication After Transduction of Granulocyte Colony-Stimulating Factor-Mobilized D34+Cells From HIV-1-Infected Donors Using Retroviral Vectors Containing Anti-HIV-1 Genes," (1997) *Blood* 89:2259-2267.

Bender, M.A. et al., "Evidence that the packaging signal of Moloney murine leukemia virus extends into the gag region," (1987) *J. Virol.* 61:1639-1646.

Bitter, G.A. et al., "Expression and Secretion Vectors for Yeast," (1987) *Methods Enzymol.* 153:516-544.

Blaese, R.M. et al., "T Lymphocyte-Directed Gene Therapy for ADA−SCID: Initial Trial Results After 4 Years," (1995) *Science* 270:475-480.

Blind, M. et al., "Cytoplasmic RNA modulators of an inside-out signal-transduction cascade," (1999) *Proc. Natl. Acad. Sci. USA* 96:3606-3610.

Boado, R.J. et al., "Drug Delivery of Antisense Molecules to the Brain for Treatment of Alzheimer's Disease and Cerebral AIDS," (1998) *J. Pharm. Sci.* 87:1308-1315.

Bolton, A.E. and W.M. Hunter, "The Labelling of Proteins to High Specific Radioactivities by Conjugation to a $^{125}$I-Containing Acylating Agent," (1973) *Biochem. J.* 133:529-539.

Bonyhadi, M.L., "RevM10-expressing T cells derived in vivo from transduced human hematopoietic stem-progenitor cells inhibit human immunodeficiency virus replication," (1997) *J. Virol.* 71:4707-4716.

Bordignon, C. et al., "Gene Therapy in Peripheral Blood Lymphocytes and Bone Marrow for ADA− Immunodeficient Patients," (1995) *Science* 270:470-475.

Boulay, J.-L. and H. Récipon, "Expression Vectors and Delivery Systems," (1998) *Curr. Opin. Biotechnol.* 9:445-450.

Brody, E.N. and L. Gold, "Aptamers as Therapeutic and Diagnosis Agents," (2000) *J. Biotechnol.* 74:5-13.

Broglie, R. et al., "Light-Regulated Expression of a Pea Ribulose-1,5-Bisphosphate Carboxylase Small Subunit Gene in Transformed Plant Cells," (1984) *Science* 224:838-843.

Buller, R.M. et al., "Decreased Virulence of Recombinant Vaccinia Virus Expression Vectors is Associated With a Thymidine Kinase-Negative Phenotype," (1985) *Nature* 317:813-815.

Burge, C. and S. Karlin, "Finding the Genes in Genomic DNA," (1997) *J. Mol. Biol.* 268:78-94.

Burge, C. and S. Karlin, "Prediction of Complete Gene Structures in Human Genomic DNA," (1998) *Curr. Opin. Struct. Biol.* 8:346-354.

Burton, D.R., "A large array of human monoclonal antibodies to type 1 human immunodeficiency virus from combinatorial libraries of asymptomatic seropositive individuals," (1991) *Proc. Natl. Acad. Sci. USA* 88:10134-10137.

Capecchi, M.R., "Altering the Genome by Homologous Recombination," (1989) *Science* 244:1288-1292.

Campbell, Monoclonal Antibody Technology, Elsevier Science Publishers, NY, Chapter 1, pp. 1-32 (1986).

Caruthers, M.H. et al., "New chemical methods for synthesizing polynucleotides," (1980) *Nucleic Acids Symp. Ser.* 7:215-223.

Cavazzana-Calvo, M. et al., "Gene Therapy of Human Severe Combined Immunodeficiency (SCID)-X1 Disease," (2000) *Science* 288:669-672.

Chang, C.-C. et al., "Evolution of a Cytokine Using DNA Family Shuffling," (1999) *Nat. Biotechnol.* 17:793-797.

Chicz, R.M. and F.Z. Regnier, "High-Performance Liquid Chromatography: Effective Protein Purification by Various Chromatographic Modes," (1990) *Methods Enzymol.* 182:392-421.

Christians, F.C. et al., "Directed Evolution of Thymidine Kinase for AZT Phosphorylation Using DNA Family Shuffling," (1999) *Nat. Biotechnol.* 17:259-264.

Clarke, M.L. et al., "Comparative Analysis of Artificial Antisense RNA Regulation in Fission Yeast and Human Cells," (2000) *Biochem. Biophys. Res. Commun.* 268:8-13.

Colbere-Garapin, F. et al., "A New Dominant Hybrid Selective Marker for Higher Eukaryotic Cells," (1981) *J. Mol. Biol.* 150:1-14.

Cole, S.P. et al., "Human monoclonal antibodies," (1984) *Mol. Cell Biol.* 62:109-120.

Coruzzi, G. et al., "Tissue-Specific and Light-Regulated Expression of a Pea Nuclear Gene Encoding the Small Subunit of rebulose-1,5-Bisphosphate Carboxylase," (1984) *EMBO J.* 3:1671-1680.

Cote, R.J. et al., "Generation of human monoclonal antibodies reactive with cellular antig.," (1983) *Proc. Natl. Acad. Sci. USA* 80:2026-2030.

Crameri, A. et al., "Improved Green Fluorescent Protein by Molecular Evoluation Using DNA Shuffling," (1996) *Nat. Biotechnol.* 14:315-319.

Creighton, "Proteins, Structure and Molecular Properties," *W.H. Freeman*, NY, pp. 28-60 (2008).

Crystal, R.G. et al., "A Phase 1 Study, in Cystic Fibrosis Patients, of the Safety, Toxicity, and Biological Efficacy of a Single Administration of a Replication Deficient, Recombinant Adenovirus Carrying the cDNA of the Normal Cystic Fibrosis Transmembrane Conductance Regulator Gene in the Lung," (1995) *Hum. Gene. Therapy* 6:643-666.

Crystal, et al., "Evaluation of Repeat Administration of a Replication Deficient, Recombinant Adenovirus Containing the Normal

(56) References Cited

OTHER PUBLICATIONS

Cystic Fibrosis Transmembrane Conductance Regulator cDNA to the Airways of Individuals with Cystic Fibrosis," *Human Gene Therapy*, pp. 667-703 (1995).
Crystal, R.G., "Transfer of Genes to Humans: Early Lessons and Obstacles to Success," (1995) *Science* 270:404-410.
Csete, M.E. et al., "Efficient Gene Transfer to Pancreatic Islets Mediated by Adenoviral Vectors," (1995) *Transplantation* 27:263-268.
Di Nicola et al., "Gene transfer into human dendritic antigen-presenting cells by vaccinia virus and adenovirus vectors," *Cancer Gene Therapy*, vol. 5, No. 6, pp. 350-356 (1998).
Dryga, S.A. et al., "Identification of Mutations in a Sindbis Virus Variant Able to Establish Persisent Infection in BHK Cells: The Importance of a Mutation in the nsP2 Gene," (1997) *Virology* 228:74-83.
Dull, T. et al., "A Third-Generation Lentivirus Vector with a Conditional Packaging System," (1998) *J. Virol.* 72:8463-8471.
Duplaa, C. et al., "Quantitative analysis of polymerase chain reaction products using biotinylated dUTP incorporation," (1993) *Anal. Biochem.* 212:229-236.
Eddy, S.R., "Hidden Markov Models," (1996) *Curr. Opin. Struct. Biol.* 6:361-365.
Engelhard, E.K. et al., "The insect tracheal system: a conduit for the systemic spread of Autographa californica M nuclear polyhedrosis virus," (1994) *Proc. Natl. Acad. Sci. USA* 91:3224-3227.
Fields, S. and O. Song, "A Novel Genetic System to Detect Protein-Protein Interactions," (1989) *Nature* 340:245-246.
Gatti, R.A. et al., "Localization of an Ataxia-Telangiectasia Gene to Chromosome," (1988) *Nature* 336:577-580.
Gee et al., "Potential Therapeutic Usefulness of Intermolecular Triplex DNA," *Mol. & Immuno. Approaches*, pp. 163-177 (1994).
Goins, W.F. et al., "Herpes Simplex Virus Type 1 Vector-Mediated Expression of Nerve Growth Factor Protects Dorsal Root Ganglion Neurons from Peroxide Toxicity," (1999) *J. Virol.* 73:519-532.
Goldman, C.K. et al., "In Vitro and In Vivo Gene Delivery Mediated by a Synthetic Polycationic Amino Polymer," (1997) *Nat. Biotechnol.* 15:462-466.
Gossen, M. and H. Bujard, "Tight control of gene expression in mammalian cells by tetracycline-responsive promoters," (1992) *Proc. Natl. Acad. Sci. USA* 89:5547-5551.
Gossen, M. et al., "Transcriptional Activation by Tetracyclines in Mammalian Cells," (1995) *Science* 268:1766-1769.
Graham, F.L. and A.J. Eb, "A New Technique for the Assay of Infectivity of Human Adenovirus 5 DNA," (1973) *Virology* 52:456-467.
Harrington, J.J. et al., "Formation of *De Novo* Centromere and Construction of First-Generation Human Artificial Microchromosomes," (1997) *Nat. Genet.* 15:345-355.
Hartman, S.C. and R.C. Mulligan, "Two dominant-acting selectable markers for gene transfer studies in mammalian cells," (1988) *Proc. Natl. Acad. Sci. USA* 85:8047-8051.
Heinz-Ulrich et al., "Whole Chromosome Complementary Probe Fluorescence Staining," pp. 965-968 (1995).
Heller, R.A. et al., "Discovery and analysis of inflammatory disease-related genes using cDNA microarrays," (1997) *Proc. Natl. Acad. Sci. USA* 94:2150-2155.
Higgins, D.G. et al., "CLUSTAL V: Improved Software for Multiple Sequence Alignment," (1992) *CABIOS* 8:189-191.
Higgins, D.G. and P.M. Sharp, "Fast and Sensitive Multiple Sequence Alignments on a Microcomputer," (1989) *CABIOS* 5:151-153.
Horn, T. et al., "Synthesis of oligonucleotides on cellulose. Part II: design and synthetic strategy to the synthesis of 22 oligodeoxynucleotides coding for Gastric Inhibitory Polypeptide (GIP)," (1980) *Nucleic Acids Svmp. Ser.* 7:225-232.
Huse, W.D. et al., "Generation of a Large Combinatorial Library of the Immunoglobulin Repertoire in Phage Lambda," (1989) *Science* 246:1275-1281.

Ivics, Z. "Molecular Reconstruction of *Sleeping Beauty*, a Tc1-like Transposon from Fish, and Its Transposition in Human Cells," (1997) *Cell* 91:501-510.
Janne, J. et al., *Biotechnol. Annu. Rev.*, 4:55-74 (1998).
Kimmel, A.R., "Identification and Characterization of Specific Clones: Strategy for Confirming the Validity of Presumptive Clones," (1987) *Methods Enzvmol.* 152:507-511.
Kohler, G. et al., "Continuous Cultures of Fused Cells Secreting Antibody of Predefined Specificity," (1975) *Nature* 256:495-497.
Lagerstrom, M. et al., "Capture PCR: efficient amplification of DNA fragments adjacent to a known sequence in human and YAC DNA," (1991) *PCR Methods Applic.* 1:111-119.
Lander, E.S. and D. Botstein, "Strategies for studying heterogeneous genetic traits in humans by using a linkage map of restriction fragment length polymorphisms," (1986) *Proc. Natl. Acad. Sci. USA* 83:7353-7357.
Liu, X. et al., Herpes Simplex Virus Mediated Gene Transfer to Primate Ocular Tissues, (1999) *Exp. Eye Res.* 169:385-395.
Logan, J. and T. Shenk, "Adenovirus tripartite leader sequence enhances translation of mRNAs late after infection," (1984) *Proc. Natl. Acad. Sci. USA* 81:3655-3659.
Lowy, I. et al., "Isolation of Tranforming DNA: Cloning the Hamster aprt Gene," (1980) *Cell* 22:817-823.
Marshall, A. and J. Hodgson, "DNA Chips: an Array of Possibilities," (1998) *Nat. Biotechnol.* 16:27-31.
Muth, J.D., "Recent advances in gene mutagenesis by site-directed recombination," (1996) *Clin. Invest.* 97:1999-2002.
McGregor, D.P. et al., "Spontaneous Assembly of Bivalent Single Chain Antibody Fragments in *Escherichia coli*," (1994) *Mol. Immunol.* 31:219-226.
Melby, P.C. et al., "Quantitative Measurement of Human Cytokine Gene Expression by Polymerase Chain Reaction," (1993) *J. Immunol. Methods* 159:235-244.
Mendoza, L.G. et al., "High-throughput microarray-based enzyme-linked immunosorbent assay (ELISA)," (1999) *Biotechniques* 27:778-788.
Miller, A.D., "Progress Toward Human Gene Therapy," (1990) *Blood* 76:271-278.
Morgan, R.A. and W.F. Anderson, "Human Gene Therapy," (1993) *Annu. Rev. Biochem.* 62:191-217.
Morris, M.G. et al., "A new peptide vector for efficient delivery of oligonucleotides into mammalian cells," (1997) *Nucleic Acids Res.* 25:2730-2736.
Morrison, S.L. et al., "Chimeric human antibody molecules: mouse antigen-binding domains with human constant region domains," (1984) *Proc. Natl. Acad. Sci. USA* 81:6851-6855.
Neuberger, M.S. et al., "Recombinant Antibodies Possessing Novel Effector Functions," (1984) *Nature* 312:604-608.
Neumann, E. et al., "Gene Transfer Into Mouse Lyoma Cells by Electroporation in High Electric Fields," (1982) *EMBO J.* 1:841-845.
Nuwaysir, E.F. et al., "Microarrays and Toxicology: The Advent of Toxicogenomics," (1999) *Mol. Carcinog.* 24:153-159.
Orlandi, R. et al., Cloning immunoglobulin variable domains for expression by the polymerase chain reaction, (1989) *Proc. Natl. Acad. Sci. USA* 86:3833-3837.
Poeschla, E. et al., "Development of HIV Vectors for Anti-HIV Gene Therapy," (1996) *Proc. Natl. Acad. Sci. USA* 93:11395-11399.
Ranga, U. et al., "Cell and viral regulatory elements enhance the expression and function of a human immunodeficiency virus inhibitory gene," (1997) *J. Virol.* 71:7020-7029.
Ranga, U. et al., "Enhanced T cell engraftment after retroviral delivery of an antiviral gene in HIV-infected individuals," (1998) *Proc. Natl. Acad. Sci.* USA 95:1201-1206.
Rao, V.B., "Direct Sequencing of Polymerase Chain Reaction-Amplified DNA," (1994) *Anal. Biochem.* 216:1-14.
Rhodes, C.A., "Transformation of Maize by electroporation of Embryos," (1995) *Methods Mol. Biol.* 55:121-131.
Riviere, I. et al., "Effects of Retroviral Vector Design on Expression of Human Adenosine Deaminase in Murine Bone Marrow Transplant Recipients Engrafted with Genetically Modified Cells," (1995) *Proc. Natl. Acad. Sci. USA* 92:6733-6737.

(56) References Cited

OTHER PUBLICATIONS

Roberge, J.Y. et al., "A Strategy for a Convergent Synthesis of N-Linked Glycopeptides on a Solid Support," (1995) *Science* 269:202-204.
Rossi, F.M.V. and H.M. Blau, "Recent Advances in Inducible Gene Expression Systems," (1998) *Curr. Opin. Biotechnol.* 9:451-456.
Sandig, V. et al., "Gene Transfer into Hepatocytes and Human Liver Tissue by Baculorirus Vectors," (1996) *Hum. Gene Ther.* 7:1937-1945.
Sarkar, G., "Restriction-Site PCR: A Direct Method of Unkown Sequence Retrieval Adjacent to a Known Locus by Using Universal Primers," (1993) *PCR Methods Applic.* 2:318-322.
Scanlon, K.J. et al., "Oligonucleotide-Mediated Modulation of Mammalian Gene Expression," (1995) *FASEB J.* 9:1288-1296.
Scharf, D. et al., "Heat Stress Promoters and Transcription Factors," (1994) *Results Probl. Cell Differ.* 20:125-162.
Schena, M. et al., "Quantitative Monitoring of Gene Expression Patterns with a Complementary DNA Microarray," (1995) *Science* 270:467-470.
Scorer, C.A. et al., "Rapid Selection Using G418 of High Copy Number Transformants of *Pichia pastoris* for High-Level Foreign Gene Expression," (1994) *Bio/Technology.* 12:181-184.
Shalon, D. et al., "A DNA Microarray System for Analyzing Complex DNA Samples Using Two-Color Fluorescent Probe Hybridization," (1996) *Genome Res.* 6:639-645.
Sonnhammer, et al., Proc. Sixth to delineate transmembrane segments on protein Intl. Conf. on Intelligent Systems for Mol. sequences and determine orientation. Biol. Glasgow et al., eds., The Am. Assoc. for Artificial Intelligence (AAAI) Press, Menlo Park, CA, and MIT Press, Cambridge, MA, pp. 175-182 (1998).
Sonnhammer, et al., Pfam: multiple sequence alignments and HMM-profiles of protein domains, *Nucleic Acids Res.*, vol. 26, No. 1, pp. 320-322 (1998).
Steiner et al., "Expression profiling in toxicolagypotentials and limitations," *Tox. Lits.* pp. 467-471 (2000).
Su, L., "Hematopoietic Stem Cell-Based Gene Therapy for Acquired Immunodeficiency Syndrome: Efficient Transduction and Expression of RevM10 in Myeloid Cells In Vivo and In Vitro," (1997) *Blood* 89:2283-2290.
Takamatsu, N., "Expression of Bacterial Chloramphenicol Acetyltransferase Gene in Tobacco Plants Mediated by TRV-RNA," (1987) *EMBO J.* 6:307-311.
Takeda, S. et al., "Construction of Chimaeric Processed Immunoglobulin Genes Containing Mouse Variable and Human Constant Region Sequences," (1985) *Nature* 314:452-454.
Thomson, J.A. et al., Embryonic Stem Cell Lines Derived from Human Blastocysts, (1998) *Science* 282:1145-1147.
Trask, B.J., "Fluorescence in situ Hybridization," (1991) *Trends Genet.* 7:149-154.
Triglia, T. et al., "A procedure for in vitro amplification of DNA segments that lie outside the boundaries of known sequences," (1988) *Nucleic Acids Res.* 16:8186.
Uckert, W. and W. Walther, "Retrovirus-Mediated Gene Transfer in Cancer Therapy," (1994) *Pharmacol. Ther.* 63:323-347.
Van Heeke, G. and S.M. Schuster, "Expression of Human Synthetase in *Escherichia coli*," (1989) *J. Biol. Chem.* 264:5503-5509.
Verma, I.M. and N. Somia, "Gene therapy—promises, problems and prospects," (1997) *Nature,* 18:389:239-242.
Wagner, K.U. et al., "Cre-mediated gene deletion in the mammary gland," (1997) *Nucleic Acids Res.*, 25:4323-4330.
Wahl, G.M. and S.L. Berger, "Molecular Hybridization of Immobilized Nucleic Acids: Theoretical Concepts and Practical Considerations," (1987) *Methods Enzymol.* 152:399-407.
Wigler, M. et al., "Transfer of Purified Herpes Virus Thymidine Kinase Gene to Cultured Mouse Cells," (1977) *Cell* 11:223-232.
Wigler, M. et al., "Transformation of mammalian cells with an amplifiable dominant-acting gene," (1980) *Proc. Natl. Acad. Sci. USA* 77:3567-3570.

Winter, G. et al., "Man-Made Antibodies," (1991) *Nature* 349:293-299.
Xu, H. et al., "Viral Transduction of trkA Into Cultured Nodose and Spinal Motor Newrons Conveys NGF Responsiveness," (1994) *Dev. Biol.* 163:152-161.
Yu, M. et al., "A Hairpin Ribozyme Inhibits Expression of Diverse Strains of Human Immunodeficiency Virus Type 1," (1993) *Proc. Natl. Acad. Sci. USA* 90:6340-6344.
Zabner, J. et al., "Adenovirus-Mediated Gene Transfer Transiently Corrects the Chloride Transport Defect in Masai Epithelia of Patients with Cystic Fibrosis," (1993) *Cell* 75:207-216.
Zufferey, R. et al., "Self-Inactivating Lentivirus Vector for Safe and Efficient In Vivo Gene Delivery," (1998) *J. Virol.* 72:9873-9880.
Alberts, B. et al., "Signal Peptides and Signal Patches Direct Proteins to the Corrct Cellular Address," (1994), *Molecular Biology of the Cell*, Garland Publishing, New York, NY, pp. 557-560,582-592.
Assoian, R. K. et al., "Transforming Growth Factor-β in Human Platelets," (1983), *J. Biol. Chem.*, 258: 7155-7160.
Attwood, T.K. et al., "The Prints Database of Protein Fingerprints: A Novel Information Resource for Computational Molecular Biology," (1997), *J. Chem. Inf. Comput. Sci.*, 37:417-424.
Ayad, S. et al., (1994), The Extracellular Matrix Facts Book. Academic Press, San Diego, CA, pp. 2-16.
Bairoch, A. et al., "The Prosite database," (1997), *Nucleic Acids Res.*, 25:217-221.
Barclay, A. N. et al., "The Analysis and Architecture of the Leucocyte Cell Surface," (1995) *The Leucocyte Antigen Facts Book*, Academic Press, San Diego, CA, pp. 17-20.
Bergsma, D. J. et al., "The Cyclophilin Multigene Family of Peptidyl-Prolyl Isomerases," (1091), *J. Biol. Chem.*, 286: 23204-23214.
Bonaldo et al., "Normalization and Subtraction: Two Approaches to Facilitate Gene Discovery," *Genome Research*, (1996), 6:791-806.
Chretien, M. et al., "From β-lipotropin to β-endorphin and 'pro-opio-melanocortin'" 1979), *Canad. J. Biochem.*, 57: 1111-1121.
Claverie, J.M. and S. Audic, "The Statistical Significance of Nucleotide Position-Weight Matrix Matches," (1997) peptides. CABIOS 12:431-439.
Conley, C. A. et al., "Crossveinless 2 Contains Cysteine-rich Domains and is Required for High Levels of BMP-like Activity During the Formation of the Cross Veins in *Drosophila*," (2000), *Development*, 127: 3947-3959.
Coss, M. et al., "Molecular Cloning, DNA Sequence Analysis, and Biochemical Characterization of a Novel 65-kDa FK506-binding Protein (FKBP65)," (1995), *J. Biol. Chem.*, 279: 29336-29341.
Danielson, P. E. et al., "Four Structurally Distinct Neuron-Specific Olfactomedin-Related Glycoproteins Produced by Differential Promoter Utilization and Alternative mRNA Splicing From a Single Gene," (1994), *J. Neurosci. Res.*, 38: 468-478.
De La Fuente, M. A. et al., "CD84 Leukocyte Antigen is a New Member of the Ig Superfamily," (1997), *Blood*, 90: 2398-2405.
Dear, T.NH. et al., "Novel Genes for Potential Ligand-Binding Proteins in Subregions of the Olfactory Mucosa," (1991) *EMBO J.*, 10 (10), 2813-2819.
Deutsch, D. et al., "Tiffelin mRNA is Expressed in a Human Ameloblastoma Tumor," (1998), *Connect. Tissue Res.*, 39 : 177-184.
Ewing, B. et al., "Base-Calling of Automated Sequencer Traces Using Phred. I. Accuracy Assessment" (1998), *Genome Res.* 8:175-185.
Ewing, B. et al., "Base-Calling of Automated Sequencer Traces Using Phred. II. Error Probabilities," (1998), Genorne Res., 8:186-194.
Firestein, G. S., "Mechanisms of Tissue Destruction and Cellular Activation in Rheumatoid Arthritis," (1992), *Curr. Opin. Rheumatol.*, 4: 348-354.
Foreman, K. et al., "Identification and Characterizatrion of a Gene That is Coamplified with Dihydrofolate Reductase in a Methotrexate-Resistant CHO Cell Line," (1989) *Mol. Cell. Biol.* 9, 1137-1147.
Friedman, P. A. et al., "Vitamin K-Dependent Carboxylation," (1987), *Int. J. Biochem.*, 19: 1-7.

(56) References Cited

OTHER PUBLICATIONS

Garoff, H. el al., (1998), "Recent Advances in Gene Expression Using Alphavirus Vectors." *Curr. Opin. Biotechnol.* 9: 464-469.
Golub, E. S. et al., "Measuring Antigen-Antibody Reactions," (1997), *Immunology : A Synthesis. Sinauer Associates*, pp. 113-115.
Gordon et al., "Consed: A Graphical Tool for Sequence Finishing," University of assembling DNA sequences, Seattle, WA., Cussed a graphical tool for viewing and editing Phrap, (1998) Genome Res. 8:195-202.
Gribskov, M. et al., "Profile Scanning for Three-Dimentional Structural Patterns in Protein Sequences," (1988), *CABIOS*, 4:61-66.
Gribskov, M. et al., (1989), "Methods specified "HIGH" value for that sequence patterns defined in Prosite." Enzymol., 183:146-159.
Harrington, M. G., "Eiutlon of Protein from Gels," (1990), *Methods Enzymol.*, 182: 488-495.
Henikoff, et al., "Blocks Databases and its Applications," (1996) "Methods for gene families, sequence homology," Enzymol. 266:88-105.
Henikoff, S. et al., "Automated Assembly of Protein Blocks for Database Searching," (1991), *Nucleic Acids Res.*, 19:6565-6572.
Horikoshi, N. et al., "Isolation of Differentially Expressed cDNAs from p53-Dependent Apoptotic Cells: Activation of the Human Homologue of the *Drosophila peroxidasin* Gene," (1999), *Biochem. Biophy. Res. Commun.*, 261: 864-869.
Horrevoets, A.J. et al., Vascular Endothelial Genes that are Responsive to Tumor Necrosis Factor-α In Vitro are Expressed in Atherosclerotic Lesions, including Inhibitor of Apoptosis Protein-1, Stannin, and Two Novel Genes, (1999), *Blood*, 93 (10), 3418-3431.
Hunter, T., "Prolyl Isomerases and Nuclear Function," (1998), *Cell*, 92: 141-143.
Itoh et al., Cloning and Expressions of Three Mammalian Homologues of *Drosophila stit* Suggest Possible Roles for *Stit* in the Formation and Maintenance of the Nervous System, (1998), *Brain Res. Mol. Brain Res.*, 62: 175-186.
Iwai, N. et al., "Human SA Gene Locus as a Candidate Locus for Essential Hypertension," (1994), *Hypertension* 23: 375-380.
Jeong, M. et al., Thioredoxin-dependent Hydroperoxide Peroxidase Activity of Bacterioferritin Comigratory Protein (BCP) as a New Member of the Thiol-specific Antioxidant Protein (TSA)/Alkyl Hydroperoxide Perosidase C (AhpC) Family, (2000), pp. 113-115, 275: 2924-2930).
Kladney, R.D. et al., "GP73, a novel Golgi-localized Protein Upregulated by Viral Infection," (2000), *Gene*, 249 (1-2), 53-65.
Kaplan, F. et al., "A Novel developmentally Regulated Gene in Lung Mesenchyme: Homology to a Tumor-Derived Trypsin Inhibitor," (1999), *Am, J. Physiol.*, 276 (6), L1027-L1036.
Kopin, A.S. et al., "Secrelin: Structure of the Precursor and Tissue Distribution of the mRNA." (1990), *Proc. Natl. Acad. Sci. USA*, 87, 2299-2303.
Koths, K. et al., "Cloning and Characterization of a Human Mac-2-binding Protein, a New Member of the Superfamily Defined by the Macrophage Scavenger Receptor Cysleine-rich Domain," (1993), *J. Biol. Chem.*, 268: 14245-14249.
Kozbor, D. et al., "Specific Immunoglobulin Production and Enhanced Tumorigenicity Following Ascites Growth of Human Hybridomas," (1985), *J. Immunol. Methods*, 81: 31-42.
Krogh, A. et al., "Hidden Markov Models in Computational Biology," (1994), *J. Mol. Biol. PFAM htts: Probability value= hidden Markov model (HMM)-based databases of*, 235:1501-1531.
Krude, H. et al., "Severe early-onset obesity, adrenal insufficiency and red hair pigmentation caused by POMC mutatons in humans," (1998), *Nature Genet.*, 19: 155-157.
Kulkarni, N. H. et al., "Characterization and differential expression of a human gene family of olfactomedin-related proteins," (2000), *Genet. Res.*, 76: 41-50.
Kulman, J. D. et al., "Identification of two Novel Transmembrane γ-Carboxyglutamic Acid Proteins Expressed Broadly in Fatal and Adult Tissues," (2001), *Proc. Natl. Acad. Sci. USA*, 98: 1370-1375.

Leverson, J. D. et al., "Point Mutations in v-Myb Disrupt a Cyclophilin-Catalyzed Negative Regulatory Mechanism," (1998), *Mol. Cell.*, 1: 203-211.
Liang, Y. et al., "Mammalian Homologues of the *Drosophila slit* Protein are Ligands of the Heparan Sulfate Proteoglycan Glypican-1 in Brain," (1999), *J. Biol. Chem.*, 274: 17885-17892.
Lodish et al., "Cell to Cell Signaling: Hormones and Receptors," (1995), *Molecular Cell Biology*, pp. 856-864, Scientific American Books Inc., New York, NY.
Loftus, B.J. et al., Genome Duplications and Other Features in 12 Mb of DNA Sequence from Human Chromosome 16p and 16q, (1999), *Genomics*, 60 (3), 295-308.
Lueking, A. et al., "Protein Microarrays for Gene Expression and Antibdy Screening," (1999), *Anal. Biochem.*, 270: 103-111.
Luong, A. et al., "Molecular Characterization of Human Acetyl-CoA Synthelase, an Enzyme Regulated by Sterol Regulatory Element-binding Proteins," (2000), *J. Biol. Chem.*, 275: 26458-26466.
Martin, C. R. et al., "Neuroendocrine Systems," (1985), *Endocrine Physiology*, pp. 57-62, Oxford University Press, New York, NY.
Muro et al., "Scieroderma Diagnosis with Recombinant Protein," (1995), *Molecular Biology and Biotechnology*, pp. 853-859, Wiley VCH, New York NY.
Mignatti, P. et al., "Biology and Biochemistry of Proteinases in Tumor Invasion," (1993), *Physiol. Rev.*, 73: 161-195.
Morimoto, T. et al., Calcium-Oependent Transmitter Secretion from Fibroblasts: Modulation by Synaptotagmin I, (1995), *Neuron*, 15: 689-696).
Morris, M. C. et al., "A new peptide vector for efficient delivery of Olignocleotides into Mammalian Cells," (1997), *Nucleic Acids Res.*, 25 (14): 2730-2736.
Munemitsu et al., "Molecular Cloning and Expression of a G25K cDNA, the Human Homolog of the Yeast Cell Cycle Gene CDC42," *Molecular & Cellular 8lo.*, pp. 5977-5982 (1990).
Nelson, R. E., "Peroxidasin: A Novel Enzyme-Matrix Protein of *Drosophila* Development," (1994), *EMBO. J.*, 13: 3438-3447.
Ohta Y. et al., Autocrine Motility Factor Receptor Expression Associates with Tumor Progression in Thymoma, (2000), *Int. J. Oncol.*, 17: 259-264.
Ohta, K. et al., "Plexin: A Novel Neuronal Cell Surface Molecule that Mediates Cell Adhesion via a Homophilic Binding Mechanism in the Presence of Calcium Ions," (1995), *Cell*, 14: 1189-1199.
Paine, C. T. et al., Identification of Tuftelin- and Amelogenin-Interacting Proteins Using the Yeast Two-Hybrid System, (1998), *Connect Tissue Res.*, 38: pp. 257-267.
Parker, J. D. et al., "Targeted Gene Walking Polymerase Chain Reaction," (1991), *Nucleic Acids Res.*, 19: pp. 3055-3060.
Pearson, "Rapid and Sensitive Sequence Comparison with FASTP and FASTA," (1990), *Methods Enzymol.*, 183: pp. 63-98.
Pearson, W.R. et al., "Improved Tools for Biological Sequence Comparison," (1988), *Natl. Acad Sci. USA* 85: pp. 2444-2448.
Persson, et al., "Prediction of Transmembrane Segments in Proteins Utilising Multiple Sequence Alignments," (1994) *J. Mol. Biol.*, 237: pp. 182-192.
Persson, et al., "Topology Prediction of Membrane Proteins," (1996), *Protein Sci.* 5: pp. 363-371.
Pimentel, E., "Regulation of Cell Functions," (1994), *Handbook of Growth Factors*, pp. 1-9, CRC Press, Ann Arbor, MI.
Plouzek, C. A. et al., "Isolation and Characterization of a Human Amnion Epithelial Cell Line That Expresses the Pregnancy-Specific $β_1$-Glycoprotein Gene," (1991), *Endocrinology*, 129: 950-958.
Plouzek, C. A. et al., "Differential Gene Expression in the Amnion, Chorion, and Trophoblast of the Human Placenta," (1993), *Placenta*, 14: 277-285.
Price, C. M., "Fluorescence In Situ Hybridization," (1993), *Blood Rev.*, 7: 127-134.
Raper, J. A., "Semaphorins and their receptors in vertebrates and invertebrates," (2000), *Curr. Opin. Neurobiol.*, 10: 88-94.
Ray, J. M. et al., "The role of matrix metalloproteases and their Inhibitors in tumour invasion, metastasis and anglogenesis," (1994), *Eur. Respir. J.*, 7: 2062-2072.

(56) References Cited

OTHER PUBLICATIONS

Reponen, P. et al., "92-kDa Type IV Collagenase and TIMP-3, But Not 72-kDa Type IV Collagenase or TIMP-1 or TIMP-2, Are Highly Expressed During Mouse Embryo Implanation," (1995), *Dev. Dyn.*, 202: 388-396.

Rossi, J. J., "Therapeutic: Antisense and Ribozymes," (1995), *Br. Med. Bull.*, 51 (1) : 217-225.

Ruoslahti, E., "Integrins as Signaling Molecules and Targets for Tumor Therapy," (1997), *Kidney Int.* 51: 1413-1417.

Schena, M. et al., "Parallel Human Genome Analysis: Microarray-based Expression Monitoring of 1000 Genes," (1996), *Proc. Natl. Acad. Sci. USA*, 93: 10614-10619.

Scherer P.E. et al., "Cloning of Cell-Specific Secreted and Surface Proteins by Subtractive Antibody Screening," (1998), *Nature Biotechnol.*, 16:581-586.

Schreiber, S. L., "Cnemistry and Biology of the Immunophilins and Their Immunosuppressive Ligands," (1991), *Science*, 251: 283-287.

Schwarze, S. R. et al., "In Vivo Protein Transduction: Delivery of a Biologically Active Protein into he Mouse," (1999), *Science*, 285: 1569-1572.

Shen, P. et al., "Population Genetic Implications from Sequence Variation in four Y Chromosome Genes," (2000), *Proc. Natl. Acad. Sci. USA*, 97 (13), 7354-7359.

Sjaastad, M. D. et al., "Integrin-Mediated Calcium Signaling and Regulation of Cell Adhesion by Intracellelar Calcium," (1997), *BioEssays*, 19: 47-55.

Slater, J. E. et al., "The latex Allergen Hev b 5 transcript is Widely Distributed After Subcutaneous Injection in BALB/c Mice of its DNA Vaccine," (1998), *J. Allergy Clin. Immunol.*, 102 (3): 469-475.

Smith, T.F., "Identification of Common Molecular Subsequences," (1981), *J. Mol. Biol.* 147:195-97.

Soares et al., "Construction and characterization of a normalized cDNA Library," *PNAS* (1994) 91:9228-9232.

Swaroop et al., "A simple and efficient cDNA library subtraction procedure: Isolation of Human Retina-Specific cDNA Clones," *NAR*, (1991), 19:1954.

Murry, "Agrobacterium-Mediated Plant Transformation," *The McGraw Hill Yearbook of Science and Technology*, (1992), pp. 191-196, McGraw Hill, New York NY.

Theopold, U. et al., "Helix pomatia Lectin, an Inducer of *Drosophila* Immune Response, Binds to Hemomucin, A Novel Surface Mucin," (1996), *J. Biol. Chem.*, 217: 12708-12715).

Toh, H., "Sequence Analysis of Firefly Luciferase Family Reveals a Conservative Sequence Motif." (1991), *Protein Seq. Data Anal.*, 4: 111-117.

Toribara, N. W. et al., "Human Gastric Mucin," (1993), *J. Biol. Chem.*, 268:5879-5885.

Toribara, N. W. et al., The Carboxyl-terminal Sequence of the Human Secretory Mucin, MUC6, (1997), *J. Biol. Chem.*, 272: 16398-16403.

Ullrich, A., et al., "The Secreted Tumor-Associated Antigen 90K is a Potent Immune Stimulator," (1994), *J. Biol. Chem.*, 269: 18401-18407.

Vermeer, C., "γ-Carboxyglutarnate-containing Proteins and the Vitamin K-dependent Carboxylase," (1990), *Biochem. J.*, 266: 625-636.

Watson, S. et al., "Angiotensin," (1994), *The G-protein Linked Receptor Facts Book*, pp. 194; 252; 284; 55; 111, Academic Press, San Diego CA.

Winberg, M. L. et al., "Plexin A is a Neuronal Semaphorin Receptor that Controls Axon Guidance," (1998), *Cell*, 95: 903-916.

Winter, J. et al., "The Expression of Heat Shock Protein and Cognate Genes During Plant Development," (1991), *Results Probi. Cell Differ.*, 17: 85-105.

Yokoyama, M. et al., "Identification and Cloning of Neuroblastoma-Specific and Nerve Tissues-Specific Genes through Compiled Expression Profiles," (1996), *DNA Res.*, 3: 311-320.

Zhou, X. et al., "Nodal is a Novel TGF-β-like Gene Expressed in the Mouse Node During Gastrulation," (1993), *Nature*, 361 (6412), 543-547.

Bertenshaw et al., "Marked Differences between Metalloproteases Meprin A and B in Substrate and Peptide Bond Specificity," *The Journal of Biological Chemistry*, vol. 276, No. 16, Issue of Apr. 2001, pp. 13248-13255.

Portela-Gomes et al., "Co-localization of Neuroendocrine Hormones in the Human Fetal Pancreas," *European Journal of Endocrinology*, 1999, pp. 526-533.

Kopin et al., "Secretin: Structure of the Precursor and Tissue Distribution of the mRNA," *Proc. Natl. Acad. Sci.*, vol. 87, Mar. 1990, pp. 2299-2303.

Holtmann et al., "Critical Contributions of Amino-Terminal Extracellular Domains in Agonist Binding and Activation of Secretin and Vasoactive Intestinal Polypeptide Receptors," *The Journal of Biological Chemistry*, vol. 270, No. 24, 1995, pp. 14394-14398.

Du et al., "Human VPAC1 Receptor Selectivity Filter," *The Journal of Biological Chemistry*, vol. 277, No. 40, 2002, pp. 37016-37022.

Luking et al., "The Protein Family of RNA Helicases," *Critical Reviews in Biochemistry and Molecular Biology*, 33 (4), 1998, pp. 259-296.

Ohara et al, "Homo Sapiens MRNA for KIAA1595 Protein, XP-002213527," 2001, 2 pgs.

Nagase et al., "Prediction of the Coding Sequences of Unidentified Human Genes. XVII. The Complete Sequences of 100 New cDNA Clones From Brain Which Code for Large Proteins in vitro," 2000, pp. 273-281.

Gunnes et al., "Cardiovascular effects of secretin infusion in man", *Scand. J. clin. Lab. Invest.*, vol. 43, 1983 (pp. 637-642).

Gunnes et al., "Peripheral Distribution of the Increased Cardiac Output by Secretin during Acute Ischemic Left Ventricular Failure", *The Journal of Pharmacology and Experimental Therapeutics*, vol. 244, No. 3, 1987 (pp. 1057-1061).

Gunnes et al., "Cardiac effects of secretin; an approach to its mechanisms of action as shown by beta-adrenergic blockade and measurement of left ventricular dimensions in dogs", *Scand J Clin Lab Invest*, vol. 49, 1989 (pp. 701-706).

S.S. Hong et al., "Inhibitory Effect of Duodenal Factors Against Ulceration of Stomach in Rats" *Yonsei Medical Journal*, vol. 12, 1971 (pp. 34-41).

Kato et al., "Secretin Stimulates Exocytosis in Isolated Bile Duct Epithelial Cells by a Cyclic AMP-mediated Mechanism", *The Journal of Biological Chemistry*, vol. 267, No. 22, 1992 (pp. 15523-15529).

Mundorf et al., *The American Journal of Gastroenterology*, vol. 90, No. 9, Sep. 1995 (p. 1611).

Perry et al., *Journal of Child and Adolescent Psychopharmacology*, vol. 8, No. 4, 1998 (pp. 247-248).

Bork (Genome Research 2000; 10, 398-400).

Misoka et al., "Efficient Purification and Analysis for Stability of Human Secretin Precursor-Like Peptide Produced in *Escherichia coli*," *Biotechnology Letters*, vol. 13, No. 8, pp. 603-608 (1991).

Whitmore et al., "Human secretin (SCT): gene structure, chromosome location, and distribution of MRNA," *Cytogenet Cell Genet.*, vol. 90, pp. 47-52 (2000).

Carlquist 1985 IRCS Med. Sci., vol. 13, pp. 217-218 (1985).

SEQUENCE LISTING

<160> NUMBER OF SEQ ID NOS: 130

<210> SEQ ID NO 1
<211> LENGTH: 351
<212> TYPE: PRT
<213> ORGANISM: Homo sapiens
<220> FEATURE:
<221> NAME/KEY: misc_feature
<223> OTHER INFORMATION: Incyte ID No: 2719959CD1

<400> SEQUENCE: 1

```
Met Asn Gly Thr Glu Leu Asp Arg Leu Gln Leu Gly Ser Thr Ile
  1               5                  10                  15

Thr Tyr Gln Cys Asp Ser Ala Ile Arg Phe Leu Thr Pro Ser Ser
                 20                  25                  30

His His Leu Cys Asp Trp Ala Asp Gly Lys Pro Ser Trp Asp Gln
                 35                  40                  45

Val Leu Pro Ser Cys Asn Ala Pro Cys Gly Gln Tyr Thr Gly
                 50                  55                  60

Ser Glu Gly Val Val Leu Ser Pro Asn Tyr Pro His Asn Tyr Thr
                 65                  70                  75

Ala Gly Gln Ile Cys Leu Tyr Ser Ile Thr Val Pro Lys Glu Phe
                 80                  85                  90

Val Val Phe Gly Gln Phe Ala Tyr Phe Gln Thr Ala Leu Asn Asp
                 95                 100                 105

Leu Ala Glu Leu Phe Asp Gly Thr His Ala Gln Ala Arg Leu Leu
                110                 115                 120

Ser Ser Leu Ser Gly Ser His Ser Gly Glu Thr Leu Pro Leu Ala
                125                 130                 135

Thr Ser Asn Gln Ile Leu Leu Arg Phe Ser Ala Lys Ser Gly Ala
                140                 145                 150

Ser Ala Arg Gly Phe His Phe Val Tyr Gln Ala Val Pro Arg Thr
                155                 160                 165

Ser Asp Thr Gln Cys Ser Ser Val Pro Glu Pro Arg Tyr Gly Arg
                170                 175                 180

Arg Ile Gly Ser Glu Phe Ser Ala Gly Ser Ile Val Arg Phe Glu
                185                 190                 195

Cys Asn Pro Gly Tyr Leu Leu Gln Gly Ser Thr Ala Leu His Cys
                200                 205                 210

Gln Ser Val Pro Asn Ala Leu Ala Gln Trp Asn Asp Thr Ile Pro
                215                 220                 225

Ser Cys Val Val Pro Cys Ser Gly Asn Phe Thr Gln Arg Arg Gly
                230                 235                 240
```

-continued

```
Thr Ile Leu Ser Pro Gly Tyr Pro Glu Pro Tyr Gly Asn Asn Leu
            245                 250                 255

Asn Cys Ile Trp Lys Ile Ile Val Thr Glu Gly Ser Gly Ile Gln
        260                 265                 270

Ile Gln Val Ile Ser Phe Ala Thr Glu Gln Asn Trp Asp Ser Leu
    275                 280                 285

Glu Ile His Asp Gly Gly Asp Val Thr Ala Pro Arg Leu Gly Ser
290                 295                 300

Phe Ser Gly Thr Thr Val Pro Ala Leu Leu Asn Ser Thr Ser Asn
            305                 310                 315

Gln Leu Tyr Leu His Phe Gln Ser Asp Ile Ser Val Ala Ala Ala
        320                 325                 330

Gly Phe His Leu Glu Tyr Lys Ser Lys Val Asn Ser Phe Cys Ile
    335                 340                 345

Gln Leu Pro Leu Leu Tyr
            350

<210> SEQ ID NO 2
<211> LENGTH: 1463
<212> TYPE: PRT
<213> ORGANISM: Homo sapiens
<220> FEATURE:
<221> NAME/KEY: misc_feature
<223> OTHER INFORMATION: Incyte ID No: 7473618CD1

<400> SEQUENCE: 2

Met Glu Pro Arg Leu Phe Cys Trp Thr Thr Leu Phe Leu Leu Ala
 1               5                  10                  15

Gly Trp Cys Leu Pro Gly Leu Pro Cys Pro Ser Arg Cys Leu Cys
            20                  25                  30

Phe Lys Ser Thr Val Arg Cys Met His Leu Met Leu Asp His Ile
        35                  40                  45

Pro Gln Val Ser Gln Gln Thr Thr Val Leu Asp Leu Arg Phe Asn
    50                  55                  60

Arg Ile Arg Glu Ile Pro Gly Ser Ala Phe Lys Lys Leu Lys Asn
65                  70                  75

Leu Asn Thr Leu Leu Leu Asn Asn Asn His Ile Arg Lys Ile Ser
            80                  85                  90

Arg Asn Ala Phe Glu Gly Leu Glu Asn Leu Leu Tyr Leu Tyr Leu
        95                  100                 105

Tyr Lys Asn Glu Ile His Ala Leu Asp Lys Gln Thr Phe Lys Gly
    110                 115                 120

Leu Ile Ser Leu Glu His Leu Tyr Ile His Phe Asn Gln Leu Glu
125                 130                 135

Met Leu Gln Pro Glu Thr Phe Gly Asp Leu Leu Arg Leu Glu Arg
            140                 145                 150

Leu Phe Leu His Asn Asn Lys Leu Ser Lys Ile Pro Ala Gly Ser
        155                 160                 165

Phe Ser Asn Leu Asp Ser Leu Lys Arg Leu Arg Leu Asp Ser Asn
    170                 175                 180

Ala Leu Val Cys Asp Cys Asp Leu Met Trp Leu Gly Glu Leu Leu
185                 190                 195

Gln Gly Phe Ala Gln His Gly His Thr Gln Ala Ala Ala Thr Cys
            200                 205                 210

Glu Tyr Pro Arg Arg Leu His Gly Arg Ala Val Ala Ser Val Thr
        215                 220                 225
```

-continued

Val Glu Glu Phe Asn Cys Gln Ser Pro Arg Ile Thr Phe Glu Pro
            230                 235                 240

Gln Asp Val Glu Val Pro Ser Gly Asn Thr Val Tyr Phe Thr Cys
            245                 250                 255

Arg Ala Glu Gly Asn Pro Lys Pro Glu Ile Ile Trp Ile His Asn
            260                 265                 270

Asn His Ser Leu Asp Leu Glu Asp Thr Arg Leu Asn Val Phe
            275                 280                 285

Asp Asp Gly Thr Leu Met Ile Arg Asn Thr Arg Glu Ser Asp Gln
            290                 295                 300

Gly Val Tyr Gln Cys Met Ala Arg Asn Ser Ala Gly Glu Ala Lys
            305                 310                 315

Thr Gln Ser Ala Met Leu Arg Tyr Ser Ser Leu Pro Ala Lys Pro
            320                 325                 330

Ser Phe Val Ile Gln Pro Gln Asp Thr Glu Val Leu Ile Gly Thr
            335                 340                 345

Ser Thr Thr Leu Glu Cys Met Ala Thr Gly His Pro His Pro Leu
            350                 355                 360

Ile Thr Trp Thr Arg Asp Asn Gly Leu Glu Leu Asp Gly Ser Arg
            365                 370                 375

His Val Ala Thr Ser Ser Gly Leu Tyr Leu Gln Asn Ile Thr Gln
            380                 385                 390

Arg Asp His Gly Arg Phe Thr Cys His Ala Asn Asn Ser His Gly
            395                 400                 405

Thr Val Gln Ala Ala Ala Asn Ile Ile Val Gln Ala Pro Pro Gln
            410                 415                 420

Phe Thr Val Thr Pro Lys Asp Gln Val Val Leu Glu Glu His Ala
            425                 430                 435

Val Glu Trp Leu Cys Glu Ala Asp Gly Asn Pro Pro Pro Val Ile
            440                 445                 450

Val Trp Thr Lys Thr Gly Gly Gln Leu Pro Val Glu Gly Gln His
            455                 460                 465

Thr Val Leu Ser Ser Gly Thr Leu Arg Ile Asp Arg Ala Ala Gln
            470                 475                 480

His Asp Gln Gly Gln Tyr Glu Cys Gln Ala Val Ser Ser Leu Gly
            485                 490                 495

Val Lys Lys Val Ser Val Gln Leu Thr Val Lys Pro Lys Gly Leu
            500                 505                 510

Ala Val Phe Thr Gln Leu Pro Gln Asp Thr Ser Val Glu Val Gly
            515                 520                 525

Lys Asn Ile Asn Ile Ser Cys His Ala Gln Gly Glu Pro Gln Pro
            530                 535                 540

Ile Ile Thr Trp Asn Lys Glu Gly Val Gln Ile Thr Glu Ser Gly
            545                 550                 555

Lys Phe His Val Asp Asp Glu Gly Thr Leu Thr Ile Tyr Asp Ala
            560                 565                 570

Gly Phe Pro Asp Gln Gly Arg Tyr Glu Cys Val Ala Arg Asn Ser
            575                 580                 585

Phe Gly Leu Ala Val Thr Asn Met Phe Leu Thr Val Thr Ala Ile
            590                 595                 600

Gln Gly Arg Gln Ala Gly Asp Asp Phe Val Glu Ser Ser Ile Leu
            605                 610                 615

```
Asp Ala Val Gln Arg Val Asp Ser Ala Ile Asn Ser Thr Arg Arg
            620                 625                 630

His Leu Phe Ser Gln Lys Pro His Thr Ser Ser Asp Leu Leu Ala
            635                 640                 645

Gln Phe His Tyr Pro Arg Asp Pro Leu Ile Val Glu Met Ala Arg
            650                 655                 660

Ala Gly Glu Ile Phe Glu His Thr Leu Gln Leu Ile Arg Glu Arg
            665                 670                 675

Val Lys Gln Gly Leu Thr Val Asp Leu Glu Gly Lys Glu Phe Arg
            680                 685                 690

Tyr Asn Asp Leu Val Ser Pro Arg Ser Leu Ser Leu Ile Ala Asn
            695                 700                 705

Leu Ser Gly Cys Thr Ala Arg Arg Pro Leu Pro Asn Cys Ser Asn
            710                 715                 720

Arg Cys Phe His Ala Lys Tyr Arg Ala His Asp Gly Thr Cys Asn
            725                 730                 735

Asn Leu Gln Gln Pro Thr Trp Gly Ala Ala Leu Thr Ala Phe Ala
            740                 745                 750

Arg Leu Leu Gln Pro Ala Tyr Arg Asp Gly Ile Arg Ala Pro Arg
            755                 760                 765

Gly Leu Gly Leu Pro Val Gly Ser Arg Gln Pro Leu Pro Pro Pro
            770                 775                 780

Arg Leu Val Ala Thr Val Trp Ala Arg Ala Ala Ala Val Thr Pro
            785                 790                 795

Asp His Ser Tyr Thr Arg Met Leu Met His Trp Gly Trp Phe Leu
            800                 805                 810

Glu His Asp Leu Asp His Thr Val Pro Ala Leu Ser Thr Ala Arg
            815                 820                 825

Phe Ser Asp Gly Arg Pro Cys Ser Ser Val Cys Thr Asn Asp Pro
            830                 835                 840

Pro Cys Phe Pro Met Asn Thr Arg His Ala Asp Pro Arg Gly Thr
            845                 850                 855

His Ala Pro Cys Met Leu Phe Ala Arg Ser Ser Pro Ala Cys Ala
            860                 865                 870

Ser Gly Arg Pro Ser Ala Thr Val Asp Ser Val Tyr Ala Arg Glu
            875                 880                 885

Gln Ile Asn Gln Gln Thr Ala Tyr Ile Asp Gly Ser Asn Val Tyr
            890                 895                 900

Gly Ser Ser Glu Arg Glu Ser Gln Ala Leu Arg Asp Pro Ser Val
            905                 910                 915

Pro Arg Gly Leu Leu Lys Thr Gly Phe Pro Trp Pro Ser Gly
            920                 925                 930

Lys Pro Leu Leu Pro Phe Ser Thr Gly Pro Pro Thr Glu Cys Ala
            935                 940                 945

Arg Gln Glu Gln Glu Ser Pro Cys Phe Leu Ala Gly Asp His Arg
            950                 955                 960

Ala Asn Glu His Leu Ala Leu Val Ala Met His Thr Leu Trp Phe
            965                 970                 975

Arg Glu His Asn Arg Val Ala Thr Glu Leu Ser Ala Leu Asn Pro
            980                 985                 990

His Trp Glu Gly Asn Thr Val Tyr Gln Glu Ala Arg Lys Ile Val
            995                1000                1005

Gly Ala Glu Leu Gln His Ile Thr Tyr Ser His Trp Leu Pro Lys
```

-continued

```
                1010                1015                1020
Val Leu Gly Asp Pro Gly Thr Arg Met Leu Arg Gly Tyr Arg Gly
                1025                1030                1035
Tyr Asn Pro Asn Val Asn Ala Gly Ile Ile Asn Ser Phe Ala Thr
                1040                1045                1050
Ala Ala Phe Arg Phe Gly His Thr Leu Ile Asn Pro Ile Leu Tyr
                1055                1060                1065
Arg Leu Asn Ala Thr Leu Gly Glu Ile Ser Glu Gly His Leu Pro
                1070                1075                1080
Phe His Lys Ala Leu Phe Ser Pro Ser Arg Ile Ile Lys Glu Gly
                1085                1090                1095
Gly Ile Asp Pro Val Leu Arg Gly Leu Phe Gly Val Ala Ala Lys
                1100                1105                1110
Trp Arg Ala Pro Ser Tyr Leu Leu Ser Pro Glu Leu Thr Gln Arg
                1115                1120                1125
Leu Phe Ser Ala Ala Tyr Ser Ala Ala Val Asp Ser Ala Ala Thr
                1130                1135                1140
Ile Ile Gln Arg Gly Arg Asp His Gly Ile Pro Pro Tyr Val Asp
                1145                1150                1155
Phe Arg Val Phe Cys Asn Leu Thr Ser Val Lys Asn Phe Glu Asp
                1160                1165                1170
Leu Gln Asn Glu Ile Lys Asp Ser Glu Ile Arg Gln Lys Leu Arg
                1175                1180                1185
Lys Leu Tyr Gly Ser Pro Gly Asp Ile Asp Leu Trp Pro Ala Leu
                1190                1195                1200
Met Val Glu Asp Leu Ile Pro Gly Thr Arg Val Gly Pro Thr Leu
                1205                1210                1215
Met Cys Leu Phe Val Thr Gln Phe Gln Arg Leu Arg Asp Gly Asp
                1220                1225                1230
Arg Phe Trp Tyr Glu Asn Pro Gly Val Phe Thr Pro Ala Gln Leu
                1235                1240                1245
Thr Gln Leu Lys Gln Ala Ser Leu Ser Arg Val Leu Cys Asp Asn
                1250                1255                1260
Gly Asp Ser Ile Gln Gln Val Gln Ala Asp Val Phe Val Lys Ala
                1265                1270                1275
Glu Tyr Pro Gln Asp Tyr Leu Asn Cys Ser Glu Ile Pro Lys Val
                1280                1285                1290
Asp Leu Arg Val Trp Gln Asp Cys Cys Ala Asp Cys Arg Ser Arg
                1295                1300                1305
Gly Gln Phe Arg Ala Val Thr Gln Glu Ser Gln Lys Lys Arg Ser
                1310                1315                1320
Ala Gln Tyr Ser Tyr Pro Val Asp Lys Asp Met Glu Leu Ser His
                1325                1330                1335
Leu Arg Ser Arg Gln Gln Asp Lys Ile Tyr Val Gly Glu Asp Ala
                1340                1345                1350
Arg Asn Val Thr Val Leu Ala Lys Thr Lys Phe Ser Gln Asp Phe
                1355                1360                1365
Ser Thr Phe Ala Ala Glu Ile Gln Glu Thr Ile Thr Ala Leu Arg
                1370                1375                1380
Glu Gln Ile Asn Lys Leu Glu Ala Arg Leu Arg Gln Ala Gly Cys
                1385                1390                1395
Thr Asp Val Arg Gly Val Pro Arg Lys Ala Glu Glu Arg Trp Met
                1400                1405                1410
```

-continued

```
Lys Glu Asp Cys Thr His Cys Ile Cys Glu Ser Gly Gln Val Thr
            1415                1420                1425

Cys Val Val Glu Ile Cys Pro Pro Ala Pro Cys Pro Ser Pro Glu
            1430                1435                1440

Leu Val Lys Gly Thr Cys Cys Pro Val Cys Arg Asp Arg Gly Met
            1445                1450                1455

Pro Ser Asp Ser Pro Glu Lys Arg
            1460

<210> SEQ ID NO 3
<211> LENGTH: 401
<212> TYPE: PRT
<213> ORGANISM: Homo sapiens
<220> FEATURE:
<221> NAME/KEY: misc_feature
<223> OTHER INFORMATION: Incyte ID No: 3564136CD1

<400> SEQUENCE: 3

Met Gly Leu Lys Ala Leu Cys Leu Gly Leu Leu Cys Val Leu Phe
  1               5                  10                  15

Val Ser His Phe Tyr Thr Pro Met Pro Asp Asn Ile Glu Glu Ser
                 20                  25                  30

Trp Lys Ile Met Ala Leu Asp Ala Ile Ala Lys Thr Cys Ala Asn
                 35                  40                  45

Val Cys Ile Phe Val Glu Met Arg Tyr His His Ile Tyr Glu Glu
                 50                  55                  60

Phe Ile Ser Met Ile Phe Arg Leu Asp Tyr Thr Gln Pro Leu Ser
                 65                  70                  75

Asp Glu Tyr Ile Thr Val Thr Asp Thr Thr Phe Val Asp Ile Pro
                 80                  85                  90

Val Arg Leu Tyr Leu Pro Lys Arg Lys Ser Glu Thr Arg Arg Arg
                 95                 100                 105

Ala Val Ile Tyr Phe His Gly Gly Gly Phe Cys Phe Gly Ser Ser
                110                 115                 120

Lys Gln Arg Ala Phe Asp Phe Leu Asn Arg Trp Thr Ala Asn Thr
                125                 130                 135

Leu Asp Ala Val Val Val Gly Val Asp Tyr Arg Leu Ala Pro Gln
                140                 145                 150

His His Phe Pro Ala Gln Phe Glu Asp Gly Leu Ala Ala Val Lys
                155                 160                 165

Phe Phe Leu Leu Glu Lys Ile Leu Thr Lys Tyr Gly Val Asp Pro
                170                 175                 180

Thr Arg Ile Cys Ile Ala Gly Asp Ser Ser Gly Gly Asn Leu Ala
                185                 190                 195

Thr Ala Val Thr Gln Gln Val Gln Asn Asp Ala Glu Ile Lys His
                200                 205                 210

Lys Ile Lys Met Gln Val Leu Leu Tyr Pro Gly Leu Gln Ile Thr
                215                 220                 225

Asp Ser Tyr Leu Pro Ser His Arg Glu Asn Glu His Gly Ile Val
                230                 235                 240

Leu Thr Arg Asp Val Ala Ile Lys Leu Val Ser Leu Tyr Phe Thr
                245                 250                 255

Lys Asp Glu Ala Leu Pro Trp Ala Met Arg Arg Asn Gln His Met
                260                 265                 270

Pro Leu Glu Ser Arg His Leu Phe Lys Phe Val Asn Trp Ser Ile
```

```
                        275                 280                 285

Leu Leu Pro Glu Lys Tyr Arg Lys Asp Tyr Val Tyr Thr Glu Pro
                290                 295                 300

Ile Leu Gly Gly Leu Ser Tyr Ser Leu Pro Gly Leu Thr Asp Ser
            305                 310                 315

Arg Ala Leu Pro Leu Leu Ala Asn Asp Ser Gln Leu Gln Asn Leu
        320                 325                 330

Pro Leu Thr Tyr Ile Leu Thr Cys Gln His Asp Leu Ile Arg Asp
    335                 340                 345

Asp Gly Leu Met Tyr Val Thr Arg Leu Arg Asn Val Gly Val Gln
            350                 355                 360

Val Val His Glu His Ile Glu Asp Gly Ile His Gly Ala Leu Ser
        365                 370                 375

Phe Met Thr Ser Pro Phe Tyr Leu Arg Leu Gly Leu Arg Ile Arg
    380                 385                 390

Asp Met Tyr Val Ser Trp Leu Asp Lys Asn Leu
            395                 400

<210> SEQ ID NO 4
<211> LENGTH: 271
<212> TYPE: PRT
<213> ORGANISM: Homo sapiens
<220> FEATURE:
<221> NAME/KEY: misc_feature
<223> OTHER INFORMATION: Incyte ID No: 624334CD1

<400> SEQUENCE: 4

Met Gln Ala Ala Cys Trp Tyr Val Leu Phe Leu Leu Gln Pro Thr
 1               5                  10                  15

Val Tyr Leu Val Thr Cys Ala Asn Leu Thr Asn Gly Gly Lys Ser
                20                  25                  30

Glu Leu Leu Lys Ser Gly Ser Ser Lys Ser Thr Leu Lys His Ile
            35                  40                  45

Trp Thr Glu Ser Ser Lys Asp Leu Ser Ile Ser Arg Leu Leu Ser
        50                  55                  60

Gln Thr Phe Arg Gly Lys Glu Asn Asp Thr Leu Asp Leu Asp Leu Arg
    65                  70                  75

Tyr Asp Thr Pro Glu Pro Tyr Ser Glu Gln Asp Leu Trp Asp Trp
            80                  85                  90

Leu Arg Asn Ser Thr Asp Leu Gln Glu Pro Arg Pro Arg Ala Lys
        95                 100                 105

Arg Arg Pro Ile Val Lys Thr Gly Lys Phe Lys Lys Met Phe Gly
    110                 115                 120

Trp Gly Asp Phe His Ser Asn Ile Lys Thr Val Lys Leu Asn Leu
            125                 130                 135

Leu Ile Thr Gly Lys Ile Val Asp His Gly Asn Gly Thr Phe Ser
        140                 145                 150

Val Tyr Phe Arg His Asn Ser Thr Gly Gln Gly Asn Val Ser Val
    155                 160                 165

Ser Leu Val Pro Pro Thr Lys Ile Val Glu Phe Asp Leu Ala Gln
            170                 175                 180

Gln Thr Val Ile Asp Ala Lys Asp Ser Lys Ser Phe Asn Cys Arg
        185                 190                 195

Ile Glu Tyr Glu Lys Val Asp Lys Ala Thr Lys Asn Thr Leu Cys
    200                 205                 210
```

-continued

```
Asn Tyr Asp Pro Ser Lys Thr Cys Tyr Gln Glu Gln Thr Gln Ser
            215                 220                 225

His Val Ser Trp Leu Cys Ser Lys Pro Phe Lys Val Ile Cys Ile
            230                 235                 240

Tyr Ile Ser Phe Tyr Ser Thr Asp Tyr Lys Leu Val Gln Lys Val
            245                 250                 255

Cys Pro Asp Tyr Asn Tyr His Ser Asp Thr Pro Tyr Phe Pro Ser
            260                 265                 270

Gly

<210> SEQ ID NO 5
<211> LENGTH: 201
<212> TYPE: PRT
<213> ORGANISM: Homo sapiens
<220> FEATURE:
<221> NAME/KEY: misc_feature
<223> OTHER INFORMATION: Incyte ID No: 7483393CD1

<400> SEQUENCE: 5

Met Arg Pro Leu Leu Val Leu Leu Leu Gly Leu Ala Ala Gly
  1               5                  10                  15

Ser Pro Pro Leu Asp Asp Asn Lys Ile Pro Ser Leu Cys Pro Gly
                 20                  25                  30

Leu Pro Gly Pro Arg Gly Asp Pro Gly Pro Arg Gly Glu Ala Gly
                 35                  40                  45

Pro Ala Gly Pro Thr Gly Pro Ala Gly Glu Cys Ser Val Pro Pro
                 50                  55                  60

Arg Ser Ala Phe Ser Ala Lys Arg Ser Glu Ser Arg Val Pro Pro
             65                  70                  75

Pro Ser Asp Ala Pro Leu Pro Phe Asp Arg Val Leu Val Asn Glu
             80                  85                  90

Gln Gly His Tyr Asp Ala Val Thr Gly Lys Phe Thr Cys Gln Val
                 95                 100                 105

Pro Gly Val Tyr Tyr Phe Ala Val His Ala Thr Val Tyr Arg Ala
                110                 115                 120

Ser Leu Gln Phe Asp Leu Val Lys Asn Gly Glu Ser Ile Ala Ser
                125                 130                 135

Phe Phe Gln Phe Phe Gly Gly Trp Pro Lys Pro Ala Ser Leu Ser
                140                 145                 150

Gly Gly Ala Met Val Arg Leu Glu Pro Glu Asp Gln Val Trp Val
                155                 160                 165

Gln Val Gly Val Gly Asp Tyr Ile Gly Ile Tyr Ala Ser Ile Lys
                170                 175                 180

Thr Asp Ser Thr Phe Ser Gly Phe Leu Val Tyr Ser Asp Trp His
                185                 190                 195

Ser Ser Pro Val Phe Ala
                200

<210> SEQ ID NO 6
<211> LENGTH: 121
<212> TYPE: PRT
<213> ORGANISM: Homo sapiens
<220> FEATURE:
<221> NAME/KEY: misc_feature
<223> OTHER INFORMATION: Incyte ID No: 1799943CD1

<400> SEQUENCE: 6

Met Ala Pro Arg Pro Leu Leu Leu Leu Leu Leu Leu Leu Gly Gly
```

```
            1               5              10              15
        Ser Ala Ala Arg Pro Ala Pro Pro Arg Ala Arg Arg His Ser Asp
                        20                  25                  30

Gly Thr Phe Thr Ser Glu Leu Ser Arg Leu Arg Glu Gly Ala Arg
                        35                  40                  45

Leu Gln Arg Leu Leu Gln Gly Leu Val Gly Lys Arg Ser Glu Gln
                        50                  55                  60

Asp Ala Glu Asn Ser Met Ala Trp Thr Arg Leu Ser Ala Gly Leu
                        65                  70                  75

Leu Cys Pro Ser Gly Ser Asn Met Pro Ile Leu Gln Ala Trp Met
                        80                  85                  90

Pro Leu Asp Gly Thr Trp Ser Pro Trp Leu Pro Pro Gly Pro Met
                        95                 100                 105

Val Ser Glu Pro Ala Gly Ala Ala Ala Glu Gly Thr Leu Arg Pro
                       110                 115                 120

Arg

<210> SEQ ID NO 7
<211> LENGTH: 186
<212> TYPE: PRT
<213> ORGANISM: Homo sapiens
<220> FEATURE:
<221> NAME/KEY: misc_feature
<223> OTHER INFORMATION: Incyte ID No: 2013095CD1

<400> SEQUENCE: 7

Met Asp Thr Phe Ser Thr Lys Ser Leu Ala Leu Gln Ala Gln Lys
          1               5                  10                  15

Lys Leu Leu Ser Lys Met Ala Ser Lys Ala Val Val Ala Val Leu
                         20                 25                  30

Val Asp Asp Thr Ser Ser Glu Val Leu Asp Glu Leu Tyr Arg Ala
                         35                 40                  45

Thr Arg Glu Phe Thr Arg Ser Arg Lys Glu Ala Gln Lys Met Leu
                         50                 55                  60

Lys Asn Leu Val Lys Val Ala Leu Lys Leu Gly Leu Leu Leu Arg
                         65                 70                  75

Gly Asp Gln Leu Gly Gly Glu Glu Leu Ala Leu Leu Arg Arg Phe
                         80                 85                  90

Arg His Arg Ala Arg Cys Leu Ala Met Thr Ala Val Ser Phe His
                         95                100                 105

Gln Val Asp Phe Thr Phe Asp Arg Arg Val Leu Ala Ala Gly Leu
                        110                115                 120

Leu Glu Cys Arg Asp Leu Leu His Gln Ala Val Gly Pro His Leu
                        125                130                 135

Thr Ala Lys Ser His Gly Arg Ile Asn His Val Phe Gly His Leu
                        140                145                 150

Ala Asp Cys Asp Phe Leu Ala Ala Leu Tyr Gly Pro Ala Glu Pro
                        155                160                 165

Tyr Arg Ser His Leu Arg Arg Ile Cys Glu Gly Leu Gly Arg Met
                        170                175                 180

Leu Asp Glu Gly Ser Leu
                        185

<210> SEQ ID NO 8
<211> LENGTH: 436
<212> TYPE: PRT
```

-continued

<213> ORGANISM: Homo sapiens
<220> FEATURE:
<221> NAME/KEY: misc_feature
<223> OTHER INFORMATION: Incyte ID No: 4674740CD1

<400> SEQUENCE: 8

```
Met Val Gly Phe Gly Ala Asn Arg Arg Ala Gly Arg Leu Pro Ser
 1               5                  10                  15

Leu Val Leu Val Val Leu Leu Val Val Ile Val Val Leu Ala Phe
                20                  25                  30

Asn Tyr Trp Ser Ile Ser Ser Arg His Val Leu Leu Gln Glu Glu
                35                  40                  45

Val Ala Glu Leu Gln Gly Gln Val Gln Arg Thr Glu Val Ala Arg
                50                  55                  60

Gly Arg Leu Glu Lys Arg Asn Ser Asp Leu Leu Leu Val Asp
                65                  70                  75

Thr His Lys Lys Gln Ile Asp Gln Lys Glu Ala Asp Tyr Gly Arg
                80                  85                  90

Leu Ser Ser Arg Leu Gln Ala Arg Glu Gly Leu Gly Lys Arg Cys
                95                 100                 105

Glu Asp Asp Lys Val Lys Leu Gln Asn Asn Ile Ser Tyr Gln Met
               110                 115                 120

Ala Asp Ile His His Leu Lys Glu Gln Leu Ala Glu Leu Arg Gln
               125                 130                 135

Glu Phe Leu Arg Gln Glu Asp Gln Leu Gln Asp Tyr Arg Lys Asn
               140                 145                 150

Asn Thr Tyr Leu Val Lys Arg Leu Glu Tyr Glu Ser Phe Gln Cys
               155                 160                 165

Gly Gln Gln Met Lys Glu Leu Arg Ala Gln His Glu Glu Asn Ile
               170                 175                 180

Lys Lys Leu Ala Asp Gln Phe Leu Glu Glu Gln Lys Gln Glu Thr
               185                 190                 195

Gln Lys Ile Gln Ser Asn Asp Gly Lys Glu Leu Asp Ile Asn Asn
               200                 205                 210

Gln Val Val Pro Lys Asn Ile Pro Lys Val Ala Glu Asn Val Ala
               215                 220                 225

Asp Lys Asn Glu Glu Pro Ser Ser Asn His Ile Pro His Gly Lys
               230                 235                 240

Glu Gln Ile Lys Arg Gly Gly Asp Ala Gly Met Pro Gly Ile Glu
               245                 250                 255

Glu Asn Asp Leu Ala Lys Val Asp Asp Leu Pro Pro Ala Leu Arg
               260                 265                 270

Lys Pro Pro Ile Ser Val Ser Gln His Glu Ser His Gln Ala Ile
               275                 280                 285

Ser His Leu Pro Thr Gly Gln Pro Leu Ser Pro Asn Met Pro Pro
               290                 295                 300

Asp Ser His Ile Asn His Asn Gly Asn Pro Gly Thr Ser Lys Gln
               305                 310                 315

Asn Pro Ser Ser Pro Leu Gln Arg Leu Ile Pro Gly Ser Asn Leu
               320                 325                 330

Asp Ser Glu Pro Arg Ile Gln Thr Asp Ile Leu Lys Gln Ala Thr
               335                 340                 345

Lys Asp Arg Val Ser Asp Phe His Lys Leu Lys Gln Ser Arg Phe
               350                 355                 360
```

-continued

```
Phe Asp Glu Asn Glu Ser Pro Val Asp Pro Gln His Gly Ser Lys
            365                 370                 375

Leu Ala Asp Tyr Asn Gly Asp Asp Gly Asn Val Gly Glu Tyr Glu
        380                 385                 390

Ala Asp Lys Gln Ala Glu Leu Ala Tyr Asn Glu Glu Glu Asp Gly
    395                 400                 405

Asp Gly Gly Glu Glu Asp Val Gln Asp Asp Glu Glu Arg Glu Leu
410                 415                 420

Gln Met Asp Pro Ala Asp Tyr Gly Lys Gln His Phe Asn Asp Val
            425                 430                 435

Leu

<210> SEQ ID NO 9
<211> LENGTH: 134
<212> TYPE: PRT
<213> ORGANISM: Homo sapiens
<220> FEATURE:
<221> NAME/KEY: misc_feature
<223> OTHER INFORMATION: Incyte ID No: 146907CD1

<400> SEQUENCE: 9

Met Gly Ser Gly Pro Ser Cys Ile Ile Ala Leu Cys Pro Pro Pro
  1               5                  10                  15

Ser Ser Leu Gln Pro Ser Arg Leu Gly Leu Leu Phe Ala Pro Pro
             20                  25                  30

Ala Glu Arg Gly Ile His Ser Arg Pro Leu Ser Ser Trp Ala Gly
         35                  40                  45

Met Phe Ser Thr Ser Ser Asp Asp Pro Ser Leu Arg Gly Phe Pro
     50                  55                  60

Leu Gly Leu Pro Gly Leu Ser Ser Leu His Cys Pro Ala Leu Leu
 65                  70                  75

Pro Arg Pro Val Val Ala Val Gly Thr Cys Leu Arg Ala Ser Ser
                 80                  85                  90

Leu Leu Leu Cys Pro Pro His Pro Gln Ala Met Ala Ala Val Arg
             95                 100                 105

Leu Gly Thr Trp Leu Leu Leu Phe Met Gln Gln Leu Gln Asp Leu
        110                 115                 120

Ala Gln Arg Leu Val Pro Ser Arg Leu Ser Ile Asn Ile Tyr
    125                 130

<210> SEQ ID NO 10
<211> LENGTH: 172
<212> TYPE: PRT
<213> ORGANISM: Homo sapiens
<220> FEATURE:
<221> NAME/KEY: misc_feature
<223> OTHER INFORMATION: Incyte ID No: 1513563CD1

<400> SEQUENCE: 10

Met Cys Ser Thr Lys Gly Met Trp His Val Ala Pro Gly Arg Val
  1               5                  10                  15

His Pro Ala Arg Gly Gln Leu Phe Ser Cys Leu Gly Leu Thr Leu
             20                  25                  30

Thr Thr Gly Leu Trp Gly Val Leu Gln Pro Lys Cys Pro Pro Cys
         35                  40                  45

Pro Pro His Ile Ser Val Arg Gly Gly His Ala Gln Ala Asn Val
     50                  55                  60

Leu Ser Gln Pro Ala Ala Gly Ala Ala Leu Pro Arg Arg Ala Trp
```

```
                65                  70                  75
Glu Val Leu Gly Met Pro Gln Arg Phe Ser Ser Cys Leu Ala Leu
             80                  85                  90

Ala Trp Pro Ser Ala Ser Arg Ile Asn Leu Arg Ser Val Glu Gln
             95                 100                 105

Pro Arg Glu Thr Gln Ile Trp Leu Arg Thr Ala Tyr Gly Gln Glu
            110                 115                 120

Gly Cys Lys Ser Ser Gln Ala Lys Pro Trp Ala Leu Ala Pro
            125                 130                 135

Ala Ala Ala Trp Leu Trp Thr Gln Leu Glu Pro Gly Arg Lys Ser
            140                 145                 150

Ala Thr Pro His Arg Arg Pro Leu Arg Leu Gly Lys His Leu Arg
            155                 160                 165

Lys Lys Leu Leu Gln Lys Arg
            170

<210> SEQ ID NO 11
<211> LENGTH: 80
<212> TYPE: PRT
<213> ORGANISM: Homo sapiens
<220> FEATURE:
<221> NAME/KEY: misc_feature
<223> OTHER INFORMATION: Incyte ID No: 3144709CD1

<400> SEQUENCE: 11

Met Ile Ile Ser Ile Ile Ile Cys Leu Val Trp Ser Ala Leu Asn
 1               5                  10                  15

Cys Leu Gln Ser Pro Phe Thr Cys Thr Ala Gly Gly Asn Cys Ala
             20                  25                  30

Val Trp Ala Gly Pro Val Leu Glu Ala Tyr Pro Val Lys Ser Val
             35                  40                  45

Ser Ala Leu Gly Glu Ser Asn Met Tyr Pro Phe Arg Leu Leu Thr
             50                  55                  60

Val Tyr Val Val Leu Met Tyr Leu Tyr Leu Phe Leu Phe Phe Leu
             65                  70                  75

Cys Leu Cys His Ile
             80

<210> SEQ ID NO 12
<211> LENGTH: 92
<212> TYPE: PRT
<213> ORGANISM: Homo sapiens
<220> FEATURE:
<221> NAME/KEY: misc_feature
<223> OTHER INFORMATION: Incyte ID No: 4775686CD1

<400> SEQUENCE: 12

Met Ala Ser Gln Thr Ser Cys Ile Ile Trp Pro Leu Ala Thr Leu
 1               5                  10                  15

Pro His Pro Ile Ser Ser Phe Ala Leu Tyr Ser Ser Tyr Thr Val
             20                  25                  30

Arg Gly Val Pro Lys Thr Ser Arg Trp Val Arg Pro Gln Asp Leu
             35                  40                  45

His Met Cys Cys Ser Leu Tyr Leu His Arg Ser Phe Leu Phe Ser
             50                  55                  60

Cys Leu Leu Asn Ser Tyr Leu Pro Ser Gly Leu Ile Ser Thr Phe
             65                  70                  75

Ser Pro Leu Leu Val Cys Cys Ser Tyr Leu Arg Ser Asn Ser Arg
```

-continued

```
                    80                  85                  90

Glu Met

<210> SEQ ID NO 13
<211> LENGTH: 90
<212> TYPE: PRT
<213> ORGANISM: Homo sapiens
<220> FEATURE:
<221> NAME/KEY: misc_feature
<223> OTHER INFORMATION: Incyte ID No: 5851038CD1

<400> SEQUENCE: 13

Met Ser Arg Pro Cys Leu Ser Leu Ala Ser Trp Cys Thr Leu Ser
  1               5                  10                  15

Ser Thr Leu Cys Ser Gly Thr Gly Leu Leu Gly Ser Pro Leu Leu
                 20                  25                  30

His Leu Ala Cys Pro Ser Ser His Arg Gly Ala Ala Gln Ala Phe
                 35                  40                  45

Pro Leu Gln Gly Trp Leu Thr Val His Gly Arg Asp Ser Ser Pro
                 50                  55                  60

Cys Cys Val Leu Ile Ala His Arg Gly Gly Ser Ser Ala Gly His
                 65                  70                  75

Phe Ala Asp Arg Leu Trp Ser Leu Ser Leu Leu Leu Ser Arg Gly
                 80                  85                  90

<210> SEQ ID NO 14
<211> LENGTH: 354
<212> TYPE: PRT
<213> ORGANISM: Homo sapiens
<220> FEATURE:
<221> NAME/KEY: misc_feature
<223> OTHER INFORMATION: Incyte ID No: 71850066CD1

<400> SEQUENCE: 14

Met Pro Leu Val Val Phe Cys Gly Leu Pro Tyr Ser Gly Lys Ser
  1               5                  10                  15

Arg Arg Ala Glu Glu Leu Arg Val Ala Leu Ala Ala Glu Gly Arg
                 20                  25                  30

Ala Val Tyr Val Val Asp Asp Ala Ala Val Leu Gly Ala Glu Asp
                 35                  40                  45

Pro Ala Val Tyr Gly Asp Ser Ala Arg Glu Lys Ala Leu Arg Gly
                 50                  55                  60

Ala Leu Arg Ala Ser Val Glu Arg Arg Leu Ser Arg His Asp Val
                 65                  70                  75

Val Ile Leu Asp Ser Leu Asn Tyr Ile Lys Gly Phe Arg Tyr Glu
                 80                  85                  90

Leu Tyr Cys Leu Ala Arg Ala Ala Arg Thr Pro Leu Cys Leu Val
                 95                 100                 105

Tyr Cys Val Arg Pro Gly Gly Pro Ile Ala Gly Pro Gln Val Ala
                110                 115                 120

Gly Ala Asn Glu Asn Pro Gly Arg Asn Val Ser Val Ser Trp Arg
                125                 130                 135

Pro Arg Ala Glu Glu Asp Gly Arg Ala Gln Ala Ala Gly Ser Ser
                140                 145                 150

Val Leu Arg Glu Leu His Thr Ala Asp Ser Val Val Asn Gly Ser
                155                 160                 165

Ala Gln Ala Asp Val Pro Lys Glu Leu Glu Arg Glu Glu Ser Gly
                170                 175                 180
```

```
Ala Ala Glu Ser Pro Ala Leu Val Thr Pro Asp Ser Glu Lys Ser
            185                 190                 195

Ala Lys His Gly Ser Gly Ala Phe Tyr Ser Pro Glu Leu Leu Glu
            200                 205                 210

Ala Leu Thr Leu Arg Phe Glu Ala Pro Asp Ser Arg Asn Arg Trp
            215                 220                 225

Asp Arg Pro Leu Phe Thr Leu Val Gly Leu Glu Glu Pro Leu Pro
            230                 235                 240

Leu Ala Gly Ile Arg Ser Ala Leu Phe Glu Asn Arg Ala Pro Pro
            245                 250                 255

Pro His Gln Ser Thr Gln Ser Gln Pro Leu Ala Ser Gly Ser Phe
            260                 265                 270

Leu His Gln Leu Asp Gln Val Thr Ser Gln Val Leu Ala Gly Leu
            275                 280                 285

Met Glu Ala Gln Lys Ser Ala Val Pro Gly Asp Leu Leu Thr Leu
            290                 295                 300

Pro Gly Thr Thr Glu His Leu Arg Phe Thr Arg Pro Leu Thr Met
            305                 310                 315

Ala Glu Leu Ser Arg Leu Arg Arg Gln Phe Ile Ser Tyr Thr Lys
            320                 325                 330

Met His Pro Asn Asn Glu Asn Leu Pro Gln Leu Ala Asn Met Phe
            335                 340                 345

Leu Gln Tyr Leu Ser Gln Ser Leu His
            350

<210> SEQ ID NO 15
<211> LENGTH: 101
<212> TYPE: PRT
<213> ORGANISM: Homo sapiens
<220> FEATURE:
<221> NAME/KEY: misc_feature
<223> OTHER INFORMATION: Incyte ID No: 2488934CD1

<400> SEQUENCE: 15

Met Ser Trp Asn Leu Lys Ala Cys Pro Phe Leu Val Leu Leu Cys
  1               5                  10                  15

Lys Ala Val Ile Ser Ser Met Glu Gly Met Val Phe Arg Gln Phe
             20                  25                  30

Phe Phe Phe Phe Arg Asp Gly Val Leu Leu Cys Arg Ser Gly Trp
             35                  40                  45

Ser Ala Val Ala Pro Phe Gln Leu Thr Ala Thr Ser Thr Ser Trp
             50                  55                  60

Val Gln Val Ile Leu Leu Leu Gln Pro Pro Lys Trp Leu Gly Leu
             65                  70                  75

Gln Ala Pro Ala Thr Thr Pro Gly Leu Phe Cys Ile Phe Ser Arg
             80                  85                  90

Asp Gly Val Ser Pro Cys Trp Pro Gly Trp Ser
             95                 100

<210> SEQ ID NO 16
<211> LENGTH: 74
<212> TYPE: PRT
<213> ORGANISM: Homo sapiens
<220> FEATURE:
<221> NAME/KEY: misc_feature
<223> OTHER INFORMATION: Incyte ID No: 2667946CD1

<400> SEQUENCE: 16
```

```
Met Met Leu Thr Leu Val Tyr Pro Pro Leu Ser Phe Arg Asn Gln
 1               5                  10                  15

Thr Leu Leu Ile Ser Leu Asn Pro His Met Cys Pro Ser Leu Asn
                 20                  25                  30

Ala Phe Leu Cys Pro Pro Glu Val Gln Thr Ile Gln Asp Ser Val
                 35                  40                  45

Phe Ile Ile Pro Met Ser Phe Phe Met Gly Phe Leu Asn Leu Glu
                 50                  55                  60

Tyr Pro Gln Arg Gln Phe Lys Ile Phe Lys Pro Met Gln Pro
                 65                  70
```

<210> SEQ ID NO 17
<211> LENGTH: 100
<212> TYPE: PRT
<213> ORGANISM: Homo sapiens
<220> FEATURE:
<221> NAME/KEY: misc_feature
<223> OTHER INFORMATION: Incyte ID No: 2834555CD1

<400> SEQUENCE: 17

```
Met Ala Leu Ser Trp Ser Ile Thr Ala Asn Ile Leu Ala Val Ser
 1               5                  10                  15

Gly Tyr Pro Val Glu Gly Ile Gly Trp Ser Val Val Cys Ile Ser
                 20                  25                  30

Asn Val Asn Lys Asn Ser Val Leu Val Gln Arg Ala Ser Ser Met
                 35                  40                  45

Ser Ser Asp Lys Thr Gly Arg Ala Tyr Phe Pro Ile Tyr Gln Leu
                 50                  55                  60

Gln Asp Trp Pro Phe Leu Gly Gln Leu Thr Arg His Leu Glu Arg
                 65                  70                  75

Arg Ala Leu Asn Ser Lys Ile Ile Phe Leu Val Ile Ala Leu Asn
                 80                  85                  90

Ala Ala Thr Ala Trp Ser Ser Ala Leu Ile
                 95                  100
```

<210> SEQ ID NO 18
<211> LENGTH: 94
<212> TYPE: PRT
<213> ORGANISM: Homo sapiens
<220> FEATURE:
<221> NAME/KEY: misc_feature
<223> OTHER INFORMATION: Incyte ID No: 5544174CD1

<400> SEQUENCE: 18

```
Met Ser Val Arg Leu Cys Val Cys Val Cys Leu Ser Leu Val Ser
 1               5                  10                  15

Leu Ser Pro Phe Ser His Ser Phe Ala Leu Cys Pro Cys Val Arg
                 20                  25                  30

Val Cys Val Cys Val Leu Gly His Met Cys Pro Val Arg Gln Arg
                 35                  40                  45

Thr Val Ser Ser Thr Ser Ala Phe Leu Val Val Ser Leu Ser Pro
                 50                  55                  60

Arg Leu Cys Leu Ala Cys Val Ala Arg Cys Gln Ser Phe Phe Trp
                 65                  70                  75

Arg Phe Gln Phe Arg Phe Val Lys Val Gln Met Arg Trp Gly Ala
                 80                  85                  90

Ala Ser Leu Ser
```

-continued

```
<210> SEQ ID NO 19
<211> LENGTH: 143
<212> TYPE: PRT
<213> ORGANISM: Homo sapiens
<220> FEATURE:
<221> NAME/KEY: misc_feature
<223> OTHER INFORMATION: Incyte ID No: 1728049CD1

<400> SEQUENCE: 19

Met Gly Met Ala Gly Leu Pro Ser Glu Leu Leu Ala Val Leu Gly
  1               5                  10                  15

Gln Thr Pro Gly Ser Gln Trp Pro Cys Ser Glu Ala Trp Leu Cys
                 20                  25                  30

Leu Pro Thr Trp Gly Gln Pro Gly Pro Pro His Pro Ala Ala
                 35                  40                  45

Gly Asp Trp Pro Ser Leu Pro Ala Ser Thr Phe Val Thr Thr Gly
                 50                  55                  60

Phe Gly Arg Ser Pro Leu Ala Arg Lys Pro Glu Cys Arg Ala Gly
                 65                  70                  75

Arg Arg Arg Arg Arg Asn Leu Thr Phe Arg Ala Asn Gln Val Ser
                 80                  85                  90

Pro Arg Asp Thr Ala Ala Val Trp Gly Val Arg Glu Gly Ser Leu
                 95                 100                 105

Pro Leu Arg Arg Gln Cys Leu Leu Gly Leu Trp Arg Met His Ser
                110                 115                 120

Gln Asp Leu Glu Trp Arg Glu Ser Leu Glu Glu Gly Pro Ser Pro
                125                 130                 135

Val Pro Gln Ala Arg Pro His Glu
                140

<210> SEQ ID NO 20
<211> LENGTH: 116
<212> TYPE: PRT
<213> ORGANISM: Homo sapiens
<220> FEATURE:
<221> NAME/KEY: misc_feature
<223> OTHER INFORMATION: Incyte ID No: 2425121CD1

<400> SEQUENCE: 20

Met Ser Arg Cys Asp Ser Arg Val His Trp Ala Leu Leu Gly Ala
  1               5                  10                  15

Pro Leu Leu Leu Ser Glu Ile Gly Ala Cys Trp Arg Ala Pro
                 20                  25                  30

Gln Val Ala Val Leu Gly Cys Arg Pro Val Pro Leu Ser Pro Ser
                 35                  40                  45

Ser Gly Ser Gln Arg Val Leu Cys Leu Asn Leu Val Asp Ser Ser
                 50                  55                  60

Tyr Pro Thr Arg Val Ala Cys Ser Thr Cys Ser Leu Gln Cys Ala
                 65                  70                  75

Val Gly Ala Pro Gly Pro Arg Gly Ala Gln Asp Thr Asn Ser Pro
                 80                  85                  90

Ser Leu His Leu Gly Cys Ser Gly Asn Glu Gly Lys Ser Thr Phe
                 95                 100                 105

Leu Pro Gln Glu Val Gly Ser Leu Ala Thr Met
                110                 115

<210> SEQ ID NO 21
<211> LENGTH: 76
```

```
<212> TYPE: PRT
<213> ORGANISM: Homo sapiens
<220> FEATURE:
<221> NAME/KEY: misc_feature
<223> OTHER INFORMATION: Incyte ID No: 2817925CD1

<400> SEQUENCE: 21

Met Ala Lys His Leu Thr Ser Ser Leu Val Ala Trp Leu Leu Ser
 1               5                  10                  15

Ser Arg Thr Ser Arg Ala Pro Leu Phe Ala Phe Pro Ser Phe Phe
            20                  25                  30

Leu Leu Leu Leu Gln Gln Thr Ser Cys Asp Leu Glu Asp Gly Cys
        35                  40                  45

His Met Leu Glu Glu Thr Glu Gly Arg Asn Pro Asp Asp Phe Thr
    50                  55                  60

Glu Leu Pro Lys Gln Phe Leu Thr Val Tyr Ser Gly Ser Leu Thr
65                  70                  75

Lys

<210> SEQ ID NO 22
<211> LENGTH: 116
<212> TYPE: PRT
<213> ORGANISM: Homo sapiens
<220> FEATURE:
<221> NAME/KEY: misc_feature
<223> OTHER INFORMATION: Incyte ID No: 4000264CD1

<400> SEQUENCE: 22

Met Pro Arg Ala Thr Pro Ala Trp Gln Leu Leu Ala Gly Phe Pro
 1               5                  10                  15

Leu Ile Ser Gly Val Gly Leu Leu Ser Gln Gly Leu Gly Leu
            20                  25                  30

Pro Leu Arg Pro Gly Pro Ala Phe Pro Arg Leu Arg Gln Glu Asp
        35                  40                  45

Arg Pro Arg Pro His Cys Leu Pro Gln Val Gln Pro Gly Gln Gly
    50                  55                  60

Ser Pro Pro Glu Leu Thr Val Ser Arg Val Pro Leu Gly Trp Ser
65                  70                  75

Arg Gln Arg Ser Pro Ser Leu Tyr Leu Leu Ser Gln Pro Ser Glu
            80                  85                  90

Ala Ser Ala Gln Ala Gln Ala Leu Arg Cys Gln Ser Cys Leu Ser
        95                 100                 105

Arg Leu Arg Lys Arg Thr Pro Gly Ala Pro Gln
    110                 115

<210> SEQ ID NO 23
<211> LENGTH: 210
<212> TYPE: PRT
<213> ORGANISM: Homo sapiens
<220> FEATURE:
<221> NAME/KEY: misc_feature
<223> OTHER INFORMATION: Incyte ID No: 4304004CD1

<400> SEQUENCE: 23

Met Ala Leu Pro Gln Met Cys Asp Gly Ser His Leu Ala Ser Thr
 1               5                  10                  15

Leu Arg Tyr Cys Met Thr Val Ser Gly Thr Val Val Leu Val Ala
            20                  25                  30

Gly Thr Leu Cys Phe Ala Trp Trp Ser Glu Gly Asp Ala Thr Ala
        35                  40                  45
```

Gln Pro Gly Gln Leu Ala Pro Pro Thr Glu Tyr Pro Val Pro Glu
            50                  55                  60

Gly Pro Ser Pro Leu Leu Arg Ser Val Ser Phe Val Cys Cys Gly
            65                  70                  75

Ala Gly Gly Leu Leu Leu Ile Gly Leu Leu Trp Ser Val Lys
            80                  85                  90

Ala Ser Ile Pro Gly Pro Pro Arg Trp Asp Pro Tyr His Leu Ser
            95                  100                 105

Arg Asp Leu Tyr Tyr Leu Thr Val Glu Ser Ser Glu Lys Glu Ser
            110                 115                 120

Cys Arg Thr Pro Lys Val Val Asp Ile Pro Thr Tyr Glu Glu Ala
            125                 130                 135

Val Ser Phe Pro Val Ala Glu Gly Pro Pro Thr Pro Pro Ala Tyr
            140                 145                 150

Pro Thr Glu Glu Ala Leu Glu Pro Ser Gly Ser Arg Asp Ala Leu
            155                 160                 165

Leu Ser Thr Gln Pro Ala Trp Pro Pro Ser Tyr Glu Ser Ile
            170                 175                 180

Ser Leu Ala Leu Asp Ala Val Ser Ala Glu Thr Thr Pro Ser Ala
            185                 190                 195

Thr Arg Ser Cys Ser Gly Leu Val Gln Thr Ala Arg Gly Gly Ser
            200                 205                 210

<210> SEQ ID NO 24
<211> LENGTH: 195
<212> TYPE: PRT
<213> ORGANISM: Homo sapiens
<220> FEATURE:
<221> NAME/KEY: misc_feature
<223> OTHER INFORMATION: Incyte ID No: 4945912CD1

<400> SEQUENCE: 24

Met Gly Leu Ala Gly Thr Cys Cys Leu Arg Ala Arg Pro Leu Pro
  1                   5                  10                  15

Gly Gly Arg Gly Val Cys Pro Leu Pro Gly Ala Arg Val Pro Ala
            20                  25                  30

Leu Ala Leu Ala Thr Ala Met Leu His Val Leu Ala Ser Leu Pro
            35                  40                  45

Leu Leu Leu Leu Leu Val Thr Ser Ala Ser Thr His Ala Trp Ser
            50                  55                  60

Arg Pro Leu Trp Tyr Gln Val Gly Leu Asp Leu Gln Pro Trp Gly
            65                  70                  75

Cys Gln Pro Lys Ser Val Glu Gly Cys Arg Gly Gly Leu Ser Cys
            80                  85                  90

Pro Gly Tyr Trp Leu Gly Pro Gly Ala Ser Arg Ile Tyr Pro Val
            95                  100                 105

Ala Ala Val Met Ile Thr Thr Thr Met Leu Met Ile Cys Arg Lys
            110                 115                 120

Ile Leu Gln Gly Arg Arg Ser Gln Ala Thr Lys Gly Glu His
            125                 130                 135

Pro Gln Val Thr Thr Glu Pro Cys Gly Pro Trp Lys Arg Arg Ala
            140                 145                 150

Pro Ile Ser Asp His Thr Leu Leu Arg Gly Val Leu His Met Leu
            155                 160                 165

Asp Ala Leu Leu Val His Ile Glu Gly His Leu Arg His Leu Ala

```
                    170                 175                 180

Thr Gln Arg Gln Ile Gln Ile Lys Gly Thr Ser Thr Gln Ser Gly
                    185                 190                 195

<210> SEQ ID NO 25
<211> LENGTH: 140
<212> TYPE: PRT
<213> ORGANISM: Homo sapiens
<220> FEATURE:
<221> NAME/KEY: misc_feature
<223> OTHER INFORMATION: Incyte ID No: 7230481CD1

<400> SEQUENCE: 25

Met Phe Ser Lys Met Glu Val Phe Trp Lys Leu Leu Leu Leu Val
 1               5                  10                  15

Gly Val Glu Ala Arg Val Cys Ile Leu Gln Cys Leu Val Lys Gly
                20                  25                  30

Phe Leu Leu Pro Gln Phe Gly Gln Gly His Pro Lys Ala Thr Val
                35                  40                  45

Ala His Asn Ile Lys Leu Asp Gln Val Pro Glu Leu His Val Val
                50                  55                  60

Gly Gln Gly Ile Leu Leu Thr Leu Gly Leu Phe Phe Thr Val Val
                65                  70                  75

Ile Pro Arg Ser His Val Met Met Met Leu Arg Cys Ser Ala Gly
                80                  85                  90

Cys Ala Ser Gln Trp Leu Pro Pro Asp Thr Arg Trp Ser Cys Arg
                95                 100                 105

Phe Ala Glu Ser Ser Thr Cys Cys Ser Leu Pro Leu Ala Arg Ile
               110                 115                 120

Asn Val Pro Arg Tyr Leu Ala Leu Cys Ser Ser Val Ser Gln Ser
               125                 130                 135

Gln Ser Leu Pro Trp
               140

<210> SEQ ID NO 26
<211> LENGTH: 585
<212> TYPE: PRT
<213> ORGANISM: Homo sapiens
<220> FEATURE:
<221> NAME/KEY: misc_feature
<223> OTHER INFORMATION: Incyte ID No: 71947526CD1

<400> SEQUENCE: 26

Met Val Cys Arg Glu Gln Leu Ser Lys Asn Gln Val Lys Trp Val
 1               5                  10                  15

Phe Ala Gly Ile Thr Cys Val Ser Val Val Ile Ala Ala Ile
                20                  25                  30

Val Leu Ala Ile Thr Leu Arg Arg Pro Gly Cys Glu Leu Glu Ala
                35                  40                  45

Cys Ser Pro Asp Ala Asp Met Leu Asp Tyr Leu Leu Ser Leu Gly
                50                  55                  60

Gln Ile Ser Arg Arg Asp Ala Leu Glu Val Thr Trp Tyr His Ala
                65                  70                  75

Ala Asn Ser Lys Lys Ala Met Thr Ala Ala Leu Asn Ser Asn Ile
                80                  85                  90

Thr Val Leu Glu Ala Asp Val Asn Val Glu Gly Leu Gly Thr Ala
                95                 100                 105

Asn Glu Thr Gly Val Pro Ile Met Ala His Pro Pro Thr Ile Tyr
```

-continued

```
                    110                 115                 120
Ser Asp Asn Thr Leu Glu Gln Trp Leu Asp Ala Val Leu Gly Ser
                125                 130                 135
Ser Gln Lys Gly Ile Lys Leu Asp Phe Lys Asn Ile Lys Ala Val
                140                 145                 150
Gly Pro Ser Leu Asp Leu Leu Arg Gln Leu Thr Glu Glu Gly Lys
                155                 160                 165
Val Arg Arg Pro Ile Trp Ile Asn Ala Asp Ile Leu Lys Gly Pro
                170                 175                 180
Asn Met Leu Ile Ser Thr Glu Val Asn Ala Thr Gln Phe Leu Ala
                185                 190                 195
Leu Val Gln Glu Lys Tyr Pro Lys Ala Thr Leu Ser Pro Gly Trp
                200                 205                 210
Thr Thr Phe Tyr Met Ser Thr Ser Pro Asn Arg Thr Tyr Thr Gln
                215                 220                 225
Ala Met Val Glu Lys Met His Glu Leu Val Gly Gly Val Pro Gln
                230                 235                 240
Arg Val Thr Phe Pro Val Arg Ser Ser Met Val Arg Ala Ala Trp
                245                 250                 255
Pro His Phe Ser Trp Leu Leu Ser Gln Ser Glu Arg Tyr Ser Leu
                260                 265                 270
Thr Leu Trp Gln Ala Ala Ser Asp Pro Met Ser Val Glu Asp Leu
                275                 280                 285
Leu Tyr Val Arg Asp Asn Thr Ala Val His Gln Val Tyr Tyr Asp
                290                 295                 300
Ile Phe Glu Pro Leu Leu Ser Gln Phe Lys Gln Leu Ala Leu Asn
                305                 310                 315
Ala Thr Arg Lys Pro Met Tyr Tyr Thr Gly Gly Ser Leu Ile Pro
                320                 325                 330
Leu Leu Gln Leu Pro Gly Asp Asp Gly Leu Asn Val Glu Trp Leu
                335                 340                 345
Val Pro Asp Val Gln Gly Ser Gly Lys Thr Ala Thr Met Thr Leu
                350                 355                 360
Pro Asp Thr Glu Gly Met Ile Leu Leu Asn Thr Gly Leu Glu Gly
                365                 370                 375
Thr Val Ala Glu Asn Pro Val Pro Ile Val His Thr Pro Ser Gly
                380                 385                 390
Asn Ile Leu Thr Leu Glu Ser Cys Leu Gln Gln Leu Ala Thr His
                395                 400                 405
Pro Gly His Trp Gly Ile His Leu Gln Ile Val Glu Pro Ala Ala
                410                 415                 420
Leu Arg Pro Ser Leu Ala Leu Ala Arg Leu Ser Ser Leu Gly
                425                 430                 435
Leu Leu His Trp Pro Val Trp Val Gly Ala Lys Ile Ser His Gly
                440                 445                 450
Ser Phe Ser Val Pro Gly His Val Ala Gly Arg Glu Leu Leu Thr
                455                 460                 465
Ala Val Ala Glu Val Phe Pro His Val Thr Val Ala Pro Gly Trp
                470                 475                 480
Pro Glu Glu Val Leu Gly Ser Gly Tyr Arg Glu Gln Leu Leu Thr
                485                 490                 495
Asp Met Leu Glu Leu Cys Gln Gly Leu Trp Gln Pro Val Ser Phe
                500                 505                 510
```

```
Gln Met Gln Ala Met Leu Leu Gly His Ser Thr Ala Gly Ala Ile
            515                 520                 525

Gly Arg Leu Leu Ala Ser Ser Pro Arg Ala Thr Val Thr Val Glu
            530                 535                 540

His Asn Pro Ala Gly Gly Asp Tyr Ala Ser Val Arg Thr Ala Leu
            545                 550                 555

Leu Ala Ala Arg Ala Val Asp Arg Thr Arg Val Tyr Tyr Arg Leu
            560                 565                 570

Pro Gln Gly Tyr His Lys Asp Leu Leu Ala His Val Gly Arg Asn
            575                 580                 585

<210> SEQ ID NO 27
<211> LENGTH: 95
<212> TYPE: PRT
<213> ORGANISM: Homo sapiens
<220> FEATURE:
<221> NAME/KEY: misc_feature
<223> OTHER INFORMATION: Incyte ID No: 6843919CD1

<400> SEQUENCE: 27

Met Lys Gly Ser Arg Ala Leu Leu Leu Val Ala Leu Thr Leu Phe
  1               5                  10                  15

Cys Ile Cys Arg Met Ala Thr Gly Glu Asp Asn Asp Glu Phe Phe
                 20                  25                  30

Met Asp Phe Leu Gln Thr Leu Val Gly Thr Pro Glu Glu Leu
                 35                  40                  45

Tyr Glu Gly Thr Leu Gly Lys Tyr Asn Val Asn Glu Asp Ala Lys
                 50                  55                  60

Ala Ala Met Thr Glu Leu Lys Ser Cys Arg Asp Gly Leu Gln Pro
                 65                  70                  75

Met His Lys Ala Glu Leu Val Lys Leu Leu Val Gln Val Leu Gly
                 80                  85                  90

Ser Gln Asp Gly Ala
                 95

<210> SEQ ID NO 28
<211> LENGTH: 347
<212> TYPE: PRT
<213> ORGANISM: Homo sapiens
<220> FEATURE:
<221> NAME/KEY: misc_feature
<223> OTHER INFORMATION: Incyte ID No: 5866451CD1

<400> SEQUENCE: 28

Met His Ala His Cys Leu Pro Phe Leu Leu His Ala Trp Trp Ala
  1               5                  10                  15

Leu Leu Gln Ala Gly Ala Ala Thr Val Ala Thr Ala Leu Leu Arg
                 20                  25                  30

Thr Arg Gly Gln Pro Ser Ser Pro Ser Pro Leu Ala Tyr Met Leu
                 35                  40                  45

Ser Leu Tyr Arg Asp Pro Leu Pro Arg Ala Asp Ile Ile Arg Ser
                 50                  55                  60

Leu Gln Ala Glu Asp Val Ala Val Asp Gly Gln Asn Trp Thr Phe
                 65                  70                  75

Ala Phe Asp Phe Ser Phe Leu Ser Gln Gln Glu Asp Leu Ala Trp
                 80                  85                  90

Ala Glu Leu Arg Leu Gln Leu Ser Ser Pro Val Asp Leu Pro Thr
                 95                 100                 105
```

-continued

Glu Gly Ser Leu Ala Ile Glu Ile Phe His Gln Pro Lys Pro Asp
            110                 115                 120

Thr Glu Gln Ala Ser Asp Ser Cys Leu Glu Arg Phe Gln Met Asp
            125                 130                 135

Leu Phe Thr Val Thr Leu Ser Gln Val Thr Phe Ser Leu Gly Ser
            140                 145                 150

Met Val Leu Glu Val Thr Arg Pro Leu Ser Lys Trp Leu Lys His
            155                 160                 165

Pro Gly Ala Leu Glu Lys Gln Met Ser Arg Val Ala Gly Glu Cys
            170                 175                 180

Trp Pro Arg Pro Thr Pro Pro Ala Thr Asn Val Leu Leu Met
            185                 190                 195

Leu Tyr Ser Asn Leu Ser Gln Glu Gln Arg Gln Leu Gly Gly Ser
            200                 205                 210

Thr Leu Leu Trp Glu Ala Glu Ser Ser Trp Arg Ala Gln Glu Gly
            215                 220                 225

Gln Leu Ser Trp Glu Trp Gly Lys Arg His Arg His His Leu
            230                 235                 240

Pro Asp Arg Ser Gln Leu Cys Arg Lys Val Lys Phe Gln Val Asp
            245                 250                 255

Phe Asn Leu Ile Gly Trp Gly Ser Trp Ile Ile Tyr Pro Lys Gln
            260                 265                 270

Tyr Asn Ala Tyr Arg Cys Gly Glu Cys Pro Asn Pro Val Gly
            275                 280                 285

Glu Glu Phe His Pro Thr Asn His Ala Tyr Ile Gln Ser Leu Leu
            290                 295                 300

Lys Arg Tyr Gln Pro His Arg Val Pro Ser Thr Cys Cys Ala Pro
            305                 310                 315

Val Lys Thr Lys Pro Leu Ser Met Leu Tyr Val Asp Asn Gly Arg
            320                 325                 330

Val Leu Leu Asp His His Lys Asp Met Ile Val Glu Glu Cys Gly
            335                 340                 345

Cys Leu

<210> SEQ ID NO 29
<211> LENGTH: 63
<212> TYPE: PRT
<213> ORGANISM: Homo sapiens
<220> FEATURE:
<221> NAME/KEY: misc_feature
<223> OTHER INFORMATION: Incyte ID No: 1310222CD1

<400> SEQUENCE: 29

Met Asp Ile Lys Gly Gln Leu Thr Val Ala Arg Leu Ser Pro Met
  1               5                  10                  15

Ser Leu Ala Arg Pro Lys Glu Arg Thr Arg Pro His Gly Val Cys
            20                  25                  30

Gln Ser Cys Ser Pro Pro Gln Leu Ser Ser Val Ser Gln Met Thr
            35                  40                  45

Pro Gln Arg Pro Ala Ser Ser Leu Asn Ala Gly Arg Cys Gly Val
            50                  55                  60

Ser Asp Cys

<210> SEQ ID NO 30
<211> LENGTH: 208

```
<212> TYPE: PRT
<213> ORGANISM: Homo sapiens
<220> FEATURE:
<221> NAME/KEY: misc_feature
<223> OTHER INFORMATION: Incyte ID No: 1432223CD1

<400> SEQUENCE: 30

Met Gly Glu Val Glu Ile Ser Ala Leu Ala Tyr Val Lys Met Cys
 1               5                  10                  15

Leu His Ala Ala Arg Tyr Pro His Ala Ala Val Asn Gly Leu Phe
                20                  25                  30

Leu Ala Pro Ala Pro Arg Ser Gly Glu Cys Leu Cys Leu Thr Asp
                35                  40                  45

Cys Val Pro Leu Phe His Ser His Leu Ala Leu Ser Val Met Leu
                50                  55                  60

Glu Val Ala Leu Asn Gln Val Asp Val Trp Gly Ala Gln Ala Gly
                65                  70                  75

Leu Val Val Ala Gly Tyr Tyr His Ala Asn Ala Ala Val Asn Asp
                80                  85                  90

Gln Ser Pro Gly Pro Leu Ala Leu Lys Ile Ala Gly Arg Ile Ala
                95                 100                 105

Glu Phe Phe Pro Asp Ala Val Leu Ile Met Leu Asp Asn Gln Lys
               110                 115                 120

Leu Val Pro Gln Pro Arg Val Pro Pro Val Ile Val Leu Glu Asn
               125                 130                 135

Gln Gly Leu Arg Trp Val Pro Lys Asp Lys Asn Leu Val Met Trp
               140                 145                 150

Arg Asp Trp Glu Glu Ser Arg Gln Met Val Gly Ala Leu Leu Glu
               155                 160                 165

Asp Arg Ala His Gln His Leu Val Asp Phe Asp Cys His Leu Asp
               170                 175                 180

Asp Ile Arg Gln Asp Trp Thr Asn Gln Arg Leu Asn Thr Gln Ile
               185                 190                 195

Thr Gln Trp Val Gly Pro Thr Asn Gly Asn Gly Asn Ala
               200                 205

<210> SEQ ID NO 31
<211> LENGTH: 256
<212> TYPE: PRT
<213> ORGANISM: Homo sapiens
<220> FEATURE:
<221> NAME/KEY: misc_feature
<223> OTHER INFORMATION: Incyte ID No: 1537636CD1

<400> SEQUENCE: 31

Met Gln Gly Arg Gly Ala Asp Gln Ser Gly Pro Glu Leu Val Leu
 1               5                  10                  15

Arg Cys Gly Phe Glu Ser Leu Pro Arg Gln Leu Val Ile Val Ser
                20                  25                  30

Thr Arg Pro Arg Arg Asn Phe Leu Leu Cys Lys Ile Val Ile Arg
                35                  40                  45

Ile Ile Thr Cys Gln Gly Ser Cys Gly His Pro Ile Arg Ser Phe
                50                  55                  60

His Gln Arg Arg Ala Tyr Gly Ala Ser Glu Ala Glu Asn Val Ala
                65                  70                  75

Val Lys Arg Leu Lys Ser Lys Thr Arg Ser Gly Asp Leu Lys Glu
                80                  85                  90
```

-continued

```
Asp Gly Leu Lys Lys Arg Gly Asn Glu Leu Gln Thr Arg Glu Phe
             95                 100                 105

Pro Leu Tyr Lys Val Thr Leu Gln Gln Leu Val Tyr Pro Ala Pro
            110                 115                 120

Cys Leu Leu Arg Ser Ser Asn Leu Gln Lys Ser Cys Lys Asn Thr
            125                 130                 135

Arg Leu Lys Ala Ala Val His Tyr Thr Val Gly Cys Leu Cys Glu
            140                 145                 150

Glu Val Ala Leu Asp Lys Glu Met Gln Phe Ser Lys Gln Thr Ile
            155                 160                 165

Ala Ala Ile Ser Glu Leu Thr Phe Arg Gln Cys Glu Asn Phe Ala
            170                 175                 180

Lys Asp Leu Glu Met Phe Ala Arg His Ala Lys Arg Thr Thr Ile
            185                 190                 195

Asn Thr Glu Asp Val Lys Leu Leu Ala Arg Arg Ser Asn Ser Leu
            200                 205                 210

Leu Lys Tyr Ile Thr Asp Lys Ser Glu Glu Ile Ala Gln Ile Asn
            215                 220                 225

Leu Glu Arg Lys Ala Gln Lys Lys Lys Ser Glu Asp Gly Ser
            230                 235                 240

Lys Asn Ser Arg Gln Pro Ala Glu Ala Gly Val Val Glu Ser Glu
            245                 250                 255

Asn

<210> SEQ ID NO 32
<211> LENGTH: 229
<212> TYPE: PRT
<213> ORGANISM: Homo sapiens
<220> FEATURE:
<221> NAME/KEY: misc_feature
<223> OTHER INFORMATION: Incyte ID No: 1871333CD1

<400> SEQUENCE: 32

Met Asp Leu Leu Gln Phe Leu Ala Phe Leu Phe Val Leu Leu Leu
  1               5                  10                  15

Ser Gly Met Gly Ala Thr Gly Thr Leu Arg Thr Ser Leu Asp Pro
             20                  25                  30

Ser Leu Glu Ile Tyr Lys Lys Met Phe Glu Val Lys Arg Arg Glu
             35                  40                  45

Gln Leu Leu Ala Leu Lys Asn Leu Ala Gln Leu Asn Asp Ile His
             50                  55                  60

Gln Gln Tyr Lys Ile Leu Asp Val Met Leu Lys Gly Leu Phe Lys
             65                  70                  75

Val Leu Glu Asp Ser Arg Thr Val Leu Thr Ala Ala Asp Val Leu
             80                  85                  90

Pro Asp Gly Pro Phe Pro Gln Asp Glu Lys Leu Lys Asp Ala Phe
             95                 100                 105

Ser His Val Val Glu Asn Thr Ala Phe Phe Gly Asp Val Val Leu
            110                 115                 120

Arg Phe Pro Arg Ile Val His Tyr Tyr Phe Asp His Asn Ser Asn
            125                 130                 135

Trp Asn Leu Leu Ile Arg Trp Gly Ile Ser Phe Cys Asn Gln Thr
            140                 145                 150

Gly Val Phe Asn Gln Gly Pro His Ser Pro Ile Leu Ser Leu Met
            155                 160                 165
```

```
Ala Gln Glu Leu Gly Ile Ser Glu Lys Asp Ser Asn Phe Gln Asn
                170                 175                 180

Pro Phe Lys Ile Asp Arg Thr Glu Phe Ile Pro Ser Thr Asp Pro
                185                 190                 195

Phe Gln Lys Ala Leu Arg Glu Glu Lys Arg Arg Lys Glu
                200                 205                 210

Glu Lys Arg Lys Glu Ile Arg Lys Gly Pro Arg Ile Ser Arg Ser
                215                 220                 225

Gln Ser Glu Leu

<210> SEQ ID NO 33
<211> LENGTH: 327
<212> TYPE: PRT
<213> ORGANISM: Homo sapiens
<220> FEATURE:
<221> NAME/KEY: misc_feature
<223> OTHER INFORMATION: Incyte ID No: 7153010CD1

<400> SEQUENCE: 33

Met Glu Lys Ser Ile Trp Leu Leu Ala Cys Leu Ala Trp Val Leu
  1               5                  10                  15

Pro Thr Gly Ser Phe Val Arg Thr Lys Ile Asp Thr Thr Glu Asn
                 20                  25                  30

Leu Leu Asn Thr Glu Val His Ser Ser Pro Ala Gln Arg Trp Ser
                 35                  40                  45

Met Gln Val Pro Pro Glu Val Ser Ala Glu Ala Gly Asp Ala Ala
                 50                  55                  60

Val Leu Pro Cys Thr Phe Thr His Pro His Arg His Tyr Asp Gly
                 65                  70                  75

Pro Leu Thr Ala Ile Trp Arg Ala Gly Glu Pro Tyr Ala Gly Pro
                 80                  85                  90

Gln Val Phe Arg Cys Ala Ala Ala Arg Gly Ser Glu Leu Cys Gln
                 95                 100                 105

Thr Ala Leu Ser Leu His Gly Arg Phe Arg Leu Leu Gly Asn Pro
                110                 115                 120

Arg Arg Asn Asp Leu Ser Leu Arg Val Glu Arg Leu Ala Leu Ala
                125                 130                 135

Asp Asp Arg Arg Tyr Phe Cys Arg Val Glu Phe Ala Gly Asp Val
                140                 145                 150

His Asp Arg Tyr Glu Ser Arg His Gly Val Arg Leu His Val Thr
                155                 160                 165

Ala Ala Pro Arg Ile Val Asn Ile Ser Val Leu Pro Ser Pro Ala
                170                 175                 180

His Ala Phe Arg Ala Leu Cys Thr Ala Glu Gly Glu Pro Pro Pro
                185                 190                 195

Ala Leu Ala Trp Ser Gly Pro Ala Leu Gly Asn Ser Leu Ala Ala
                200                 205                 210

Val Arg Ser Pro Arg Glu Gly His Gly His Leu Val Thr Ala Glu
                215                 220                 225

Leu Pro Ala Leu Thr His Asp Gly Arg Tyr Thr Cys Thr Ala Ala
                230                 235                 240

Asn Ser Leu Gly Arg Ser Glu Ala Ser Val Tyr Leu Phe Arg Phe
                245                 250                 255

His Gly Ala Ser Gly Ala Ser Thr Val Ala Leu Leu Leu Gly Ala
                260                 265                 270
```

```
Leu Gly Phe Lys Ala Leu Leu Leu Gly Val Leu Ala Arg Ala
            275                 280                 285

Ala Arg Arg Arg Pro Glu His Leu Asp Thr Pro Asp Thr Pro Pro
                290                 295                 300

Arg Ser Gln Ala Gln Glu Ser Asn Tyr Glu Asn Leu Ser Gln Met
            305                 310                 315

Asn Pro Arg Ser Pro Pro Ala Thr Met Cys Ser Pro
            320                 325

<210> SEQ ID NO 34
<211> LENGTH: 104
<212> TYPE: PRT
<213> ORGANISM: Homo sapiens
<220> FEATURE:
<221> NAME/KEY: misc_feature
<223> OTHER INFORMATION: Incyte ID No: 7996779CD1

<400> SEQUENCE: 34

Met Asp Phe Ser Ser Ser Asn Ser Cys Leu Ser Leu Trp Pro Val
  1               5                  10                  15

Gln Met Pro Phe Leu Ser Trp Thr Leu Pro Pro Ser Val Thr Gly
             20                  25                  30

Glu Ser Leu Pro Pro Leu Gln Val Thr Asp Thr Ser Val Thr Ser
             35                  40                  45

Ser Lys Leu Pro Arg Pro Gln Ala His Gln Val Ser Pro Glu Leu
             50                  55                  60

Leu Cys Gly His Ser Ala Tyr His Ser Arg Ile Asn Thr Ser Pro
 65                  70                  75

Gly Met Tyr Phe Met Thr Ala Ser Ser Pro Val Ser Lys Pro His
             80                  85                  90

Gly Gly Arg Asp Arg Val Cys Leu Gly Gln Ser Cys Ile Ser
             95                 100

<210> SEQ ID NO 35
<211> LENGTH: 82
<212> TYPE: PRT
<213> ORGANISM: Homo sapiens
<220> FEATURE:
<221> NAME/KEY: misc_feature
<223> OTHER INFORMATION: Incyte ID No: 640025CD1

<400> SEQUENCE: 35

Met Ala Met Leu Thr Pro Thr Gln Leu Gly Ala Ser Ala Gly Leu
  1               5                  10                  15

Leu Gly Cys Gly Phe Leu Pro Ala Cys Leu Leu Gln Leu Cys
             20                  25                  30

Gly Leu Ala Met Ala Leu Pro Pro Leu Ser Leu Leu Pro Cys Leu
             35                  40                  45

Pro Leu Ser Ser Phe Ser Gln Lys Ala Arg Phe His His Val Leu
             50                  55                  60

Thr Thr Asn Cys Leu Pro Ser Leu Val Gly Val Thr Ala Val Gly
 65                  70                  75

His Leu Gln Ala Leu Val Glu
             80

<210> SEQ ID NO 36
<211> LENGTH: 367
<212> TYPE: PRT
<213> ORGANISM: Homo sapiens
<220> FEATURE:
```

<221> NAME/KEY: misc_feature
<223> OTHER INFORMATION: Incyte ID No: 1545079CD1

<400> SEQUENCE: 36

```
Met Val Ser Arg Ser Cys His Cys Arg Cys Ser Thr Ala Ser Ser
 1               5                  10                  15

Ser Cys Trp Ala Arg Ser Ser Arg Gly Gly Cys Gly Gly Gly Leu
                20                  25                  30

Pro Pro Ser Pro Ser Pro Ala Phe Pro Arg Ser Thr Pro Ala Ala
                35                  40                  45

Ser Arg Ser Pro Ser Ile Leu Leu Gly Val Val Pro Leu Ser
                50                  55                  60

Cys Pro Ala Gln Arg Arg Gly Arg Val Ser Trp Thr Gly Ser Trp
                65                  70                  75

Leu Gly Ala Ser Leu Pro Pro Gly Ser Gly Pro Gly Arg Met Ser
                80                  85                  90

Pro Ala Arg Arg Cys Arg Gly Met Arg Ala Ala Val Ala Ala Ser
                95                 100                 105

Val Gly Leu Ser Glu Gly Pro Ala Gly Ser Arg Ser Gly Arg Leu
               110                 115                 120

Phe Arg Pro Pro Ser Pro Ala Pro Ala Ala Pro Gly Ala Arg Leu
               125                 130                 135

Leu Arg Leu Pro Gly Ser Gly Ala Val Gln Ala Ala Ser Pro Glu
               140                 145                 150

Arg Ala Gly Trp Thr Glu Ala Leu Arg Ala Ala Val Ala Glu Leu
               155                 160                 165

Arg Ala Gly Ala Val Val Ala Val Pro Thr Asp Thr Leu Tyr Gly
               170                 175                 180

Leu Ala Cys Ala Ala Ser Cys Ser Ala Ala Leu Arg Ala Val Tyr
               185                 190                 195

Arg Leu Lys Gly Arg Ser Glu Ala Lys Pro Leu Ala Val Cys Leu
               200                 205                 210

Gly Arg Val Ala Asp Val Tyr Arg Tyr Cys Arg Val Arg Val Pro
               215                 220                 225

Glu Gly Leu Leu Lys Asp Leu Leu Pro Gly Pro Val Thr Leu Val
               230                 235                 240

Met Glu Arg Ser Glu Glu Leu Asn Lys Asp Leu Asn Pro Phe Thr
               245                 250                 255

Pro Leu Val Gly Ile Arg Ile Pro Asp His Ala Phe Met Gln Asp
               260                 265                 270

Leu Ala Gln Met Phe Glu Gly Pro Leu Ala Leu Thr Ser Ala Asn
               275                 280                 285

Leu Ser Ser Gln Ala Ser Ser Leu Asn Val Glu Glu Phe Gln Asp
               290                 295                 300

Leu Trp Pro Gln Leu Ser Leu Val Ile Asp Gly Gly Gln Ile Gly
               305                 310                 315

Asp Gly Gln Ser Pro Glu Cys Arg Leu Gly Ser Thr Val Val Asp
               320                 325                 330

Leu Ser Val Pro Gly Lys Phe Gly Ile Ile Arg Pro Gly Cys Ala
               335                 340                 345

Leu Glu Ser Thr Thr Ala Ile Leu Gln Gln Lys Tyr Gly Leu Leu
               350                 355                 360

Pro Ser His Ala Ser Tyr Leu
               365
```

```
<210> SEQ ID NO 37
<211> LENGTH: 70
<212> TYPE: PRT
<213> ORGANISM: Homo sapiens
<220> FEATURE:
<221> NAME/KEY: misc_feature
<223> OTHER INFORMATION: Incyte ID No: 2668150CD1

<400> SEQUENCE: 37

Met Glu Ser Gln Ser Ile Ser Pro Leu Cys Ser Phe Leu Leu Thr
 1               5                  10                  15

Leu Thr Ala Thr Phe Pro Ile Val Ser Arg Gly Arg Val Asp Ile
                20                  25                  30

Val Ser Val Val Lys Leu Gln Lys Val Cys Cys Leu Leu Gly Thr
                35                  40                  45

Ala Lys Tyr Phe Ser Val Ser Asp Lys Gln Ile Ile Ser Asn Cys
                50                  55                  60

Ser Asn Ser Ile Ser Thr Leu Ile Arg Gly
                65                  70

<210> SEQ ID NO 38
<211> LENGTH: 73
<212> TYPE: PRT
<213> ORGANISM: Homo sapiens
<220> FEATURE:
<221> NAME/KEY: misc_feature
<223> OTHER INFORMATION: Incyte ID No: 2804787CD1

<400> SEQUENCE: 38

Met Cys Lys Leu Arg Ser Leu Trp Phe Leu Gly Leu Gly Gln Val
 1               5                  10                  15

Thr Val Phe Thr Val Ile Thr Gly Val Ser Glu Gly Pro Ala Arg
                20                  25                  30

Ile Ala Ser Thr Ser Gly Ile Met Pro Arg Pro Leu Gly Ala Ala
                35                  40                  45

Ser Gly Gln Gln Ser Ser Pro Val Cys Tyr Ser Val Phe Leu Leu
                50                  55                  60

Ser Gln Gly Ser Ser Asp Asn Ile Ser Arg Glu Thr Gly
                65                  70

<210> SEQ ID NO 39
<211> LENGTH: 76
<212> TYPE: PRT
<213> ORGANISM: Homo sapiens
<220> FEATURE:
<221> NAME/KEY: misc_feature
<223> OTHER INFORMATION: Incyte ID No: 4003882CD1

<400> SEQUENCE: 39

Met Thr Leu Trp Leu Cys His Asn Val Cys Ile Leu Gln Val Tyr
 1               5                  10                  15

Met Lys Gln Ile Leu Met Asp Val Gly Trp Leu Pro Phe Thr Leu
                20                  25                  30

Ser Tyr Leu Lys Met His Leu Glu Thr Leu Leu Arg Lys Leu Leu
                35                  40                  45

Met Leu Leu Val Leu Leu Phe Cys Cys Ser Val Cys Pro Gln
                50                  55                  60

Val Val Glu Ser Leu Lys Thr Gln Lys Asp Asn Asn Val Val Asn
                65                  70                  75
```

Pro

<210> SEQ ID NO 40
<211> LENGTH: 80
<212> TYPE: PRT
<213> ORGANISM: Homo sapiens
<220> FEATURE:
<221> NAME/KEY: misc_feature
<223> OTHER INFORMATION: Incyte ID No: 4737462CD1

<400> SEQUENCE: 40

```
Met Leu Phe Leu Leu Gln Glu Ile Leu Leu Ala Leu Val Leu Ser
  1               5                  10                  15

Val Leu Gln Val Ser Gly Gly Leu Ile Ile Ser Gly Thr Pro Ala
                 20                  25                  30

Leu Ile Val Leu Pro Ser Leu Arg Asp Phe Leu Phe His Met Ser
                 35                  40                  45

Thr Leu His Thr Ser Ile Lys His Ile Glu Ser His Val Leu Cys
                 50                  55                  60

Met Tyr Ala Trp Cys Phe Pro Asn Trp Glu Leu Ser Ser Asn Val
 65                  70                  75

Lys Ser Leu Ser Ile
                 80
```

<210> SEQ ID NO 41
<211> LENGTH: 73
<212> TYPE: PRT
<213> ORGANISM: Homo sapiens
<220> FEATURE:
<221> NAME/KEY: misc_feature
<223> OTHER INFORMATION: Incyte ID No: 4921634CD1

<400> SEQUENCE: 41

```
Met Trp Phe Ala Phe Leu Ser Leu Leu Val Leu Leu Ala Leu Cys
  1               5                  10                  15

Phe Ser Thr Glu Ile Thr Cys Leu Ala Phe Ala Leu Lys Val Val
                 20                  25                  30

Lys Ala Pro His Pro His Met Phe Leu Pro Leu Ile Cys His Arg
                 35                  40                  45

Asp Pro Gln Cys Cys Tyr Leu Cys Ile Met Cys Val Gly Arg Val
                 50                  55                  60

Val Ser Ser Ile Arg Arg Arg Tyr Leu Ser Ser Leu
                 65                  70
```

<210> SEQ ID NO 42
<211> LENGTH: 116
<212> TYPE: PRT
<213> ORGANISM: Homo sapiens
<220> FEATURE:
<221> NAME/KEY: misc_feature
<223> OTHER INFORMATION: Incyte ID No: 6254942CD1

<400> SEQUENCE: 42

```
Met Ala Ser Ser Ser Asp Gly Ile Ser Leu Ser Tyr Arg Pro Val
  1               5                  10                  15

Val Thr Gly Gln Asp Arg Met Met Asp Thr Glu Val Leu Ser Leu
                 20                  25                  30

Leu Ser Ser Val Ala Leu Pro Ser Leu Leu Ala Ser Glu Ser
                 35                  40                  45

Phe Asp Ser Ile Tyr Pro Gly Ile Phe Cys Val Leu Met Phe Ser
                 50                  55                  60
```

-continued

```
Ser Gly Leu Ala Ser Ala Val Leu Ile Gly Arg Ala Leu Ser Phe
             65                  70                  75

Gln Ala Ile Leu Lys Gly Gly Gln Ser Lys Gly Gln Ser Leu Asn
             80                  85                  90

Pro Phe Cys Gly Leu Asn Asn Leu Arg Ile Lys Ser Ser Val Leu
             95                 100                 105

Leu Ile Pro Val Leu Leu Cys Gln Thr Leu Ser
            110                 115

<210> SEQ ID NO 43
<211> LENGTH: 95
<212> TYPE: PRT
<213> ORGANISM: Homo sapiens
<220> FEATURE:
<221> NAME/KEY: misc_feature
<223> OTHER INFORMATION: Incyte ID No: 6747838CD1

<400> SEQUENCE: 43

Met Gly Pro Leu Ser Ala Leu Leu Ser Gln Ser Leu Leu Leu Ser
  1               5                  10                  15

Cys Thr Ala Pro Arg Glu Arg Leu Pro Gly Gly Gly Trp Pro Gly
             20                  25                  30

Thr Pro Gly Met Gly Pro Leu Arg Ser Gly Thr Ser Ala Pro Ser
             35                  40                  45

Ser Ile Val Arg Lys Gly Arg Gly Ser Leu Arg Ala Leu Ala Tyr
             50                  55                  60

Ala Thr Pro Ser Gly Gly Glu Ala Arg Val Leu Cys Leu Phe Ser
             65                  70                  75

Gln Tyr Gly Phe Ser His Arg Ala Lys Val Thr Arg Asp Val Ser
             80                  85                  90

Gln Ser Lys Thr Gly
             95

<210> SEQ ID NO 44
<211> LENGTH: 138
<212> TYPE: PRT
<213> ORGANISM: Homo sapiens
<220> FEATURE:
<221> NAME/KEY: misc_feature
<223> OTHER INFORMATION: Incyte ID No: 7050585CD1

<400> SEQUENCE: 44

Met Gln Leu Phe Trp His Val Ser Leu Leu Leu Leu Trp Arg Leu
  1               5                  10                  15

Gly Asp Trp Pro Pro Glu His Ala Asp Leu Ile Leu Glu Val Gly
             20                  25                  30

Val Glu Arg Glu Asn Trp Leu Ser Val Glu Leu Leu Leu Leu Val
             35                  40                  45

Arg Gly Gln Leu Lys Phe Arg Asp Leu Leu Arg Lys Lys Gly
             50                  55                  60

Arg Met His Thr Val Arg Arg Leu Asp Leu Ser Ala Thr Phe Lys
             65                  70                  75

Ile Phe Leu His Phe Thr Val Lys Leu Pro Ser Thr Phe Ser
             80                  85                  90

Met Ser Pro Ser Pro Asn His His Gly Met Glu Ala Asp Gln
             95                 100                 105

Leu Lys Arg Leu Ala Arg Ser Pro Ser Ser Pro Gly Leu Pro Arg
            110                 115                 120
```

Thr Ser Tyr Asp Asn Leu Phe Asn His Ile Ser Tyr Ala Asp Ser
            125                 130                 135

Phe Ile Ser

<210> SEQ ID NO 45
<211> LENGTH: 134
<212> TYPE: PRT
<213> ORGANISM: Homo sapiens
<220> FEATURE:
<221> NAME/KEY: misc_feature
<223> OTHER INFORMATION: Incyte ID No: 3880321CD1

<400> SEQUENCE: 45

Met Ser Asn Thr Gly Leu Met Leu Ser Ser His Val Cys Phe Cys
  1               5                  10                  15

Phe Cys Phe Ser Leu Phe Leu Phe Val Cys Leu Phe Phe Asp Thr
                 20                  25                  30

Lys Ser Arg Ser Ile Ala Gln Ala Gly Val Gln Trp His Asp Leu
                 35                  40                  45

Ser Ser Leu Glu Pro Pro Pro Pro Gly Phe Lys Arg Phe Ser His
                 50                  55                  60

Leu Arg Leu Leu Ser Ser Trp Asp Tyr Arg His Val Pro Pro Cys
                 65                  70                  75

Pro Ala Asn Phe Cys Ile Phe Ser Arg Asp Gly Val Ser Pro Cys
                 80                  85                  90

Trp Pro Gly Trp Ser Trp Leu Leu Pro Ser Ser Asp Pro Pro Ala
                 95                 100                 105

Leu Gly Ser Gln Ser Ala Gly Ile Thr Gly Met Ser His Cys Ala
                110                 115                 120

Trp Pro Ile Phe Val Phe Phe Asp Gly Ala Arg Tyr Pro Asp
                125                 130

<210> SEQ ID NO 46
<211> LENGTH: 570
<212> TYPE: PRT
<213> ORGANISM: Homo sapiens
<220> FEATURE:
<221> NAME/KEY: misc_feature
<223> OTHER INFORMATION: Incyte ID No: 3950005CD1

<400> SEQUENCE: 46

Met Arg Pro Trp Leu Arg His Leu Val Leu Gln Ala Leu Arg Asn
  1               5                  10                  15

Ser Arg Ala Phe Cys Gly Ser His Gly Lys Pro Ala Pro Leu Pro
                 20                  25                  30

Val Pro Gln Lys Ile Val Ala Thr Trp Glu Ala Ile Ser Leu Gly
                 35                  40                  45

Arg Gln Leu Val Pro Glu Tyr Phe Asn Phe Ala His Asp Val Leu
                 50                  55                  60

Asp Val Trp Ser Arg Leu Glu Glu Ala Gly His Arg Pro Pro Asn
                 65                  70                  75

Pro Ala Phe Trp Trp Val Asn Gly Thr Gly Ala Glu Ile Lys Trp
                 80                  85                  90

Ser Phe Glu Glu Leu Gly Lys Gln Ser Arg Lys Ala Ala Asn Val
                 95                 100                 105

Leu Gly Gly Ala Cys Gly Leu Gln Pro Gly Asp Arg Met Met Leu
                110                 115                 120

-continued

```
Val Leu Pro Arg Leu Pro Glu Trp Trp Leu Val Ser Val Ala Cys
            125                 130                 135

Met Arg Thr Gly Thr Val Met Ile Pro Gly Val Thr Gln Leu Thr
            140                 145                 150

Glu Lys Asp Leu Lys Tyr Arg Leu Gln Ala Ser Arg Ala Lys Ser
            155                 160                 165

Ile Ile Thr Ser Asp Ser Leu Ala Pro Arg Val Asp Ala Ile Ser
            170                 175                 180

Ala Glu Cys Pro Ser Leu Gln Thr Lys Leu Leu Val Ser Asp Ser
            185                 190                 195

Ser Arg Pro Gly Trp Leu Asn Phe Arg Glu Leu Leu Arg Glu Ala
            200                 205                 210

Ser Thr Glu His Asn Cys Met Arg Thr Lys Ser Arg Asp Pro Leu
            215                 220                 225

Ala Ile Tyr Phe Thr Ser Gly Thr Thr Gly Ala Pro Lys Met Val
            230                 235                 240

Glu His Ser Gln Ser Ser Tyr Gly Leu Gly Phe Val Ala Ser Gly
            245                 250                 255

Arg Arg Trp Val Ala Leu Thr Glu Ser Asp Ile Phe Trp Asn Thr
            260                 265                 270

Thr Asp Thr Gly Trp Val Lys Ala Ala Trp Thr Leu Phe Ser Ala
            275                 280                 285

Trp Pro Asn Gly Ser Cys Ile Phe Val His Glu Leu Pro Arg Val
            290                 295                 300

Asp Ala Lys Val Ile Leu Asn Thr Leu Ser Lys Phe Pro Ile Thr
            305                 310                 315

Thr Leu Cys Cys Val Pro Thr Ile Phe Arg Leu Leu Val Gln Glu
            320                 325                 330

Asp Leu Thr Arg Tyr Gln Phe Gln Ser Leu Arg His Cys Leu Thr
            335                 340                 345

Gly Gly Glu Ala Leu Asn Arg Asp Val Arg Glu Lys Trp Lys His
            350                 355                 360

Gln Thr Gly Val Glu Leu Tyr Glu Gly Tyr Gly Gln Ser Glu Thr
            365                 370                 375

Val Val Ile Cys Ala Asn Pro Lys Gly Met Lys Ile Lys Ser Gly
            380                 385                 390

Ser Met Gly Lys Ala Ser Pro Pro Tyr Asp Val Gln Ile Val Asp
            395                 400                 405

Asp Glu Gly Asn Val Leu Pro Pro Gly Glu Glu Gly Asn Val Ala
            410                 415                 420

Val Arg Ile Arg Pro Thr Arg Pro Phe Cys Phe Phe Asn Cys Tyr
            425                 430                 435

Leu Asp Asn Pro Glu Lys Thr Ala Ala Ser Glu Gln Gly Asp Phe
            440                 445                 450

Tyr Ile Thr Gly Asp Arg Ala Arg Met Asp Lys Asp Gly Tyr Phe
            455                 460                 465

Trp Phe Met Gly Arg Asn Asp Asp Val Ile Asn Ser Ser Ser Tyr
            470                 475                 480

Arg Ile Gly Pro Val Glu Val Glu Ser Ala Leu Ala Glu His Pro
            485                 490                 495

Ala Val Leu Glu Ser Ala Val Val Ser Ser Pro Asp Pro Ile Arg
            500                 505                 510

Gly Glu Val Val Lys Ala Phe Ile Val Leu Thr Pro Ala Tyr Ser
```

-continued

```
                515                 520                 525

Ser His Asp Pro Glu Ala Leu Thr Arg Glu Leu Gln Glu His Val
                530                 535                 540

Lys Arg Val Thr Ala Pro Tyr Lys Tyr Pro Arg Lys Val Ala Phe
                545                 550                 555

Val Ser Glu Leu Ala Lys Asp Gly Phe Trp Lys Asp Pro Lys Glu
                560                 565                 570

<210> SEQ ID NO 47
<211> LENGTH: 1325
<212> TYPE: PRT
<213> ORGANISM: Homo sapiens
<220> FEATURE:
<221> NAME/KEY: misc_feature
<223> OTHER INFORMATION: Incyte ID No: 3043830CD1

<400> SEQUENCE: 47

Met Ser Ala Pro Asp Glu Gly Arg Arg Asp Pro Pro Lys Pro Lys
  1               5                  10                  15

Gly Lys Thr Leu Gly Ser Phe Phe Gly Ser Leu Pro Gly Phe Ser
                 20                  25                  30

Ser Ala Arg Asn Leu Val Ala Asn Ala His Ser Ser Ser Gly Ala
                 35                  40                  45

Lys Asp Leu Val Cys Ser Lys Met Ser Arg Ala Lys Asp Ala Val
                 50                  55                  60

Ser Ser Gly Val Ala Ser Val Asp Val Ala Lys Gly Val Val
                 65                      70                  75

Gln Gly Gly Leu Asp Thr Thr Arg Ser Ala Leu Thr Gly Thr Lys
                 80                  85                      90

Glu Ala Val Ser Ser Gly Val Thr Gly Ala Met Asp Met Ala Lys
                 95                 100                 105

Gly Ala Val Gln Gly Gly Leu Asp Thr Ser Lys Ala Val Leu Thr
                110                 115                 120

Gly Thr Lys Asp Thr Val Ser Thr Gly Leu Thr Gly Ala Val Asn
                125                 130                 135

Val Ala Lys Gly Thr Val Gln Ala Gly Val Asp Thr Thr Lys Thr
                140                 145                 150

Val Leu Thr Gly Thr Lys Asp Thr Val Thr Thr Gly Val Met Gly
                155                 160                 165

Ala Val Asn Leu Ala Lys Gly Thr Val Gln Thr Gly Val Glu Thr
                170                 175                 180

Ser Lys Ala Val Leu Thr Gly Thr Lys Asp Ala Val Ser Thr Gly
                185                 190                 195

Leu Thr Gly Ala Val Asn Val Ala Arg Gly Ser Ile Gln Thr Gly
                200                 205                 210

Val Asp Thr Ser Lys Thr Val Leu Thr Gly Thr Lys Asp Thr Val
                215                 220                 225

Cys Ser Gly Val Thr Ser Ala Met Asn Val Ala Lys Gly Thr Ile
                230                 235                 240

Gln Thr Gly Val Asp Thr Ser Lys Thr Val Leu Thr Gly Thr Lys
                245                 250                 255

Asp Thr Val Cys Ser Gly Val Thr Gly Ala Met Asn Val Ala Lys
                260                 265                 270

Gly Thr Ile Gln Thr Gly Val Asp Thr Ser Lys Thr Val Leu Thr
                275                 280                 285
```

-continued

```
Gly Thr Lys Asp Thr Val Cys Ser Gly Val Thr Gly Ala Met Asn
            290                 295                 300
Val Ala Lys Gly Thr Ile Gln Thr Gly Val Asp Thr Thr Lys Thr
            305                 310                 315
Val Leu Thr Gly Thr Lys Asn Thr Val Cys Ser Gly Val Thr Gly
            320                 325                 330
Ala Val Asn Leu Ala Lys Glu Ala Ile Gln Gly Gly Leu Asp Thr
            335                 340                 345
Thr Lys Ser Met Val Met Gly Thr Lys Asp Thr Met Ser Thr Gly
            350                 355                 360
Leu Thr Gly Ala Ala Asn Val Ala Lys Gly Ala Met Gln Thr Gly
            365                 370                 375
Leu Asn Thr Thr Gln Asn Ile Ala Thr Gly Thr Lys Asp Thr Val
            380                 385                 390
Cys Ser Gly Val Thr Gly Ala Met Asn Leu Ala Arg Gly Thr Ile
            395                 400                 405
Gln Thr Gly Val Asp Thr Thr Lys Ile Val Leu Thr Gly Thr Lys
            410                 415                 420
Asp Thr Val Cys Ser Gly Val Thr Gly Ala Ala Asn Val Ala Lys
            425                 430                 435
Gly Ala Val Gln Gly Gly Leu Asp Thr Thr Lys Ser Val Leu Thr
            440                 445                 450
Gly Thr Lys Asp Ala Val Ser Thr Gly Pro Thr Gly Ala Val Asn
            455                 460                 465
Val Ala Lys Gly Thr Val Gln Thr Gly Val Asp Thr Thr Lys Thr
            470                 475                 480
Val Leu Thr Gly Thr Lys Asp Thr Val Cys Ser Gly Val Thr Ser
            485                 490                 495
Ala Val Asn Val Ala Lys Gly Ala Val Gln Gly Gly Leu Asp Thr
            500                 505                 510
Thr Lys Ser Val Val Ile Gly Thr Lys Asp Thr Met Ser Thr Gly
            515                 520                 525
Leu Thr Gly Ala Ala Asn Val Ala Lys Gly Ala Val Gln Thr Gly
            530                 535                 540
Val Asp Thr Ala Lys Thr Val Leu Thr Gly Thr Lys Asp Thr Val
            545                 550                 555
Thr Thr Gly Leu Val Gly Ala Val Asn Val Ala Lys Gly Thr Val
            560                 565                 570
Gln Thr Gly Met Asp Thr Thr Lys Thr Val Leu Thr Gly Thr Lys
            575                 580                 585
Asp Thr Ile Tyr Ser Gly Val Thr Ser Ala Val Asn Val Ala Lys
            590                 595                 600
Gly Ala Val Gln Thr Gly Leu Lys Thr Thr Gln Asn Ile Ala Thr
            605                 610                 615
Gly Thr Lys Asn Thr Phe Gly Ser Gly Val Thr Gly Ala Val Asn
            620                 625                 630
Val Ala Lys Gly Ala Val Gln Thr Gly Val Asp Thr Ala Lys Thr
            635                 640                 645
Val Leu Thr Gly Thr Lys Asp Thr Val Thr Thr Gly Leu Met Gly
            650                 655                 660
Ala Val Asn Val Ala Lys Gly Thr Val Gln Thr Ser Val Asp Thr
            665                 670                 675
Thr Lys Thr Val Leu Thr Gly Thr Lys Asp Thr Val Cys Ser Gly
```

```
                    680                 685                 690
Val Thr Gly Ala Ala Asn Val Ala Lys Gly Ala Val Gln Thr Gly
                695                 700                 705
Val Asp Thr Thr Lys Ser Val Leu Thr Gly Thr Lys Asp Ala Val
                710                 715                 720
Ser Thr Gly Leu Thr Gly Ala Val Asn Leu Ala Lys Gly Thr Val
                725                 730                 735
Gln Thr Gly Met Asp Thr Thr Lys Thr Val Leu Thr Gly Thr Lys
                740                 745                 750
Asp Ala Val Cys Ser Gly Val Thr Gly Ala Ala Asn Val Ala Lys
                755                 760                 765
Gly Ala Val Gln Thr Gly Val Asp Thr Ala Lys Thr Val Leu Thr
                770                 775                 780
Gly Thr Lys Asp Thr Val Thr Thr Gly Leu Met Gly Ala Val Asn
                785                 790                 795
Val Ala Lys Gly Thr Val Gln Thr Ser Val Asp Thr Thr Lys Thr
                800                 805                 810
Val Leu Thr Gly Thr Lys Asp Thr Val Cys Ser Gly Val Thr Gly
                815                 820                 825
Ala Ala Asn Val Ala Lys Gly Ala Val Gln Gly Gly Leu Asp Thr
                830                 835                 840
Thr Lys Ser Val Leu Thr Gly Thr Lys Asp Thr Val Ser Thr Gly
                845                 850                 855
Leu Thr Gly Ala Val Asn Leu Ala Lys Gly Thr Val Gln Thr Gly
                860                 865                 870
Val Asp Thr Ser Lys Thr Val Leu Thr Gly Thr Lys Asp Thr Val
                875                 880                 885
Cys Ser Gly Val Thr Gly Ala Val Asn Val Ala Lys Gly Thr Val
                890                 895                 900
Gln Thr Gly Val Asp Thr Ala Lys Thr Val Leu Ser Gly Ala Lys
                905                 910                 915
Asp Ala Val Thr Thr Gly Val Thr Gly Ala Val Asn Val Ala Lys
                920                 925                 930
Gly Thr Val Gln Thr Gly Val Asp Ala Ser Lys Ala Val Leu Met
                935                 940                 945
Gly Thr Lys Asp Thr Val Phe Ser Gly Val Thr Gly Ala Met Ser
                950                 955                 960
Met Ala Lys Gly Ala Val Gln Gly Gly Leu Asp Thr Thr Lys Thr
                965                 970                 975
Val Leu Thr Gly Thr Lys Asp Ala Val Ser Ala Gly Leu Met Gly
                980                 985                 990
Ser Gly Asn Val Ala Thr Gly Ala Thr His Thr Gly Leu Ser Thr
                995                1000                1005
Phe Gln Asn Trp Leu Pro Ser Thr Pro Ala Thr Ser Trp Gly Gly
               1010                1015                1020
Leu Thr Ser Ser Arg Thr Thr Asp Asn Gly Gly Glu Gln Thr Ala
               1025                1030                1035
Leu Ser Pro Gln Glu Ala Pro Phe Ser Gly Ile Ser Thr Pro Pro
               1040                1045                1050
Asp Val Leu Ser Val Gly Pro Glu Pro Ala Trp Glu Ala Ala Ala
               1055                1060                1065
Thr Thr Lys Gly Leu Ala Thr Asp Val Ala Thr Phe Thr Gln Gly
               1070                1075                1080
```

-continued

Ala Ala Pro Gly Arg Glu Asp Thr Gly Leu Leu Ala Thr Thr His
         1085                1090                1095

Gly Pro Glu Glu Ala Pro Arg Leu Ala Met Leu Gln Asn Glu Leu
    1100                1105                1110

Glu Gly Leu Gly Asp Ile Phe His Pro Met Asn Ala Glu Glu Gln
         1115                1120                1125

Ala Gln Leu Ala Ala Ser Gln Pro Gly Pro Lys Val Leu Ser Ala
    1130                1135                1140

Glu Gln Gly Ser Tyr Phe Val Arg Leu Gly Asp Leu Gly Pro Ser
         1145                1150                1155

Phe Arg Gln Arg Ala Phe Glu His Ala Val Ser His Leu Gln His
    1160                1165                1170

Gly Gln Phe Gln Ala Arg Asp Thr Leu Ala Gln Leu Gln Asp Cys
         1175                1180                1185

Phe Arg Leu Ile Glu Lys Ala Gln Gln Ala Pro Glu Gly Gln Pro
    1190                1195                1200

Arg Leu Asp Gln Gly Ser Gly Ala Ser Ala Glu Asp Ala Ala Val
         1205                1210                1215

Gln Glu Glu Arg Asp Ala Gly Val Leu Ser Arg Val Cys Gly Leu
    1220                1225                1230

Leu Arg Gln Leu His Thr Ala Tyr Ser Gly Leu Val Ser Ser Leu
         1235                1240                1245

Gln Gly Leu Pro Ala Glu Leu Gln Gln Pro Val Gly Arg Ala Arg
    1250                1255                1260

His Ser Leu Cys Glu Leu Tyr Gly Ile Val Ala Ser Ala Gly Ser
         1265                1270                1275

Val Glu Glu Leu Pro Ala Glu Arg Leu Val Gln Ser Arg Glu Gly
    1280                1285                1290

Val His Gln Ala Trp Gln Gly Leu Glu Gln Leu Leu Glu Gly Leu
         1295                1300                1305

Gln His Asn Pro Pro Leu Ser Trp Leu Val Gly Pro Phe Ala Leu
    1310                1315                1320

Pro Ala Gly Gly Gln
         1325

<210> SEQ ID NO 48
<211> LENGTH: 228
<212> TYPE: PRT
<213> ORGANISM: Homo sapiens
<220> FEATURE:
<221> NAME/KEY: misc_feature
<223> OTHER INFORMATION: Incyte ID No: 002479CD1

<400> SEQUENCE: 48

Met Gly Leu Arg Pro Val Pro Ser Tyr Gln Thr Glu Ser Ala Pro
 1               5                  10                  15

Gly Pro Met Gly Ser Leu Pro Ser Glu Glu Ala Val Gly Trp His
             20                  25                  30

Ser Gln Val Leu Pro Leu Leu Pro Val Leu Ala Gln Arg Ser Ser
         35                  40                  45

Arg Ile Arg Ala Ala Leu Leu Gly Ser Phe Gln Ala Ala Pro Ile
     50                  55                  60

His Thr Pro Arg Leu Arg Cys Leu Phe Met Trp Lys Val Pro Arg
 65                  70                  75

Gly Leu Phe Ser Ala Val Cys Thr Gln Lys Asp Leu Val Met Leu

```
                    80                  85                  90
Ile Ala Gln Met Ala Gly Gly Cys Leu Phe Pro Trp Val Ser Leu
                95                 100                  105

Phe Gly Leu Trp Asp Ala Gly Ala Leu Pro Met Met Ser Gly Thr
               110                 115                  120

Ser Pro Leu Gly Gly Pro Ala Thr Leu Thr Ile Pro Arg Ala His
               125                 130                  135

Leu Gly Thr Pro Gly Thr Cys Pro Thr Pro Thr Leu Gly Thr Gly
               140                 145                  150

Ser Thr Ser Phe Pro Leu Ser Thr Ser His Ser Leu Ala Phe Ser
               155                 160                  165

Lys Lys Leu Asn Gln Glu Met Glu Gly Thr Leu Glu Thr Leu Ile
               170                 175                  180

Ser Glu Gly His Leu Asp Ser Gly Leu Asp Leu Ile Pro Ala Pro
               185                 190                  195

Trp Arg Pro Arg Arg Glu Asp His Leu Ile Pro Ser Val Gln Asp
               200                 205                  210

Leu Leu Val Thr Trp Gln Asp Leu His Leu His Phe Asn Phe Leu
               215                 220                  225

Lys Lys Val

<210> SEQ ID NO 49
<211> LENGTH: 80
<212> TYPE: PRT
<213> ORGANISM: Homo sapiens
<220> FEATURE:
<221> NAME/KEY: misc_feature
<223> OTHER INFORMATION: Incyte ID No: 1395420CD1

<400> SEQUENCE: 49

Met Lys Arg Arg His His Leu Leu Ser Asn Asn Ser Gln Glu Gln
  1               5                  10                  15

Pro Phe Leu Ile His Thr Cys Leu Leu Thr Pro Ser Ala His Phe
                 20                  25                  30

Phe Lys Leu His Leu Met Pro Cys Lys Ser Pro Tyr Ser Pro Gly
                 35                  40                  45

Leu Leu Ser Ser Gln Phe Ser Leu Leu Tyr Thr Thr Ser Gln Gly
                 50                  55                  60

Ser His Leu His Thr His Gly Phe Asn Cys Phe Leu His Ser Leu
                 65                  70                  75

Arg Thr Ile Glu Phe
                 80

<210> SEQ ID NO 50
<211> LENGTH: 538
<212> TYPE: PRT
<213> ORGANISM: Homo sapiens
<220> FEATURE:
<221> NAME/KEY: misc_feature
<223> OTHER INFORMATION: Incyte ID No: 1634103CD1

<400> SEQUENCE: 50

Met Ala Ala Glu Gln Asp Pro Glu Ala Arg Ala Ala Arg Pro
  1               5                  10                  15

Leu Leu Thr Asp Leu Tyr Gln Ala Thr Met Ala Leu Gly Tyr Trp
                 20                  25                  30

Arg Ala Gly Arg Ala Arg Asp Ala Ala Glu Phe Glu Leu Phe Phe
                 35                  40                  45
```

-continued

Arg Arg Cys Pro Phe Gly Gly Ala Phe Ala Leu Ala Ala Gly Leu
            50                  55                  60
Arg Asp Cys Val Arg Phe Leu Arg Ala Phe Arg Leu Arg Asp Ala
            65                  70                  75
Asp Val Gln Phe Leu Ala Ser Val Leu Pro Pro Asp Thr Asp Pro
            80                  85                  90
Ala Phe Phe Glu His Leu Arg Ala Leu Asp Cys Ser Glu Val Thr
            95                  100                 105
Val Arg Ala Leu Pro Glu Gly Ser Leu Ala Phe Pro Gly Val Pro
            110                 115                 120
Leu Leu Gln Val Ser Gly Pro Leu Leu Val Val Gln Leu Leu Glu
            125                 130                 135
Thr Pro Leu Leu Cys Leu Val Ser Tyr Ala Ser Leu Val Ala Thr
            140                 145                 150
Asn Ala Ala Arg Leu Arg Leu Ile Ala Gly Pro Glu Lys Arg Leu
            155                 160                 165
Leu Glu Met Gly Leu Arg Arg Ala Gln Gly Pro Asp Gly Gly Leu
            170                 175                 180
Thr Ala Ser Thr Tyr Ser Tyr Leu Gly Gly Phe Asp Ser Ser Ser
            185                 190                 195
Asn Val Leu Ala Gly Gln Leu Arg Gly Val Pro Val Ala Gly Thr
            200                 205                 210
Leu Ala His Ser Phe Val Thr Ser Phe Ser Gly Ser Glu Val Pro
            215                 220                 225
Pro Asp Pro Met Leu Ala Pro Ala Ala Gly Glu Gly Pro Gly Val
            230                 235                 240
Asp Leu Ala Ala Lys Ala Gln Val Trp Leu Glu Gln Val Cys Ala
            245                 250                 255
His Leu Gly Leu Gly Val Gln Glu Pro His Pro Gly Glu Arg Ala
            260                 265                 270
Ala Phe Val Ala Tyr Ala Leu Ala Phe Pro Arg Ala Phe Gln Gly
            275                 280                 285
Leu Leu Asp Thr Tyr Ser Val Trp Arg Ser Gly Leu Pro Asn Phe
            290                 295                 300
Leu Ala Val Ala Leu Ala Leu Gly Glu Leu Gly Tyr Arg Ala Val
            305                 310                 315
Gly Val Arg Leu Asp Ser Gly Asp Leu Leu Gln Gln Ala Gln Glu
            320                 325                 330
Ile Arg Lys Val Phe Arg Ala Ala Ala Gln Phe Gln Val Pro
            335                 340                 345
Trp Leu Glu Ser Val Leu Ile Val Ser Asn Asn Ile Asp Glu
            350                 355                 360
Glu Ala Leu Ala Arg Leu Ala Gln Glu Gly Ser Glu Val Asn Val
            365                 370                 375
Ile Gly Ile Gly Thr Ser Val Val Thr Cys Pro Gln Gln Pro Ser
            380                 385                 390
Leu Gly Gly Val Tyr Lys Leu Val Ala Val Gly Gly Gln Pro Arg
            395                 400                 405
Met Lys Leu Thr Glu Asp Pro Glu Lys Gln Thr Leu Pro Gly Ser
            410                 415                 420
Lys Ala Ala Phe Arg Leu Leu Gly Ser Asp Gly Ser Pro Leu Met
            425                 430                 435

-continued

```
Asp Met Leu Gln Leu Ala Glu Glu Pro Val Pro Gln Ala Gly Gln
                440                 445                 450

Glu Leu Arg Val Trp Pro Pro Gly Ala Gln Glu Pro Cys Thr Val
            455                 460                 465

Arg Pro Ala Gln Val Glu Pro Leu Leu Arg Leu Cys Leu Gln
        470                 475                 480

Gly Gln Leu Cys Glu Pro Leu Pro Ser Leu Ala Glu Ser Arg Ala
    485                 490                 495

Leu Ala Gln Leu Ser Leu Ser Arg Leu Ser Pro Glu His Arg Arg
500                 505                 510

Leu Arg Ser Pro Ala Gln Tyr Gln Val Val Leu Ser Glu Arg Leu
            515                 520                 525

Gln Ala Leu Val Asn Ser Leu Cys Ala Gly Gln Ser Pro
                530                 535

<210> SEQ ID NO 51
<211> LENGTH: 73
<212> TYPE: PRT
<213> ORGANISM: Homo sapiens
<220> FEATURE:
<221> NAME/KEY: misc_feature
<223> OTHER INFORMATION: Incyte ID No: 2422023CD1

<400> SEQUENCE: 51

Met Asp Ser Ala Ala Leu Ala Ala Leu Pro Val Thr Phe Ala Pro
 1               5                  10                  15

Arg Ala Trp Gly Gly Gly Cys Glu Glu Thr Leu Arg Ser Phe Pro
             20                  25                  30

Met Glu Glu Gly Arg Pro Ala Val Thr Arg Val Leu Ala Arg Val
         35                  40                  45

Arg Val Pro Gly Ala Gly Leu Thr Arg Pro Pro Asp Cys Leu Gly
     50                  55                  60

Leu Pro Arg Trp Pro Pro Arg Gly Ala Ala Val Thr Leu
 65                  70

<210> SEQ ID NO 52
<211> LENGTH: 108
<212> TYPE: PRT
<213> ORGANISM: Homo sapiens
<220> FEATURE:
<221> NAME/KEY: misc_feature
<223> OTHER INFORMATION: Incyte ID No: 4241771CD1

<400> SEQUENCE: 52

Met Asn Ile Leu Gly Tyr Arg Val Ser Gly Ile Ser Phe Phe Leu
 1               5                  10                  15

Leu Phe Leu Asn Gly Leu Leu Ser Cys Gln Pro Asn Ile Tyr Tyr
             20                  25                  30

Ile Ala Asn Ser Ser Leu Val Cys Asp Glu Tyr Ser Arg Pro Ala
         35                  40                  45

Phe Ile Pro Gly Leu Gln Lys Met Phe Asp Asp Ala Val Glu Ile
     50                  55                  60

Ser Ala Leu Gly Arg Val Gln Trp Leu Thr Pro Val Ile Ser Ala
 65                  70                  75

Leu Trp Glu Ala Lys Gly Gly Gly Ser Pro Glu Val Arg Ser Ser
             80                  85                  90

Arg Pro Val Trp Pro Val Trp Gln Asn Pro Ile Ser Thr Lys Asn
         95                 100                 105
```

Thr Lys Asn

```
<210> SEQ ID NO 53
<211> LENGTH: 80
<212> TYPE: PRT
<213> ORGANISM: Homo sapiens
<220> FEATURE:
<221> NAME/KEY: misc_feature
<223> OTHER INFORMATION: Incyte ID No: 5046408CD1

<400> SEQUENCE: 53
```

Met Ser Thr Ile Val Tyr Ile Leu Phe Phe Ser Gly Phe Leu Asn
 1               5                  10                  15

Ser Ser Gly Gly Ser Arg Trp Gly Leu Gln His His Leu Gly Gly
             20                  25                  30

Cys His Gly Glu Gly Ile Gly Ser Cys Gln Gly Asn Leu Glu Glu
         35                  40                  45

Thr Leu Leu Thr Gly Pro Phe Gln Ala Pro Tyr Pro Gly Pro Pro
     50                  55                  60

Glu Gln Ala Ala Trp Thr Gly Val Ser Gly Cys Gly Cys Pro Asp
 65                  70                  75

Val Leu Thr Leu Glu
             80

```
<210> SEQ ID NO 54
<211> LENGTH: 87
<212> TYPE: PRT
<213> ORGANISM: Homo sapiens
<220> FEATURE:
<221> NAME/KEY: misc_feature
<223> OTHER INFORMATION: Incyte ID No: 6271376CD1

<400> SEQUENCE: 54
```

Met Gln Leu Leu Val Trp Leu Cys Leu Leu Gly Ala Ser His Ala
 1               5                  10                  15

Gly Leu Ser Pro Ser Asp Leu His Ser Gly Thr Phe Pro Gly Cys
             20                  25                  30

Ala Glu Thr His Gly Phe Met Ser Cys Ala Glu Pro Ser Pro Val
         35                  40                  45

Asp Ser Gly Glu Asp Arg Lys Ile Leu Leu Asp Ser Arg Pro Trp
     50                  55                  60

Phe Leu Asn Leu Ser Pro Ile Gly Ile Cys Gly Arg Val Ile Leu
 65                  70                  75

Cys Cys Val Gly Ala Val Leu Cys Ile Val Gly His
             80                  85

```
<210> SEQ ID NO 55
<211> LENGTH: 78
<212> TYPE: PRT
<213> ORGANISM: Homo sapiens
<220> FEATURE:
<221> NAME/KEY: misc_feature
<223> OTHER INFORMATION: Incyte ID No: 7032326CD1

<400> SEQUENCE: 55
```

Met Thr Gly Val Ser Leu Arg Thr Gln Pro Leu Asp Ser Asn Ala
 1               5                  10                  15

Leu Phe Leu Ala Leu Ser Ser Gln Leu Gly Trp Ala Leu Gly Pro
             20                  25                  30

Arg Ser Pro Val Ala Ser Pro Gly Gly Leu Arg Gly His Arg Leu
         35                  40                  45

-continued

Ser Leu Ala Ser Gln Ile Pro Gly Ser Leu Gly Cys Ala Glu Asn
            50                  55                  60

Pro Lys Gly Phe Gln Gly Gly Glu Ser Val Glu Cys Val Arg Asp
65                  70                  75

Ser Leu Arg

<210> SEQ ID NO 56
<211> LENGTH: 108
<212> TYPE: PRT
<213> ORGANISM: Homo sapiens
<220> FEATURE:
<221> NAME/KEY: misc_feature
<223> OTHER INFORMATION: Incyte ID No: 7078691CD1

<400> SEQUENCE: 56

Met Asp Cys Thr Leu Leu Ser Leu Leu Ser Val Leu Leu Leu Gly
1               5                   10                  15

Pro Gly Ile Cys Gln Gly Cys Leu Leu Val Ala Thr Ser Asp Ala
            20                  25                  30

Gln Gln Gly Lys Gln Glu Gly Met Arg Pro Leu Ser Gln Gly Ser
            35                  40                  45

Glu Leu Thr Arg Cys His Val Leu Pro Arg Ala Val Ser Gln Ser
            50                  55                  60

Lys Leu Asp Asp Gln Ala Glu Pro Lys Ser Glu Glu Ile Asn Ser
65                  70                  75

Phe Cys Asp Glu Ala Val Ala Arg Val Trp Val Gln Gly Val Gly
            80                  85                  90

Asn Asn Leu Asp Gln Arg Leu Asn Leu Pro Pro Pro Pro Pro Ala
            95                  100                 105

Ile Arg Thr

<210> SEQ ID NO 57
<211> LENGTH: 81
<212> TYPE: PRT
<213> ORGANISM: Homo sapiens
<220> FEATURE:
<221> NAME/KEY: misc_feature
<223> OTHER INFORMATION: Incyte ID No: 7089352CD1

<400> SEQUENCE: 57

Met Lys Pro Cys Ala Arg Gly Leu Ser Val Phe Ser Cys Val Val
1               5                   10                  15

Cys Val Leu Cys Leu Val Trp Pro Cys Leu Ala Ser Gly Arg Phe
            20                  25                  30

Thr Gly Gly Arg Cys Met Cys Phe Cys Glu Val Ser Arg Gly Glu
            35                  40                  45

Leu Lys Arg Ser Arg Glu Glu Ala Leu Pro Leu Pro Asp Arg
            50                  55                  60

Leu Ser Pro Ser Ser Ala Ile Arg Ser Gly Trp Ile Leu Ala Gly
            65                  70                  75

Arg Gly Ser Ser Arg Leu
                80

<210> SEQ ID NO 58
<211> LENGTH: 146
<212> TYPE: PRT
<213> ORGANISM: Homo sapiens
<220> FEATURE:
<221> NAME/KEY: misc_feature
<223> OTHER INFORMATION: Incyte ID No: 7284533CD1

<400> SEQUENCE: 58

```
Met Met Pro Trp Lys Met Leu Leu Lys Val Thr Ser Thr Leu Leu
 1               5                  10                  15

Ala Leu Pro Tyr Gly Ser Ser Val Pro Ala Gly Pro Pro Leu
             20                  25                  30

Phe Ser Cys Ser Pro Leu Leu Ala Ser Val Ala Thr Ser Trp Ala
             35                  40                  45

Leu Ala Thr Leu Leu Leu Phe Ser Pro Cys Leu Leu Gly Thr Ser
             50                  55                  60

Pro Ala His Pro Leu Ser Ala Asp Cys Leu Arg Pro Gln Ser Leu
             65                  70                  75

Ile Phe Ser Val Tyr Met Arg Phe Leu Gly Lys Cys Phe Gln Thr
             80                  85                  90

Glu Ala Leu Ser Ile Phe His Thr Ile Ile Thr Pro Lys Ile Ser
             95                  100                 105

Ile Ser Ile Leu Asp His Thr Pro Glu Leu Gln Asp Leu His Ile
             110                 115                 120

Gln Thr Thr Arg Ile Glu Ile Pro Thr Gly Ile Ser Gln Asp Asn
             125                 130                 135

Leu Lys Phe Asn Leu Phe Lys Asn Met Asn Ser
             140                 145
```

<210> SEQ ID NO 59
<211> LENGTH: 92
<212> TYPE: PRT
<213> ORGANISM: Homo sapiens
<220> FEATURE:
<221> NAME/KEY: misc_feature
<223> OTHER INFORMATION: Incyte ID No: 7482209CD1

<400> SEQUENCE: 59

```
Met Phe Arg Leu Phe Thr Cys Ile Cys Val Cys Ser Ser Ala Gly
 1               5                  10                  15

Ala Ser Asn Ser Asp Thr Thr Arg Glu Tyr Arg His Pro Cys Arg
             20                  25                  30

Asn Cys Gln Phe Val Lys Ser Lys Ser Trp Thr Gln Met Ser Cys
             35                  40                  45

His Cys His Arg Thr Ala Ser Leu Cys Gly Ser Cys Cys Ser Leu
             50                  55                  60

Gly Glu Leu Lys Arg Leu Phe Pro Thr Leu Asn His Thr Ser Phe
             65                  70                  75

Cys Ser Leu Leu Tyr Thr His Arg Ile Arg Thr Arg Gln His Ser
             80                  85                  90

Pro Ser
```

<210> SEQ ID NO 60
<211> LENGTH: 119
<212> TYPE: PRT
<213> ORGANISM: Homo sapiens
<220> FEATURE:
<221> NAME/KEY: misc_feature
<223> OTHER INFORMATION: Incyte ID No: 7482314CD1

<400> SEQUENCE: 60

```
Met Gly Arg Thr Arg Val Cys Ser Trp Leu Cys Leu Ser Thr Ala
 1               5                  10                  15
```

```
Cys Ala Leu Thr Thr Ser Met Cys Cys Leu Leu Ala Ser Val Trp
                 20                  25                  30

Pro Val Asp Ser Leu Met Ala Arg Leu Ile Leu Ile Asn Ile Cys
             35                  40                  45

Trp Val Pro Thr Met Ala Gln Ala Leu Glu Ile Ile Val Lys Ser
             50                  55                  60

Ser Pro Leu Pro Gln Leu Leu Val Cys Leu Leu Asn Thr Leu Val
             65                  70                  75

Leu Cys Cys Ala Glu Arg Thr Ser Val His Met Pro Ala Ile Thr
             80                  85                  90

Leu Val Glu Pro Asn Phe Tyr Lys Leu Ser Phe Arg Trp Arg Asp
             95                 100                 105

Ser Val Phe Leu Ser Tyr Asn Thr Tyr Arg Asn Thr Asn Ile
            110                 115

<210> SEQ ID NO 61
<211> LENGTH: 92
<212> TYPE: PRT
<213> ORGANISM: Homo sapiens
<220> FEATURE:
<221> NAME/KEY: misc_feature
<223> OTHER INFORMATION: Incyte ID No: 7482339CD1

<400> SEQUENCE: 61

Met Gly Phe Pro Leu Leu Val Pro Leu Gly Leu Arg Val Val Ile
 1               5                  10                  15

Thr Leu Cys Leu Ala Ser Val Trp Ser Cys His Leu Ser Leu Leu
                 20                  25                  30

Val Ser Leu Tyr Pro Ala His Ser Thr Cys Asn Gln Ser Phe Val
             35                  40                  45

Lys Leu Pro Ser Val Ala Leu Ser Leu Pro Ser Phe Ser Cys Arg
             50                  55                  60

Val Leu Tyr Lys Arg Ala Leu Ala Ser Lys Gly Gln Leu Ala Val
             65                  70                  75

Glu Thr Ala Leu Arg Ala Arg Thr Ser Val Met Trp Ile Ser Gly
             80                  85                  90

Cys Ser

<210> SEQ ID NO 62
<211> LENGTH: 107
<212> TYPE: PRT
<213> ORGANISM: Homo sapiens
<220> FEATURE:
<221> NAME/KEY: misc_feature
<223> OTHER INFORMATION: Incyte ID No: 7949557CD1

<400> SEQUENCE: 62

Met Cys His His Ile Trp Leu Ile Phe Asn Phe Leu Asn Arg Ile
 1               5                  10                  15

Trp Val Leu Ser Cys Cys Leu Gly Trp Ser Arg Thr Ala Glu Phe
                 20                  25                  30

Lys Arg Ser Ser Cys His Asp Leu Pro Glu Arg Trp Asp Tyr Arg
             35                  40                  45

Gln Glu Pro Leu Cys Pro Ala Ser Gln Asn Ser Leu Met Arg Ile
             50                  55                  60

Gly Leu Ala Phe Arg Glu Arg Ala Ser Lys Pro Pro Ile Cys Pro
             65                  70                  75

Ala Gln Pro Pro Thr Pro Ser Trp Gln Cys Ser Cys Ser Ser Leu
```

-continued

```
                     80                  85                  90

Lys Arg Gln Glu Asp Ala Gly Glu Gly Arg Gly Glu Val Val Ser
                 95                 100                 105

Trp Arg

<210> SEQ ID NO 63
<211> LENGTH: 497
<212> TYPE: PRT
<213> ORGANISM: Homo sapiens
<220> FEATURE:
<221> NAME/KEY: misc_feature
<223> OTHER INFORMATION: Incyte ID No: 1555909CD1

<400> SEQUENCE: 63

Met Ser Cys Val Leu Gly Gly Val Ile Pro Leu Gly Leu Leu Phe
  1               5                  10                  15

Leu Val Cys Gly Ser Gln Gly Tyr Leu Leu Pro Asn Val Thr Leu
                 20                  25                  30

Leu Glu Glu Leu Leu Ser Lys Tyr Gln His Asn Glu Ser His Ser
                 35                  40                  45

Arg Val Arg Arg Ala Ile Pro Arg Glu Asp Lys Glu Glu Ile Leu
                 50                  55                  60

Met Leu His Asn Lys Leu Arg Gly Gln Val Gln Pro Gln Ala Ser
                 65                  70                  75

Asn Met Glu Tyr Met Thr Trp Asp Asp Glu Leu Glu Lys Ser Ala
                 80                  85                  90

Ala Ala Trp Ala Ser Gln Cys Ile Trp Glu His Gly Pro Thr Ser
                 95                 100                 105

Leu Leu Val Ser Ile Gly Gln Asn Leu Gly Ala His Trp Gly Arg
                110                 115                 120

Tyr Arg Ser Pro Gly Phe His Val Gln Ser Trp Tyr Asp Glu Val
                125                 130                 135

Lys Asp Tyr Thr Tyr Pro Tyr Pro Ser Glu Cys Asn Pro Trp Cys
                140                 145                 150

Pro Glu Arg Cys Ser Gly Pro Met Cys Thr His Tyr Thr Gln Ile
                155                 160                 165

Val Trp Ala Thr Thr Asn Lys Ile Gly Cys Ala Val Asn Thr Cys
                170                 175                 180

Arg Lys Met Thr Val Trp Gly Glu Val Trp Glu Asn Ala Val Tyr
                185                 190                 195

Phe Val Cys Asn Tyr Ser Pro Lys Gly Asn Trp Ile Gly Glu Ala
                200                 205                 210

Pro Tyr Lys Asn Gly Arg Pro Cys Ser Glu Cys Pro Pro Ser Tyr
                215                 220                 225

Gly Gly Ser Cys Arg Asn Asn Leu Cys Tyr Arg Glu Glu Thr Tyr
                230                 235                 240

Thr Pro Lys Pro Glu Thr Asp Glu Met Asn Glu Val Glu Thr Ala
                245                 250                 255

Pro Ile Pro Glu Glu Asn His Val Trp Leu Gln Pro Arg Val Met
                260                 265                 270

Arg Pro Thr Lys Pro Lys Lys Thr Ser Ala Val Asn Tyr Met Thr
                275                 280                 285

Gln Val Val Arg Cys Asp Thr Lys Met Lys Asp Arg Cys Lys Gly
                290                 295                 300

Ser Thr Cys Asn Arg Tyr Gln Cys Pro Ala Gly Cys Leu Asn His
```

```
                        305                 310                 315
Lys Ala Lys Ile Phe Gly Ser Leu Phe Tyr Glu Ser Ser Ser Ser
                320                 325                 330
Ile Cys Arg Ala Ala Ile His Tyr Gly Ile Leu Asp Asp Lys Gly
                335                 340                 345
Gly Leu Val Asp Ile Thr Arg Asn Gly Lys Val Pro Phe Phe Val
                350                 355                 360
Lys Ser Glu Arg His Gly Val Gln Ser Leu Ser Lys Tyr Lys Pro
                365                 370                 375
Ser Ser Ser Phe Met Val Ser Lys Val Lys Val Gln Asp Leu Asp
                380                 385                 390
Cys Tyr Thr Thr Val Ala Gln Leu Cys Pro Phe Glu Lys Pro Ala
                395                 400                 405
Thr His Cys Pro Arg Ile His Cys Pro Ala His Cys Lys Asp Glu
                410                 415                 420
Pro Ser Tyr Trp Ala Pro Val Phe Gly Thr Asn Ile Tyr Ala Asp
                425                 430                 435
Thr Ser Ser Ile Cys Lys Thr Ala Val His Ala Gly Val Ile Ser
                440                 445                 450
Asn Glu Ser Gly Gly Asp Val Asp Val Met Pro Val Asp Lys Lys
                455                 460                 465
Lys Thr Tyr Val Gly Ser Leu Arg Asn Gly Val Gln Ser Glu Ser
                470                 475                 480
Leu Gly Thr Pro Arg Asp Gly Lys Ala Phe Arg Ile Phe Ala Val
                485                 490                 495
Arg Gln

<210> SEQ ID NO 64
<211> LENGTH: 1338
<212> TYPE: DNA
<213> ORGANISM: Homo sapiens
<220> FEATURE:
<221> NAME/KEY: misc_feature
<223> OTHER INFORMATION: Incyte ID No: 2719959CB1

<400> SEQUENCE: 64
ggaagagaca cagcagaggc tcacaccttc tcccccgtg ggcgcctgt tcccgcccc       60 cgcgcgtggg gggaacgccc gtcgtccgct aacacccgcc cccgtctcct ccactttggg  120 ggatccccc cccccgggtc cgggccccgc cccaaaaatg gggttccgac ccgttccgca   180
ttccgatgac ccccgggcct ccaggtccca tgaattaaaa gagaccacgg gaagcttgtt  240
ttgacccagg aatataatga atggaacaga gttggacaga cttcaacttg gctccaccat  300
cacctaccag tgtgactctg ctataagatt cttgaccccc tcatcccatc acctgtgtga  360
ttgggctgat gggaaacccct cctgggacca agtgctgccc tcctgcaatg ctccctgtgg  420
aggccagtac acgggatcag aagggagtagt tttatcacca aactaccccc ataattacac  480
agctggtcaa atatgcctct attccatcac ggtaccaaag gaattcgtgg tcttttggaca  540 gtttgcctat ttccagacag ccctgaatga tttggcagaa ttatttgatg aacccatgc   600 acaggccaga cttctcagct cactctcggg gtctcactca ggggaaacat tgcccttggc  660
tacgtcaaat caaattctgc tccgattcag tgcaaagagc ggtgcctctg cccgcggctt  720
ccacttcgtg tatcaagctg ttcctcgtac cagtgacacc caatgcagct ctgtccccga  780
gcccagatac ggaaggagaa ttggttctga gttttctgcc ggctccatcg tccgattcga  840
```

| | |
|---|---|
| gtgcaacccg ggatacctgc ttcagggttc cacggcgctc cactgccagt ccgtgcccaa | 900 |
| cgccttggca cagtggaacg acacgatccc cagctgtgtg gtaccctgca gtggcaattt | 960 |
| cactcaacga agaggtacaa tcctgtcccc cggctaccct gagccatacg gaaacaactt | 1020 |
| gaactgtata tggaagatca tagttacgga gggctcggga attcagatcc aagtgatcag | 1080 |
| ttttgccacg gagcagaact gggactccct tgagatccac gatggtgggg atgtgaccgc | 1140 |
| acccagactg ggaagcttct caggcaccac agtaccggca ctgctgaaca gtacttccaa | 1200 |
| ccaactctac ctgcatttcc agtctgacat tagtgtggca gctgctggtt ccacctgga | 1260 |
| atacaaaagt aaggtcaact ctttctgtat acagcttcca ctgttatact gagtcatttt | 1320 |
| tttaaagaaa aaataaac | 1338 |

<210> SEQ ID NO 65
<211> LENGTH: 5093
<212> TYPE: DNA
<213> ORGANISM: Homo sapiens
<220> FEATURE:
<221> NAME/KEY: misc_feature
<223> OTHER INFORMATION: Incyte ID No: 7473618CB1

<400> SEQUENCE: 65

| | |
|---|---|
| tgggcttcaa gaggacagct ggaggctaag aggtcgggtt tttcatcaaa tgcgcagtgg | 60 |
| aagtaatttt ggaaaagttt gtttgcatta tgctgcctaa acacggtgt tttagaaaga | 120 |
| ggcttttgca ttgaaaagct tctcgtcctc gcctctggga gtctagtgct tcctagagct | 180 |
| gcttgtgccc tcagccctgt aatgtgatat ccctcctcct ggattggtca gaggggtgtc | 240 |
| cttttccctgg gagctgcttt ccaccacggc tcccaaactt ggctcagtcc agcagccacc | 300 |
| atcaccacca ctgcggttgc tgctgcagct gcggctgctg ctctccctcc ggctgcttct | 360 |
| tcgcgtggcc agcagcgaat ggagcgatgg agcccagact gttctgctgg accactctct | 420 |
| ttctcctggc cgggtggtgc ctgccagggt tgccctgccc cagccggtgc ctttgcttta | 480 |
| agagcaccgt ccgctgcatg cacttgatgc tggaccacat tcctcaggta tcacagcaga | 540 |
| ccacagttct agacttgagg tttaacagaa taagagaaat tccagggagc gccttcaaga | 600 |
| aactcaagaa tttgaacaca cttctgctga caacaacca catcagaaag atttccagaa | 660 |
| atgcttttga aggacttgaa aatttgctat atctgtacct gtataagaat gaaatccatg | 720 |
| cactagataa gcaaacattt aaaggactca tatctttgga acatctgtat attcatttca | 780 |
| accaactaga aatgctacag ccagagacct ttggagacct tctgagatta gagcgactat | 840 |
| ttttgcataa caacaaatta tctaaaattc cagctgggag cttttctaat ctggattcat | 900 |
| taaaaagatt gcgtctggat tccaacgccc tggtttgtga ctgtgatctg atgtggctgg | 960 |
| gggagctttt acaaggcttt gcccaacacg gccacaccca ggctgcggct acctgcgaat | 1020 |
| atcccaggag actccatggg cgtgcagttg cttcagtaac agtagaggaa ttcaattgcc | 1080 |
| agagcccccg aattacttt gagccgcagg atgtggaggt accatcagga ataccgtct | 1140 |
| acttcacctg ccgggcggaa ggaaacccca aacctgagat tatttggata cacaacaacc | 1200 |
| actcattgga tttggaagat gatactcgac ttaatgtgtt tgatgatggc acactcatga | 1260 |
| tccgaaacac cagagagtca gaccaaggtg tctatcagtg catggccaga aattccgctg | 1320 |
| gggaagccaa gacacagagt gccatgctca gatactccag tcttccagcc aaaccaagct | 1380 |
| ttgtaatcca gcctcaggac acagaggttt taattggcac cagcacaact ttggaatgta | 1440 |
| tggccacagg ccacccacac cctcttatca cttggaccag ggacaatgga ttggagctgg | 1500 |

```
atggatccag gcatgtggca acgtccagtg gactttactt acagaacatc acacaacggg    1560
atcatggtcg atttacctgt catgccaaca atagccacgg cactgttcaa gctgcagcaa    1620
acataattgt acaagctcct ccacaattta cagtaacccc caaggatcaa gtggtgctgg    1680
aagaacatgc tgtagagtgg ctctgtgaag ctgacggcaa cccacctcct gttattgtct    1740
ggacaaaaac aggagggcag ctccctgtgg aaggccagca tacagttctc tcctctggca    1800
ctttgagaat tgaccgtgca gcacagcacg atcaaggcca atatgaatgt caagcagtca    1860
gttcgttggg ggtgaaaaag gtgtctgtgc agctgactgt aaaacccaaa ggtcttgcag    1920
tgtttactca acttcctcag gatacaagtg tcgaggttgg aaagaatata aacatttcat    1980
gtcatgctca aggagaacca cagcccataa ttacttggaa taaggaaggt gtgcagatta    2040
ctgagagtgg taaattccat gtggatgatg aaggcacgct gactatctac gacgcagggt    2100
tccctgacca gggaagatat gaatgtgtgg ctcggaattc ttttggcctt gctgtgacca    2160
acatgttcct acagtcacg gctatacagg gtagacaagc tggcgatgac tttgttgaat    2220
cttccattct tgatgctgta cagagagttg acagtgcaat taactccaca cgaagacatt    2280
tgttttcaca aaaacctcac acctccagtg acctgctggc tcaatttcat tacccgcgtg    2340
acccactgat tgtggaaatg caagagcag gggagatttt tgagcacacg ctgcagctga    2400
tacgggaacg tgtgaagcag gggctcactg tggacttgga aggcaaagaa ttccggtaca    2460
atgacttggt gtccccgcgc tccctcagcc tcatcgccaa tttatctgga tgcacagctc    2520
gcaggcctct gccaaactgc tccaaccggt gtttccatgc gaagtaccgc gcccacgacg    2580
gcacgtgcaa caacctgcag cagcccacgt ggggcgcggc gctgaccgcc ttcgcgcgcc    2640
tgctgcagcc agcctaccgg gacggcatcc gcgcgccccg cgggctcggc cttcctgtgg    2700
gctcccgcca gccccccccg ccgcccggc tggtcgccac agtgtgggcg cgcgcggcgg    2760
ccgtcacccc cgaccacagc tacacgcgca tgctcatgca ctggggctgg tttctagagc    2820
acgacttgga ccacacagtg cctgcgctga gcacagcccg cttctcggat gggcggccgt    2880
gcagctccgt ctgcaccaac gaccctcctt gtttccccat gaacacccgg cacgccgacc    2940
cccgggcac ccacgcgccc tgcatgctct tcgcgcgctc cagccccgcg tgtgccagcg    3000
gccgtccctc tgcgacggtg gattcagtct atgcacgaga gcagatcaac cagcaaacag    3060
cctacatcga tggctccaac gtttacggga gctcggagcg ggaatcccag gctctcagag    3120
acccttcggt gcctcggggt ctcctgaaga caggcttcc ttggcctccc tccggaaagc    3180
ccttattgcc cttttctaca ggcccaccca ccgagtgcgc gcgacaggag caggagagcc    3240
cctgtttcct ggccggggac caccgggcca acgagcatct ggctctggtc gccatgcaca    3300
ccctgtggtt ccgggaacac aacagggtgg ccacggagct gtccgccctg aaccccccact    3360
gggagggaaa cacggtttac caggaagcca ggaagatcgt gggcgcggag ctgcagcaca    3420
tcacctacag ccactggctg cctaaggtcc tgggggaccc tggcactagg atgctgaggg    3480
gttaccgagg ctacaacccc aacgtgaatg caggcatcat taactctttt gctactgcag    3540
cctttagatt tggccacaca ttaatcaatc ctattcttta ccgactgaat gccaccttag    3600
gtgaaatttc cgaaggccac cttccgttcc ataaagcgct cttttcaccg tccagaataa    3660
tcaaggaagg tgggatagac ccggttctcc gggggctgtt tggcgtggct gctaaatggc    3720
ggcacccctc ctaccttctc agtcctgagc tgacccagag gctcttctcc gcggcttatt    3780
ctgcggccgt ggattcggct gccaccatca ttcaaagggg tagagaccac gggatcccac    3840
catatgttga cttcagagtt ttctgtaatt tgacttcagt taagaacttt gaggatcttc    3900
```

| | |
|---|---|
| aaaatgaaat taaagattca gagattagac aaaaactgag aaagttgtac ggctctccag | 3960 |
| gtgacattga cctctggccc gcccttatgg ttgaagacct gattcctggt acaagagtgg | 4020 |
| gaccaacact tatgtgcctg tttgttaccc agtttcagcg gctaagagat ggagataggt | 4080 |
| tctggtatga aaaccctgga gtatttaccc cggcacaact cactcagctg aagcaggcgt | 4140 |
| ccctgagccg ggtgctttgt gacaatggtg acagcattca gcaagtgcag gctgatgtct | 4200 |
| ttgtaaaggc agaataccca caggattacc tgaactgcag cgagatcccg aaggtggacc | 4260 |
| tgcgagtgtg gcaagactgc tgtgcagact gtaggagtag aggacagttc agagcagtga | 4320 |
| cgcaagagtc tcaaaagaaa cgctcagctc aatacagcta tcctgttgat aaggatatgg | 4380 |
| agttaagtca tctaagaagt aggcaacaag ataaaatata tgtgggtgaa gatgctagaa | 4440 |
| atgtgacagt tctggcaaaa acaaagttct cccaagattt cagcacgttt gcagcggaaa | 4500 |
| ttcaggaaac catcacagca ctcagagagc agataaacaa gctggaggca cgcctgaggc | 4560 |
| aggcagggtg tacagatgtt agaggggttc aaggaaggc cgaggagcgc tggatgaaag | 4620 |
| aagactgcac tcactgcatt tgtgagagtg gccaggtcac ctgtgtggtg gagatttgtc | 4680 |
| ccccggctcc ctgtcccagt cctgaattgg tgaaaggaac ctgctgtcca gtttgcagag | 4740 |
| accgaggaat gccaagtgat tccccagaga agcgctaata aaagttttgt gctgttgagc | 4800 |
| cccaaatggg aaatttctca ggaagagaca tttaggactt cagaactttt aacttgtagt | 4860 |
| cacattgttg atatggaaac cactgactta agcaacttag ttcatctaat cttacatata | 4920 |
| cttacgatct tttattttt cattttctaa cataccttga aataattcca aactaaaagc | 4980 |
| cataaagtgc atatgaagtg tttgatcata agaaatattt cttactgtaa gctgtcagtt | 5040 |
| ttatatgcca cacctggaaa taaaagaat atcatggaat atttaaaaaa aaa | 5093 |

```
<210> SEQ ID NO 66
<211> LENGTH: 1392
<212> TYPE: DNA
<213> ORGANISM: Homo sapiens
<220> FEATURE:
<221> NAME/KEY: misc_feature
<223> OTHER INFORMATION: Incyte ID No: 3564136CB1

<400> SEQUENCE: 66
```

| | |
|---|---|
| atggggctaa aagctctctg tttggggctg ctttgtgttc ttttgtctc tcattttac | 60 |
| acacccatgc cagacaacat tgaagaaagc tggaaaataa tggccttgga tgccatcgct | 120 |
| aaaacttgtg ctaatgtttg tatttttgta gaaatgaggt atcaccacat ttatgaagag | 180 |
| tttatatcca tgatattcag gctggattat acccaaccac tttcagatga atacatcaca | 240 |
| gtgactgata caacatttgt tgacattcca gtacgattgt acttgccaaa agaaagtca | 300 |
| gaaacccgaa ggcgagctgt gatatatttt catggtggtg gttttgttt tggaagttcc | 360 |
| aaacagaggg cttttgactt cctgaataga tggacggcaa acacgcttga tgctgttgtt | 420 |
| gtaggcgtgg actataggct ggctcctcaa caccactttc ctgctcagtt tgaagatggc | 480 |
| cttgctgcag tcaaattttt tcttttggaa aaattctta caaatatgg agtggatccc | 540 |
| acccgaatct gcattgcggg agacagttct ggggcaatt tagcaacagc ggtcactcaa | 600 |
| caggtgcaga atgatgctga aataaaacat aaaatcaaga tgcaagtctt actttacccct | 660 |
| ggcttacaga taacagattc ttatttgcca tctcaccgag aaaatgagca tggtatagtt | 720 |
| ttgaccaggg atgtagccat aaaactcgtg agcttatatt tcaccaagga tgaagcactt | 780 |
| ccctgggcaa tgagaagaaa ccaacacatg cctctggagt caagacatct gtttaagttt | 840 |

| | |
|---|---|
| gttaactgga gtattcttct tcctgagaag tatagaaaag actatgtata tactgaacca | 900 |
| attcttggag gacttagtta ttcattgcca ggacttacag acagcagagc attacccttg | 960 |
| ttggccaatg attctcagtt acagaatttg ccactaacct atattcttac ttgtcaacat | 1020 |
| gatctcataa gagatgatgg acttatgtat gttacaagac ttcgaaatgt tggagtccaa | 1080 |
| gttgttcatg aacatattga ggatggaatt catggagctt tatcattcat gacttcacca | 1140 |
| ttttatttac gtctaggtct taggataaga gatatgtatg taagttggct ggataagaat | 1200 |
| ttataaatat gtgatgtgta tgtatagccc ttacatagtg gattgtaatt tgtgatattt | 1260 |
| tgtggttttg gagcaaagaa caatgtcatt tgagttatct aaatctacat ttgcaacatt | 1320 |
| tgtagcagtt aatgtgtgtc cttgaagagt tattaaattt tctgacttgc agaccctgaa | 1380 |
| aaaaaaaaaa aa | 1392 |

<210> SEQ ID NO 67
<211> LENGTH: 2390
<212> TYPE: DNA
<213> ORGANISM: Homo sapiens
<220> FEATURE:
<221> NAME/KEY: misc_feature
<223> OTHER INFORMATION: Incyte ID No: 624334CB1

<400> SEQUENCE: 67

| | |
|---|---|
| tgcaccgtga atccaactgt gccaagcctt ggctcccgcg aaccaatcct gagcgcgacc | 60 |
| cgggcactgg gacggcgact ccgccaaagc tggacgaggc agccggaccc gtctgcgctc | 120 |
| gagcatggag acggagcgcc tgggagggca cgtccggggc gctggagacg ccaggcccga | 180 |
| gtagcttctc catggagcct gcccagagcg gtcccttctc gcaggattcg ccccaagtcc | 240 |
| tgtgcggctg ctgagagcgc tccttgctct gtaaagtgga tgtcaggtgg atctatgttt | 300 |
| ctgaaggaac aaagactcaa agaaggcacc gccaaggaag tttgagacgc gggagaatgc | 360 |
| aggctgcgtg ctggtacgtg cttttcctcc tgcagcccac cgtctacttg gtcacatgtg | 420 |
| ccaatttaac gaacggtgga aagtcagaac ttctgaaatc aggaagcagc aaatccacac | 480 |
| taaagcacat atggacagaa agcagcaaag acttgtctat cagccgactc ctgtcacaga | 540 |
| cttttcgtgg caaagagaat gatacagatt tggacctgag atatgacacc ccagaacctt | 600 |
| attctgagca agacctctgg gactggctga ggaactccac agaccttcaa gagcctcggc | 660 |
| ccagggccaa gagaaggccc attgttaaaa cgggcaagtt taagaaaatg tttggatggg | 720 |
| gcgattttca ttccaacatc aaaacagtga agctgaacct gttgataact gggaaaattg | 780 |
| tagatcatgg caatgggaca tttagtgttt atttcaggca taattcaact ggtcaaggga | 840 |
| atgtatctgt cagcttggta ccccctacaa aaatcgtgga atttgacttg gcacaacaaa | 900 |
| ccgtgattga tgccaaagat tccaagtctt ttaattgtcg cattgaatat gaaaaggttg | 960 |
| acaaggctac caagaacaca ctctgcaact atgaccttc aaaaacctgt taccaggagc | 1020 |
| aaacccaaag tcatgtatcc tggctctgct ccaagccctt taaggtgatc tgtatttaca | 1080 |
| tttcctttta tagtacagat tataaactgg tacagaaagt gtgccctgac tacaactacc | 1140 |
| acagtgacac accttacttt ccctcgggat gaaggtgaac atgggggtga gactgaagcc | 1200 |
| tgaggaatta aaggtcatat gacagggctg ttacctcaaa gaagaaggtc acatctgttg | 1260 |
| cctggaatgt gtctacactg ctgctcttgt caactggctg caaaatacac tagtggaaaa | 1320 |
| cactctgatg taatttctgc ccagtcagct tcatccctca gtataattgt aaatcatcac | 1380 |
| agattttgaa ttcacacctg aagacatgct ctcacatata gaggtacaca aacacaccgt | 1440 |

| | |
|---|---|
| catgcacatt tcagcttgcg tctatcatga ttcctgttga gagggctttc attgtctgac | 1500 |
| tcataatggt tcaggatcaa ctatcatcaa acggaaggat taactagaca gagaatgttt | 1560 |
| ctaacagttg ctgttatgga aatctctttt aaagtcttga gtacatgcta atcaataatc | 1620 |
| tccactcatg cattcctact gcttggagta gctgtactgg taaatactac tgtaggagta | 1680 |
| tctgcttgtt aaaatggaaa aatgtgtctt tagagctcag tattctttat tttacaaaca | 1740 |
| caacaaaatg tagtaacttt tttccagcat acagtaggca cattcaaagt ggtccaagat | 1800 |
| ggctcttttt tctttgaaag gggcctgttc tcagtaaaga tgagcaaaca tttggaattt | 1860 |
| acatgtgggc agacattggg ataacaactt tcatcaccaa tcattggact tttgtgaagt | 1920 |
| cgacaccagc taaggctgct aaaataagt tctgatcatt atataagaag ggaaatgcct | 1980 |
| ggcagacacc atgtaagtta taagtgtctg tcttatcttt actacacata ttgtaacaaa | 2040 |
| ttcaatatcc tagtcttcat ttgtatgaat ggtttgtatt gtacatagtt taaccaagtg | 2100 |
| ttatttgagc tgcttattaa tattaacttg tacttgtctc tctgcttgtt attggttaag | 2160 |
| aaaaaaggat atgaggaatt cattttatca atgtagctgt gaaggccatt aaaaagacaa | 2220 |
| acttaatgta cagagcattt attcagatca agtattgttg aaagctatac atatacaaca | 2280 |
| ttacagtctg tctgtattta gatattttat ttctggaaaa aatgaaatgt acataaaaat | 2340 |
| aaaacactta aagttgagtt tcaataaaaa aaaaaaaaaa aaaaaaaaaa | 2390 |

<210> SEQ ID NO 68
<211> LENGTH: 3248
<212> TYPE: DNA
<213> ORGANISM: Homo sapiens
<220> FEATURE:
<221> NAME/KEY: misc_feature
<223> OTHER INFORMATION: Incyte ID No: 7483393CB1

<400> SEQUENCE: 68

| | |
|---|---|
| gcaggagtca ggcgtgagcc cctccccaca gtccacctgt ggaggcctcc tctctggccc | 60 |
| aaggggcttc ttcagcagcc ctaactaccc agacccttac ccccccaaca cccactgcgt | 120 |
| gtggcatatc caggtggcca cagaccacgc aatacagctc aagatcgaag ccctcagcat | 180 |
| agagagtgtg gcctcttgcc ttttgatcg cttggaactc tcccctgagc ctgaaggccc | 240 |
| cctcctcagg gttgtggaa gggtgcctcc ccccacgctc aacaccaatg ccagccacct | 300 |
| cctggtggtc ttcgtctctg acagcagtgt ggaaggattt ggtttccatg cctggtacca | 360 |
| ggctatggcc cctgggcgcg ggagctgtgc ccatgatgag ttccgctgtg accagctcat | 420 |
| ctgcctgcta cctgactcag tgtgtgatgg ttttgccaac tgtgctgacg gcagtgatga | 480 |
| gaccaattgc agtgccaagt ctcgggtg tgggggaat ctgactggcc tccagggcac | 540 |
| tttctctact cccagctacc tgcagcagta ccctcaccaa ctgctctgca cctggcatat | 600 |
| ctcggtgcct gccggacaca gcatagaact acagttccac aacttcagcc tggaggctca | 660 |
| ggacgagtgc aagtttgact acgtggaggt gtatgagacc agcagctcag ggccttcag | 720 |
| cctcctgggc aggttctgtg gagcagagcc accccccac ctcgtctcct cgcaccatga | 780 |
| gctggctgtg ctgtttagga cagatcatgg catcagcagt ggaggcttct cagccaccta | 840 |
| cctggccttc aatgccacgg agaaccctg tgggcccagt gagctctcct gccaggcagg | 900 |
| agggtgtaag ggtgtgcagt ggatgtgtga catgtggaga gactgcaccg atggcagcga | 960 |
| tgacaactgc agcggcccct tgttcccacc cccagagctg gcctgtgagc ctgtccaggt | 1020 |
| ggagatgtgc ctcggtctga gctacaacac cacagccttc cctaacatct gggtgggcat | 1080 |

```
gatcacccag gaggaggtgg tagaggtcct cagcggttac aagagcctga caagcctgcc    1140
ctgctaccag catttccgga ggctcctgtg tgggctgctt gtgccccgtt gcaccccact    1200
aggcagtgtt ctgcccectt gccgctctgt ctgccaggaa gcggagcacc agtgccagtc    1260
tggcctggca ctactgggca cccctggcc cttcaactgc aacaggctgc cagaggcagc    1320
tgacctggaa gcttgtgccc agccctgacc ctgaagccgg ccctgccct cttcctgccc    1380 gtcctctttt gccggtcagg gctggcacgc aggggaacaa aggaaggagc atcagcaggg    1440
tctctaccca tccttctctg gggctcccag ggaggggaa gagaagtcct cagctggggc    1500
tcatgggacc ctaccaccct ccctgctcct tcctgtccct ttaccggtcc caggctgctg    1560
actggcccca cactgtgcca ccggacaatc gagaccactt cccatccagg cctcttcccc    1620
tttccatctg cttttttcagc ttctccatcg cctgccttct gaccttttcc ttgattcaac    1680
aaaaatgtac tgagcatcta ttcatgtggc aggccctgt cctaggccct agggatccaa    1740
ctggctgtct gcctctagaa ctctccaccc tcatctctct gcgtatttct ccctgaaatg    1800
gggtctggtc cttggtctct gccactgccc tgcctctcct ctggccctgg aacaggagg    1860 tgccctgtgt gtccgtctct cgaagttctg cctctctgtg cccagctcaa gtctctctcc    1920
ccctcctttc tcccctaaa ctttggccgg ccgccgggcg acaccacgag ttatttccca    1980
gctatttccc ggtccgggag ctcttggccc ctgaacaact ggtttcctct tggagtctgg    2040
gaggaggaaa gcggagccgg cagggagcga accaggactg gggtgacggc agggcagggg    2100
gcgcctggcc ggggagaagc gcggggctg gagcaccacc aactggaggg tccggagtag    2160
cgagcgcccc gaaggaggcc atcggggagc cgggaggggg gactgcgaga ggaccccggc    2220
gtccgggctc ccggtgccag cgctatgagg ccactcctcg tcctgctgct cctgggcctg    2280
gcggccggct cgcccccact ggacgacaac aagatcccca gcctctgccc gggactgccg    2340
ggacctcgag gggaccccgg gccgcgagga gaggcgggac ccgcggggcc caccgggcct    2400
gccggggagt gctcggtgcc tccgcgatcc gccttcagcg ccaagcgctc cgagagccgg    2460
gtgcctccgc cgtctgacgc acccttgccc ttcgaccgcg tgctggtgaa cgagcaggga    2520
cattacgacg ccgtcaccgg caagttcacc tgccaggtgc tgggggtcta ctacttcgcc    2580
gtccatgcca ccgtctaccg ggccagcctg cagtttgatc tggtgaagaa tggcgaatcc    2640
attgcctctt tcttccagtt tttcgggggg tggcccaagc cagcctcgct ctcggggggg    2700
gccatggtga ggctggagcc tgaggaccaa gtgtgggtgc aggtgggtgt gggtgactac    2760
attggcatct atgccagcat caagacagac agcaccttct ccggatttct ggtgtactcc    2820
gactggcaca gctccccagt ctttgcttag tgcccactgc aaagtgagct catgctctca    2880
ctcctagaag gagggtgtga ggctgacaac caggtcatcc aggagggctg ccccctgg    2940 aatattgtga atgactaggg aggtggggta gagcactctc cgtcctgctg ctggcaagga    3000
atgggaacag tggctgtctg cgatcaggtc tggcagcatg gggcagtggc tggatttctg    3060
cccaagacca gaggagtgtg ctgtgctggc aagtgtaagt cccccagttg ctctggtcca    3120
ggagcccacg gtggggtgct ctcttcctgg tcctctgctt ctctggatcc tccccacccc    3180
ctcctgctcc tggggccggc ccttttctca gagatcactc aataaaccta agaaccctca    3240
aaaaaaaa                                                             3248
```

<210> SEQ ID NO 69
<211> LENGTH: 520
<212> TYPE: DNA

```
<213> ORGANISM: Homo sapiens
<220> FEATURE:
<221> NAME/KEY: misc_feature
<223> OTHER INFORMATION: Incyte ID No: 1799943CB1

<400> SEQUENCE: 69
ggccgtggcc gcagcgctca gctcctgcgc cccgaccccg ccatggcccc ccggcccctc      60
ctgctgctgc tgctgctcct cgggggctcc gccgcgcgcc ccgcgccccc cagggcccgg     120
cgacactcag acgggacgtt caccagcgag ctcagccgcc tgcggagggg cgcgcggctc     180
cagcggctgc tacagggcct ggtggggaag cgcagcgagc aggacgcaga gaacagcatg     240
gcctggacca ggctcagcgc gggtctgctc tgcccgtcag gtccaacat gcccatcctg      300
caggcctgga tgcccctgga cgggacctgg tctccctggc tgcccccctgg gcctatggtt     360
tcagaaccag ctggcgctgc tgcagaagga accttgcggc ccagatgagg aaggaaccc      420
ctcaccacct gcccggccca ggagcgcagc tgcatttggg gtgggggca ggatggggga     480
gaggggagg ggtggtactt ggcaccaata aacggaggag                            520

<210> SEQ ID NO 70
<211> LENGTH: 2108
<212> TYPE: DNA
<213> ORGANISM: Homo sapiens
<220> FEATURE:
<221> NAME/KEY: misc_feature
<223> OTHER INFORMATION: Incyte ID No: 2013095CB1

<400> SEQUENCE: 70
gcactgggac cacaggcatg aaccacaggc ttgaattata ggctgcagtg cggtggcatg      60
gtcttagctc actgcaacct ccgcctcccg ggctcaaggg attctcctgc ctcagcctcc     120
caagtagcgg ggattgcggg cacccatcac caagcctggc taattttgt attttagta      180
gagagaaaca tgggtttcac catgtttgcc aggctggtct cgcactccta acctcgatct     240
caggcgatcc gcctgcctag gcatcccaaa ttgctgggat tacaggcgtg agccactgcg     300
tccggcatga cacttttaa agaaacaaat tccgttaggc cctctggggt ctgtggtgtt      360
gtcacctctt ctgtgtgagg agtgccccaa cgtgcaaaac tgaggctgg tctgtgtccc      420
ccgcaggcca tggacaccctt cagcaccaag agcctggctc tgcaggcgca aagaagctc     480
ctgagtaaga tggcgtccaa ggcagtggtg gccgtgctgg tggatgacac cagcagtgag     540
gtgctggatg agctgtaccg cgccaccagg gagttcacgc gcagccgcaa ggaggcccag     600
aagatgctca agaacctggt caaggtggcc ctgaagctgg gactgctgct gcgtggggac     660
cagctgggcg gtgaggagct ggcgctgctg cggcgcttcc gccaccgggc gcgctgcctg     720
gccatgacgg ccgtcagctt ccaccaggtg gacttcacct tcgaccggcg cgtgctggcc     780
gccgggctgc tcgagtgccg cgacctgctg caccaggccg tgggtcccca cctgaccgcc     840
aagtcccacg gccgcatcaa ccacgtgttc ggccacctag ccgactgcga cttcctggct     900
gcgctctacg gccccgccga gccctaccgc tccacctgc gcaggatctg cgagggcctg     960
ggccggatgc tggacgaggg cagcctctga accccggcgc gcccaaccg cgcccctcgc    1020
gcctttgggg gctctcctgc tgggcgcggg tggggtttgt gggttttttt ccacctcttt    1080
tctcccaatc ggactccggc caaactcccc tagacagatg ggtgacctgt ctcctttgag    1140
aggatgctga ggcatctgta gcagctgttt caaacaccaa tgtcacctct cctcctggcc    1200
cccgcccaat ggggagagga atttgggcc tactctgggg gaccacctt cacccgtttg      1260
tactttctgg gccacgccga cccctgggtc gcttgatgta aaagccaaaa gctgctgcct    1320
```

```
cccacttgga tcatgtcgcc tgggattttc atccctcgca caaggactac gggttcacac    1380
ggtgaactgg gggaagggaa gtgttagggg gcaagtcgcg gcaccccccc ttccataaac    1440
tcacgtccta acccccagga cctcagaaga tgatctgatt tggaaatagg atcattacag    1500
atggaattag ttcagatgat ctcatcttgg agtagggtgg gccccaattc aaggactggg    1560
gtccttaaaa aaagggggcc tggggcaggg cgcggtggct cacgcctgta atcccagcac    1620
tttgagaggc tgaggcgggc ggatcacgag gtctcgaact cctgggctca agcgacctac    1680
ctacctcggc ctcacaaagt gtgcacattg taatatcgtg atttcatatt tggagaatca    1740
gcaaccaacc agccaaccat gttgctttta taagacagag ctgagaaagc aaagcttggc    1800
tgtcgtcttg gctctggtac cacccacgag atgcgggcga ttctcagctc agggcgtgga    1860
ggcgtggtgt gggggagtct atttgccatt tttgtttgtc agcaggggc agggggttctc    1920
aaagattgca aaatgctgct gcaggtcagg aaggttattt gggtgcctg tggggaggt     1980
gaaacaaggt cccatgactg ttttgcagaa ccttgtctgt ggagggtaga ggttgcggca    2040
ggggcctgtg ggccttactt ggtgagaagg taggtctagc tggctccatt cagtatttga    2100
gacatttg                                                            2108
```

<210> SEQ ID NO 71
<211> LENGTH: 2219
<212> TYPE: DNA
<213> ORGANISM: Homo sapiens
<220> FEATURE:
<221> NAME/KEY: misc_feature
<223> OTHER INFORMATION: Incyte ID No: 4674740CB1

<400> SEQUENCE: 71

```
cccacgcgtc cggaggtgtt gggtttgggg gacgctggca gctgggttct cccggttccc      60
ttgggcaggt gcagggtcgg gttcaaagcc tccggaacgc gttttggcct gatttgagga     120
gggggcggg gagggacctg cggcttgcgg ccccgccccc ttctccggct cgcagccgac      180
cggtaagccc gcctcctccc tcggccggcc ctggggccgt gtccgccggg caactccagc     240
cgaggcctgg gcttctgcct gcaggtgtct gcggcgaggc ccctagggta cagcccgatt     300
tggccccatg gtgggtttcg gggccaaccg gcgggctggc cgcctgccct ctctcgtgct     360
ggtggtgctg ctggtggtga tcgtcgtcct cgccttcaac tactgagca tctcctcccg     420
ccacgtcctg cttcaggagg aggtggccga gctgcagggc caggtccagc gcaccgaagt     480
ggcccgcggg cggctggaaa agcgcaattc ggacctcttg ctgttggtgg acacgcacaa     540
gaaacagatc gaccagaagg aggccgacta cggccgcctc agcagccggc tgcaggccag     600
agagggcctc gggaagagat gcgaggatga caaggttaaa ctacagaaca acatatcgta     660
tcagatggca gacatacatc atttaaagga gcaacttgct gagcttcgtc aggaatttct     720
tcgacaagaa gaccagcttc aggactatag gaagaacaat acttaccttg tgaagaggtt     780
agaatatgaa agttttcagt gtggacagca gatgaaggaa ttgagagcac agcatgaaga     840
aaatattaaa aagttagcag accagttttt agaggaacaa aagcaagaga cccaaaagat     900
tcaatcaaat gatggaaagg aattggatat aaacaatcaa gtagtaccta aaatattcc     960
aaaagtagct gagaatgttg cagataagaa tgaagaaccc tcaagcaatc atattccaca    1020
tgggaaagaa caaatcaaaa gaggtggtga tgcagggatg cctggaatag aagagaatga    1080
cctagcaaaa gttgatgatc ttccccctgc tttaaggaag cctcctattt cagtttctca    1140
acatgaaagt catcaagcaa tctcccatct tccaactgga caacctctct ccccaaatat    1200
```

```
gcctccagat tcacacataa accacaaatgg aaaccccggt acttcaaaac agaatccttc     1260
cagtcctctt cagcgtttaa ttccaggctc aaacttggac agtgaaccca gaattcaaac     1320
agatatacta aagcaggcta ccaaggacag agtcagtgat ttccataaat tgaagcaaag     1380
ccgattcttt gatgaaaatg aatccctgt tgatccgcag catggctcta aactggcgga      1440
ttataatggg gatgatggta acgtaggtga gtatgaggca gacaagcagg ctgagctggc     1500
ttacaatgag gaagaagatg tgtgatggtgg agaggaagac gtccaagatg atgaagaacg    1560
agagcttcaa atggatcctg cagactatgg aaagcaacat ttcaatgatg tcctttaagt    1620
cctaaaggaa tgcttcagaa aacctaaagt gctgtaaaat gaaatcattc tactttgtcc    1680
tttctgactt ttgttgtaaa gacgaattgt atcagttgta aagatacatt gagatagaat    1740
taaggaaaaa ctttaatgaa ggaatgtacc catgtacata tgtgaacttt tcatattgt     1800 attatcaagg tatagacttt tttggttatg atacagttaa gccaaaaaca gctaatcttt    1860
gcatctaaag caaactaatg tatatttcac attttattga ccgacttat ttccacaaat     1920 agataaacag gacaaaatag ttgtacaggt tatatgtggc atagcataac cacagtaaga    1980
acagaacaga tattcagcag aaaactttt tatactctaa ttctgttta cttttgcgaa      2040 caccgagttc tagcctttgt ttcccaggct gggagtgcag gggccaatct gggctccatg    2100
gaaactcggc ctccggggtt caggaatttc tgcgtcaact ccaagtatgg gttaagggac    2160
cacacatgcc cgttttgtgt tattaagtaa agcttccaaa acggccctgg cgggggtaa     2219

<210> SEQ ID NO 72
<211> LENGTH: 1678
<212> TYPE: DNA
<213> ORGANISM: Homo sapiens
<220> FEATURE:
<221> NAME/KEY: misc_feature
<223> OTHER INFORMATION: Incyte ID No: 146907CB1

<400> SEQUENCE: 72
ttcccccggt gccctttttc ccccccccct tttttttttt tttttttttt tttttttttt      60
tttttttttt ttaagacagg gtctcactct gccgcccagg ctggagtgca gtggcacaaa     120
tagggctcac tgcagcgttg aaatcctggg ttcaagtgat cctcctgcat cagccgcctg     180
tgtagctggg accacaggca tgtgtcacca tgcctggcta atttttttgat tgtatttaga   240 gatgggttt cgccatgtta cccaggctgc ctcctaaagt gctgagacta cgggcgtgag     300
ccaccacacc cagcctaacg tcatattctg aggtttagga tgaatgtgaa ttttgggggg    360
tcttgattta acccactaaa ctatcctcca tcacaaatcc tgtccacata ggagagagct    420
gaggtttccc tgagtttgga ggatggggtc tggcccctcc tgcatcatcg ccttgtgtcc    480
tccaccttcc tccctccagc ctagccgcct gggccttctc ttcgctcctc cagctgagag    540
aggcatccat tccagacccc tctcctcttg ggctggaatg ttctccacat cttcagatga    600
tccctctctc agagggttcc ccctcggcct ccctggtctt tcttcattgc attgtcctgc    660
tttgctgcct cggccagtgg tcgctgttgg aacttgtctc cgtgcaagct cgctgcttct    720 ctgccccca caccccagg ccatggctgc cgtgaggttg gggacctggt tgctcttgtt     780
catgcagcag ctccaggatc tggctcagcg cctggtgcca agcagactct caataaacat    840
ttactgaata aacaaaagga atcaatgacc agccctcat gaatgccag cgtctccttc      900 ttgagaaatt tccagcagaa caaggaggtc agctgtggcc aaaactagcgg acccttttgc   960 cttcctttac agctggattt aggatacaaa gcctgaaaaa cactgccatc taatggactc    1020
```

-continued

| | |
|---|---|
| acaggagaag tgttttgttt ctaaattaca accacatatt caaacaatgg gctgaaggac | 1080 |
| caaacacgcc gtccacagga gaaaacgtta aaggagcggt cctggcctgc actccactct | 1140 |
| gcacagagca cgcagatgat ccctagggtc tgtctcagac ggaagccaga tatttagtgt | 1200 |
| tgccagataa aacacaggac gcccagttaa atttgaagtt cagataaaca atgaggaact | 1260 |
| ttttagtata agtatgaccc aaatattgca tggaacgtat ttatgctaaa aagttacgcg | 1320 |
| tttatctgaa cttcaaattt aactggcaac tctacaagga ctgggtgggg agggtcctct | 1380 |
| ttggctgact ggctctcaca agggcatgtt cctgagaggc acagaagata aagctgtcaa | 1440 |
| tttgcaattg agagggattt acaccagcca gagaacggtg gctagcagag cgctgtccga | 1500 |
| ggtgctgaat tcaaagacaa gagcactaaa aagaatgtcc tttggaggtt ccaagaaaat | 1560 |
| tcagacctac gtgcctatca ttaagagcag gggtctccaa cacccagaaa cacatttttc | 1620 |
| cccatggaga aacacaccca cattttta ccccatggag aatttactaa acttttttt | 1678 |

<210> SEQ ID NO 73
<211> LENGTH: 2374
<212> TYPE: DNA
<213> ORGANISM: Homo sapiens
<220> FEATURE:
<221> NAME/KEY: misc_feature
<223> OTHER INFORMATION: Incyte ID No: 1513563CB1

<400> SEQUENCE: 73

| | |
|---|---|
| gtgcagcctt catgctttga tctggaaaga gcagctgcaa gcgggcctgg gtctccaaga | 60 |
| tagtggtcac acaggaggac cgctggaaac ataccaacac gtgcagtctc ccctccaagc | 120 |
| tattcatgct gtttgtggaa tctctctcaa acataagtgt caggtgtgtg tcgtcccaac | 180 |
| gggtcctgtg ctgtgaatag atccatgtgc agcacaaagg gaatgtggca cgtggcccca | 240 |
| ggaagagttc acccggccag ggggcagttg ttcagttgcc tggggctgac actgaccact | 300 |
| ggcctctggg gtgtcctgca gcccaaatgc ccaccttgcc ctcctcacat ctcagtcagg | 360 |
| ggaggccatg cccaagccaa tgtgctgtca cagcctgcag cggggggcagc acttcctcgg | 420 |
| agggcctggg aggtgctggg gatgcccccag cgcttctctt cctgcctcgc cctggcatgg | 480 |
| cccagcgcct ctaggatcaa cttacgatcc gtggagcagc cccgggaaac ccaaatctgg | 540 |
| ctcaggacag cgtacgggca ggagggctgt aaatcatccc aggctaagcc tccgtgggca | 600 |
| ctggctcctg ccgcagcctg gctatggact cagttagaac caggtagaaa gtcagcgaca | 660 |
| ccccacagaa ggccactgcg gctaggtaaa cacctgagaa agaaactgct ccagaagaga | 720 |
| tgacgtgggc ttccaggagc atggaggagg tggcacttga acttttagga aactccttag | 780 |
| atgagataaa gtgggggttg gaggtggcga aaagaggggta accctgggaa agtcagtcag | 840 |
| aacccatggc agaagactgc aggagaggca ggggagggggc ttcggggacc actgtggaca | 900 |
| gagctctgaa agcaccctgg ccaaagcccc tcctgaggtg acagagcgtg ggaggaggct | 960 |
| gcactgggcc tgcgtgccat cctcacccct gttccccgct ggcgccaggc cctgccttct | 1020 |
| tggtacctgt gccaacagga gagccctcac cagccgatct tgtcactctc cgtggtgaca | 1080 |
| gtgtcttggc cagctgtggc ccctagtttc tagcagcgtt tctcagtgtc cttgccctt | 1140 |
| ctgagaaggc aggcgggagg cacacggtgc cctgttcttc cccgtttgtc cagttgcttg | 1200 |
| caaagcagag aatgagtagg agtgaacccg agtgacttca cccgccctgt ccccacgtc | 1260 |
| aggacaggct tgaggcctct ctgggcgtga gcgaggaaac caggctgctc taacttctga | 1320 |
| agagtgggct ctggctcaag actccaatcg gccagaagcc cacagagatc aaagcactag | 1380 |

```
caagttcagc tgtcctggcc ctcgggtaga acccacgggc gtgcctgggt gcggctccac      1440
ccacatgccc cactgtcagc ccaggcagga gccttcctgg ccgggctcag gatctgcctg      1500
cagcccagcc aggccatcac ccagccccga tgcatcctgg cactgcacgc ttactcttca      1560
caagcactta tacgcggatg gcctccgaga ccctgcctcc ctggtctgct gaggtcaggc      1620
caggtctccc acggagccgg gcagctccac accccaccac ctggcaccgt taggtttcag      1680
atctcccgtg tggtgtttga tgtcggcttt tgttcctacc ttgggagttt ggattgtttc      1740
ctctggtgtc tttgtttacc ttcctcactg ttctacctcc tggccaggtc tcagcttagc      1800
ttccctggtg tggggtgttt ttcaagcctt ccagccacag ctgtctcccc tcaggctgga      1860
cggctccggg gtgacagggc ttcaccctct gcctgcagac ccctggtggg cacatctcac      1920
aggcttccgt cttgctgagt tgggtacgga ggcagaagtg gggtgtggag gaaagtcaga      1980
gggaaatctg cttcagaaag gaagggtctt tagacacaaa gactggaggc ccttccccgc      2040
ccgcacggga gctgccatcg tgggtctcat gcacgtcaag accttcccac atccaaactc      2100
agcttccagc agggattttg actttggatg acaaggcttt atttgtaaat atgctcttaa      2160
tatgcaactt tgagaataaa atagaaacat catgtatttt aaaatataag atgaagtgtg      2220
acgcactgta tacaatttaa tatatatttt tagggttttg ttatttaaga aaatggaatg      2280
taatggtact tttacaaaag agaaaaaatg ttatttttac tttctggaaa aaataaatat      2340
tctcattgtt gtagaaagaa aaaaaaaaaa aaaa                                 2374

<210> SEQ ID NO 74
<211> LENGTH: 842
<212> TYPE: DNA
<213> ORGANISM: Homo sapiens
<220> FEATURE:
<221> NAME/KEY: misc_feature
<223> OTHER INFORMATION: Incyte ID No: 3144709CB1

<400> SEQUENCE: 74
gaaataacca ctccgtttct attcttaaac cttaccattt tgttttgtt ttgttttttt        60 gagtcagagt tttgttcttg ttgcctaggc tggagtgcag tggtgcgatc tcggctcact      120
gcaacctcca cctcccgggt tcaagtgatt ctcctgcctc agcctcccaa gtagctggga      180
ttacaggcac ccgccaccac acctggctaa ttttttttgta tttttagtag agatggggtt      240
tcaccatgtt ggccaggctg gtctcgaact cctgacctca ggtgatccgc ccgcctcggc      300
ctcccaaagt gctgggatta caggcgtgag ccaccgcgcc cagccaaacc ttactatttt      360
tttaaagaat ttttttccaga gtttaatttc tgacatagct taagttttcc agtaactcta      420
aactccatct cctttatcgt cattaagtca ttcacaaaaa gccaggagaa gcatttggaa      480
agggcatgat aatcagtata ataatttgcc ttgtgtggtc agcacttaac tgtttacaaa      540
gccctttcac atgcacagca ggtgggaact gcgcggtgtg ggctgggcct gtgctggaag      600
catatcccgt gaaaagtgtt agtgccttag gtgaaagcaa catgtatccc tttagactac      660
taacggtata tgttgttctt atgtatttgt atttatttct attttttcta tgtttatgtc      720
atatttaaac gatatcctac tgcttgttgg tattacccta aactgtttaa ataaagagct      780
ctatttttaa agaaaaaagg tacaaaaaaa aaaaaaaagg gcggccgctc gcgatctaga      840
ac                                                                    842

<210> SEQ ID NO 75
<211> LENGTH: 837
```

```
<212> TYPE: DNA
<213> ORGANISM: Homo sapiens
<220> FEATURE:
<221> NAME/KEY: misc_feature
<223> OTHER INFORMATION: Incyte ID No: 4775686CB1

<400> SEQUENCE: 75
ccaggtgtgg tgtgagtgcc tataatccca gctactcggg aggctgaggc aggagaatcg    60
cttgaacttg ggaggcggag gttgcagtga gcagagatca tgccactgca ctccagcctg   120
ggcgacgagt gatattgtca ctgtctcccc cttgctaacc tcctaggtgc ttaggataaa   180
acgtcaaata tttaacatgg cttcacagac atcttgtatc atttggcccc tggctacctt   240
acctcaccca atttcctcct tgctctgta ctctagctac actgtccgag gagttcctaa    300
aacatcacgc tgggtccgac cacaggatct tcacatgtgc tgctccctct atctgcatcg   360
ctctttcctc ttctcttgtt tgcttaactc ctatttaccc tcgggcttaa tcagcacttt   420
ctcacctctc ctagtctgtt gctcttattt aagatcaaac agcagagaaa tgtgaagtcc   480
actgacttcc gggtggaaca gggttcagta tgccaattaa attattgggt gctggctggg   540
cacggtggct cacacctgta atcccagcac tttgaaggg cggggcgggt agatcacttg    600
aggtcaggag tttgagagga caacatgatg aaactccgtc tctgctgaaa cgcaaaagtt   660
agctgggctt ggtcgtgggc acctgtggtc ccagctgctc gggaggctga ggcgggagaa   720
tcgcttggac gcaggagggg gagggtgcgg tgagccgaga tcgcaccact gtactctagc   780
ctgagcgaca gggtgactcc atctcaaaaa aaaaaacaa aaaaaaaaa aaggggg       837

<210> SEQ ID NO 76
<211> LENGTH: 828
<212> TYPE: DNA
<213> ORGANISM: Homo sapiens
<220> FEATURE:
<221> NAME/KEY: misc_feature
<223> OTHER INFORMATION: Incyte ID No: 5851038CB1

<400> SEQUENCE: 76
gtaaaaaaaa cacgacaggt tgacagttac ctggaaaggt ggggaacagg tggtgaagaa    60
cacatttttt cgatgttcat ggtacttaca taacataaat gaataaaata gggccaacat   120
ggaaaagaaa acaaaatgaa ggaaaatgtc aaattgccat cctgaacacc agcaccgcct   180
gtaattagcg ttcctggctg cagccacatc tgcggtcctg ctcctcatga agccgtcctc   240
cgtgccatgt cccggccatg cctgtcctta gcttcctggt gcacactgtc ctccaccttg   300
tgttcaggca cagggctgct tggctcaccc ttgctgcacc tggcctgtcc gtcctcccac   360
cgcggtgccg cccaggcctt cccactgcag ggctggctaa cggtgcatgg aagagactcg   420
agtccgtgtt gtgtcctcat agcccaccga ggaggcagca gtgccggaca tttcgcggat   480
aggttgtggt ctctgagtct cctcctctca agaggatgag atttgtctgt gttattgtca   540
aaactcttat ttgtcacgcc gcgggttatg tgtcagtaac aaaaagctga gatttaggcc   600
ggtgtttctt actggtgcag ccctttaaatg cacacctgcg aatgttcagt gcaccttccg   660
cttcctggct ctatttcagt caaacctgag gtcgtagtga aagtcggtga ggaattcttt   720
ggaacttcct gattggctgt gtccttgcct ccttgtcttc ccgcagattt gatttgtatc   780
cactgtcacc agcactgctc acttaggact ttctggatcc ggacccag            828

<210> SEQ ID NO 77
<211> LENGTH: 1696
<212> TYPE: DNA
```

```
<213> ORGANISM: Homo sapiens
<220> FEATURE:
<221> NAME/KEY: misc_feature
<223> OTHER INFORMATION: Incyte ID No: 71850066CB1

<400> SEQUENCE: 77
gccaatggtc gctccctgag aggatgccgc tcgtggtgtt ttgcgggctg ccgtacagcg      60
gcaagagccg gcgtgctgaa gagttgcgcg tggcgctggc tgccgagggc cgcgcggtgt     120
acgtggtgga cgacgcagct gtcctgggcg cagaggaccc agcggtgtac ggcgattctg     180
cccgtgagaa ggcattgcgt ggagctctgc gagcctccgt ggaacggcgc ctgagtcgcc     240
acgacgtggt catcctggac tcgcttaact acatcaaagg tttccgttac gagctctact     300
gcctggcacg ggcggcgcgc accccgctct gcctggtcta ctgcgtacgg cccggcggcc     360
cgatcgcggg acctcaggtg gcgggcgcga acgagaaccc tggccggaac gtcagtgtga     420
gttggcggcc acgcgctgag gaggacggga gagcccaggc ggcgggcagc agcgtcctca     480
gggaactgca tactgcggac tctgtagtaa atggaagtgc ccaggccgac gtacccaagg     540
aactggagcg agaagaatcc ggggctgcgg agtctccagc tcttgtgact ccggattcag     600
agaaatctgc aaagcatggg tccggtgcct tttactctcc cgaactcctg gaggccctaa     660
cgctgcgctt tgaggctccc gattctcgga atcgctggga ccggcctttta ttcactttgg     720
tgggcctaga ggaccgttg cccctggcgg ggatccgctc tgccctgttt gagaaccggg     780
ccccaccacc ccatcagtct acgcagtccc agcccctcgc ctccggcagc tttctgcacc     840
agttggacca ggtcacgagt caagtactgg ccggattgat ggaagcgcag aagagcgctg     900
tccccgggga cttgctcacg cttcctggta ccacagagca cttgcggttt acccggccct     960
tgaccatggc agaactgagt cgccttcgtc gccagtttat ttcgtacact aaaatgcatc    1020
ccaacaatga gaacttgccg caactggcca acatgtttct tcagtatttg agccagagcc    1080
tgcactgacc agaggaggta gggggggaagc catggcttct gatctccact ccactttatt    1140
tctctgggaa aaataggctg caggtctcca gagcatatcg atgcagtact gtactagagc    1200
tgttgtgact gattcactca aactttcctg catacccctg tgccaggcct tgggtttaca    1260
gcataagttc agactaaaga gaatggagaa ctattgtggt gcaacctggc aaatccctca    1320
gaggacagag ctaaggtgga cagggattac ctagattgga tcctacttgg gctatcacag    1380
agcattgacc attggcttcc ctcatctgag gcgtgggaga gcagactgga tagatgagaa    1440
ttgtttttaaa acaattgtga acagaaactg aagatggtac agttctacat ctgcacctgc    1500
ccttttttca taccacaaaa gtattttttg agtactgtac tgacttttg ctagtttcta    1560
ttctgggacc gagttcacag ataaatccat tggtttgtat ccttgagaaa ctttgttttt    1620
gtggaagtaa gaaagttatc tactagatta tttcctctaa taaaatcttt taaaatagtc    1680
taaaaaaaaa aaaagg                                                    1696

<210> SEQ ID NO 78
<211> LENGTH: 841
<212> TYPE: DNA
<213> ORGANISM: Homo sapiens
<220> FEATURE:
<221> NAME/KEY: misc_feature
<223> OTHER INFORMATION: Incyte ID No: 2488934CB1

<400> SEQUENCE: 78
ggcgctctca gattgttttg tagagttcaa atgtaaatat tgtttcatt tatggtcctt       60
ttggttataa gtaacagaaa tcaactctaa aaagattttt attataggtt agattatgtc     120
```

```
atggaacctt aaggcttgtc cctttctagt tcttttgtgt aaagcggtga tttcttccat    180
ggagggaatg gtatttaggc aattttttt ttttttcga gatggagtct tgctctgtcg      240
ctcaggctgg agtgcagtgg caccatttca gctcactgca acttccacct cctgggttca    300
agtgattctc ctgcttcagc ctcccaagtg gctgggattg caggcacccg ccaccacacc    360
cggcttattt tgtatttta gtagagatgg ggtttcaccg tgttggccgg ctggtcttg      420 aactcctgac ctcaagtgat ctccccacct tggccttcca aagtgctagg attacaggcg    480
cctagcctag gcagtcattt tcaaaaaaca agcatgactc accaaaagtt ttaagatttt    540
ctgtgataat gttcttattg aggcttacat tatattacag tttcttgaat ctaaaatgat    600
gtaccctctt agaatatata catcatgctt cattggtctc aggggctga ttttatcag     660 gcgagatttg ctagttttca caatatgtcc tctaagttgg catgtatagc taaacaggct    720
ttcataaaaa tatacaattt agttaatgaa atttgggata tagtcttta tgattgacat    780 aattttgcta aatagactgt ctctgattta ttaggtatca ccactcttat tttgttttac    840
t                                                                    841
```

<210> SEQ ID NO 79  
<211> LENGTH: 2752  
<212> TYPE: DNA  
<213> ORGANISM: Homo sapiens  
<220> FEATURE:  
<221> NAME/KEY: misc_feature  
<223> OTHER INFORMATION: Incyte ID No: 2667946CB1

<400> SEQUENCE: 79

```
gggacattgc tccggggaga aagggcccca agattaaaaa accatctaga gttagctttc    60
ggaaatcatg ttaaacataa agagatatga cttaaaaatg ttgtcatctg aactgtcaat    120
ttccataaat agcttaaata tagtgaaaaa ttgagaggtt cttgaagcca ctaagtctaa    180 taaaaaatg caattccatg gggttttcgg ttttctgctt tttccttagg gtcctcaaag     240
atgaggaagg ctttgtcttt gtgagaaagc tcattctagt cacttcaaaa catactggaa    300
aaatagcata tgagctaatt tggttttctgt gacatgatga ttctattccc ctattacctg   360
tcacatgaga gccagttagg actaagaaaa caccagggtg gttaaatggt aaattttatg    420
ttatgcatat ttggccactg tatatattta aaaattgagg ctctacagga gctcttgttt    480
atgtgggcta tgcctatcaa tgtttacctt agtagtcagt aaaactggga tttttttttc    540
aaaggaacac cattatgaat agatgatgct aacattggtg tatccaccac tcagcttcag    600
aaatcaaact ttactgatat ccttgaatcc ccatatgtgt ccttccctga atgcattcct    660
ttgtccccca gaagtacaga ctatccagga ttcagtgttt atcattccca tgtctttctt    720
tatgggtttt ctaaatttag aatatcccca gagacagttt aaaattttta agccaatgca    780
gccataacac agtatgtgta ttattttgga acttttattg acttggttca tccaccctc     840 caggtgccat tggtcaccca accccctcca aagcagaggg gcagttctct ctagtacttt    900
attagctgcc ttgatgtctt gtttccagtc ccttcagaaa ttatggtgga gatacacaca    960
tacacattaa tggaataaac actcttccct cctctccctt ggggctcctt ccccaaaga    1020 ggtccattgt ccacaagtac tcatttgtgg gactcaatat gttcccagcc acaacaagag   1080
cattacatta gaataggagc taacatgtgg gaatcagcat atgttagaa ttacatctta    1140 cacactgaaa aatgcactgg aagagcagcc attattgaca gagacggtcc tggctaatag   1200
atctgcctag ttttaggctg cttaggggaa caggggtcct ggaataagaa gccccacccc    1260
```

```
ctcctatgaa gagaggaaag ctggagacaa aaagaggaag caagagatga attgcaaaaa    1320
actaatcaga ttgcaacctc aaggtaacat tttgcataat aagttctaac aatgttttct    1380
tgtttatatc agcctcctcc tcttagcctg gcttactagg ctggtgttta attccaatgc    1440
ttctggttta atttattcaa ctttattatc cttactatag tagcctcccc tagcgttctc    1500
ccctacctct caaaggtctc atctaagtgt gtataaagct gttaaataga ggagaggaat    1560
caggatgaac tgcacagcat tttcttaagg cctgtgggtt ctggagccta tgcttcagca    1620
actgaagctg aactgtgtgg ttgttgctaa cattggtgta tccaccacta agcctcagaa    1680
ataaaacttt actgatatct ttgaatccca tgtgtgtcct tccctgaatg cattgctttg    1740
tcacccagag gtaacagcta tccagcattc agtgcttatc atccccatgt ctttctttat    1800
tggttttcta aatttggaat atccctggag acaactttgg caactgaagc taaactgtga    1860
tggttgttga cctctgatgt gctactttt aatcaagaac ttattttccc tctttctctc    1920
tcagctccca caggcccatt ctggtgactc atgacttgta tacacagaac aacagagaaa    1980
agaaaaatag aattagataa acaagcaggg gcaacagtga gggctatgtc ttacaaagaa    2040
ccatttttaa ttgaattcat tttctctctt gaaattcttt ttttttttccc tcaaaagtgg    2100 gaaaaaattc tcaaataaca acagcaaacc aagaaagcag cttagtctgc actgcatttg    2160
catttcttag tttcattccc tattcaaaaa tgtcttaggc aaatgtgtgg gaatgaacat    2220
gcactttaaa attatgggac ctagtagatt taatggagtg agccctggat tgggagccag    2280
gggacctggc tttgaatggt cccaacccag gcacttattt accttagttt cttcacttat    2340
aaaattaaac acaccatcta ctgatgaatg gataaacaaa atgtgatata tccacagaag    2400
ggaatcttgt tcagctgtga gaaggaatga agtatggaca tgtgctataa tgtggatgtg    2460
cgttaaagac attatgctaa gtgaaagaag ccagacacaa agaccataca tttcacgatt    2520
ccacttacat gaaatgtaca gaatagctaa atctaaggac ataaagtagg ttagctaatg    2580
ggtacaggtt tcattctggg ttgatgaaat gttccaaaat tgattgtgct gatggttgta    2640
tttaaaactc tgcatatact gaaaaccatt taattgtaca ttttaaatga gtgaattgta    2700
tgctatgtga attatatctc aataaagttt gttccaacaa aaaaaaaaa gg             2752

<210> SEQ ID NO 80
<211> LENGTH: 934
<212> TYPE: DNA
<213> ORGANISM: Homo sapiens
<220> FEATURE:
<221> NAME/KEY: misc_feature
<223> OTHER INFORMATION: Incyte ID No: 2834555CB1

<400> SEQUENCE: 80
ctcatattgc ctggttttaa gatgtggcct gggatcacca tattgatctt cccatgccag      60
ctgctcccat gatggttgtg tgtttattta gacctgtgat gatgtctcag acagtacatg     120
gttccctgaa ctgctttgca acttcagtga tgttgtatgg cattgagctg gtccatcact     180
gccaacatcc tggctgtctc aggttaccct gtagaaggaa tcggatggtc agtggtgtgc     240
atcagtaatg taaacaagaa cagtgttctt gtacagaggg ccagcagcat gagcagtgat     300
aagacaggta gggcctattt tcccatctac caactccagg actggccatt cctgggtcag     360
ttgaccagac acctggaaag aagagctctc aactccaaga ttattttctt agtaatagct     420
ttaaatgcag ccacagcttg gtcgtctgcc ttaaatgat ttgatatgtt ttgcaattta      480
ctgtcctgct gaaagcattc atattatgag ggaaaaaacc atacaaatca tcgctaaatc     540
```

```
tgttatttttt aaatgtttgg cctttttcta tacccttttgg attcaagcat taattgggtt    600
tccaaagtaa ttgaatagaa atcatattgc ttataaaaaa gaaaaaaact tttgagtcac    660
aggatgtaag ataaacatac aaaaatgaat tttatttcat aatagcaatc tatactagca    720
atgaacaagt gggcaatgaa attaaaaatg tggtatcatt tacagtcact taaaaaaaga    780
tgctaggtca ggcgtggtgg ttcacgcatg tattcccagc attttgggag gcttaggcag    840
gaggattact ttagcctggg agttcgagac cagcctcggc aacaaagtga daccccgtct    900
ctacaagaaa taaaaaacta ggcaagtgtg gtgg                                934
```

<210> SEQ ID NO 81
<211> LENGTH: 815
<212> TYPE: DNA
<213> ORGANISM: Homo sapiens
<220> FEATURE:
<221> NAME/KEY: misc_feature
<223> OTHER INFORMATION: Incyte ID No: 5544174CB1

<400> SEQUENCE: 81

```
cgggcaagca gcgcgggatc ccaggttcag gcctgcacgg acggtgtgcc agtgagtctc     60
ttcaaaaaag gagaggtttg cttgtgtgcc cgtgggctgc tctctcacta gtgggttgta    120
gtcgtggaga gcagaaccct gaaaattcag gggctgcctg ggtgtaggtg ttaccgtgcc    180
actgctgtat gtctgtgcgt ttgtgtgtgt gcgtatgtct ctctcttgtt tctctctctc    240
ccttttctca ctcttttgct ctgtgtccct gtgtgcgtgt gtgtgtgtgt gtgttgggac    300
atatgtgccc tgtgcgccag aggacggtat cttctacgtc cgcctttctt gtggtcagcc    360 tctcccgcg tctctgcctg gcttgcgtgg cccgttgtca gtcattttc tggcggttcc      420 agtttaggtt tgtgaaggtc cagatgagat ggggagctgc gtctctctca taagaattta    480
aatcacctcc ccaccctgag aggcctcttt tccaggataa aggcctccac ccccaagcca    540
aggataatag cctcaccgga gaggtcattg tctacctgca ggagcagtgc agagcgacct    600
gaaagaaggt ggttctcatt cgtctctctc tttcatctcc ttgagaaatc tagccacagg    660
gtaacacagg tttcgagagg atgggaacgg gacgtggcaa ggatctgtga gtgtgcaggc    720
tgtgtttcac atatcattaa acatagtcta gtgagggttc tgcagataac tggcatttaa    780
gtttgtttca ttgaatcaag gaaaaagaca aatac                               815
```

<210> SEQ ID NO 82
<211> LENGTH: 1242
<212> TYPE: DNA
<213> ORGANISM: Homo sapiens
<220> FEATURE:
<221> NAME/KEY: misc_feature
<223> OTHER INFORMATION: Incyte ID No: 1728049CB1

<400> SEQUENCE: 82

```
tgcatgtgtg tccacgtgtg cacccgtgtt cgtgtgtgat gcgtgtgtgt gcacacacat     60
ctctgtgtgt attcctagca ctcatagctg ccctggatcc atatccagct ctcgtgccac    120
ttcctgtgtg acctttgagca gccagcagcc ccgtgggtta gccccctggg gagacatggc   180
caggttgggc aggacgtggg tgtagggctt gtgatgccaa ccctgtgcca gtcgggaggc    240
ccagggcatg gggatggccg ggctacccag cgagctgttg gctgtgctgg gacagacccc    300
aggctcccag tggccctgct ctgaagcgtg gctctgtctc cccacctggg ggcagccagg    360
tccccctccc caccccgccg caggagactg gccgtccctg ccagcctcga cgtttgtgac    420
```

| | |
|---|---|
| aactggcttc ggccggagcc ccctggccag gaagcccgag tgcagagctg gaaggaggag | 480 |
| gagaagaaac ctcaccttca gggcaaacca ggtcagcccc agagacaccg ctgctgtttg | 540 |
| gggtgtacgt gaagggagcc ttcctctgag gaggcaatgc ctgctggggc tttggaggat | 600 |
| gcattcacag gacctagaat ggagggaaag cctggaggaa ggacccagcc ccgtgcccca | 660 |
| ggcccgccct catgaataga gaccctagct gtttcagagt accttgttac agactcatgg | 720 |
| tgatgatgga atgtctgctt ctggcagctt gagggactgg ggtggctggg gtgttgctga | 780 |
| cctggaggag ggcagggtgc agggtggggc tgggcctgga ggccactcag gtgtctgtgg | 840 |
| ggctgggtca gggcagtcca gtgggcgtgt ggggcattag ggaggcaggg ctggggccag | 900 |
| ctgtgctgtg ctgaggtcag gctccttcca agctgtgtcc tggtcacgtt gggcctggtg | 960 |
| gcccaggtcc cagaggctca ccctgctcct tctccaggga gacccttgtc cccgccaat | 1020 |
| gtccctgctc tgcctggcga gacggtgacc tccccagtca gggtgagtag tggtggggag | 1080 |
| ccgggcaggg gcccagccct ccggcatcct caccgcccct ccgttcccag ctgcaccccg | 1140 |
| actacctctc cccggaggag atacagaggc agctgcagga catcgagagg cggctggacg | 1200 |
| ccctggagct ccgcggcgtg gagctggaga acgactgcg ac | 1242 |

<210> SEQ ID NO 83
<211> LENGTH: 4217
<212> TYPE: DNA
<213> ORGANISM: Homo sapiens
<220> FEATURE:
<221> NAME/KEY: misc_feature
<223> OTHER INFORMATION: Incyte ID No: 2425121CB1

<400> SEQUENCE: 83

| | |
|---|---|
| gccggtggcc ctgctgcacg gaggtcgtcg ggctggtgcg tggaccggcg ctgcgccgag | 60 |
| tctgagggag gggcgcccgt cttaacgggc gcagctgttg gctgtgtcca agttaccggc | 120 |
| tctagcagtt atagaggcaa tccttgtggg attgacaggt gcatttgggg gcgcccccc | 180 |
| tccatgtcgg agttcgcccc ggcttggctt ctctcccggt gtccatcgtg ttctttggaa | 240 |
| ggccatggat ttttctccgt gcgtctctgt cttcttcagt tgtcgactta tcgaatttct | 300 |
| cgatctcagc catatcgggt ttgtcaaaca tggtttcgga ggaaaatcca agcgaggcgc | 360 |
| acgagtacga gcgaagtctg gtctgcgcca gtggccacca ctgtcctcca gcctgcattt | 420 |
| tggggaggct gtgaatgggc acgtttgcca accccccccc cccagtagag cccaggaccc | 480 |
| tcctctctca gcttgccagt gccctgccct ccacatggcg gggaacagca tcaatgaggt | 540 |
| ccttgctccc tgagagcctc tctggaacct gcccactttt ctcaacatgt atattctgct | 600 |
| ttgtagtctg aggttgattt tctagaggcg aggaagggc tgagttctgc cctcgtgctg | 660 |
| ttcgctggtg ctgatcaggg ccaagacgac ccttccctct cccccacagc ctgttgaggt | 720 |
| gccgttgacg tggacagcgc ccctccctta agatgccccc ttgccgttgc catgagccgc | 780 |
| tgtgactcac gcgtgcactg ggccttgctt ggtgctcccc cctcctcct gtctgagatc | 840 |
| ggagcttgct ggagagcacc ccaggtcgcc gtgcttggct gcaggccgt ccctctctcc | 900 |
| ccatcctcgg gttcccagcg tgttttgtgc ttgaacttgg tggactcatc ttaccccaca | 960 |
| agagtggcct gctcaacctg cagcctccaa tgtgccgtag gcgctccagg tccccgtggc | 1020 |
| gcccaggaca ccaactctcc ctccctgcac ttaggatgtt ctggaaatga ggggaaatcc | 1080 |
| acattcctgc cccaggaggt gggaagcctg gcaacgatgt agcttcccct gagatgcggt | 1140 |
| atgatcaggc ctcagcaact actcaggagg caaaggtgtt tggaaagcaa accccaaacc | 1200 |

```
tcccggcacg gcatgtgctc tgcttccgtc cctcaccgcc tgcacaaggt cgttgagact    1260
tttctagaac tccccggggt tgtatttatg gccttcaagc aaacaaattg aaaagcagtc    1320
aaggaggagt tcagatagaa aagtgctgga gatacacatc tttccttcaa aggaaatgta    1380
atttatttcc aaccgctgcc tcagacgggg gtttcacatg ttgtgaagtc acatcttgaa    1440
tgactgtcac cctcatcctt ccccaaaaag ctaaataagg gcctttggca tcaatgcgtg    1500
cattctccac ctttccgcgg cttgcgcttg gatttctgag tggctttctt cagggagccc    1560
ttgtggtcat gtgtctttaa tgctgctccc catgccccca ggccaggcca gcacgctcag    1620
gtgatagcga gtgggggccag gagaccccccc tgccctgccc agtggacaga tctgccccag    1680
ccctgctgtg gggacgggcc ctctatcatt taaccacata cattaggttg cttttcagca    1740
aaatgtcagc tttcctccca ttatgcagga gagagaaggg gcgcaggtgt atctccttag    1800
agtacacctt ggagctggat cactaagaaa cagtcctcag actggtcctt ccgacacagg    1860
cagagagtga actggatcgc tggccccctgg gatgctgcgc tgtctgtgat tagagagaag    1920
tggccagtgt cccgtctgtg attagacaga aaccccctgtg gcagactcct ccctctccca    1980
tgaagaaaga aatatttact tagatattac tgtttcaaaa cacaaacttt attcccctta    2040
gagaagaaat actgccctta aatagactgt tgaaatatta atggccccccc catttaatca    2100
gtgtgtctgc ggcttttcttc gcgtcacatg tccgcattgg caggtgattc tggaaaggga    2160
ttctgggaaa ccaacaagtc tttttttaaat ctttgagttg tatgagaaag tatttaagtt    2220
caccagtgta gtaaacaccc accccagagc agcggtaagc aaacctaaat ctgaaaaccc    2280
attcttactg tcttttcacca tgagatgctg gttttggtgt aaaatgacag cacttggttt    2340
ggggttttgc acctgttggg tagaactgtt cttgtctgag gtcctcaccc tctacagatg    2400
ggcctcaggg cctggaggtg ggcagatggg gccagagtgg ccagcagaga cttgcatggg    2460
ctctgaaagc cccagagctc aggcctaagg ctgctaggtg agaccagcag gcagctgtgg    2520
catccgacct tgggacgccc aagctgggca gccgctccat gtgccccaaa caggatatcc    2580
tcatgaatgt gaggagaggc tggctcaggg cttggttttc attttggcct ggcacagggt    2640
acctgtaggg agcactcccc caacctgagg atggtgaaac catatgatag agactccttg    2700
tcgaagtcca catcggactg atctagaatg ccccgtgggg ggattgcatg gcctttgcct    2760
tgagatgcag gtgaaagaaa ggaaccaaac aaggcatgag tgtgttgggg aatcttccca    2820
gtggagcaaa cccccttaac acaccagctg ttgggaacag ctgcccctaa atccaattaa    2880
accctcatct ccctggtgct gaacagtcta cactggccca ggaagctaac gtctgagccg    2940
cttggagagc tttggtaaac agaagacact ggaagcccac tcggtcagca gctgggcatg    3000
aggatgtcag gggcctttgg acttgaggaa ggacagtcca ggtgcatgga atcctaatgg    3060
gcctcatgca gacactggaa gcagcccagc ccctgcccca ataccacagc cctggggtgt    3120
cccctgacat tcctggaggt ccctgggcaa atgcatttcc tgcctgggtt ctcagggtag    3180
gagaacagag aaggctccaa gggtgttggg agtgagccag ggctggtct ggggagtggg    3240
tctcacgcac tgctcaggtt ggcacgaggg acctcccca tcccaaccca gccccaaggg    3300
tcccagcagg gctctcagca tggctgtttt gagggtacac aggtggctgg agaggggtgg    3360
ggcagttgca tggtgggtgg caaagtgtgc atttagaagc tgcttcgtgg cgttaagaac    3420
gggggggagag ggaccagcac tgtaacgtta gaaataattc cttcttgcag acttgaaaag    3480
catcagtttc cctcccacgg ctgggttttt gtgtctgaaa tacatctaat tctccagact    3540
gcagcccctc tcagccccga gcacctgagc gctggggagg cccttattga gctcagcctg    3600
```

-continued

```
gagagggagg ggtcgcacgg gtcccggggg caggtctcct gcactggctc ttcccttctg        3660
ccagcttgga atttggttct catcttgcca caggggtgcg tttcctaaag ggcagccgga        3720
gcagctcaaa ggtgacaact gagatgcatt tctaggcagg ggcagggaag gccaacccac        3780
cttgcagcca gttttctgtt tctgtaaata gcagtgtata gagatggaag ggcagcgtgg        3840
gtgtatccac agatgggttt aggttttttt tttggatgtt ttctattacc tcattcagca        3900
actttatgtt tcacaatgac tcaatgatgc tttatttata ttgtttgtac tgtaattaaa        3960
accattgaca gacatttcac tttgcttgtt atttcatatg atcttgtttt gattaaatat        4020
gccagtttgt attttcctgc cttgggattt ttttgtgtcc gctgtacagt attctaaggg        4080
aaaaagaaaa agaaagatgt gtaaagtaac agagagaggt ggctatggtg tagagacctc        4140
tttctaataa agaaatgaaa atatgtctac aaaaaaaaaa aaaaaaaaaa aaaaaaaaa         4200 agaaaaaaaa aaaaaaa                                                      4217

<210> SEQ ID NO 84
<211> LENGTH: 1301
<212> TYPE: DNA
<213> ORGANISM: Homo sapiens
<220> FEATURE:
<221> NAME/KEY: misc_feature
<223> OTHER INFORMATION: Incyte ID No: 2817925CB1

<400> SEQUENCE: 84
gtgggccaca ctgttaagcc ggtcaggttc acaacgtccg tgaagatggg ccacccacat          60
acgcggatca ccatgggact cagacacact gggaagcgga gtgctcagaa ggcagaatgc         120
ggaggtaatt gcacggggaa agccgtacag ggccggtctc acaagtgccg agattcgggt         180
ccacagttta gagagcccct gctgcacttc taatacagtc ccggaaagac ggggccagaa         240
cttaggaggg gagcgctttg cagcaacttt tcaagaaaag gggaaaattt aagcaccata         300
ctgttatgtg gtccttgtac ccagaggccc tgttcagctc cagtgatcag ctctcttagg         360
gcacaccctc caaggtgcct aaatgccatc ccaggattgg ttccagtgtc tattatctgt         420
ttgactccaa atggccaaac acctgacttc ctctctggta gcctggcttt tatcttctag         480
gacatccagg gcccctctct ttgccttccc ctctttcttc cttctactgc ttcagcagac         540
atcatgtgac cttgaggatg gatgtcacat gctggaggaa acagaaggcc gaaaccctga         600
tgacttcaca gagctgccaa aacagttcct gactgtttat tccgggtctt taacaaagtg         660
atgaaaagaa atccttgcag tatgaaaaca acttttctat tccatggagc caaacctcat         720
tataacagat aacgtgaccc tcagcgatat cccaagtatt ttcctgttct catctatact         780
atggcaaagg ggcaaatacc tctcagtaaa gaaagaaata acaacttcta tcttgggcga         840
ggcatttctt ctgttagaac tttgtacacg gaataaaata gatctgtttg tgcttatctt         900
tctccttaga attattgaat ttgaagtctt tcccagggtg ggggtggagt gaagctgggg         960
tttcataagc acatagatag tagtgtctct tagcttccgt ttaaatatgg gggtagcgat        1020
gtggagggcc cagaagtatc agagaggaga gacaggctgc tctgattgcc tttgtaaaat        1080
gcacatttga gcttgtgcaa agccctgggc ctgagctcag aaaaagcaag gccaggaatg        1140
aggctcttgg ttcagttccc ctgcacaccc tgggcgggga ggggttgtta gagtcatgga        1200
acccctattt tttttttttt tttttttttt gaccgggtct tgcttggtca cccagccaga        1260
gtgcagaggt atgtgcacag ctcactgcag cctcaacttc c                           1301
```

```
<210> SEQ ID NO 85
<211> LENGTH: 2148
<212> TYPE: DNA
<213> ORGANISM: Homo sapiens
<220> FEATURE:
<221> NAME/KEY: misc_feature
<223> OTHER INFORMATION: Incyte ID No: 4000264CB1

<400> SEQUENCE: 85
cagccatgag caggacctgg ccaaccagcg ccggcaggga aggcaggtct cccaggttcg      60
ccttgaggaa gccgagggtc atctcccgga attccttgat ggaggtgccc cgggtgggct     120
tgtcaaacag taccagctcc cgccgggggg ccgcatccga ccgggccttg gagtcgaggg     180
tctcctcaat gccacacttg atggttacat ccttgtcccg ccagagcccg ctgtacacct     240
gctggcccgg ggccaccgag aggcaggtcc tccactccac catatgcagc tcacacaggt     300
cctggcagac ggagcccgag atgatcccct tgcggtactg gtcacactga ggagacaggt     360
gcaggcgtgc cgggcgggc agccacaccc ctgccccact gagcccctgc cacaggccc      420 gaagctggca ggggcctcca cttgctgcag ttggaaagct gccagcccct cacacaggca     480
gtgccggggc cctgggtcat gccattggtg gctgcaggat ggggctgtcg gctgcagggg     540
cagccccgcc aaccctccgg tccggtcccg tccccaccat cctggctcct gtaacaggac     600
ggcacagcaa aggccactgc ctggacatga gacacacacc acacccagtg tcgacccac      660 gccagggcca gaggcaggaa cctggaggca gctctccgcc cagccgaccc agctctggac     720
catccaggca ttggccggtg aactagaatt cacactagtc cctaatatct acaccaccag     780
ctgccacacg cgcgctctct gcctgactct tcattcctgc ctcgggtgac gccaggaggg     840
aggatgcacc ccctgactca tggcgccctc cctgcccgga atagtaagtg agacatttct     900
gaacttgttt cctatgatgg tgctgactgg actgcgtctt ccatctgaag gccaggagc      960 tgccccaccc aggcagggct ttccctggga cgccaggaag aacaaaaggg tgggctcttg    1020
gtgccagagc gatggatggt caggctggca gaacctggac aggagtcaga cacgagccat    1080
agggcctctg tcagagaagc aaccccctgg acacagggca aacagctggg tgtcatcccg    1140
tgaagggcac cgcgtccagc ccctctgctc ccgtcaggg cggctgcca gccattctgc      1200 actgggcact catgggggct ctcacgacag atcctgatgc ccagagccac acctgcatgg    1260
cagcttctgg ctgggtttcc actaatctca ggtgtgggtc tcctcctgtc caaggactt     1320 ggcctccctc ttcggcccgg cccagccttc cccaggctga ggcaggagga caggccgcgg    1380
cctcactgtt tgcctcaagt gcagccagga cagggctcac caccagagct gacagtctca    1440
agggtacccc tggggtggag ccggcaacgg agcccagcc tctacctcct ctcccagccc     1500
tccgaggcca gtgcccaggc tcaagcgctc cgttgtcaga gctgtttgtc aaggctgaga    1560
aaacggaccc ctggggcccc acaatgactc cgggcctgtc cttcccggtc ccacaggccc    1620
cctccttagc cagacccca gggagacttt gttagcagta attacatcag gcctggggct     1680
ggctgccgcc cctcctcagc ccccacccta gctccaggag cctggcagcc cctcaatccc    1740
agcgccccac gggaggtgat ggagggatgg agctggcccg cccctctggc gggggagaa     1800 ttcctggatg tacagcctca gttgccatgg agcctggcca agcaggcttg gagggagctg    1860
gggaagggag ctgcggaaca ccccgccctc cagggtaggg ggaggaggga gggtccccgc    1920
cccccacaca ccaaggatgg ggacagaagt gagatgggcc aagctggagg ccgaggaccc    1980
cgccaccgtg agtcatgaag gcagcgtctt gtcccgcgca gcaagaaaac gccggctctt    2040
cgtcaagaca gagacaggca aatgacggaa aactgcacac ttgtccaacc ctccaccttg    2100
```

```
caggcaggc ctttgccacc gagtcactcc cgtcccagac cagcagta              2148

<210> SEQ ID NO 86
<211> LENGTH: 1141
<212> TYPE: DNA
<213> ORGANISM: Homo sapiens
<220> FEATURE:
<221> NAME/KEY: misc_feature
<223> OTHER INFORMATION: Incyte ID No: 4304004CB1
<220> FEATURE:
<221> NAME/KEY: unsure
<222> LOCATION: 916, 942
<223> OTHER INFORMATION: a, t, c, g, or other

<400> SEQUENCE: 86
cctggagctg cccgaggacg cggaggagag acccgagggt cgccgctggt agggtcgctc     60
agccctggcg tcctccacca ccacaccttc acctgcgccc ggctccctgc gcgcctggac    120
agcgcctgct gcccgcctcc cgatggccct gccccagatg tgtgacggga gccacttggc    180
ctccaccctc cgctattgca tgacagtcag cggcacagtg gttctggtgg ccggacgct    240
ctgcttcgct tggtggagcg aaggggatgc aaccgcccag cctggccagc tggccccacc    300
cacggagtat ccggtgcctg agggcccag ccccctgctc aggtccgtca gcttcgtctg    360
ctgcggtgca ggtggcctgc tgctgctcat tggcctgctg tggtccgtca aggccagcat    420
cccagggcca cctcgatggg acccctatca cctctccaga gacctgtact acctcactgt    480
ggagtcctca gagaaggaga gctgcaggac ccccaaagtg gttgacatcc ccacttacga    540
ggaagccgtg agcttcccag tggccgaggg ccccccaaca ccacctgcat accctacgga    600
ggaagccctg gagccaagtg gatcgaggga tgccctgctc agcacccagc ccgcctggcc    660
tccacccagc tatgagagca tcagccttgc tcttgatgcc gtttctgcag agacgacacc    720
gagtgccaca cgctcctgct caggcctggt tcagactgca cggggaggaa gttaaaggct    780
cctagcaggt cctgaatcca gagacaaaaa tgctgtgcct tctccagagt cttatgcagt    840
gcctgggaca cagtaggcac tcagcaaacg ttcgttgttg aaggctgtcc tatttatcta    900
ttgctgtata acaaancagc ccagaattta gtgggttaaa antaaatcca ttttattatg    960
tttcaaaaaa aaaaaaaaa agggggggcgc cgaatattga gctcgtggac cgcggattta   1020
attccggacg ggaccttgag gggggggtga agagatcgaa tataagattt cagaacggcg   1080
acctcggggg ggcgcgggaa caattcgcct ataggggcga ataaggcgcc aagggggagt   1140
a                                                                  1141

<210> SEQ ID NO 87
<211> LENGTH: 855
<212> TYPE: DNA
<213> ORGANISM: Homo sapiens
<220> FEATURE:
<221> NAME/KEY: misc_feature
<223> OTHER INFORMATION: Incyte ID No: 4945912CB1

<400> SEQUENCE: 87
caaacttctg ggctcaagcc atccacctgc ctcaacctcc caaagtgctg ggattccagg     60
tgtgtgccac tacacccagc ctagggccca gcttcaaaag gaggtgctcc ctcagtttgg    120
ggccagctag gcccgctggg acagcaggac ccagaaccca ggtctgccgt tgtcctcaag    180
ccctggactc cagccccctg accacagcca gtttctggcc aggctgctca tgaaaggcca    240
tgggcctggc tggaacctgc tgccttagag ccaggcctct tccgggggc aggggcgttt    300
```

```
gcccgttgcc aggtgcccgg gttccggccc tggcactagc gacggccatg ctgcatgtgc    360
tggcctcgct gcctttgctg ctcctgctgg tgacgtctgc ctccacccac gcctggtcga    420
gacccctctg gtaccaggtg gggctggact tgcagccctg ggggtgtcag ccaaagagtg    480
tggagggctg taggggtggc ctgagctgtc ctggctactg gctgggccct ggagcaagcc    540
gcatctaccc cgtggctgcg gtcatgatca ccaccacgat gctgatgatc tgccgcaaga    600
tactgcaggg gcggcggcgc tcacaggcca ccaagggtga gcatccgcag gtgaccactg    660
agccctgcgg accctggaaa cggcgggccc caatctcaga ccacaccctg ctccgtgggg    720
tcctgcacat gctggatgcc ctcctggtcc acatcgaagg ccacctacgt catctagcca    780
cccagcggca aatccaaata aaggggactt ccacccagag tgggtgaccg aaaaaaaaaa    840
aaaaaaaaaa aattg                                                     855

<210> SEQ ID NO 88
<211> LENGTH: 617
<212> TYPE: DNA
<213> ORGANISM: Homo sapiens
<220> FEATURE:
<221> NAME/KEY: misc_feature
<223> OTHER INFORMATION: Incyte ID No: 7230481CB1

<400> SEQUENCE: 88
gggtgaggtt gtcaagcggt ccctggtgga gtcctacact cacccaaaca gcagcgagac     60
agagcagagg gagaacatca ataccgtcat gaactggttc accaaggaag actttgactt    120
tgtgacactg agctacagag agccagataa cgtgggacat tgattcgggc cagaggcaga    180
gaacagcaag ttgatgattc agcaaatcga caggaccatc tggtatctgg tgggagccac    240
tgagaagcac agcctgcaga gcacctcagc atcatcatca catgagaccg tgggatgacc    300
accgtgaaga agagacccaa tgtcaacaag atcccttgtc caactacatg aagttcaggg    360
acttggtcaa gtttgatatt gtgggctaca gtggctttgg gatgcccctg cccaaattgg    420
ggcaagagga aaccctttac caggcactga agaatgcata ccctcgcctc cacacctaca    480
agaaggagga gcttccagaa cacctccatc ttgctaaaca tgaccgggtt ctgccaattg    540
tgatgtatgc caactctggt tacagtatca ataggtaag ttcattctaa aatgaataaa     600
gtcaccttag atctagg                                                  617

<210> SEQ ID NO 89
<211> LENGTH: 2460
<212> TYPE: DNA
<213> ORGANISM: Homo sapiens
<220> FEATURE:
<221> NAME/KEY: misc_feature
<223> OTHER INFORMATION: Incyte ID No: 71947526CB1

<400> SEQUENCE: 89
gaattaggtg ctgctgggag ctcctgcctc ccacaggatt ccagctgcag ggagcctcag     60
ggactctggg ccgcacggag ttgggggcat tccccagaga gcgtcgccat ggtctgcagg    120
gagcagttat caaagaatca ggtcaagtgg gtgtttgccg gcattacctg tgtgtctgtg    180
gtggtcattg ccgcaatagt ccttgccatc accctgcggc ggccaggctg tgagctggag    240
gcctgcagcc ctgatgccga catgctggac tacctgctga gcctgggcca gatcagccgg    300
cgagatgcct tggaggtcac ctggtaccac gcagccaaca gcaagaaagc catgacagct    360
gccctgaaca gcaacatcac agtcctggag gctgacgtca atgtagaagg gctcggcaca    420
gccaatgaga caggagttcc catcatggca cacccccccca ctatctacag tgacaacaca    480
```

```
ctggagcagt ggctggacgc tgtgctgggc tcttcccaaa agggcatcaa actggacttc      540
aagaacatca aggcagtggg ccccteectg gacctectge ggcagctgac agaggaaggc      600
aaagtccggc ggcccatatg gatcaacgct gacatcttaa agggccccaa catgctcatc      660
tcaactgagg tcaatgccac acagttcctg gccctggtcc aggagaagta tcccaaggct      720
accctatctc caggctggac caccttctac atgtccacgt ccccaaacag gacgtacacc      780
caagccatgg tggagaagat gcacgagctg gtgggaggag tgccccagag ggtcaccttc      840
cctgtacggt cttccatggt gcgggctgcc tggccccact tcagctggct gctgagccaa      900
tctgagaggt acagcctgac gctgtggcag gctgcctcgg accccatgtc ggtggaagat      960
ctgctctacg tccgggataa cactgctgtc caccaagtct actatgacat ctttgagcct     1020
ctcctgtcac agttcaagca gctggccttg aatgccacac ggaaaccaat gtactacacg     1080
ggaggcagcc tgatccctct tctccagctg cctggggatg acggtctgaa tgtggagtgg     1140
ctggttcctg acgtccaggg cagcggtaaa acagcaacaa tgaccctccc agacacagaa     1200
ggcatgatcc tgctgaacac tggcctcgag ggaactgtgg ctgaaaaccc cgtgcccatt     1260
gttcatactc caagtggcaa catcctgacg ctggagtcct gcctgcagca gctgccacca     1320
catcccggac actggggcat ccatttgcaa atagtggagc ccgcagccct ccggccatcc     1380
ctggccttgc tggcacgcct ctccagcctt ggctcttgc attggcctgt gtgggttggg     1440
gccaaaatct cccacgggag ttttcggtc cccggccatg tggctggcag agagctgctt     1500
acagctgtgg ctgaggtctt cccccacgtg actgtggcac caggctggcc tgaggaggtg     1560
ctgggcagtg gctacaggga acagctgctc acagatatgc tagagttgtg ccaggggctc     1620
tggcaacctg tgtccttcca gatgcaggcc atgctgctgg ccacagcac agctggagcc     1680 ataggcaggc tgctggcatc ctcccccgg gccaccgtca cagtggagca aacccagct     1740 gggggcgact atgcctctgt gaggacagca ttgctggcag ctagggctgt ggacaggacc     1800
cgagtctact acaggctacc ccagggctac cacaaggact tgctggctca tgttggtaga     1860
aactgagcac ccagggtgg tgggtcagcg gacctcaggg cggaggcttc ccacggggag     1920
gcaggaagaa ataaaggtct ttggctttct ccaggcactg tatgtgagtc cttggggaca     1980
ggatggagtg ggagtgggca tgatgtggcc actgagggca tctagagggt ctggaggctg     2040
ggggccagat cattccggtt gtccaagaga aactgctcac aagccttgaa ggtggtgtag     2100
aactcagagg agaggccggc acgttggtg gtcacatagt tgagaacacc tggggtggcc     2160
tggttgtagt aggataccgtt ggtcagctgg tccccctcgc gccagaggca gaagcctgag     2220
cagagggtct ctccgcgtct gtactctggc gtctctcggt gtgtgggcag cgtgaccgac     2280
ctcagcgcga tgcataggg gtccccattg tcacaaggct tccgcctcga ggccaggatc     2340
acgaagtcct ggggctttgt gtgaccctcg agggcagggc tggtgacgtg gtagatggcg     2400
tcgtcctcgt ctacctgctg cactagctcc acgctccggt agtgcttgtc ccactctggc     2460
```

<210> SEQ ID NO 90
<211> LENGTH: 431
<212> TYPE: DNA
<213> ORGANISM: Homo sapiens
<220> FEATURE:
<221> NAME/KEY: misc_feature
<223> OTHER INFORMATION: Incyte ID No: 6843919CB1

<400> SEQUENCE: 90

```
ccggcatgaa ggggagccgt gccctcctgc tggtggccct caccctgttc tgcatctgcc       60
```

```
ggatggccac aggggaggac aacgatgagt ttttcatgga cttcctgcaa acactactgg    120
tggggacccc agaggagctc tatgagggga ccttgggcaa gtacaatgtc aacgaagatg    180
ccaaggcagc aatgactgaa ctcaagtcct gcagagatgg cctgcagcca atgcacaagg    240
cggagctggt caagctgctg gtgcaagtgc tgggcagtca ggacggtgcc taagtggacc    300
tcagacatgg ctcagccata ggacctgcca cacaagcagc cgtggacaca acgcccacta    360
ccacctccca catggaaatg tatcctcaaa ccgtttaatc aataaagcct cttccgcaaa    420
aaaaaaaaaa a                                                         431
```

<210> SEQ ID NO 91
<211> LENGTH: 1050
<212> TYPE: DNA
<213> ORGANISM: Homo sapiens
<220> FEATURE:
<221> NAME/KEY: misc_feature
<223> OTHER INFORMATION: Incyte ID No: 5866451CB1

<400> SEQUENCE: 91

```
atgcacgccc actgcctgcc cttccttctg cacgcctggt gggccctact ccaggcgggt     60
gctgcgacgg tggccactgc gctcctgcgt acgcggggggc agccctcgtc gccatcccct   120
ctggcgtaca tgctgagcct ctaccgcgac ccgctgccga gggcagacat catccgcagc   180
ctacaggcag aagatgtggc agtggatggg cagaactgga cgtttgcttt tgacttctcc   240
ttcctgagcc aacaagagga tctggcatgg gctgagctcc ggctgcagct gtccagccct   300
gtggacctcc ccactgaggg ctcacttgcc attgagattt ccaccagcc aaagcccgac    360 acagagcagg cttcagacag ctgcttagag cggtttcaga tggacctatt cactgtcact   420
ttgtcccagg tcaccttttc cttgggcagc atggttttgg aggtgaccag gcctctctcc   480
aagtggctga agcaccctgg ggccctggag aagcagatgt ccagggtagc tggagagtgc   540
tggccgcggc cccccacacc gcctgccacc aatgtgctcc ttatgctcta ctccaacctc   600
tcgcaggagc agaggcagct gggtgggtcc accttgctgt gggaagccga gagctcctgg   660
cgggcccagg agggacagct gtcctgggag tggggcaaga ggcaccgtcg acatcacttg   720
ccagacagaa gtcaactgtg tcggaaggtc aagttccagg tggacttcaa cctgatcgga   780
tggggctcct ggatcatcta ccccaagcag tacaacgcct atcgctgtga gggcgagtgt   840
cctaatcctg ttggggagga gtttcatccg accaaccatg catacatcca gagtctgctg   900
aaacgttacc agccccaccg agtcccttcc acttgttgtg ccccagtgaa gaccaagccg   960
ctgagcatgc tgtatgtgga taatggcaga gtgctcctag atcaccataa agacatgatc   1020
gtggaagaat gtgggtgcct ctgaagatga                                    1050
```

<210> SEQ ID NO 92
<211> LENGTH: 1822
<212> TYPE: DNA
<213> ORGANISM: Homo sapiens
<220> FEATURE:
<221> NAME/KEY: misc_feature
<223> OTHER INFORMATION: Incyte ID No: 1310222CB1

<400> SEQUENCE: 92

```
ctagaggttg ttagacccctt ttttatgttt tttaattaat cagtcacttg taaaagcaaa     60
caagcggtcc atcccctttt caaggtcact tttttgatgg taccgaagat ccatgggaca    120
ttaagggaca gctaactgtg gccagactca gccccatgtc cttggccagg cccaaggaga    180
```

| | |
|---|---|
| ggactcggcc ccatggggtg tgccagtctt gcagtccgcc ccagctgagt agcgtgagcc | 240 |
| agatgacgcc acagagaccc gcctcttccc tgaacgcggg tcggtgtgga gtcagtgact | 300 |
| gctgactcag ggagctcctt ggccccgtgg gcactgtgcc agggctgggg ccttctgctg | 360 |
| ctgccacacc cagctcaggc ctgggccagc ccctgccccc agcccactga ggggtgggc | 420 |
| ttactccctg ggcagtcttg ggggccagag ctgaggccag tccatattac agtggctggg | 480 |
| ctgtttttt cagtagcccc tagcattggc tgggattcct gttcctgggt gcgcctccac | 540 |
| ctcccttctg atgtttcctg gctatggtgg ggtgggaacc tcagtttccc ccaaagtctt | 600 |
| ccctggatgc tggcttcagg ttgaagtccc tggttcttcc agttcctcac gggttaggta | 660 |
| ggggctcctg catcaccttc agaatccagt tccaaccccc actctcctta ggctttgtgc | 720 |
| tctgctctgc cctgccaggc tgcccttgtc catgtgagta gcatgggcgg gtggtgggga | 780 |
| cggcagtggt gatgaagggg gtgcaccaca ggcctcatga agcagttccc acatgggcgt | 840 |
| gtggctgggg cgtggccacc acagagcaca tggctgtgtc taggcgcaag cactttagca | 900 |
| gtatctgttt acatgcgcaa ggatcaagcc gactacctgt gctgtctact gggacagcag | 960 |
| tctccgagct actccgtacc tccctctgcc aggtcgtgga gttaggcccc agtccctact | 1020 |
| tgtcactggt tcccactgtg ctcctaactg tgcagcacct gggagctctg gcctggggct | 1080 |
| ggaggccctg gtaggagctg cagttggagg ccgttctgtg cccagcagcg gtgagtggct | 1140 |
| cccatgggcc ctgtgtctgc agggagccag ggctgcggca catgtgctgt gaaactggca | 1200 |
| cccacctggc gtgctgctgc cgccacttgc ttcctgcagc acctcctacc ctgctccgtg | 1260 |
| tcctcctct ccccgcgcct ggctcaggag tgctggaaaa gctcacgcct cggcctggga | 1320 |
| gcctggcctc ttgatatacc tcgagcttcc cctgtgctcc ccagccccag gaccactggc | 1380 |
| cccttggcct gaggggctgg gggccccacg acctgcagcg tcgagtccgg gagagagccc | 1440 |
| ggagcggcgt gccatctcgg ctcggccttg ctgagagcct ccgccctggc tttctccctg | 1500 |
| tctggattca gtggctcacg ttggtgctac acagctagaa tagatatatt tagagagaga | 1560 |
| gatatttta agacaaagcc cacaattagc tgtccttaa caccgcagaa ccccctccca | 1620 |
| gaagaagagc gatccctcgg acggtccggg cgggcaccct cagccgggct cttttgcagaa | 1680 |
| gcagcaccgc tgactgtggg cccggccctc agatgtgtac atatacggct atttcctatt | 1740 |
| ttactgttct tcagatttag tacttgtaaa taaacacaca cattaaggag agattaaaca | 1800 |
| ttttgctaa aaaaaaaaa aa | 1822 |

<210> SEQ ID NO 93
<211> LENGTH: 855
<212> TYPE: DNA
<213> ORGANISM: Homo sapiens
<220> FEATURE:
<221> NAME/KEY: misc_feature
<223> OTHER INFORMATION: Incyte ID No: 1432223CB1

<400> SEQUENCE: 93

| | |
|---|---|
| cggacggtgg gcgcggcggc cagctagggg cgcgggaagg cggggctcgg atgcaatcgg | 60 |
| gacctcctcc tggactgggc cggggggcgga ctccggacc cagggcgccc ggagccggcg | 120 |
| ggctacctgc gagtcgagtt agcgttgtcg ccgaaccgaa gcctcgctcg ccatggggga | 180 |
| ggtggagatc tcggccctgg cctacgtgaa gatgtgcctg catgctgccc ggtacccaca | 240 |
| cgccgcagtc aacgggctgt ttttggcgcc agcgccgcgg tctggagaat gcctgtgcct | 300 |
| caccgactgt gtgcccctct tccacagcca cctggccctg tccgtcatgt tggaggtcgc | 360 |

```
cctcaaccag gtggatgtgt ggggagcaca ggccggtctg gtggtggctg gttactacca    420
tgccaatgca gctgtgaacg atcagagccc tgggcccctg gccttgaaaa ttgctgggcg    480
aattgcagaa ttcttccctg atgcagtact tattatgttg gataatcaga aactggtgcc    540
tcagcctcgt gtgccccegg tcatcgtcct ggagaaccaa ggtctccgct gggtccctaa    600
ggataagaac ttagtgatgt ggagggactg ggaagagtca cggcagatgg tgggagctct    660
actggaagat cgggcccacc agcaccttgt ggactttgac tgccaccttg atgcatccg     720 gcaggactgg accaaccagc ggctcaacac tcaaatcacc cagtgggttg gtcccactaa    780
tggaaatgga aatgcctgag ccagggccag cggggcccgg ttccaataaa gagacttggg    840
ctgaaaaaaa aaaaa                                                     855
```

<210> SEQ ID NO 94
<211> LENGTH: 1440
<212> TYPE: DNA
<213> ORGANISM: Homo sapiens
<220> FEATURE:
<221> NAME/KEY: misc_feature
<223> OTHER INFORMATION: Incyte ID No: 1537636CB1

<400> SEQUENCE: 94

```
ctggcctgcg ctggctgggg aggaagcggt tctagggag  cgtgcgggcg ccggggtccg     60
gcgacgagag gccaccttct ggccttgcga tgaatcctcg gtttccctt  ctcagatggg    120 gttttcgtga gggtacaacg tcggcattag acattccagg tgacgcccgt acgcggtggg    180
cggttcgggc cggagctctg gaacgctggc cctggaggcg tcgacccctc gttactgatg    240
cagggacgcg gtgcggacca gtcaggccca gagctcgtcc ttagatgtgg gttcgaatct    300
ctgccccgcc aacttgtgat cgtatcgact cggcccagac gcaatttct  tctctgcaaa    360 atcgtcataa gaataatcac ttgtcagggt agctgcgggc atcccattcg ttcctttcat    420
cagcgccggg catatggggc gtcagaggct gagaacgttg ccgtgaagag cttaaaagc     480 aagacccgga gtggcgacct taagaggac  ggactgaaga aacgcgggaa tgagctccag    540
acgcgggagt ttcctctcta caaagttaca ctgcagcagc ttgtctaccc tgccccttgt    600
cttttgagaa gttcaaacct tcagaaaagt tgcaagaaca cgaggctaaa ggcagcagtt    660
cactatactg tgggttgtct ttgcgaggaa gttgcattgg acaaagagat gcagttcagc    720
aaacagacca ttgcggccat ttcggagctg actttccgac agtgtgaaaa ttttgccaaa    780
gaccttgaaa tgtttgcaag acatgcgaaa agaaccacaa ttaacactga agatgtgaag    840
ctcttagcca ggaggagtaa ttcactgcta aaatacatca cagacaaaag tgaagagatt    900
gctcagatta acctagaacg aaaagcacag aagaaaaaga agtcagagga tggaagcaaa    960
aattcaaggc agccagcaga ggctggagtg gtggaaagtg agaattaaag tccctcgccg   1020
cttggaaagt gcagccttct acaggtagag ccacctagaa atgcatatgg ctgcaaagga   1080
aactttgaag ggttaaatag agatttaaaa aaataaaata aaaaggctgg gctagggtgc   1140
tttttgtgct gaattctcca cattgttaac tgccaaagct agttttagag aatgagaaag   1200
tcttaagcaa aatactccca ggtctcactc cagaacataa aaatggtgtg tgatcgaatg   1260
gtatatatta gaaattacat ctgttgtaat taaaattgtg tgagcaatta acatggttg    1320 acttttcaa  gcaaaaatca gttcatcttt tgatgtaatt ttctaggcta aatggcaatc   1380
tctgaaagat gaataaagct atatttattt agcttaaaaa aaaaaaaaaa aaaaaaaaa    1440
```

<210> SEQ ID NO 95

<211> LENGTH: 1389
<212> TYPE: DNA
<213> ORGANISM: Homo sapiens
<220> FEATURE:
<221> NAME/KEY: misc_feature
<223> OTHER INFORMATION: Incyte ID No: 1871333CB1

<400> SEQUENCE: 95

| | | | | | |
|---|---|---|---|---|---|
| ccgtttgctc | ccgctttcag | ttgctttgct | gttagcctgt | tggaccttcg | agcctagctg | 60 |
| ctcgcacagg | actcggccac | ctgcccttcc | tgcaccgact | ggccaggagt | tcagagcctc | 120 |
| atgctgagcc | aggaggagct | ccgggtgacg | catacggcag | atcgggatt | gagaggctga | 180 |
| aaaactcaag | aggtttggat | atggaccttc | ttcaattcct | ggccttcctc | tttgtcctgc | 240 |
| ttttgtctgg | gatgggagcc | acaggcacct | tgaggacctc | cctggaccca | agcctggaga | 300 |
| tctacaagaa | gatgtttgag | gtgaagcggc | gggagcagct | gttggcactg | aagaacctgg | 360 |
| cacagctgaa | cgacatccac | cagcagtaca | agatccttga | tgtcatgctc | aagggctct | 420 |
| ttaaggtgct | ggaggactcc | cggacagtgc | tcaccgctgc | tgatgtgctc | ccagatgggc | 480 |
| ccttccccca | ggacgagaag | ctgaaggatg | ctttctccca | cgtggtggag | aacacggcct | 540 |
| tcttcggcga | tgtggtgctg | cgcttcccga | ggattgtgca | ctattacttt | gaccacaact | 600 |
| ccaactggaa | cctcctcatc | cgctggggta | tcagtttctg | caaccagaca | ggcgtcttca | 660 |
| accaggggcc | ccactcgccc | atcctcagcc | tgatggccca | ggagctgggg | atcagtgaga | 720 |
| aagactccaa | cttccagaac | ccatttaaaa | tcgaccgcac | agagttcatt | cccagcactg | 780 |
| accctttcca | gaaggccctg | agagaagaag | agaaacgccg | aaagaaagag | gagaagcgga | 840 |
| aggagatccg | aaaaggccca | aggatctcca | gatcccagtc | tgagttatag | ccctggagca | 900 |
| gctcagggct | caggggggcca | caaggaggca | ggtcggagg | aagaagaggt | ggaggtgtgg | 960 |
| ttgtggtgga | gagcaccagc | tagccccttc | cagaagggga | ggccacattt | gcccggcccc | 1020 |
| ctggagctgg | gtctgagccc | cagctgaagg | gactgagcct | cagatggctg | gattttctct | 1080 |
| caggggcctc | ctgctgaagg | ggccttcaga | ggatttatg | ctggaaatat | gaccctgtgc | 1140 |
| agactgctgg | gggaggcagg | aggatgcctg | cctggaccct | gttggtggct | gaagacctct | 1200 |
| ggccagctgg | cttccgccct | tggtggggaa | gcagcagaac | taggttctga | gccacgggtc | 1260 |
| agggtgccac | cctgctgctg | gccccactgt | gtcacagagc | tgcctggcac | aggtcccagc | 1320 |
| ccctctgcag | agacacaata | aaagccagca | gaccctttga | aaaaaaaaa | aaaaaaaaa | 1380 |
| aaaaaaaaa | | | | | | 1389 |

<210> SEQ ID NO 96
<211> LENGTH: 1500
<212> TYPE: DNA
<213> ORGANISM: Homo sapiens
<220> FEATURE:
<221> NAME/KEY: misc_feature
<223> OTHER INFORMATION: Incyte ID No: 7153010CB1

<400> SEQUENCE: 96

| | | | | | |
|---|---|---|---|---|---|
| cagatgctca | cagcatggaa | aagtccatct | ggctgctggc | ctgcttggcg | tgggttctcc | 60 |
| cgacaggctc | atttgtgaga | actaaaatag | atactacgga | gaacttgctc | aacacagagg | 120 |
| tgcacagctc | gccagcgcag | cgctggtcca | tgcaggtgcc | accgaggtg | agcgcggagg | 180 |
| caggcgacgc | ggcagtgctg | ccctgcacct | tcacgcaccc | gcaccgccac | tacgacgggc | 240 |
| cgctgacggc | catctggcgc | gcgggcgagc | cctatgcggg | cccgcaggtg | ttccgctgcg | 300 |
| ctgcggcgcg | gggcagcgag | ctctgccaga | cggcgctgag | cctgcacggc | cgcttccggc | 360 |

```
tgctgggcaa cccgcgccgc aacgacctct cgctgcgcgt cgagcgcctc gccctggctg      420
acgaccgccg ctacttctgc cgcgtcgagt tcgccgcgca cgtccatgac cgctacgaga      480
gccgccacgg cgtccggctg cacgtgacag ccgcgccgcg gatcgtcaac atctcggtgc      540
tgcccagtcc ggctcacgcc ttccgcgcgc tctgcactgc cgaaggggag ccgccgcccg      600
ccctcgcctg gtccggcccg gccctgggca cagcttggc agccgtgcgg agcccgcgtg       660
agggtcacgg ccacctagtg accgccgaac tgcccgcact gacccatgac ggccgctaca      720
cgtgtacggc cgccaacagc ctgggccgct ccgaggccag cgtctacctg ttccgcttcc      780
atggcgccag cggggcctcg acggtcgccc tcctgctcgg cgctctcggc ttcaaggcgc      840
tgctgctgct cggggtcctg gccgcccgcg ctgcccgccg ccgcccagag catctggaca      900
ccccggacac cccaccacgg tcccaggccc aggagtccaa ttatgaaaat ttgagccaga      960 tgaaccccg gagcccacca gccaccatgt gctcaccgtg aggagtccct cagccaccaa      1020
catccatttc agcactgtaa agaacaaagg ccagtgcgag gcttggctgg cacagccagt      1080
cctggttctc gggcaccttg gcagccccca gctgggtggc cctcccctg ctcaaggtca       1140 agaccctgct cataggaggc tcatctggcc tcctatgtgg acaaccattt cggagctccc      1200
tgatattttt gccagcattt cgtaaatgtg catacgtctg tgtgtgtgtg tgtgtgtgag      1260
agagagagag agagagtaca cgcattagct tgagcgtgaa acttccagaa atgttccctt      1320
gcccttcctt acctagaaca cctgctatag taaacgcaga caggaaactg tttacagggc      1380
ctggaggccc agtcttgtcc tcctctgtcc ccgacttgct gtgtggacct gggacactct      1440
cttcacttct ctgggtctca ttcatttact gttgaacctt ccagcacac tggcgccgta       1500

<210> SEQ ID NO 97
<211> LENGTH: 796
<212> TYPE: DNA
<213> ORGANISM: Homo sapiens
<220> FEATURE:
<221> NAME/KEY: misc_feature
<223> OTHER INFORMATION: Incyte ID No: 7996779CB1

<400> SEQUENCE: 97
tctcaggctt atttctggat tttgtaagta caagtacaga ggctgcagaa tggcctgggc       60
cttggaatct ggaagcttct ccacagcaat ttgcatgggg acacaggacg agtgaccctc      120
agggtgttca tcaccaccat cttaccctga aactttgatc agttcccaga taacttgcag      180
gaacccaata acctagaggg aagagggcag aagaaagtga aagctgtaaa caatagagac      240
ttaagatcat gagaaaacct ctaagtagga caatattcag actcgtaata cgcaccctga      300
ggtgaagggg agggcaaatg ggagtcaatt atccactctt gttcctcaaa ctcattggtc      360
accccaagat gacagaccca cttgctttca ctcacattca ctttgcgctt ctgcccgccc      420
accagccaca tggactttag ttcttccaac tcctgccttt ccctctgcc tgtgcagatg       480 cccttccttt cctggactct ccctccatct gtgactggtg aatccctacc ccacttcag      540 gtgactgaca ccagcgtcac ttcctctaag ctccccgac cacaagctca ccaggtcagc      600
ccagaactgc tttgtggtca cagtgcttat cacagtcgaa ttaataccctc accaggaatg    660 tactttatga ctgcatcctc tccagtatct aagccccatg gtggtaggga ccgtgtctgc     720
cttggtcaga gctgcatctc ttagggacac agtgcctcat tcaaaatggg tgctgggagt     780
actagccaac tgaccc                                                      796
```

```
<210> SEQ ID NO 98
<211> LENGTH: 2540
<212> TYPE: DNA
<213> ORGANISM: Homo sapiens
<220> FEATURE:
<221> NAME/KEY: misc_feature
<223> OTHER INFORMATION: Incyte ID No: 640025CB1

<400> SEQUENCE: 98
aataacagtg gtacgagctg gatcacttat acggccgcag tgtgctggaa agagttcacc      60 cagggttgt acgctgccac ccaggttccc aaggtttctc ccatctggtc agatgtcgaa     120
cacaaaatgt gggcattctg cacggaagga aagatcaggc ttctcttgct gagtgtgtga     180
agacagggag agccaggccc cagcagatgc ggcctagcac actctgattt ggttttgtgg     240
ggagggccca ggaacttggg ggtggtcttg gcattcagag ctggtgctaa aaacccagag     300
cagaagcagg gagaagggag tgaggatggg acagagaaga gcgaccactg gggatcagaa     360
cagcttttca ggggccacct tgcagcctaa aataatgccg tttcagggcc tgggcctgct     420
gtgagagcca gaatgaagca tgtgcaagat tggaatgtga aagaactgt gggggaaac     480 cagtttaat taagtggaag tgcttttgtgc ttgtgctgaa gttgcctggg cctcctgcag     540
ctctggacct cactggagcg gccccgccct gcccttgcct gcctttcttt tatgctgatg     600
ctggtgggct ttttcctgct tcaggatcca tgtaagggac tgaccaggtt catccagcct     660
taactggttc ctgcaaccca cttttaggtc tcccaccagg ggcctattgt gctgtcttcc     720
tgtgaccagc agatcctgta aggggtgat cctaattctg gggctctttg cagcaagagg     780
agaacgttct ttttcttgaa caaggtggcc ggttccctgg gagaaggctg ggaatggcac     840
gtccggccag ggcaggcggt gcggcatcct cctcctggga ttcctgtggc ctccctgtt    900 ctattcattg tttggcttcc cacccataag ctctgggata cccagggctt gcttcccagc     960
tcttctcatc tccaagcctc tgctcccctt cccaccacca ctgccatata aaatggccat    1020
gctaactcct acacaactag gagcctcagc aggattgcta ggatgtgggt tccttcctgc    1080
atgcttgctt ctgcagctgt gtggccttgc catggccctc ccaccacttt cccttctacc    1140
ttgccttcca ttgtcttcct tctcccagaa agccaggttt caccacgtgc tcaccacaaa    1200
ctgtctcccc tccctcgtag gagtcactgc agtagggcac ctgcaggccc tggtagagtg    1260
agcagggctt acgtgtacat tcttcctcac tctaaggatg tgatatctga ccctgatgtc    1320
agagaggagg tctcaggact agcattcggg gtcctttgag tgttcccaga atggtttggg    1380
gtatcacaca aaacaccaga gctgagggta gggatagagt ccccaaacac acatcctggg    1440
agcaagccac ttcatctgag cttcccatac caggagcatg gtttgtgctt tgatgggaaa    1500
cctagcaagc ccctgcactc tggggcttct cctctcctgg agcccagggc ggctctggcc    1560
cgatgatatg gcagccatag gtacaggtat tgcaggtgca gcctttctta agtaccctgc    1620
ctccactcta tagcccagct gctgctggag tccaggacct tagacccagg atgagcaaaa    1680
ggatcccacc aggttgtcca ggaccattgc cagggtgacc ccagagttct tcagacctgt    1740
gtctgatact gaatacagtg ccatgggacc ctgctccaat ctaactgcct acaacctgcc    1800 cgtcccctg ctgcagggat gttgctgcta cctcggagg ctctctgaga ctggtgtctg    1860
gtcttagatg ctgcacatag tacctggtgc tagggtctag gggctgccca agcccagca    1920 ggaacagcta ctactcatcc tgcagaggcc ttggcccaga ccagcttccc atccaaagcc    1980
tcacctggtt tccatgtcca tctcaacagt ctggccttcc tgtgactgta gcctggcagc    2040
cacaccctca gtaatcccgc acagtgagtc cagcttctct gggagcttgg ccttcagtta    2100
```

```
gcccagtcca tgagagggca gggtaatgag gaggagtaaa ggacctatct tctctgtcca    2160
cataaggaag ttgggaccac aaggtctttt atctccttgt tactcccaa ccccaccata    2220 acctcctact cagcacacag ctttatcctg gtagattata aggtgagctt ccagaacctg    2280
gcaggaggct ggtgtatccc cctgcacaga cggaagtgta tctgaatgtt gtgtatgtgg    2340
ctgatatgga agacatacat gtatgcaatc catcagcgtt taaagaagaa gattggctcc    2400
agttctgagg aggaggagga agattacaga tctattctga gtatttttta gagagttaat    2460
atttatattt ttagtaattt tctggtagaa ggaaattgca caataaaatg atttggtttg    2520
gtttgcaaaa aaaaaaaaaa                                               2540
```

<210> SEQ ID NO 99
<211> LENGTH: 2487
<212> TYPE: DNA
<213> ORGANISM: Homo sapiens
<220> FEATURE:
<221> NAME/KEY: misc_feature
<223> OTHER INFORMATION: Incyte ID No: 1545079CB1

<400> SEQUENCE: 99

```
tgcccaaatc tgggtaatca gactgggtat tcattggctg catttcaaag cacagcactg      60
ctttcagcca ggatgaagtg ggagtgaacc cagctgctag cagagctgcc actccaggct     120
gagagccaag taccagccac tgccagtgaa gactggcccc tttactgaag ggagttgttc     180
agagtccagc caccggccct ggggagggag agaagtcagg gtattctgct cggggatggt     240
cagggctccg cagctccatc gccagcatcc tttggaaagc cgcctctggc ggagacagcc     300 ggctggggggg gcgctccagg tttggctgag acgttcccgc caccagccgg caccgggcgc     360
cggcggccca gctgccgtaa catctcctcg caggctgcga tggtgtccag gagctgccac     420
tgccgctgct ccaccgcgtc cagcagctgc tgggcgcgct cctcccgggg cggctgtggg     480
ggtggcctcc cgccgagccc cagccccgcc ttcccgcggt ccacgccggc agcctcccgg     540
tctccttcaa tcctcctggg ggtcgtggtc cctttaagct gcccggcgca gaggcggggc     600
cgagtctcct ggaccggaag ctggctggga gcgtcacttc ctcccggaag cgggcctggg     660
cggatgtctc cggcgcgtcg gtgcaggggg atgagggccg cggtggctgc cagcgtgggg     720
ttgagcgagg ggcctgctgg ctcccggagc ggtcgcctct tccgcccgcc gagtcccgct     780
ccggcggccc ccggcgcccg gctgttgcgg ctcccgggga gcggggccgt gcaggccgcg     840
agcccggagc gcgccggctg gaccgaggcg ctgcgggccg ccgtggccga gctgcgcgcc     900
ggcgccgtgg tggccgtccc caccgatacg ctgtacggcc tggcctgcgc ggcgagctgc     960
tcggcggctc tgcgcgctgt gtaccgcctc aagggtcgca gcgaggccaa gcctctggcc    1020
gtatgcctcg gccgcgtggc cgacgtctac agatactgcc gtgtgagagt acctgagggg    1080
ctcctgaaag acctactgcc aggaccagtg accctggtga tggaacgctc ggaggagctc    1140
aacaaggacc taaacccttt tacgcctctt gtaggcattc ggattcctga tcatgctttt    1200
atgcaagact tggctcagat gtttgagggt ccgcttgctc tcactagtgc caacctcagc    1260
tcccaggcca gttctctgaa tgtcgaggag ttccaggatc tctggcctca gttgtccttg    1320
gttattgatg ggggacaaat tggggatggc cagagcccg agtgtcgcct tggctcaact    1380
gtggttgatt tgtctgtgcc cggaaagttt ggcatcattc gtccaggctg tgccctggaa    1440
agtactacag ccatcctcca acagaagtac ggactgctcc cctcacatgc gtcctacctg    1500
tgaaactctg ggaagcagga aggcccaaga cctggtgctg gatactatgt gtctgtccac    1560
```

```
tgacgactgt caaggcctca tttgcagagg ccaccggagc tagggcacta gcctgacttt      1620
taaggcagtg tgtctttctg agcactgtag accaagccct tggagctgct ggtttagcct      1680
tgcacctggg gaaaggatgt atttatttgt attttcatat atcagccaaa agctgaatgg      1740
aaaagttaag aacattccta ggtggcctta ttctaataag tttcttctgt ctgttttgtt      1800
tttcaattga aaagtaatta ataacagat ttagaatcta gtgagagcct cctctctggt       1860
gggtggtggc atttaaggtt caaccagcc agaagtgctg gtgctgttta aaagtctca        1920 ggtggctgcg tgtggtggct catgcctgta atcccaacat tctgggaggc ccaggcggga      1980
gaactgcttg agcccaggag ttcagaatca gcctgggcaa catagcaata ctccgtctca      2040
taaaaattaa taaataaaaa gtctcaggtg accaaaggct cctgaagcta gaaccaggtt      2100
tggataaaga ttgaagagcc acaggccact cttccctctg agccattggg cctagtggtg      2160
tcatgtattg taattgctcg cggggagagc agtctttttg gtgtaatagt gggatgtctg      2220
cttagttggc aggggttcag tccaaatgga agaatattgg gaagtaaacc tccactatcc      2280
tttatagcca gggactttt tcttatttat tcataaaata aattatagtt aattataccc       2340
ataacacctt tatttaaatc cagtgttctc cgcagccttt tgtctattta tatgtgtacc      2400
aagtgttaaa cataattatt attgggcatt tgaactttgt ttttctttaa agaaatgctg      2460
ctattaaaca tatttgtaaa aaaaaaa                                          2487
```

<210> SEQ ID NO 100
<211> LENGTH: 701
<212> TYPE: DNA
<213> ORGANISM: Homo sapiens
<220> FEATURE:
<221> NAME/KEY: misc_feature
<223> OTHER INFORMATION: Incyte ID No: 2668150CB1

<400> SEQUENCE: 100

```
taggaccacc taaacgtgcg tgtattcgcc aaaggacccc atatctaatg agggaaaagt        60
ggcacctgca gaccaaagaa cacacaagat ttccgaaggt ggttattcca agtgaaaaca      120
cacaactgaa agaagtccat gaggactgag tggaaattga caagaacaag gggagttcat      180
caggaacaac ttttccagga aaacttgagg ttcagatttg agaggataat atggctggat      240
gaataggaga aaataagcta ctccagagga aatgaaggaa gttaagacat ggaatcacaa      300
tccatttcac ctctttgttc ttttcttta accttaactg caaccttccc catagtaagc       360
agaggaagag tagatattgt ttctgtggtt aagttacaga aagtgtgttg cttgctaggt      420
actgcaaagt attttctgt tagtgacaag caaatcatat caaattgttc aaactcaatt      480
tcaactctta taagaggata gacatggggtt ttgaggaaat ggttatcatt tgccttgtta     540
ttacctcatc tttgagcccc aacatgtgcc tttactactt atcccagtga ttctttcaaa      600
aaattattta ataaatcaaa atattccata agtcaaaata tcttcaggtt gcggatttac      660
ctttgacttt catcttaacc aataacgttc aaaagtcccc a                          701
```

<210> SEQ ID NO 101
<211> LENGTH: 1956
<212> TYPE: DNA
<213> ORGANISM: Homo sapiens
<220> FEATURE:
<221> NAME/KEY: misc_feature
<223> OTHER INFORMATION: Incyte ID No: 2804787CB1

<400> SEQUENCE: 101

| | |
|---|---|
| ataggaatt tggcctcgag gcaagaattc ggcacgaggc tttgcattgc tttggcagag | 60 |
| gagctgaagg tgcctttggg tggagatcga tgaaccgtaa tctgagctag ggttttagat | 120 |
| cttgacctgt catttaggaa agtgcatgtg taaattgagg tctctgtggt ttcttggtct | 180 |
| tgggcaggtt actgttttca ctgtcatcac tggtgttagt gagggtcctg ccaggatagc | 240 |
| gagtaccagt ggtataatgc ccagacctct aggagctgct tcgggccaac aatccagccc | 300 |
| agtttgttac tcggtcttcc tgctgtccca ggggtcatct gacaacattt ctagggaaac | 360 |
| tgggtgatca gaatatgaac cccatgtccc tttctggaag tcagtccttg attttgttct | 420 |
| gcatcctgct tctcactcta ccaggcctct ctctgctggt tctgtttctc acagaaagca | 480 |
| acctgtctgt agagaactgg tagaggcctg agagtcagga gtattacagc tagctgcaat | 540 |
| gaaccttggg tcccttattt tacacatgaa gaaaaggagg cctcaggtgg aggattagct | 600 |
| tgcctgtggt tacagcaaga gatgtcgctt attgtctagc accatgggac tgtatcggcc | 660 |
| aagggtggtg cctgagtggc tggtcttgtt ttctttgcct cctgtttctt ttcctctccc | 720 |
| tcagccaagt ctcaggatag atgcgaagta tagtccggtt agagaaggtg aatatatgct | 780 |
| ctgggttata cgcctatgca tgtcaggtcc tgggagtgtg tgtgatgcat ggtgttccga | 840 |
| taggcaggca tgagtctgtc catatgtggt tatgaagttt ctcaatagct gatggttagg | 900 |
| tatcacgagt caggagtcct gtgagtccta ctctgttgga caaagtggtc atctttttc | 960 |
| tttgctaact ttaagttgaa agtttgtttg agggctagt ggaaaggca ttgactttaa | 1020 |
| gcaagatccg tgcctctgga cataatgaac aggcatctca tgggaacttc ccaccactgc | 1080 |
| cctggacagg ctaagcttca gaggccagtt agtcgtaagt tttattgctt catcctggtc | 1140 |
| tgcagtaagg tctgatactt cagtgtcccc atttgggaac tgagacatct gcctagaaga | 1200 |
| agagtgtaat cttgcactcg tctaagggat caggaccaca ttgccctcgg tggactgctg | 1260 |
| cacttttttg gagatttcct cccttcaaaa aaagcctact ttgtaacatt ttgtcatctg | 1320 |
| agatttcaga taccacctt tctttagttt ctcacctgtt taggcattta ggcatgctgg | 1380 |
| tctgtggcta atggtgtttc agataggaag gatggatatg tctttatcta cagcagaagt | 1440 |
| tagttacct ttcatgaggt gattagttta cttctaggtg gaaaaagaga ggactttgaa | 1500 |
| cttggtgttg tcacaggagc tgctctcatg gacaagagcc catggatttt gtggaggaag | 1560 |
| aatgtgtagg aaacaaggag aaaaatcaga agactttgca cctgtcaggg aagaactagt | 1620 |
| gaagagcaaa aaccagtgtt ttagtggatg aaatacagtt ccgagggttt ggaattaggg | 1680 |
| aagagatggc ctcagagagg agcatggaga ccatgggagg tagacctgac ttgatacttg | 1740 |
| ttggccattt taagaaccag gtatgtgtga agccttacca cagggatcag aggagcagga | 1800 |
| gcagttgatg gtgactctgt atttaaccat ttgagaaact gccaaactgt tctctaaagt | 1860 |
| ggctgtacca ttttacatgt ctaccagcag tgtataagag ttccagtatc tgcatccttg | 1920 |
| tcaacacttg ttattgtctt tttaaagtta ttaaag | 1956 |

<210> SEQ ID NO 102
<211> LENGTH: 1063
<212> TYPE: DNA
<213> ORGANISM: Homo sapiens
<220> FEATURE:
<221> NAME/KEY: misc_feature
<223> OTHER INFORMATION: Incyte ID No: 4003882CB1

<400> SEQUENCE: 102

| | |
|---|---|
| ggtcattaga atttgtcctt ttgaggacca ttggctggaa actttatact acaattgagt | 60 |

| | |
|---|---|
| gtgctatgag taagacagct tcaattgaag cctctgaaga ggaaaggaaa ataacaaaga | 120 |
| agacgctttt gtatctttt ccattatcaa taacgtcaat atagaacatg cctttttca | 180 |
| tgtgaaactt caatatgaac ttattcaaat gacactctgg ctatgtcata atgtctgcat | 240 |
| tctccaggta tatatgaaac agattttaat ggatgttggg tggcttccat tcacccttc | 300 |
| atatttgaaa atgcacttag aaactctgtt gagaaagttg cttatgctat tggtcctcct | 360 |
| tttctgttgt tgttcagtct gcccccaagt ggtagagagc ctaaaaaccc aaaaagataa | 420 |
| caacgtggtc aatccatgac ttatcagctg caattgtatg cctgattgat ttttgttgct | 480 |
| atacaacagc tgaacaattc gaaatttatc acatggaata tgaattcacc tgttcaaatc | 540 |
| atggtagtat aataattctt gaaattgcag ctgcatattt taattcatta caccaagtaa | 600 |
| ataaacttca agacattcag ccaccattca tgaaatagat ttctaaaggc ttatgtgggg | 660 |
| atcattttct ttctcttacc ctctaccctc ttgttttaaa actcctctcc ccaccatggc | 720 |
| cttatactgg aagacatttt tactcttgat ttctagcaat tgctggctgg tattgttgag | 780 |
| ttttaatatt tcagtgtgat tcagagctct gaccattttc aagttcttag gagccctctc | 840 |
| ttgtctcatt tttaaacatg gcctttgggg aatgacagtg attgtgacag atggtaaagg | 900 |
| aataagattg cactttggcg ctgcttctgt ctttgcctct tgatcttttc ccactttctc | 960 |
| aaggcaaatt atagatttcc ttttgcctct agagggacgc aaattgcagt tgccagttat | 1020 |
| atggttcttt gattctcttt ctagctctta aaaaaaaaa aag | 1063 |

<210> SEQ ID NO 103
<211> LENGTH: 495
<212> TYPE: DNA
<213> ORGANISM: Homo sapiens
<220> FEATURE:
<221> NAME/KEY: misc_feature
<223> OTHER INFORMATION: Incyte ID No: 4737462CB1

<400> SEQUENCE: 103

| | |
|---|---|
| gtttgtcatc aaggttcctc agggtttggc attaccacct cttcagtcca ttcttaaggg | 60 |
| tcctcctcac atacttaccc ttgacctcag gatgataaac cactgtctct tatctctggg | 120 |
| cctttgtgca tgctgttcct tctccaggaa atacttcttg cccttgtcct tagtgtcctt | 180 |
| caagtttcag gggggctgat catctctggg cacctgctc taatagtctt accaagtctt | 240 |
| agggattttc tgtttcacat gtccacatta cacacatcta tcaaacatat tgagtctcat | 300 |
| gttctttgta tgtatgcatg gtgctttcct aactgggagc tgagctctaa cgtgaagagc | 360 |
| ctttccattt agctttaatc tctagcagtg tcattggttg gcatatattt gaaccaacaa | 420 |
| ttaatgctgg ttgaatctaa cttgtcacac tgaagagact atttctttca ttgccggtga | 480 |
| gttagaccag aagtt | 495 |

<210> SEQ ID NO 104
<211> LENGTH: 880
<212> TYPE: DNA
<213> ORGANISM: Homo sapiens
<220> FEATURE:
<221> NAME/KEY: misc_feature
<223> OTHER INFORMATION: Incyte ID No: 4921634CB1

<400> SEQUENCE: 104

| | |
|---|---|
| gggctgtcac cccttgtga tggtgacact gatgtggtta accccgggac ggtgggtcgc | 60 |
| atccttgcct agagcagtgg tgtgtacagg gtcatccttc acagtgagga gaggtaccga | 120 |
| cgtcgtctga tgcttgacac aacccgaccc acacacatta tgcacagata gcaacactga | 180 |

```
gggtctcggt gacaaatgag tggaaggaac atatgggggt ggggggcttt cacaaccttg      240
agagcaaagg caaggcaagt tatttctgtt gagaaacaca aagccaacaa caccagcagc      300
gaaaggaatg caaaccacat cttgcttgtt taaagcagta aaggaacaaa actacatagg      360
caaggaggtg cttttgtgtc cccagccatg acttctggtt aaaaagtgca cacaaacctc      420
agacagtcaa tacactcact tcaacgcctg atgtggtgtg tttccttaag aaaaaaaatc      480
ccgggagggg aacaacactc actggggcct gttgggagag ggctgggcca ggggcatgg       540 agaacattag ggaaaagagc taatgcatgc tggtcctcat gcctagtgac agggtgacag      600
gtgcagcaaa ccaccatggc acacgtttac ctatgtaaca aacctgcaca tcctgcacat      660
gtaccctgga acttaaaaat atatataaaa taattaaaat tttaaaaaag aaaaaaaaat      720
cctaagggct gggtgcagag gctcatgcca gtgatcccag cccttgggag gctgaggtgg      780
gaggacagct tgagctcagg agttcgagat cagcctgggc aacaagggga gaccctgtct      840
ctctacacgt atatttattt taaaaaaaaa aaaaagggg                            880
```

```
<210> SEQ ID NO 105
<211> LENGTH: 2666
<212> TYPE: DNA
<213> ORGANISM: Homo sapiens
<220> FEATURE:
<221> NAME/KEY: misc_feature
<223> OTHER INFORMATION: Incyte ID No: 6254942CB1

<400> SEQUENCE: 105
```

```
caggttataa tcattgttct tcctctaaac tgcctcttgg gctttacatc aggtcaagga       60
tttttagggt ttctcaaaaa taggattctt gtcagtgtat gcatgctgag taagtcacct      120
ttctggctct aatttctggg tggccatctg ttgtccagct ctgctgccaa ctggactttc      180
cgaaagccat gtcaactaat ttttatatg ctaagacaaa tcgaatatga aagaggaag       240 aatattctag atattctaag acatttctta atttggcatc tcagaggagg taggtggaaa      300
gtaaaggaag agataatttt gggggaaaat ttgtggaaac atacaaaacg ttttgctttg      360
tatagatgct aaacagagtg ggaggcagca tatttgtaac aacaaccatt ctgacctttt      420
gaaacacaag cttttggaga agtcagggag agacacagta tgaataaaag caattaacat      480
tttctttaat gtatattttt caaagaggac cactgaatcc tgttctctaa cccaaggggc      540
agtgtaggtg gttttaagcc cacagaatat tgagatattt ctcttgtggt tttggtgggg      600
tggtgggatg cagaaggtta ttaaagatca atttaagcat cagatagact atcccttta      660 tttttttaac tttaggttc agggtacat gtgcaggttg ttatataggt aaactcatgt        720
caagtggttt tgttgtacag attattttgt cacccaggtg ctaagcctag tacccagtag      780 ttatttccc tgctcttctc cctcctccca ccctccaccc tcaagtaggc cccagtgtct       840
gttgttcctt tctttgtgtc cttgagttct catcatttag ctcctacttc taaatgagaa      900
catgtatttg gttttctgtt ctgtgttagt ttgctaagga taatggcctc cagctcagat      960
ggaatatctc tatcatatag acctgttgtt acagggcagg atcggatgat ggacactgaa     1020
gtcctcagct tgctaagttc agttgctctc cctagcctcc ttttggcttc agagtctttt     1080
gattccatct atcctggtat tttttgtgtg ctgatgttta gttctggatt ggcttcagct     1140
gtgctaatag gaagggcgtt gtcttttcaa gcaatcttaa aaggtggtca atcaaaaggc     1200
cagagtctga atcccttctg tggcttaaat aatttgagga tcaagtccag tgtcttgtta     1260
atccctgttc tactgtgcca gacactatct tgaatgcttt tatatgttca ggttcaaaat     1320
```

| | |
|---|---:|
| cgctctttca taccagggga tgatagtaac gtgtaacttg caatagattc cttcatctta | 1380 |
| gtaataagat gatcagtcta gttaggacaa aatagagatt gaataaatta acttttccaa | 1440 |
| gtttacagag taaaaatgag cagatctctg cctggttttg tgaaaagag ttagcactgg | 1500 |
| taaatagaat atttctactc ctacaccatt ctttcagtat atcatcactg aagacaggaa | 1560 |
| gataggcaca cagattcttc ctcgtagtaa ttcatagtgc actaggtgaa agagatgaag | 1620 |
| tatgtattaa aagtacaatg tgatggcatt tattattcag ataatcccag gattctagaa | 1680 |
| gaaaataaag aagagtgaca gttcagttag ggtgtgaact tccagaggag cactgcttaa | 1740 |
| gctgaacttg agagcattgt gcaaaagcac agtagtctgt taagaactag aaataaccta | 1800 |
| gcttgtgcca cttcgggagt attaagacat aagcctagaa aggtaggcaa aggttagatc | 1860 |
| ttagactgtc ttgtattttt ctcattcctg ttgattacct acctcaaaat tgaatatgtt | 1920 |
| tttcctcctg cctaacacaa aactactcaa gggcagaaat ttaaattctt ccttggtgta | 1980 |
| tgtgcaaaga aggttgaata tattcatgcc taccttattt tggactagga atacagtagt | 2040 |
| atactttccg aagacttgcc tgaatagtat ataaggtgga ggcaactgac tagttaggtc | 2100 |
| agtatttta gaaactctta atagctcata ctcttgatac caaaagcagc cctgattgtt | 2160 |
| aaagcacaca cctgcacaag aagcagtgat ggttgcattt acatttcctg ggtgcacaaa | 2220 |
| aaaaaattct caaaaagcaa ggacttacgc tttttgcaaa gcctttgaga agttactgga | 2280 |
| tcataggaag cttataacaa gaatggaaga ttcttaaata actcactttc tttggtatcc | 2340 |
| agtaacagta gatgttcaaa atatgtagct gattaatacc agcattgtga acgctgtaca | 2400 |
| accttgtggt tattactaag caagttacta ctagcttctg aaaagtagct tcataattaa | 2460 |
| tgttatttat acactgcctt ccatgacttt tactttgccc taagctaatc tccaaaatct | 2520 |
| gaaatgctac tccaatatca gaaaaaaagg gggaggtgga attatatttc ctgtgatttt | 2580 |
| aagagtacag agaatcatgc acatctctga ttagttcata tatgtctagt gtgtaataaa | 2640 |
| agtcaagatg aactctcaaa aaaaaa | 2666 |

<210> SEQ ID NO 106
<211> LENGTH: 1293
<212> TYPE: DNA
<213> ORGANISM: Homo sapiens
<220> FEATURE:
<221> NAME/KEY: misc_feature
<223> OTHER INFORMATION: Incyte ID No: 6747838CB1

<400> SEQUENCE: 106

| | |
|---|---:|
| cgcgcacctg ccccgccaca tggcgctggc tgcggtcccc gggctgcgtg gggctgatga | 60 |
| gctccatccg cagggagctg cttctcccct tttcgtgttc tatccacacg gtttatgttt | 120 |
| aaaaaccctc ttttcctatt tgccatttta tggttaaatc cttgttgaaa aatgacactt | 180 |
| gatcattagg cctttggata taattttatt ttctcccagt aatgagcagt cccactgtct | 240 |
| ttaacggaca cctaaagagt gcagagcaag gagatggagc gctggacgcc ttcaaatacc | 300 |
| gggacaacca ggatccagag cagcgaggga cccacagtgc tccctcagag gcctctggac | 360 |
| cccacgccca cacgtccctg tgaccaccca caccctcccc cgactggctt ctccatgctg | 420 |
| ctgtctccgg gacatgagtc gcctgtctgt cccccacgtg tggccaggag ggcatgagcc | 480 |
| acctgtctgt ccctacgtg tgcccaggag ggcacgagcc gcctgtctgt ctgccatgtg | 540 |
| tgcccaggag atacggtgct tttcctgcca tgtcctcaga gctgtgcatg tggcacacag | 600 |
| gaagcagttg tcacaaataa acaggaattt ggcctgtgta tgttagtcct gagaacttgg | 660 |

```
ttagcacgag tctgtttctg caagataacc cgttcctggt gagcagacag agctagtcat    720
agagcctgct ggcatgggct gtgccagggc cctgtggggt tggcagggaa gcacgtcctg    780
tgtggccagg tgtccccggg ggagagagct ctgggctgtg aatccttctg ggaggcaggc    840
gaagggccct ggccttctgt acccagtgt tcctgtgtg ccaacaggaa caggtgctta    900
```
(Note: corrected) 
```
gaagggccct ggccttctgt acccagtgt tcctgtgtg ccaacaggaa caggtgctta    900
gcatctcgtg ccatggggcc tctcagcgcc ctcctgagcc agagcttgct gttgagctgt    960
acagcgcctc gagagaggct gcctggggga ggctggcctg ggactcctgg catgggccca   1020
ctccgctcag gcacctctgc accctcctcg attgtccgta agggcagggg gtccctccgg   1080
gccctggcct atgccacacc ctccggaggt gaagccaggg tgctctgctt gttctcgcag   1140
tacggcttct ctcacagggc aaaggtcact cgtgacgtgt cccagtcaaa acggggtaa    1200 agtgtgggga aacgcacaaa gtgtgttttg ctttttagag aagagcggtt gagcacacgc   1260
catgctggct gctcaggttg gggtgcagcc tgc                                1293
```

<210> SEQ ID NO 107
<211> LENGTH: 693
<212> TYPE: DNA
<213> ORGANISM: Homo sapiens
<220> FEATURE:
<221> NAME/KEY: misc_feature
<223> OTHER INFORMATION: Incyte ID No: 7050585CB1

<400> SEQUENCE: 107

```
tatgattaat tcagcccaat atagagtttt ttctattttt ggtctagcac ctcagaatcc     60
acttccacat atatttccca gatttttata gattataaat caccaacatg caattatttt    120
ggcatgtaag ccttcttctt ctgtggagac ttggtgattg gccccagaa catgctgatc     180 tgattctaga ggtgggagta gagcgtgaga attggctttc tgttgagttg ctccttttgg    240
taagaggtca gttaaaattc agggatttat tattgaggaa gagggaaga atgcatactg     300 tgagacgcct agatctttct gccactttta agatattttt acattttact gtggtgaaac    360
tgccttctac tttttctatg tccccatcac ccccaaacca ccatggtatg aagctgatc     420 aactgaaaag acttgctcgc tccccttcaa gcccagggct tcccaggaca tcatatgaca    480
atctattcaa ccacatttcc tatgctgata gtttcatttc ctaattctct cttgatgcca    540
ttacctcatt tgcccttatc actgccagag cctagcaggc gagccaatcg tcggtcttgg    600
cttcatgtgc tgtgccagtc cccttccctt tgggccttaa tcaattctcc aggggcttct    660
tttgggcaat attagccccg ccggtttctt gga                                 693
```

<210> SEQ ID NO 108
<211> LENGTH: 860
<212> TYPE: DNA
<213> ORGANISM: Homo sapiens
<220> FEATURE:
<221> NAME/KEY: misc_feature
<223> OTHER INFORMATION: Incyte ID No: 3880321CB1

<400> SEQUENCE: 108

```
gtttgtttac tgtcctccca tcaagaccta cagcctatgc cgacattctt ctaagcagat     60
cacatgtgct tgggcacaa gtgggcattc tgaacacttt tttgtgtttt cagccatggt    120 cctctttttct caagggatac tgccagtctc catcctgatc cagatttaga aacacaacaa    180
aaacaaaaga gaagcggtga tataaaatgg aagtagaact tggcgttggc tagtggagac    240
ggcgataagg agttttgaag tgtctctcct ttgaaaggtc tttccttgttg gatcactgct    300
```

-continued

| | |
|---|---|
| cccccagtat gtctgatcct tgtgcacagc ccacctgggc tggtgggggt cggtcctcat | 360 |
| cacactgagg ctgggtttct ttaacttcag aaatgtcctg aggaataaga aatgaaacat | 420 |
| gagcaataca gggttaatgt tgtcaagcca tgtttgtttt tgttttttgtt tttctttgtt | 480 |
| tcttttttgtt tgtttgtttt ttgatacgaa gtctcgctct attgctcagg ctggagtgca | 540 |
| atggcacgat ctcagctcac tggaacctcc gcctcccggg ttcaagcgat tctcccacct | 600 |
| caggctcctg agtagctggg attacaggca tgtgccacca tgcccggcta atttttgtat | 660 |
| ttttagtaga cggggtttt caccatgttg gccaggctgg tcttggctcc tgccctcaag | 720 |
| tgatccgcct gccttgggct cccaaagtgc cgggattaca ggcatgagcc actgtgcctg | 780 |
| gcctattttt gttttctttg atggggcaag gtacccagat taagtttata gacgacagct | 840 |
| aatgataatc aagttccatg | 860 |

<210> SEQ ID NO 109
<211> LENGTH: 2738
<212> TYPE: DNA
<213> ORGANISM: Homo sapiens
<220> FEATURE:
<221> NAME/KEY: misc_feature
<223> OTHER INFORMATION: Incyte ID No: 3950005CB1

<400> SEQUENCE: 109

| | |
|---|---|
| ctgaagttcc ctgtgggagg ctgttttctg agggagctga gtgtttacag ccactcagcc | 60 |
| ctgctctgct cagctgaagc agaaaacaga gacctttttgc attactttgg ttcaagagca | 120 |
| agacaggagg cgactgcatg agaccatggc tgagacacct agtcctccag gcactgagga | 180 |
| actccagggc attctgtggg tctcatggga agccagcacc tctacctgtt cctcagaaga | 240 |
| tcgtggccac ctgggaagcc atcagcctgg gaaggcagct ggtgcctgag tacttcaact | 300 |
| tcgcccatga tgtgctggat gtgtggagtc ggctggaaga ggctggacac cgccccccaa | 360 |
| atcctgcctt ctggtgggtc aatggcacag gagcagagat caagtggagc tttgaggagc | 420 |
| tggggaagca gtccaggaag gcagccaatg tgctggggggg tgcatgcggc ctgcagcctg | 480 |
| gggacagaat gatgctggta ctcccacggc tcccggagtg gtggctggtc agtgtggctt | 540 |
| gcatgcggac agggactgtg atgattccgg gtgtgactca gctgacagag aaggacctca | 600 |
| agtaccggct gcaggcgtcc agggccaagt ccattatcac cagtgactcc ctagctccaa | 660 |
| gggtggatgc catcagtgcc gaatgcccct ccctccagac caagctgctg gtgtcagaca | 720 |
| gcagtcggcc aggctggttg aacttcaggg aactcctccg ggaggcttct acagagcaca | 780 |
| actgcatgag gacaaagagt cgagacccgc tggccatcta ctttaccagc ggaaccaccg | 840 |
| ggcccccaa gatggtcgag cactcccaga gcagctacgg actgggtttt gtggccagcg | 900 |
| gaagacggtg gtggccttg accgaatctg acatcttctg gaacacgact gacactggct | 960 |
| gggtgaaggc agcctggact ctcttctctg cctggcctaa tggatcttgc attttttgtgc | 1020 |
| atgagctgcc ccgagttgat gccaaagtta tcctgaatac tctctccaaa ttcccgataa | 1080 |
| ccacccctctg ctgtgtccca accatctttc ggctgcttgt gcaggaggat ctgaccaggt | 1140 |
| accagttttca gagcctgagg cactgtctga ccggaggaga ggccctcaac cgtgacgtga | 1200 |
| gggagaagtg gaaacaccag accggtgtgg agctgtacga aggctatggc cagtctgaaa | 1260 |
| cggttgtcat ctgtgccaat ccaaaaggca tgaaaatcaa gtctggatcc atggggaagg | 1320 |
| cgtccccacc ctacgatgtg cagattgtgg atgatgaggg caacgtcctg cctcctggag | 1380 |
| aagagggaa tgttgccgtc cgtatcagac ccactcggcc cttctgtttc ttcaattgct | 1440 |

| | | |
|---|---|---|
| atttggacaa tcctgagaag acagctgcat cagaacaagg ggacttttac atcacagggg | 1500 | |
| accgagctcg catggacaag gatggctact tttggttcat gggaagaaac gacgatgtga | 1560 | |
| tcaattcttc aagctaccgg atcgggcctg ttgaagtgga aagtgccctg gcagagcatc | 1620 | |
| ctgctgtcct ggagtcggct gtggtcagca gcccagaccc catcagggga gaggtggtaa | 1680 | |
| aggcatttat agtccttact ccagcctact cctctcatga cccagaggca ctaacgcggg | 1740 | |
| aactccagga gcatgtgaaa agggtgactg ctccatacaa ataccccagg aaggtggcct | 1800 | |
| ttgtttcaga acttgccaaa gacggtttct ggaaagatcc aaaggagtaa attgcgaagt | 1860 | |
| caggagtggg ggaaatgagg tgcaccccag gaaggcccg tagacctccg aagactccac | 1920 | |
| aagaaactaa tggatcactg gtcagtcccc atggggagca tcatctcttc gaccctaaag | 1980 | |
| atgtcaaagg tgtgcagctt ccaaacggca tccccaggat cactgggcaa tgctggaaag | 2040 | |
| agcaaaagaa tatcattggc cctgatcaca tagatgctgc gccgcctagc aaatgcttgg | 2100 | |
| tggttcgact tctccctctg tctggggca ggctcagcat ctgcccactg gtctcactaa | 2160 | |
| gagctttcag atttccctcc ataggacagg ttaccataga cttggggcac ttgtgggtac | 2220 | |
| tcattttctg ccagtgggaa tgtaaaggct tcatccttg tatgtaacca tttggcaaaa | 2280 | |
| gtatgcagga acataaaata aaatatcctt tagctcagaa attctatctt cgggagtcac | 2340 | |
| cacaaaagaa aaaatcaaa atgcagaaaa tgtgtggtgc actaagatga tcacacagca | 2400 | |
| ttaaaactaa aaaaaaaaaa gaaaaaatta acaattaaca tccaaacaac aaggaaatga | 2460 | |
| ttaacaaaac tgtagtagat taactcaatt acatatgatg tagccactaa aatatttgag | 2520 | |
| agcagtttag tatgtcttgg gaaaagtgta agctatatta atttaaaaa tcagagcaaa | 2580 | |
| aatattcata ctggagaatc ccaactctga aaaataaagg gaaaactgta gttaattgta | 2640 | |
| atcctcctgg agattgagga gggagggaga gaaattatgg atggtagttt ttcttcttcc | 2700 | |
| tttttccatt acatttctgt attttccaag tttttgga | 2738 | |

<210> SEQ ID NO 110
<211> LENGTH: 6108
<212> TYPE: DNA
<213> ORGANISM: Homo sapiens
<220> FEATURE:
<221> NAME/KEY: misc_feature
<223> OTHER INFORMATION: Incyte ID No: 3043830CB1

<400> SEQUENCE: 110

| | | |
|---|---|---|
| atgtctgctc cagacgaagg gagacgggat cccccaaac cgaagggcaa gaccctgggc | 60 | |
| agcttctttg ggtccctgcc tggcttcagc tctgcccga acctggtggc caacgcacat | 120 | |
| agctcgtccg gggccaaaga cctggtgtgt tccaagatgt ccagggccaa ggatgccgtg | 180 | |
| tcctccgggg tggccagcgt ggtggacgtg gctaaggag tggtccaggg aggcctggac | 240 | |
| accactcggt ctgcacttac gggcaccaag gaggcggtgt ccagcggggt cacaggggcc | 300 | |
| atggacatgg ctaaggggc cgtccaaggg ggtctggaca cctcgaaggc tgtcctcacc | 360 | |
| ggcaccaagg acacggtgtc cactgggctc acggggggcag tgaatgtggc caaagggacc | 420 | |
| gtacaggccg gtgtggacac caccaagact gtgctgaccg gcaccaaaga cacagtgact | 480 | |
| actgggtcg tgggggcagt gaacttggcc aaagggactg tccagactgg cgtggaaacc | 540 | |
| tccaaggctg tgctgaccgg caccaaagat gctgtgtcca ctgggctcac aggggcagtg | 600 | |
| aatgtggcca ggaagcat tcagaccggt gtggacacca gtaagactgt tctaacaggt | 660 | |
| accaaggaca ccgtctgtag tggggtgacc agtgccatga atgtggccaa aggaaccatc | 720 | |

-continued

```
cagaccggcg tggacaccag taagactgtc ctaacaggta ccaaggacac cgtctgtagt     780
ggggtgactg gtgccatgaa tgtggccaaa ggaaccatcc agaccggcgt ggacaccagt     840
aagactgtcc taacaggtac caaggacacc gtctgtagtg gggtgactgg tgccatgaat     900
gtggccaaag gaaccatcca gaccggcgtg gacaccacca agactgtcct aactggcacc     960
aagaacactg tctgcagtgg ggtgaccggt gccgtgaact tggccaaaga ggccatccag    1020
gggggcctgg ataccaccaa gtctatggtc atgggtacga agacacgat gtccactggg     1080 ctcacagggg cagcgaatgt ggccaagggg gccatgcaaa ctgggctgaa cacaacccaa    1140
aatatcgcaa caggtacaaa ggacaccgtc tgcagtgggg tgactggtgc catgaatttg    1200
gccagaggaa ccatccagac aggcgtggac accaccaaga tcgttctaac tggtaccaag    1260
gacactgtct gcagtggggt caccggtgct gcgaatgtgg ccaaaggggc cgtccagggc    1320
ggcctggaca ctacaaagtc tgtcctgact ggcactaaag atgctgtgtc cactgggccc    1380 acagggctg tgaacgtggc caaagggacc gtccagaccg gcgtagacac caccaagact    1440
gtcctaaccg gcaccaagga caccgtctgc agtggggtga ccagtgctgt gaacgtggcc    1500
aaaggggccg tccagggggg cctggacacc accaagtctg tggtcatagg tacaaaagac    1560
acgatgtcca ctgggctcac gggggcagcg aatgtggcca aggggctgt ccagacaggt    1620 gtagacacag ccaagaccgt gctgaccggc accaaggaca cagtgactac tgggctcgtg    1680
ggggcagtga atgtcgccaa agggaccgtc cagacaggc tggacaccac caaaactgtc    1740
ctaaccggta ccaaggacac catctacagt ggggtcacca gtgccgtgaa cgtggccaag    1800
ggggctgtgc aaactgggct gaaaacgacc caaaatatcg cgacaggtac aaagaacacc    1860
tttggcagtg gggtgaccgg tgctgtgaat gtggccaaag gggctgtcca gacaggtgta    1920
gacacagcca agaccgtgct gaccggcacc aaggacacag tcactactgg gctcatgggg    1980
gcagtgaatg tcgccaaagg gactgtccag accagtgtgg acaccaccaa gactgtccta    2040
actggtacca aggacaccgt ctgcagtggg gtgaccggtg ctgcgaatgt ggccaaaggg    2100
gccgtccaga cgggtgtaga cactacaaag tctgtcctga ctggcactaa agatgctgtg    2160
tccactgggc tcacagggc tgtgaacttg gccaaaggga ctgtccagac cggcatggac    2220
accaccaaga ctgtgttaac tggtaccaag gatgctgtgt gcagtggggt gaccggtgct    2280
gcgaatgtgg ccaaggggc cgtccagacg ggtgtagaca cggccaagac cgtgctgacc    2340
ggcaccaagg acacagtcac tactgggctc atgggggcag tgaatgtcgc caaagggacc    2400
gtccagacca gtgtggacac caccaagact gtcctaactg gtaccaagga caccgtctgc    2460
agtggggtga ccggtgctgc gaatgtggcc aaggggcccg tccagggggg cctggacact    2520
acaaagtctg tcctgactgg cactaaagac accgtatcca ctgggctcac agggctgtg    2580 aacttggcca aagggactgt ccagaccggc gtggacacca gcaagactgt cctgaccggt    2640
accaaggaca ccgtctgcag tggagtcact ggtgccgtaa atgtggccaa aggcaccgtc    2700
cagacaggtg tggacacagc caagacgtg ctgagtggcg ctaaggatgc agtgactact    2760
ggagtcacgg gggcagtgaa tgtggccaaa ggaaccgtgc agaccggcgt ggacgcctcc    2820
aaggctgtgc ttatgggtac caaggacact gtcttcagtg ggttaccgg tgccatgagc    2880 atggccaaag gggccgtcca gggggggcctg gacaccacca agacagtgct gaccggaacc    2940
aaagacgcag tgtccgctgg gctcatgggg tcagggaacg tggcgacagg gccacccac    3000 actggcctca gcaccttcca gaactggtta cctagtaccc ccgccacctc ctggggtgga    3060
ctcaccagtt ccaggaccac agacaatggt ggggagcaga ctgccctgag cccccaagag    3120
```

```
gccccgttct ctggcatctc cacgcccccg gatgtgctca gtgtaggccc ggagcctgcc   3180
tgggaagccg cagccactac caagggcctt gcgactgacg tggcgacgtt cacccaaggg   3240
gccgccccag gcaggagga cacgggcctt ttggccacca cacacggccc cgaagaagcc   3300
ccacgcttgg caatgctgca gaatgagttg gaggggctgg gggacatctt ccaccccatg   3360
aatgcggagg agcaagctca gctggctgcc tcccagcccg ggccaaaggt gctgtcggcg   3420
gaacagggga gctacttcgt tcgtttaggt gacctgggtc ccagcttccg ccagcgggca   3480
tttgaacacg cggtgagcca cctgcagcac ggccagttcc aagccaggga cactctggcc   3540
cagctccagg actgcttcag gctgattgaa aaggcccagc aggctccaga agggcagcca   3600
cgtctggacc agggctcagg tgccagtgcg gaggacgctg ctgtccagga ggagcgggat   3660
gccggggttc tgtccagggt ctgcggcctt tccggcagc tgcacacggc ctacagtggc   3720
ctggtctcca gcctccaggg cctgcccgcc gagctccagc agccagtggg gcgggcgcgg   3780
cacagcctct gtgagctcta tggcatcgtg gcctcagctg gctctgtaga ggagctgccc   3840
gcagagcggc tggtgcagag ccgcgagggt gtgcaccagg cttggcaggg gttagagcag   3900
ctgctggagg gcctacagca caatcccccg ctcagctggc tggtagggcc cttcgccttg   3960
cccgctggcg ggcagtagct gtaggagcct gcaggcccgg cgcggggtcg ccctgctctg   4020
tccagggagg agctgcctca gaactttctc cccgccccca aacctggatc ggttccctaa   4080
agccctagac ctttggggct gcagctggct gagcgccgag gggctgcgga ggcagtgacc   4140
ttcttaactg agccaccca cgccctgctc cgggcctgcc tgcatctccc acctcctccc   4200
cagcgctgcc tgcccctctc ggagcctggg gtcactcaga ccaccagcca agagccttcc   4260
cttgaagtcc ccaagcaagc actgcaatta ggaaagagaa aaagcagcgt gcccagcctg   4320
gaagggcatc tgtttgcccc gctagcaacc cttttatatc tagcagggct cttccagtcc   4380
tgcagcacgg gcccccagct atcagcggtg caggcagtgc tgtggcatcc caggctccgg   4440
gcagctccgt tctcatgctg aaagtgggtc tccggcctta gcacacacac cttgagggtc   4500
ttaagaacca cattccctca tagtagaaag tactagaaaa agcgacactg ccatcatcat   4560
cccaaggcag gctgctactg cctttgctga ccccgggt ggcctcacgg tggggacaaa   4620
gctgccagga gccacagcag ccacagctgg ggctttgcac cagcctggct tgagactgag   4680
cagtttgcag ggggtggggg gtgcaaaaaa caagcaaaca ggctgctgct gcctccagct   4740
gcccaccaca ggcctgcccc aggcacctgg ggctctgagg cccctgggga ggctgggccc   4800
agcagctgcc cctggagaac acagacaaag gacttccccg cagggaactg tgccctatgg   4860
agggatcaga cagggctggg aacagccaca gaggctgcgt gcctatggca cagcccttcc   4920
tccgccgcac actcccctg gtcctcagg cccacccaag cgccgggctg cagaggaagc   4980
ggggctgggg aggctgcagg catcagagac actggtggtg gcggaccggg ccgccgggcc   5040
ccgtgctctc aggctagccc aggtcgtgga ggctggcagg ctcaggtcgg gtgtgagacg   5100
tgccgtggct gcgctcagtc cagcggggag gagccgttca gccggcctc cccaggaagc   5160
catatcccca ctcacccggt aagagaacct tgtcgtcccc tttccatgct ctcctaggac   5220
acgagcccag gaacccagag cccaggggga ggaagggtgg agggccccca ggggtcacca   5280
tgtgcaccag gggccgtgag gggccggggc attcagctca gctctgaacc ggggaagctg   5340
gcacggcaag gactgcctca ggtgacgggc cgtgagaggg gacgggtcag gagccttccc   5400
aagccttctc ctcagcccga cacccatggc catcggaggc taggatgcca gacacagcca   5460
```

-continued

| | | |
|---|---|---|
| tttgcagaaa tcaggcacag tgactgcagc tcacgtccag ccaaccaagc atggggccgc | 5520 | |
| agctcaggaa gtcccttccc gccacaccac agcctaattc ttactgggac ggaggcaact | 5580 | |
| cggctacgct gggcaggacg acaaacacga dacgccactg tggaatgagc aacttcggag | 5640 | |
| cacggggtga cttgcttggg accgtgccca cgtgacagcc ccttatgcag gaggaaaag | 5700 | |
| agaagcccg agtgggaggg gaacctgtcc aaagtcacac ggtgtgtggg tgacacagct | 5760 | |
| ggggtgagtc gaggctggcc cctgaggccc atgctccctg aacgctggag accactgtcg | 5820 | |
| gctagcagcg gctctcaggg aaggcctggt ctccaccctc ccagcctagc ctcgcggacc | 5880 | |
| ctcgtcctcc ccacatcgga cctgctaccc tgcctggacc ctgggctgcc agatgcagga | 5940 | |
| agcatcaaac cccccagcct cgtgggtgcg ggcagggcg caggcagcac agcttagatg | 6000 | |
| ccctggtttg tccctcttgt ctcctgggaa gagcttgctc ccgcccagct tcctgccac | 6060 | |
| tggcctttca gggttgggct gggcccagag tgccttttag tcgcttct | 6108 | |

<210> SEQ ID NO 111
<211> LENGTH: 1110
<212> TYPE: DNA
<213> ORGANISM: Homo sapiens
<220> FEATURE:
<221> NAME/KEY: misc_feature
<223> OTHER INFORMATION: Incyte ID No: 002479CB1

<400> SEQUENCE: 111

| | | |
|---|---|---|
| ctgtgcacca ctgggcctgc ttcccctgcc ttgccccatt tccttagaca gagagaaagg | 60 | |
| gtcagatatg gcaagtcccg tctgttgacc atttcccgcc agcctctgcc atcccttctc | 120 | |
| ctgcagttgt gtcctgatgg ggctcaggcc agtaccatcc tatcagacag aatctgcacc | 180 | |
| aggtcccatg ggttccctgc cctctgagga ggctgtgggc tggcacagtc aggtcttgcc | 240 | |
| cctccttcct gtgttggctc agagaagctc tagaattaga gcagcccttc tggggtcctt | 300 | |
| ccaggccgcc ccgatccaca ccccacgtct gcgatgtctg ttcatgtgga aggtccctcg | 360 | |
| gggcctcttc agtgctgtgt gcacacagaa agacttggtc atgttgattg cacagatggc | 420 | |
| aggaggatgc ttgtttcctt gggtttccct ttttggccta tgggatgcgg gtgctctgcc | 480 | |
| catgatgtca gggacttccc cgcttggggg ccctgccaca ctcacaatcc cccgcgctca | 540 | |
| cctgggaacc cctggcactt gccctacccc cacgctgggc acgggcagca cctcttttcc | 600 | |
| cctcagcaca tccacagcc tggcattttc taaaaagctc aaccaagaaa tggagggaac | 660 | |
| actagagacc ttaataagtg aaggacatct ggattcggga ctagatttaa tcccagcacc | 720 | |
| ttggaggcca aggcgggaag atcacttgat accatcagtt caagatctgc tggtaacatg | 780 | |
| gcaagatctc catctccatt ttaatttttt aaaaaagtt taaaaagaa caaaaatggc | 840 | |
| cgggcgcggt ggctcatgcc tgtaatccca gcactttggg aggccgaggc gggtggatca | 900 | |
| cgaggtcagg agatcgaaac catcctggct aacatggtga aaaccgtct ctactaaaaa | 960 | |
| gacaaaaaat tagctggtgt ggtggtgggt tctgtagtc ccagctactc gggaggctga | 1020 | |
| ggcaggagaa tggggtgaac ccaggaagcg gacttgcagt gagctgaatc gcgtcactgc | 1080 | |
| actccagcct gggcacagag cgagtctctg | 1110 | |

<210> SEQ ID NO 112
<211> LENGTH: 1902
<212> TYPE: DNA
<213> ORGANISM: Homo sapiens
<220> FEATURE:
<221> NAME/KEY: misc_feature
<223> OTHER INFORMATION: Incyte ID No: 1395420CB1

<400> SEQUENCE: 112

```
tagaaaagat cttttgatca cctttatttt aacagaaata gctctagtgt cacatggtcc      60
tttctccctt cttgcttttg gaaggaatcc aaagctaatc tgtccctgat ccggattgca     120
cgcacctgtg cctttgggg cccttctgca ttagttcttc cttctcttct aacctcaaaa     180
atgtgttttt tctattggct ctttcccttt aacatagaag tatactcacg cttttgttga     240
atcttgaaat aaaagtcttc ctttaccaca tatctccctt taatactaca tctctcttct     300
cagccaaata cttgggaaga gaagccctga gtttgtgtca ttgttttctc acctccagtt     360
cactactttg cccactgcct gacatccagc tcactcacac acacacacaa gcccaatcac     420
taagttgcca tagctaattt gtagctttcc tgccttcctg gcaaaatttg actctgcatt     480
gggataatac atgtcgagta cctattgaac aggcactgtg ctaggtgcta ctgttataga     540
tatgaaaaga aggcatcatc tcctttctaa caactcacag gagcagccat tcctgattca     600
tacatgtctc ttgactccca gtgctcactt tttcaagctt cacttaatgc cgtgcaaatc     660
accctattct ccaggtcttc tttcttccca gttctcctta ctatacacaa cttctcaagg     720
cagtcacctc cacacccatg gcttcaattg cttttctcca t tctctgagaa caatagaatt    780
ttaaatggtt ttatttcatg tattagcttt attttataca aggtgcctca cctgctgtaa     840
ccatagattc aaagttgctc catgaaagta ataaatgaaa aatggtgatt ttttagcatg     900
taaattttag gaaatttccc cagttacgct taatggcttg atttagtgtg tatgttattt     960
ttgaaaacat atgttgggat gtcacaaatg gacttagcct acagagattt atattcaact    1020
tttgaccaga gagttccatt ttaatgtgac actgagagta aaaaactatc ttttcctcct    1080
tacctatttc tcttcctaca ttctcggcca ggaggaaggc actgctacat acccagtctt    1140
ccccagcaga gcctgagcag ctctgttttc cttctacttc ccctcttctt tcacatctca    1200
tgaccaagca cttcctattc tgtctcccaa atgatcacag acttttttcct ccacttttgt    1260
cactgccact gcccttagca ttactctgcc tttagagaaa gtctcttaat tggtttggtt    1320
gcttccttca gtctttatta tacagaccac tacacgcaca tctgacagag acttttcacc    1380
ttttttatggt tgaatgactg aaattcccag aataaaatta aaaccacccc agcatcaaat    1440
ttgaggtcaa atagaggtgg gtttgtatcc caggttcata tactgtccag cagtatggtc    1500
tcagaaaact gacctcctta agcctttgtt tgtgtatctg cctaaactca ttgagagttg    1560
ggactatttc acacatacag tgcctggcat gtagaaggga cttaatgttg aaagaagggg    1620
aggcatttta aaatccacat caaaaaaatg ttgttctgtt cgtgagccac cgcgcctggc    1680
ctgtttattc tcttaagaga gaaatgagg ggattaatgg actgtagttc tggacaaggt    1740
ggaaaactct taaagtggaa gtactgggc aagtgctctg acagggtagg atggtgcagt    1800
cagtcccttc actcagaaat cagtagaatg ttagcagttc agacttcaac cttgtgaaaa    1860
acaggtggtg gaaggaaat ccctcacagc cactgggcac ca                         1902
```

<210> SEQ ID NO 113
<211> LENGTH: 1960
<212> TYPE: DNA
<213> ORGANISM: Homo sapiens
<220> FEATURE:
<221> NAME/KEY: misc_feature
<223> OTHER INFORMATION: Incyte ID No: 1634103CB1

<400> SEQUENCE: 113

```
gggggcacct ctggtgacca agaccgggct gcgctccaaa gaggccgttg ggcctggagt      60
```

```
ggggttgggg gggtccgaga ggagttgggt gacatccccc accccatccc gggtccagct    120
gtttcagccc ctctcggcgc gccgatacta ttagccccac ccgtcctcca tcgagtcccg    180
tgccgctccc aaaccgcacg ataagcccca cagggagtgc gccataggcc ggggcgcgtc    240
acggggccgg ggcggggcgg agtccggacg tcgggagcag gatggcggcg gagcaggacc    300
ccgaggcgcg cgcggcggcg cggccgctgc tcactgacct ctaccaggcc accatggcgt    360
tgggctattg gcgcgcgggc cgggcgcggg acgccgccga gttcgagctc ttcttccgcc    420
gctgcccgtt cggcggcgcc ttcgcctggg ccgccggctt gcgcgactgt gtgcgcttcc    480
tgcgcgcctt ccgcctgcgg gacgccgacg tgcagttcct ggcctcggtg ctgccccag    540 acacggatcc tgcgttcttc gagcaccttc gggccctcga ctgctccgag gtgacggtgc    600
gagccctgcc cgagggctcc ctcgccttcc ccggagtgcc gctcctgcag gtgtccgggc    660
cgctcctggt ggtgcagctg ctggagacac cgctgctctg cctggtcagc tacgccagcc    720
tggtggccac caacgcagcg cggcttcgct tgatcgcagg gccagagaag cggctgctag    780
agatgggcct gaggcgggct cagggccccg atggggcct gacagcctcc acctacagct    840
acctgggcgg cttcgacagc agcagcaacg tgctagcggg ccagctgcga ggtgtgccgg    900
tggccgggac cctggcccac tccttcgtca cttcctttc aggcagcgag gtgcccctg    960 acccgatgtt ggcgccagca gctggtgagg gccctgggt ggacctggcg gccaaagccc    1020
aggtgtggct ggagcaggtg tgtgcccacc tggggctggg ggtgcaggag ccgcatccag    1080
gcgagcgggc agcctttgtg gcctatgcct tggcttttcc ccgggccttc cagggcctcc    1140
tggacaccta cagcgtgtgg aggagtggtc tccccaactt cctagcagtc gccttggccc    1200
tgggagagct gggctaccgg gcagtgggcg tgaggctgga cagtggtgac ctgctacagc    1260
aggctcagga gatccgcaag gtcttccgag ctgctgcagc ccagttccag gtgccctggc    1320
tggagtcagt cctcatcgta gtcagcaaca acattgacga ggaggcgctg gcccgactgg    1380
cccaggaggg cagtgaggtg aatgtcattg gcattggcac cagtgtggtc acctgccccc    1440
aacagccttc cctgggtggc gtctataagc tggtggccgt ggggggccag ccacgaatga    1500
agctgaccga ggaccccgag aagcagacgt tgcctgggag caaggctgct ttccggctcc    1560
tgggctctga cgggtctcca ctcatggaca tgctgcagtt agcagaagag ccagtgccac    1620
aggctgggca ggagctgagg gtgtggcctc caggggccca ggagccctgc accgtgaggc    1680
cagcccaggt ggagccacta ctgcggctct gcctccagca gggacagctg tgtgagccgc    1740
tcccatccct ggcagagtct agagccttgg cccagctgtc cctgagccga ctcagccctg    1800
agcacaggcg gctgcggagc cctgcacagt accaggtggt gctgtccgag aggctgcagg    1860
ccctggtgaa cagtctgtgt gcggggcagt ccccctgaga ctcggagcgg ggctgactgg    1920
aaacaacacg aatcactcac ttttccccac aaaaaaaaa                          1960
```

<210> SEQ ID NO 114
<211> LENGTH: 540
<212> TYPE: DNA
<213> ORGANISM: Homo sapiens
<220> FEATURE:
<221> NAME/KEY: misc_feature
<223> OTHER INFORMATION: Incyte ID No: 2422023CB1

<400> SEQUENCE: 114

```
gcgatcccag tttccatttc aatctgtatt cactcgtagt gagtttcctt gaatgggatt     60
tcaagcggag aatgggggag tctcacttcc ccgccgcctt gccccattgg cctgggccag    120
```

-continued

| | | |
|---|---|---|
| ttctccactc ctaggggcca agccaccct agccttggtg ggggaaaggc agggcccacc | 180 |
| cgggccagcc cgtgccctga ggggctcttg acacccacgt agaattctct acacaccagt | 240 |
| aacgggattt caattccgat ggactctgcc gccctggcgg cccttcctgt gacttttgcg | 300 |
| ccccgcgcct ggggtggggg gtgcgaagag acgctacgtt cctttccgat ggaggaaggc | 360 |
| agacctgccg tcacacgtgt gcttgcacga gtgcgtgtac ctggtgcggg actcacccgg | 420 |
| ccgccagact gcctgggcct gcccagatgg ccacctcgtg gtgctgcggt gactttgtag | 480 |
| ccaactttat aataaagtcc agtttgcctt tttggtaaaa aaaaaaaaaa aaaaaaaaa | 540 |

<210> SEQ ID NO 115
<211> LENGTH: 1321
<212> TYPE: DNA
<213> ORGANISM: Homo sapiens
<220> FEATURE:
<221> NAME/KEY: misc_feature
<223> OTHER INFORMATION: Incyte ID No: 4241771CB1

<400> SEQUENCE: 115

| | | |
|---|---|---|
| tgattttcta tacatgctca ggacagtagt ttcactcata gatgaaaagt tagaatttgg | 60 |
| atttatttga aatatataca aatattcaag tatatacata tattcaaata aatacatata | 120 |
| tgtatatatg tgtgtatata cacacataca tacacatgaa tcatcattgc cttcttgaga | 180 |
| tctcaccact ttagtcctac taaaagatgg gtggttgttg gttttttttt gttgttgttg | 240 |
| ttgttttta aattccaatc tgtatggaat gatactttaa taaaattatg tgctcggatg | 300 |
| ttgaataaat gtcaaattgc cataaaagtt tctaaacact ctcagtcact gcttatctca | 360 |
| tccctgactg gtcacaaaca gtttgtagac tggctccaac ctggaccaca tttgtatagt | 420 |
| attgacttag aatttaacag aaaattgagg acaaggaaga tgagaaagcc agtgaccacc | 480 |
| tagaaggaaa atagttaaca tggagcattg tcgagtccat gctagttacc tttagttaca | 540 |
| tattctgatt ctgttaaaaa aagagagaga cctggttaat ggtttaataa ccatggtctg | 600 |
| tcagttggtc tgtctgtctc tctccctccc tctcttttct gtaaagggcc agttagtaaa | 660 |
| tattttagat tttgtaacca actacccaac tctgcccctta tagagcaaac acaactacag | 720 |
| acattaaaac cagtgagtat ggctgtgtcc caatacactt catttccaaa aacaggcagt | 780 |
| ggggcctgac ttggcctgag gaccacagtt tgccagctcc tggtctaaga tatcatgaat | 840 |
| atcttgggat acagagtatc aggaataagt ttttcctgc tgtttcttaa tggtttattg | 900 |
| agttgtcagc ccaatatcta ctatatagct aactcctccc tggtatgtga tgagtatagt | 960 |
| aggcctgcct tcataccagg acttcagaaa atgtttgatg atgctgtaga aatatctgcc | 1020 |
| ctaggccggg tgcagtggct tacacctgta atctcagcac tttgggaggc caagggaggt | 1080 |
| ggatcacctg aggtcaggag ttcgagacca gtgtggccag tgtggcaaaa ccccatctct | 1140 |
| actaaaaata caaaaatta gctgggtgtg gtggcgggtg cctgtaatcc cagctacttg | 1200 |
| ggaggctgag gcaggagaac tgcttgaacc tgggaggtgg aggttgcagt gagccaagat | 1260 |
| tgcgccattg cactccagcc tgggtgacag agtgagactc tgtctcaaaa aaaaaaaaa | 1320 |
| a | 1321 |

<210> SEQ ID NO 116
<211> LENGTH: 536
<212> TYPE: DNA
<213> ORGANISM: Homo sapiens
<220> FEATURE:
<221> NAME/KEY: misc_feature -continued
<223> OTHER INFORMATION: Incyte ID No: 5046408CB1

<400> SEQUENCE: 116

| | | |
|---|---|---|
| cgggaattaa ttccccgggt ccacgagctt cactaatccg cgggccgctt tcatccttaa | 60 |
| tagcaggccc aaatcccaat ccttgcctcc tttccagaag aaaattccaa gacgagtgcc | 120 |
| agaaatttat ctgaaggcag cttgaaaaac atcacttcta aagagaacat taactgaggg | 180 |
| aaaactgaag gaagagtgat gaaaagtgaa aggcactcat aggaaggcat ggaaacacac | 240 |
| aaggttgaca ttcctcaggc gcagaattgc taagtaagca tatttagtgc aaatgtccac | 300 |
| catagtctat attctattct tttcaggttt tctgaacagc agtgggggct ctcgctgggg | 360 |
| tcttcagcac catcttggag gttgccatgg tgaggggatt gggagctgcc aggggaacct | 420 |
| ggaggagact cttctcacag gcccttttcca ggcccatac ccagggcccc ctgagcaggc | 480 |
| agcttggaca ggagtcagtg gctgtggatg cccagatgtc ctcaccttag agtgag | 536 |

<210> SEQ ID NO 117
<211> LENGTH: 1345
<212> TYPE: DNA
<213> ORGANISM: Homo sapiens
<220> FEATURE:
<221> NAME/KEY: misc_feature
<223> OTHER INFORMATION: Incyte ID No: 6271376CB1

<400> SEQUENCE: 117

| | | |
|---|---|---|
| gcacggctca ctaatggcgg ccccctttt ttttttttga gacagagtct cacgctctgc | 60 |
| agcccaagct ggagtgagtg gtgcaacctc agctcactgc aagcctctgc ctcccaggtt | 120 |
| caagtgattc tcctgcctta gcctcccgag tacctgggat tacaggcaca caccaccacg | 180 |
| tccagctaat ttttgtattt ttagtagaga cagggtttca ccatgttggg caggctggtc | 240 |
| tcaatccctg gacctcaagt gatccacttg ccttggcctc caaaggggt gggattacat | 300 |
| gcatgagcca ctgtgcctgg ctcacacatt tcttgaatca tgcccaggtt atgagaatag | 360 |
| agggtcaggg ccagaatctt ggaatatgag ttctagaaag ggttttcgtg ataccctggc | 420 |
| tggctttctt cacttggcat ttaaggaaac taaactcaga cgggaagagc ttgcccaaga | 480 |
| gcatgcagct actggtctgg ctgtgtctcc tcggtgccag ccatgcaggc ctctccccat | 540 |
| ctgaccttca ctcggggacc ttccctggct gtgctgaaac ccatggcttc atgagttgtg | 600 |
| ctgagccctc cccagtcgac agtggtgaag atcgaaagat tttgctggat tctagaccgt | 660 |
| ggtttctcaa tctcagccct attggtattt gcggccgggt aattctttgc tgtgtgggag | 720 |
| ctgtcctgtg tattgtagga cactgagcag catcaatggc ctctacctac tggatgcagt | 780 |
| agaccgctcc cccgacaatc tcacaaccaa ctccagacct tggcaagtgt gccctgggga | 840 |
| gcaaaatcac cttcagttaa gaaccactgc tccagagcat aagaactac tcagctttgg | 900 |
| cagaaaggga atcccaaaat ataagctcaa ttcattttat tttattttgt tttgtttttat | 960 |
| ttttatttt cattattatt attgagatga gtttcgctct ttcgcccagg ctggagtgaa | 1020 |
| gtggcacaat ctcagctcac cgcaacctcc gccctccctc cccaccacca ggttcaaggg | 1080 |
| attctcccgc ctcagcctcc cgagcagctg ggaccacagg tgcccaccac catgtctagc | 1140 |
| caattttttc atcttcagca gggacagagt ttcaccacat tggccaggct ggtctcaaac | 1200 |
| tcccgactca agcgatccac ccgcctcagc ctcccaagtg ctagggttga caggcgtgag | 1260 |
| ccaatgtgcc tgggcagtca attaaaacgc agatacagta cttttcctcc atgatcctat | 1320 |
| gtgtgataag ctgtcctgta agtgt | 1345 |

<210> SEQ ID NO 118
<211> LENGTH: 1060
<212> TYPE: DNA
<213> ORGANISM: Homo sapiens
<220> FEATURE:
<221> NAME/KEY: misc_feature
<223> OTHER INFORMATION: Incyte ID No: 7032326CB1

<400> SEQUENCE: 118

| | | | | | |
|---|---|---|---|---|---|
| agcccctaac | cgcgagtgat | ccgccagcct | cggcctcccg | aggtgccggg | attgcagacg | 60 |
| gagtctcgtt | cactcagtgc | tcaatggtgc | ccaggctgga | gtgcagtggc | gtgatctcgg | 120 |
| ctcgctacaa | cctccacctc | ccagccgcct | gccttggcct | cccaaagagc | cgagattgca | 180 |
| gcctctgccc | ggccgccacc | ccgtctggga | agtgaggagc | gtctctgcct | ggccgcccat | 240 |
| cgtctgggat | gtgaggagcg | tctctgcccg | gctgcccagt | ctgggaagtg | aggagcgcct | 300 |
| cctcccggcc | gccatcccgt | ctaggaagtg | aggagcgtct | ctgcccggcc | gcccatcgtc | 360 |
| tgagatgtgg | ggagcgccac | tgccccgccg | ccccgtccgg | gaggtgcctc | ggcttccgca | 420 |
| tctgtcgtat | gacccgtgat | ctctgggaag | ccacacagct | caaggtcttg | ggcacgtca | 480 |
| tggaggctcc | ggaagcgtca | cttaccctgt | ccctgtcggc | atcatcatcg | tcagcatcgt | 540 |
| ttaagaatca | agccctgttt | tcttcttctg | accactgggt | ggctccgcag | aattggttct | 600 |
| gtgattatcg | cgctctcaaa | ggcggccttg | gggtttgggt | gaacagtatg | ataatgctgg | 660 |
| tttgtcgtag | gtcaaaaaca | gcaaattatc | tgcaatgtca | tgtggttcta | cctaatgctt | 720 |
| gcggtgtccc | tgccctgggc | tgtttcccct | cggcttcatc | tcagcgaatc | acgaacacat | 780 |
| tccacggact | cacctccttg | gaagcctttt | ggattctctg | cgcagcccaa | gctgcccggg | 840 |
| atctgggagg | ccaggctgag | tctatggccc | cggagcccgc | ccggacttgc | cactggagac | 900 |
| ctggggccaa | gggcccatcc | gagctgggaa | gagagggcta | gaaagagagc | attagaatcg | 960 |
| aggggctggg | tgcggaggct | cacgcctgtc | atcccagcac | tttgggagcc | gagggagatg | 1020 |
| gatcacctga | ggttaggaat | tcaagagcag | cctggccaac | | | 1060 |

<210> SEQ ID NO 119
<211> LENGTH: 1192
<212> TYPE: DNA
<213> ORGANISM: Homo sapiens
<220> FEATURE:
<221> NAME/KEY: misc_feature
<223> OTHER INFORMATION: Incyte ID No: 7078691CB1

<400> SEQUENCE: 119

| | | | | | |
|---|---|---|---|---|---|
| agaatgggtt | tcgccacgtg | ggccaggctg | gtctcgaact | cctgacctca | ggtgatccgc | 60 |
| cggccttgcg | ttcccaaagt | gctgggattg | caggcgtgag | ccaccgtgcc | tgtaagcatt | 120 |
| cattcttagg | gatctgcggt | tggctggggt | ttgcccggtc | tagacaaagc | ttgactgagt | 180 |
| cagttctgca | tctcactatg | gtcaactgag | ggtgacctga | cctgggatgg | actgtaccct | 240 |
| cctgtctctc | ctgtctgtcc | tcctccttgg | accaggatt | tgtcagggat | gtcttctcgt | 300 |
| ggcaacctca | gatgctcagc | agggcaagca | ggaaggcatg | aggcctctga | gccagggctc | 360 |
| agaactgaca | cgctgccacg | tcctcccacg | tgctgtcagt | cagagcaagt | tagatgacca | 420 |
| agcagagcca | aaaagtgagg | aaataaattc | cttctgtgat | gaggccgtgg | caagggtatg | 480 |
| ggtgcaggga | gtgggaaata | atctggacca | aagactcaat | ctcccacccc | caccccctgc | 540 |
| aattaggact | taataaaagg | agtcaggagt | gcattgtccc | agtccagcag | agatcttcc | 600 |
| ctggccaata | attatctaat | aattaggagt | gttattccac | cctggggtgt | gggcccagct | 660 |

```
ttgtgctgaa tgccatggcg ggggcatcag aagaagaggg aaaagcccca attttgcctt      720
ccagagctct gttctctgag ggataagact tgtgttcccg agatggagat gagacgatgt      780
tcagtggtgt aatgctgact atggagctca gagaaagaaa ccagcaaagg ccaggaaaga      840
actacatggg aggagaagaa tggcactggc aaccggcatc cagggagcgc ttgctgcagg      900
ctgcatgctg aggcgaattt cctccacacc ttacttcctc tcataaccat cctgagaggt      960
actgggattg tccttcactt aacaggtgaa gaaacagagg cacaaagagc tccagtgact     1020
tgcctgtggt cacatagctg gtaaatgctg gcaccagcat ttgacaacag agctgagcgt     1080
atcactaggc catggtagga cacccaaatg aagggagcac caaggtcaaa cgattgcgaa     1140
gcacgtgcag ggctgaccga agggattcct gtttacttta gggcccatat tt             1192

<210> SEQ ID NO 120
<211> LENGTH: 693
<212> TYPE: DNA
<213> ORGANISM: Homo sapiens
<220> FEATURE:
<221> NAME/KEY: misc_feature
<223> OTHER INFORMATION: Incyte ID No: 7089352CB1

<400> SEQUENCE: 120
gggtctcaca tgcctgtgag cagcatgtta ccccatttac agatgggggc acagagccct       60
gagaggttga gcaatgtgcc cacagtgggc cagtagcaga ctctgagcct ggagcctggg      120
tgcttatgga gatgctcgtt caagagcgtg gggaaaagaa agggcgatca gactgttact      180
gtgtctatgt agaaaaggaa gacataagaa actccatttt gatctctttc ttttccccac      240
acaagggcat caggcagacg tgtgggctcc tgcatgggcg cctgtcttga ttgactgcgt      300
tgctcactca gcagacattt actaagcacc tgctgtatat gaagccctgt gcaagggggc      360
tgtcagtgtt cagttgtgtc gtgtgtgtcc tatgtcttgt ctggccatgt cttgcttcag      420
gcaggtttac tggtggcagg tgcatgtgct tttgtgaggt ctcgagggg gaattgaaga      480 gaagcaggga ggaagcccta cccctcctcc ctgacaggct gagccccagc tctgccatta      540
gaagtgggtg gattttggct gggcgaggta gctcacgcct gtaatcccag cactttggga      600
ggccaaggcg ggtggatcat gaggtcagga gttcaagacc cacctggcca agatggtgaa      660
actccatctc tactaaagac acaaaaatta gcc                                   693

<210> SEQ ID NO 121
<211> LENGTH: 888
<212> TYPE: DNA
<213> ORGANISM: Homo sapiens
<220> FEATURE:
<221> NAME/KEY: misc_feature
<223> OTHER INFORMATION: Incyte ID No: 7284533CB1

<400> SEQUENCE: 121
ggggtggcga cagaggaaga gggcgctgaa accaaaatgt attttgtga actacactca       60 agaattgcag tgtgtgactg catgtgtgaa gtgagaggga aagcaaaaat caagaataat      120
gccaactttt ttagcttcag cagttggcta gtggcagtgc tatttagtga gagaagttgg      180
gggttggaaa tcaagagttc atgttcttga acaagttaaa cttgagattg tcttgtgaaa      240
tcccagtagg aatctcaatg cgggtagttt ggatgtgcaa gtcttggagc tcagggtgt      300 gatccaggat agagatagaa attttgggag tgatgatagt atggaagata ctaagagcct      360
cagtctggaa gcatttacct aggaagcgca tatagacaga gaagatcaag gactgaggcc      420
```

| | |
|---|---|
| tgagacagtc agcacttaaa gggtgagcag gagaagtgcc aaggagacaa ggtgagaaca | 480 |
| gcagaagagt agccaaggcc caggatgttg ccacagaagc caggagaggt gagcatgaaa | 540 |
| acagaggagg accagctgct gggacagaag agccatatgg aagagctagc agcgtggaag | 600 |
| tgactttcaa gagcatcttc catggcatca tggaacaggg acctgactgg agaggttgga | 660 |
| agggctaagg gagctgagtg agcaggggca gtgggtacag accactcggt ggagaaattc | 720 |
| agacatgaag gggaacacca acttacaaag tccctggaag aagttccggg aaacacattt | 780 |
| ggccagtaaa tatacaaaga gacatccagc tttgctagtg atgagggaaa tgcaaatcaa | 840 |
| gacacaatgg gatatcattt tacatccatt ccactgggaa aatgtttt | 888 |

<210> SEQ ID NO 122
<211> LENGTH: 618
<212> TYPE: DNA
<213> ORGANISM: Homo sapiens
<220> FEATURE:
<221> NAME/KEY: misc_feature
<223> OTHER INFORMATION: Incyte ID No: 7482209CB1

<400> SEQUENCE: 122

| | |
|---|---|
| tgagctgagg gtattaagat ggagagtgtt ggcgtgtacg gattctgtgg gtgtaaagca | 60 |
| aagaacaaaa tgaagtgtga ttcaaggtgg gaaatagccg cttcagctcc cccaggctgc | 120 |
| agcagctacc acacaaagaa gcagtcctat ggcaatgaca ggacatctgt gtccaggatt | 180 |
| tggatttgac gaactggcag ttcctgcagg gatgacggta ctccctagtt gtgtctgaat | 240 |
| tggacgcacc agcacttgag cacacacaaa tgcacgtgaa cagacggaac atgttatggg | 300 |
| cctgttagcc aaggaatgac agaattaatc catgggcatt tgcggccagt gttgtgttaa | 360 |
| actaagggaa aaagtgaac tggaaaaagc aatgtttgtt ttatgaaaat ctcagaccca | 420 |
| atccttaggt gacagttctg gaaatgaggg gtgtctaaaa caagggcat ctgaaacttc | 480 |
| ggttttcag cttcctttcc ttgtctcatg acctctttcc tacccgctgc ctctgttttc | 540 |
| tctaatatgg aacagtgaaa atgggggcca gcaaaacaga ttgctgatgt ctgttgattt | 600 |
| tatcaaaggg aggttaga | 618 |

<210> SEQ ID NO 123
<211> LENGTH: 755
<212> TYPE: DNA
<213> ORGANISM: Homo sapiens
<220> FEATURE:
<221> NAME/KEY: misc_feature
<223> OTHER INFORMATION: Incyte ID No: 7482314CB1

<400> SEQUENCE: 123

| | |
|---|---|
| acgtggatgt gaccacaact gcatgccact ccctccaccc ccatctgcct accagctaat | 60 |
| tcaaaaaaat ttttttttgt agagatgggg tctccctgtg ttgcccaggt cagtctcgaa | 120 |
| ctcctaggct caagcaatcc tcctgccttg gcttctcaag gtgctgggat tacagacatg | 180 |
| agccactggg ctcagccatt aattttaaat tgcaagtgac atattcttta gtttattaat | 240 |
| cagcaccata tgatgtcaca gttttataac tcatttatct catttaattc tcatacccac | 300 |
| cttgtggaat tgttatcact gtcctttaca gatgaagaaa gaaactccaa gaaattaagt | 360 |
| agctggccca agtccaccca actgggatgg gcagaaccag ggtttgctct tggttgtgcc | 420 |
| tttctacagc ctgtgcctta accacatcta tgtgctgcct cttggcctct gtgtggccag | 480 |
| tagattctct catggctagg ctcatcttaa ttaacatttg ttgggtgcct actatggctc | 540 |
| aggctctaga gatcattgta aaatccagtc cactgcccca gctcctcgtg tgtcttttga | 600 |

```
acacattagt attgtgctgt gcagaaagga cttctgtgca tatgcctgct attacacttg    660
ttgaacccaa tttctacaaa ctttcattca gatggaggga ttcagtcttc ttatcatata    720
atacatacag aaataccaat atttaaatat ttatc                              755
```

<210> SEQ ID NO 124
<211> LENGTH: 386
<212> TYPE: DNA
<213> ORGANISM: Homo sapiens
<220> FEATURE:
<221> NAME/KEY: misc_feature
<223> OTHER INFORMATION: Incyte ID No: 7482339CB1

<400> SEQUENCE: 124

```
ttagttgatc atctcctatg ggcttccctt tgcttgttcc cttaggctta agggtggtga     60
taactctctg cctggccagt gtgtggtcat gtcacctctc gttgttggtg tcactgtacc    120
ctgcccactc cacctgtaac cagtccttcg tgaaactccc ttcagttgct ctgagtcttc    180
catctttctc ctgcagggtc ctttacaaaa gggctctgga atcaaagggg cagctggcgg    240
tggagacggc cctcagagca aggacatcag tgatgtggat cagcggctgc agctgaggag    300
agcgactcag tcccagtccg ctgaaggagg acatgaagt caagggagag gcagctggca    360
gacctagcag ggaccctcta aagtcc                                         386
```

<210> SEQ ID NO 125
<211> LENGTH: 524
<212> TYPE: DNA
<213> ORGANISM: Homo sapiens
<220> FEATURE:
<221> NAME/KEY: misc_feature
<223> OTHER INFORMATION: Incyte ID No: 7949557CB1

<400> SEQUENCE: 125

```
ttcggctcga gctcaagatc tgtttttaag gcatgtgtca ccacatctgg ctgattttta     60 atttttaaa tagaatctgg gtcttgtcat gttgcctagg ctggtctcgg actgctgagt    120
tcaagagatc ctcctgccac gaccttccag agcgctggga ttataggcaa gagccactgt    180
gcccagccag ccaaaactct ttaatgagga ttggtttagc atttagagag agagcgagca    240
agcctcccat ctgcccagca cagcctccca cccctcatg gcagtgtagc tgttcttctc     300
tgaagaggca ggaagatgct ggggaaggga gaggagaggt agttagttgg aggtgatgaa    360
atggtcagaa gagagaaagg agaaacaggg cagggttcgg cagtgcacag ccgggttgct    420
ggtcccattg gctgtggtca gcatggctgc cttctcctgc ttcacttcct atggccacag    480
agcccaattt ttctgcatct tcttaacact tgcagagccg gcgg                    524
```

<210> SEQ ID NO 126
<211> LENGTH: 3836
<212> TYPE: DNA
<213> ORGANISM: Homo sapiens
<220> FEATURE:
<221> NAME/KEY: misc_feature
<223> OTHER INFORMATION: Incyte ID No: 1555909CB1

<400> SEQUENCE: 126

```
cagggcgtct ccggctgctc ccattgagct gtctgctcgc tgtgcccgct gtgcctgctg     60
tgcccgcgct gtcgccgctg ctaccgcgtc tgctggacgc gggagacgcc agcgagctgg    120
tgattggagc cctgcggaga gctcaagcgc ccagctctgc cccaggagcc caggctgccc    180
cgtgagtccc atagttgctg caggagtgga gccatgagct gcgtcctggg tggtgtcatc    240
```

| | |
|---|---|
| cccttggggc tgctgttcct ggtctgcgga tcccaaggct acctcctgcc caacgtcact | 300 |
| ctcttagagg agctgctcag caaataccag cacaacgagt ctcactcccg ggtccgcaga | 360 |
| gccatcccca gggaggacaa ggaggagatc ctcatgctgc acaacaagct tcggggccag | 420 |
| gtgcagcctc aggcctccaa catggagtac atgacctggg atgacgaact ggagaagtct | 480 |
| gctgcagcgt gggccagtca gtgcatctgg gagcacgggc ccaccagtct gctggtgtcc | 540 |
| atcgggcaga acctgggcgc tcactggggc aggtatcgct ctccggggtt ccatgtgcag | 600 |
| tcctggtatg acgaggtgaa ggactacacc taccctacc cgagcgagtg caacccctgg | 660 |
| tgtccagaga ggtgctcggg gcctatgtgc acgcactaca cacagatagt ttgggccacc | 720 |
| accaacaaga tcggttgtgc tgtgaacacc tgccggaaga tgactgtctg gggagaagtt | 780 |
| tgggagaacg cggtctactt tgtctgcaat tattctccaa aggggaactg gattggagaa | 840 |
| gcccctaca agaatggccg gccctgctct gagtgcccac ccagctatgg aggcagctgc | 900 |
| aggaacaact tgtgttaccg agaagaaacc tacactccaa aacctgaaac ggacgagatg | 960 |
| aatgaggtgg aaacggctcc cattcctgaa gaaaaccatg tttggctcca accgagggtg | 1020 |
| atgagaccca ccaagcccaa gaaaacctct gcggtcaact acatgaccca agtcgtcaga | 1080 |
| tgtgacacca agatgaagga caggtgcaaa gggtccacgt gtaacaggta ccagtgccca | 1140 |
| gcaggctgcc tgaaccacaa ggcgaagatc tttggaagtc tgttctatga agctcgtct | 1200 |
| agcatatgcc gcgccgccat ccactacggg atcctggatg acaagggagg cctggtggat | 1260 |
| atcaccagga acgggaaggt cccccttcttc gtgaagtctg agagacacgg cgtgcagtcc | 1320 |
| ctcagcaaat acaaaccttc cagctcattc atggtgtcaa aagtgaaagt gcaggatttg | 1380 |
| gactgctaca cgaccgttgc tcagctgtgc ccgtttgaaa agccagcaac tcactgccca | 1440 |
| agaatccatt gtccggcaca ctgcaaagac gaaccttcct actgggctcc ggtgtttgga | 1500 |
| accaacatct atgcagatac ctcaagcatc tgcaagacag ctgtgcacgc gggagtcatc | 1560 |
| agcaacgaga gtgggggtga cgtggacgtg atgcccgtgg ataaaaagaa gacctacgtg | 1620 |
| ggctcgctca ggaatggagt tcagtctgaa agcctgggga ctcctcggga tggaaaggcc | 1680 |
| ttccggatct ttgctgtcag gcagtgaatt ccagcacca ggggagaagg ggcgtcttca | 1740 |
| ggagggcttc ggggttttgc ttttattttt attttgtcat tgcggggtat atggagagtc | 1800 |
| aggaaacttc ctttgactga tgttcagtgt ccatcacttt gtggcctgtg ggtgaggtga | 1860 |
| catctcatcc cctcactgaa gcaacagcat cccaaggtgc tcagccggac tccctggtgc | 1920 |
| ctgatcctgc tggggcctgg gggtctccat ctggacgtcc tctctccttt agagatctga | 1980 |
| gctgtctctt aaagggggaca gttgcccaaa atgttccttg ctatgtgttc ttctgttggt | 2040 |
| ggaggaagtt gatttcaacc tccctgccaa agaacaaac catttgaagc tcacaattgt | 2100 |
| gaagcattca cggcgtcgga agaggccttt tgagcaagcg ccaatgagtt tcaggaatga | 2160 |
| agtagaaggt agttatttaa aaataaaaaa cacagtccgt ccctaccaat agaggaaaat | 2220 |
| ggttttaatg tttgctggtc agacagacaa atgggctaga gtaagagggc tgcgggtatg | 2280 |
| agagaccccg gctccgccct ggcacgtgtc cttgctggcg gcccgccaca ggccccttc | 2340 |
| aatggccgca ttcaggatgg ctctatacac agcagtgctg gttatgtag agttcagcag | 2400 |
| tcacttcaga gatgtatctt gtctttgtca ggcccttcgt cttcatggcc cacctgtttt | 2460 |
| ctgccgtgac ctttggtccc attgaggact aaggatcggg acctttctt taccccctac | 2520 |
| ccgttgtggc tcccacccctg cctcggactg gtttacgtgt cctggttcac acccaggact | 2580 |

```
tttctttgca agcgaacctg tttgaagccc aagtcttaac tcctggtctc gtaaggttcc    2640
actgagacga gatgtctgag aacaaccaaa gaaggcctgc tctttgctgc ttttaaaaaa    2700
tgacaattaa atgtgcagat tccccacgca cccgatgacc tatttttttca gccgtgggag   2760 gaatggagtc tttggtacat tcctcaccga ggttagcagc tcagtttgtg gttatgaaac    2820
cgtctgtggc ctcatgacag cgagagatgg gaatacacta gaaggatctc tttccctgtt    2880
ttcgtgaaac gactcttgcc aaacgttccc gaggcgccaa ggagtgtagt acaccctggc    2940
tgccatcact ctataaaagt gcttcatgag cccagaccaa aagcccacag tgaaatgaag    3000
tacccttttg taaatagcat tttttgcag aaggtgaaaa ttccactctc taccaccggg     3060
ccagccaata gatcactttg gtgaatgcta gtttcaaatt tgattcaaaa tatttcttag    3120
gtgaaagaac tagcagaaag tcaaaaacta agatactgta gactggacaa gaaattctac    3180
ctgggcacct aggtgatgcc ttcttctttt gattgccttt ctaataaatg cagaatctga    3240
aggtaaatag gttaaaaca aaacaaaaac ccaccccttt aaggagttgg taaaaagcag     3300
ttcaactctt agcttgactg agctaaaatt cacaggacta cgtgctttgt gcattgtagt    3360
ctagtcgtaa ttcataggta ctgactcctc agccccaaat gtcggagagg aagaattcgg    3420
tcagcctgtc aggtcgtgag tccagttacc accaaacatc tgggaaactt ctgggtgctg    3480
ggtgctctgc tgctggactt ttgtggctgt gtctgtgtct gcaagataaa ttagatcgcc    3540
ctgtggggtt tgcagaatta gtgaagggtc caggacgatc ccagtgggct cgcttccaaa    3600
gcatcccact caagggagac ttgaaacttc cagtgtgagt tgaccccatc atttaaaaat    3660
aaagtccccg ggttccttaa tgcctccttc actgggcctt cctagcagga tagaaagtcc    3720
ttgcccagag caggacctgg ctgtcttttt tttttttttt ttcccgagac caagtttcac    3780
tctgttgccc actgcactcc agcctgggca acaaaacgag acttcgtctc aaaaaa       3836
```

<210> SEQ ID NO 127
<211> LENGTH: 617
<212> TYPE: DNA
<213> ORGANISM: Homo sapiens
<220> FEATURE:
<221> NAME/KEY: misc_feature
<223> OTHER INFORMATION: Incyte ID No: 7230481CB1.comp

<400> SEQUENCE: 127

```
cctagatcta aggtgacttt attcatttta gaatgaactt accctattga tactgtaacc     60
agagttggca tacatcacaa ttggcagaac ccggtcatgt ttagcaagat ggaggtgttc    120
tggaagctcc tccttcttgt aggtgtggag gcgagggtat gcattcttca gtgcctggta    180
aagggtttcc tcttgcccca atttgggcag gggcatccca aagccactgt agcccacaat    240
atcaaacttg accaagtccc tgaacttcat gtagttggac aagggatctt gttgacattg    300
ggtctcttct tcacggtggt catcccacgg tctcatgtga tgatgatgct gaggtgctct    360
gcaggctgtg cttctcagtg ctcccaccac gataccagat ggtcctgtcg atttgctgaa    420
tcatcaactt gctgttctct gcctctggcc cgaatcaatg tcccacgtta tctggctctc    480
tgtagctcag tgtcacaaag tcaaagtctt ccttggtgaa ccagttcatg acggtattga    540
tgttctccct ctgctctgtc tcgctgctgt ttgggtgagt gtaggactcc accagggacc    600
gcttgacaac ctcaccc                                                   617
```

<210> SEQ ID NO 128
<211> LENGTH: 880
<212> TYPE: DNA

```
<213> ORGANISM: Homo sapiens
<220> FEATURE:
<221> NAME/KEY: misc_feature
<223> OTHER INFORMATION: Incyte ID No: 4921634CB1.comp

<400> SEQUENCE: 128
cccccttttt ttttttttta aaataaatat acgtgtagag agacagggtc tcccttttgtt      60
gcccaggctg atctcgaact cctgagctca agctgtcctc ccacctcagc ctcccaaggg     120
ctgggatcac tggcatgagc ctctgcaccc agccctttagg attttttttt cttttttaaa    180
attttaatta ttttatatat atttttaagt tccagggtac atgtgcagga tgtgcaggtt    240
tgttacatag gtaaacgtgt gccatggtgg tttgctgcac ctgtcaccct gtcactaggc    300
atgaggacca gcatgcatta gctcttttcc ctaatgttct ccatgcccccc tggcccagcc    360
ctctcccaac aggccccagt gagtgttgtt ccctccccgg gattttttttt cttaaggaaa    420
cacaccacat caggcgttga agtgagtgta ttgactgtct gaggtttgtg tgcactttttt    480
aaccagaagt catggctggg gacacaaaag cacctccttg cctatgtagt tttgttcctt    540
tactgcttta aacaagcaag atgtggtttg cattccttttc gctgctggtg ttgttggctt    600
tgtgtttctc aacagaaata acttgccttg cctttgctct caaggttgtg aaagcccccc    660
accccccatat gttccttcca ctcatttgtc accgagaccc tcagtgttgc tatctgtgca    720
taatgtgtgt gggtcgggtt gtgtcaagca tcagacgacg tcggtacctc tcctcactgt    780
gaaggatgac cctgtacaca ccactgctct aggcaaggat gcgacccacc gtcccggggt    840
taaccacatc agtgtcacca tcacaagggg gtgacagccc                           880

<210> SEQ ID NO 129
<211> LENGTH: 888
<212> TYPE: DNA
<213> ORGANISM: Homo sapiens
<220> FEATURE:
<221> NAME/KEY: misc_feature
<223> OTHER INFORMATION: Incyte ID No: 7284533CB1.comp

<400> SEQUENCE: 129
aaaacatttt cccagtggaa tggatgtaaa atgatatccc attgtgtctt gatttgcatt     60
tccctcatca ctagcaaagc tggatgtctc tttgtatatt tactggccaa atgtgtttcc    120
cggaacttct tccagggact ttgtaagttg gtgttcccct tcatgtctga atttctccac    180
cgagtggtct gtacccactg ccctgctca ctcagctccc ttagcccttc caacctctcc     240
agtcaggtac ctgttccatg atgccatgga agatgtctctt gaaagtcact tccacgctgc   300
tagctcttcc atatggctct tctgtcccag cagctggtcc tcctctgttt tcatgctcac    360
ctctcctggc ttctgtggca acatcctggg ccttggctac tcttctgctg ttctcacctt    420
gtctccttgg cacttctcct gctcaccctt taagtgctga ctgtctcagg cctcagtcct    480
tgatcttctc tgtctatatg cgcttcctag gtaaatgctt ccagactgag gctcttagta    540
tcttccatac tatcatcact cccaaaattt ctatctctat cctggatcac accccctgagc   600
tccaagactt gcacatccaa actacccgca ttgagattcc tactgggatt tcacaagaca    660
atctcaagtt taacttgttc aagaacatga actcttgatt tccaacccccc aacttctctc    720
actaaatagc actgccacta gccaactgct gaagctaaaa aagttggcat tattcttgat    780
ttttgctttc cctctcactt cacacatgca gtcacacact gcaattcttg agtgtagttc    840
acaaaaatac attttggttt cagcgccctc ttcctctgtc gccacccc                 888
```

-continued

```
<210> SEQ ID NO 130
<211> LENGTH: 618
<212> TYPE: DNA
<213> ORGANISM: Homo sapiens
<220> FEATURE:
<221> NAME/KEY: misc_feature
<223> OTHER INFORMATION: Incyte ID No: 7482209CB1.comp

<400> SEQUENCE: 130
tctaacctcc ctttgataaa atcaacagac atcagcaatc tgttttgctg gcccccattt      60
tcactgttcc atattagaga aaacagaggc agcgggtagg aaagaggtca tgagacaagg     120
aaaggaagct gaaaaaccga agtttcagat gcccttttgtt ttagacaccc ctcatttcca    180
gaactgtcac ctaaggattg ggtctgagat tttcataaaa caaacattgc ttttttccagt   240 tcactttttc cctttagttt aacacaaacac tggccgcaaa tgcccatgga ttaattctgt    300
cattccttgg ctaacaggcc cataacatgt tccgtctgtt cacgtgcatt tgtgtgtgct    360
caagtgctgg tgcgtccaat tcagacacaa ctagggagta ccgtcatccc tgcaggaact    420
gccagttcgt caaatccaaa tcctggacac agatgtcctg tcattgccat aggactgctt    480
ctttgtgtgg tagctgctgc agcctggggg agctgaagcg gctatttccc accttgaatc    540
acacttcatt ttgttctttg ctttacaccc acagaatccg tacacgccaa cactctccat    600
cttaataccc tcagctca                                                   618
```

SECRETED PROTEINS

CROSS-REFERENCE TO RELATED APPLICATIONS

This application is a Divisional of U.S. patent application Ser. No. 14/480,328, filed Sep. 8, 2014, which is a Divisional of U.S. patent application Ser. No. 14/048,277, filed Oct. 8, 2013, now U.S. Pat. No. 8,889,833, which is a Divisional of U.S. patent application Ser. No. 12/585,371, filed Sep. 14, 2009, now U.S. Pat. No. 8,569,445, which is a Divisional of U.S. patent application Ser. No. 11/378,616, filed Mar. 20, 2006, now U.S. Pat. No. 7,608,704, which is a Divisional of U.S. patent application Ser. No. 10/416,314, filed May 8, 2003, now abandoned, which is the National Phase of PCT/US2001/047420, filed Nov. 8, 2001, and published as WO 2002/38602 on May 16, 2002, which claims priority to U.S. Provisional Patent Application Nos. 60/247,505, filed Nov. 8, 2000, 60/247,642, filed Nov. 9, 2000, 60/249,824, filed Nov. 16, 2000, 60/252,824, filed Nov. 21, 2000, 60/254,305, filed Dec. 8, 2000, and 60/256,448, filed Dec. 18, 2000. The contents of these applications are incorporated herein by reference in their entirety.

TECHNICAL FIELD

This invention relates to nucleic acid and amino acid sequences of secreted proteins and to the use of these sequences in the diagnosis, treatment, and prevention of cell proliferative, autoimmune/inflammatory, cardiovascular, neurological, and developmental disorders, and in the assessment of the effects of exogenous compounds on the expression of nucleic acid and amino acid sequences of secreted proteins.

BACKGROUND OF THE INVENTION

Protein transport and secretion are essential for cellular function. Protein transport is mediated by a signal peptide located at the amino terminus of the protein to be transported or secreted. The signal peptide is comprised of about ten to twenty hydrophobic amino acids which target the nascent protein from the ribosome to a particular membrane bound compartment such as the endoplasmic reticulum (ER). Proteins targeted to the ER may either proceed through the secretory pathway or remain in any of the secretory organelles such as the ER, Golgi apparatus, or lysosomes. Proteins that transit through the secretory pathway are either secreted into the extracellular space or retained in the plasma membrane. Proteins that are retained in the plasma membrane contain one or more transmembrane domains, each comprised of about 20 hydrophobic amino acid residues. Secreted proteins are generally synthesized as inactive precursors that are activated by post-translational processing events during transit through the secretory pathway. Such events include glycosylation, proteolysis, and removal of the signal peptide by a signal peptidase. Other events that may occur during protein transport include chaperone-dependent unfolding and folding of the nascent protein and interaction of the protein with a receptor or pore complex. Examples of secreted proteins with amino terminal signal peptides are discussed below and include proteins with important roles in cell-to-cell signaling. Such proteins include transmembrane receptors and cell surface markers, extracellular matrix molecules, cytokines, hormones, growth and differentiation factors, enzymes, neuropeptides, vasomediators, cell surface markers, and antigen recognition molecules. (Reviewed in Alberts, B. et al. (1994) Molecular Biology of The Cell, Garland Publishing, New York, N.Y., pp. 557-560, 582-592.)

Cell surface markers include cell surface antigens identified on leukocytic cells of the immune system. These antigens have been identified using systematic, monoclonal antibody (mAb)-based "shot gun" techniques. These techniques have resulted in the production of hundreds of mAbs directed against unknown cell surface leukocytic antigens. These antigens have been grouped into "clusters of differentiation" based on common immunocytochemical localization patterns in various differentiated and undifferentiated leukocytic cell types. Antigens in a given cluster are presumed to identify a single cell surface protein and are assigned a "cluster of differentiation" or "CD" designation. Some of the genes encoding proteins identified by CD antigens have been cloned and verified by standard molecular biology techniques. CD antigens have been characterized as both transmembrane proteins and cell surface proteins anchored to the plasma membrane via covalent attachment to fatty acid-containing glycolipids such as glycosylphosphatidylinositol (GPI). (Reviewed in Barclay, A. N. et al. (1995) The Leucocyte Antiaen Facts Book, Academic Press, San Diego, Calif., pp. 17-20.)

Matrix proteins (MPs) are transmembrane and extracellular proteins which function in formation, growth, remodeling, and maintenance of tissues and as important mediators and regulators of the inflammatory response. The expression and balance of MPs may be perturbed by biochemical changes that result from congenital, epigenetic, or infectious diseases. In addition, MPs affect leukocyte migration, proliferation, differentiation, and activation in the immune response. MPs are frequently characterized by the presence of one or more domains which may include collagen-like domains, EGF-like domains, immunoglobulin-like domains, and fibronectin-like domains. In addition, MPs may be heavily glycosylated and may contain an Arginine-Glycine-Aspartate (RGD) tripeptide motif which may play a role in adhesive interactions. MPs include extracellular proteins such as fibronectin, collagen, galectin, vitronectin and its proteolytic derivative somatomedin B; and cell adhesion receptors such as cell adhesion molecules (CAMs), cadherins, and integrins. (Reviewed in Ayad, S. et al. (1994) The Extracellular Matrix Facts Book, Academic Press, San Diego, Calif., pp. 2-16; Ruoslahti, E. (1997) Kidney Int. 51:1413-1417; Sjaastad, M. D. and Nelson, W. J. (1997) BioEssays 19:47-55.)

Peroxidasin is a Drosophila protein that contains both peroxidase and extracellular matrix motifs. The 1512 amino acid peroxidasin protein contains a peroxidase domain homologous to human myeloperoxidase and eosiniphil peroxidase, as well as six leucine-rich repeats, four immunoglobulin domains, and a region of thrombospondin/procollagen homology. Peroxidasin is secreted by hemocytes as they spread throughout the developing Drosophila embryo. The protein is thought to function in extracellular matrix consolidation, phagocytosis, and defense (Nelson, R. E. (1994) EMBO J. 13:3438-3447). A human homolog of the Drosophila peroxidasin gene was recently found to be upregulated in a colon cancer cell line undergoing p53 tumor suppressor-dependent apoptosis, and thus may play a role in the mechanisms of p53-dependent apoptosis (Horikoshi, N. et al. (1999) Biochem. Biophy. Res. Commun. 261:864-869).

Mucins are highly glycosylated glycoproteins that are the major structural component of the mucus gel. The physiological functions of mucins are cytoprotection, mechanical protection, maintenance of viscosity in secretions, and cellular recognition. MUC6 is a human gastric mucin that is also found in gall bladder, pancreas, seminal vesicles, and female reproductive tract (Toribara, N. W. et al. (1997) J. Biol. Chem. 272:16398-16403). The MUC6 gene has been mapped to human chromosome 11 (Toribara, N. W. et al. (1993) J. Biol. Chem. 268:5879-5885). Hemomucin is a novel *Drosophila* surface mucin that may be involved in the induction of antibacterial effector molecules (Theopold, U. et al. (1996) J. Biol. Chem. 217:12708-12715).

Tuftelins are one of four different enamel matrix proteins that have been identified so far. The other three known enamel matrix proteins are the amelogenins, enamelin and ameloblastin. Assembly of the enamel extracellular matrix from these component proteins is believed to be critical in producing a matrix competent to undergo mineral replacement. (Paine, C. T. et al. (1998) Connect Tissue Res. 38:257-267). Tuftelin mRNA has been found to be expressed in human ameloblastoma tumor, a non-mineralized odontogenic tumor (Deutsch, D. et al. (1998) Connect. Tissue Res. 39:177-184).

Olfactomedin-related proteins are extracellular matrix, secreted glycoproteins with conserved C-terminal motifs. They are expressed in a wide variety of tissues and in broad range of species, from *Caenorhabditis elegans* to *Homo sapiens*. Olfactomedin-related proteins comprise a gene family with at least 5 family members in humans. One of the five, TIGR/myocilin protein, is expressed in the eye and is associated with the pathogenesis of glaucoma (Kulkami, N. H. et al. (2000) Genet. Res. 76:41-50). Research by Yokoyama et al. (1996) found a 135-amino acid protein, termed AMY, having 96% sequence identity with rat neuronal olfactomedin-releated ER localized protein in a neuroblastoma cell line cDNA library, suggesting an essential role for AMY in nerve tissue (Yokoyama, M. et al. (1996) DNA Res. 3:311-320). Neuron-specific olfactomedin-related glycoproteins isolated from rat brain cDNA libraries show strong sequence similarity with olfactomedin. This similarity is suggestive of a matrix-related function of these glycoproteins in neurons and neurosecretory cells (Danielson, P. E. et al. (1994) J. Neurosci. Res. 38:468478).

Mac-2 binding protein is a 90-kD serum protein (90K), a secreted glycoprotein isolated from both the human breast carcinoma cell line SK-BR-3, and human breast milk. It specifically binds to a human macrophage-associated lectin, Mac-2. Structurally, the mature protein is 567 amino acids in length and is proceeded by an 18-amino acid leader. There are 16 cysteines and seven potential N-linked glycosylation sites. The first 106 amino acids represent a domain very similar to an ancient protein superfamily defined by a macrophage scavenger receptor cysteine-rich domain (Koths, K. et al. (1993) J. Biol. Chem. 268:14245-14249). 90K is elevated in the serum of subpopulations of AIDS patients and is expressed at varying levels in primary tumor samples and tumor cell lines. Ullrich et al. (1994) have demonstrated that 90K stimulates host defense systems and can induce interleukin-2 secretion. This immune stimulation is proposed to be a result of oncogenic transformation, viral infection or pathogenic invasion (Ullrich, A., et al. (1994) J. Biol. Chem. 269:18401-18407).

Semaphorins are a large group of axonal guidance molecules consisting of at least 30 different members and are found in vertebrates, invertebrates, and even certain viruses. All semaphorins contain the sema domain which is approximately 500 amino acids in length. Neuropilin, a semaphorin receptor, has been shown to promote neurite outgrowth in vitro. The extracellular region of neuropilins consists of three different domains: CUB, discoidin, and MAM domains. The CUB and the MAM motifs of neuropilin have been suggested to have roles in protein-protein interactions and are thought to be involved in the binding of semaphorins through the sema and the C-terminal domains (reviewed in Raper, J. A. (2000) Curr. Opin. Neurobiol. 10:88-94). Plexins are neuronal cell surface molecules that mediate cell adhesion via a homophilic binding mechanism in the presence of calcium ions. Plexins have been shown to be expressed in the receptors and neurons of particular sensory systems (Ohta, K. et al. (1995) Cell 14:1189-1199). There is evidence that suggests that some plexins function to control motor and CNS axon guidance in the developing nervous system. Plexins, which themselves contain complete semaphorin domains, may be both the ancestors of classical semaphorins and binding partners for semaphorins (Winberg, M. L. et al (1998) Cell 95:903-916).

Human pregnancy-specific beta 1-glycoprotein (PSG) is a family of closely related glycoproteins of molecular weights of 72 KDa, 64 KDa, 62 KDa, and 54 KDa. Together with the carcinoembryonic antigen, they comprise a subfamily within the immunoglobulin superfamily (Plouzek, C. A. and Chou, J. Y. (1991) Endocrinology 129:950-958) Different subpopulations of PSG have been found to be produced by the trophoblasts of the human placenta, and the amnionic and chorionic membranes (Plouzek, C. A. et al. (1993) Placenta 14:277-285).

Autocrine motility factor (AMF) is one of the motility cytokines regulating tumor cell migration; therefore identification of the signaling pathway coupled with it has critical importance. Autocrine motility factor receptor (AMFR) expression has been found to be associated with tumor progression in thymoma (Ohta Y. et al. (2000) Int. J. Oncol. 17:259-264). AMFR is a cell surface glycoprotein of molecular weight 78 KDa.

Hormones are secreted molecules that travel through the circulation and bind to specific receptors on the surface of, or within, target cells. Although they have diverse biochemical compositions and mechanisms of action, hormones can be grouped into two categories. One category includes small lipophilic hormones that diffuse through the plasma membrane of target cells, bind to cytosolic or nuclear receptors, and form a complex that alters gene expression. Examples of these molecules include retinoic acid, thyroxine, and the cholesterol-derived steroid hormones such as progesterone, estrogen, testosterone, cortisol, and aldosterone. The second category includes hydrophilic hormones that function by binding to cell surface receptors that transduce signals across the plasma membrane. Examples of such hormones include amino acid derivatives such as catecholamines (epinephrine, norepinephrine) and histamine, and peptide hormones such as glucagon, insulin, gastrin, secretin, cholecystokinin, adrenocorticotropic hormone, follicle stimulating hormone, luteinizing hormone, thyroid stimulating hormone, and vasopressin. (See, for example, Lodish et al. (1995) *Molecular Cell Biology*, Scientific American Books Inc., New York, N.Y., pp. 856-864.)

Pro-opiomelanocortin (POMC) is the precursor polypeptide of corticotropin (ACTH), a hormone synthesized by the anterior pituitary gland, which functions in the stimulation of the adrenal cortex. POMC is also the precursor polypeptide of the hormone beta-lipotropin (beta-LPH). Each hormone includes smaller peptides with distinct biological activities: alpha-melanotropin (alpha-MSH) and corticotropin-like intermediate lobe peptide (CLIP) are formed from ACTH; gamma-lipotropin (gamma-LPH) and beta-endorphin are peptide components of beta-LPH; while beta-MSH is contained within gamma-LPH. Adrenal insufficiency due to ACTH deficiency, resulting from a genetic mutation in exons 2 and 3 of POMC results in an endocrine disorder characterized by early-onset obesity, adrenal insufficiency, and red hair pigmentation (Chretien, M. et al. (1979) Canad. J. Biochem. 57:1111-1121; Krude, H. et al. (1998) Nature Genet. 19:155-157; Online Mendelian Inheritance in Man (OMIM) 176830).

Growth and differentiation factors are secreted proteins which function in intercellular communication. Some factors require oligomerization or association with membrane proteins for activity. Complex interactions among these factors and their receptors trigger intracellular signal transduction pathways that stimulate or inhibit cell division, cell differentiation, cell signaling, and cell motility. Most growth and differentiation factors act on cells in their local environment (paracrine signaling). There are three broad classes of growth and differentiation factors. The first class includes the large polypeptide growth factors such as epidermal growth factor, fibroblast growth factor, transforming growth factor, insulin-like growth factor, and platelet-derived growth factor. The second class includes the hematopoietic growth factors such as the colony stimulating factors (CSFs). Hematopoietic growth factors stimulate the proliferation and differentiation of blood cells such as B-lymphocytes, T-lymphocytes, erythrocytes, platelets, eosinophils, basophils, neutrophils, macrophages, and their stem cell precursors. The third class includes small peptide factors such as bombesin, vasopressin, oxytocin, endothelin, transferrin, angiotensin II, vasoactive intestinal peptide, and bradykinin, which function as hormones to regulate cellular functions other than proliferation.

Growth and differentiation factors play critical roles in neoplastic transformation of cells in vitro and in tumor progression in vivo. Inappropriate expression of growth factors by tumor cells may contribute to vascularization and metastasis of tumors. During hematopoiesis, growth factor misregulation can result in anemias, leukemias, and lymphomas. Certain growth factors such as interferon are cytotoxic to tumor cells both in vivo and in vitr. Moreover, some growth factors and growth factor receptors are related both structurally and functionally to oncoproteins. In addition, growth factors affect transcriptional regulation of both proto-oncogenes and oncosuppressor genes. (Reviewed in Pimentel, E. (1994) *Handbook of Growth Factors*, CRC Press, Ann Arbor, Mich., pp. 1-9.)

The Slit protein, first identified in *Drosophila*, is critical in central nervous system midline formation and potentially in nervous tissue histogenesis and axonal pathfinding. Itoh et al. ((1998) Brain Res. Mol. Brain Res. 62:175-186) have identified mammalian homologues of the slit gene (human Slit-1, Slit-2, Slit-3 and rat Slit-1). The encoded proteins are putative secreted proteins containing EGF-like motifs and leucine-rich repeats, both of which are conserved protein-protein interaction domains. Slit-1, -2, and -3 mRNAs are expressed in the brain, spinal cord, and thyroid, respectively (Itoh, A. et al., sura). The Slit family of proteins are indicated to be functional ligands of glypican-1 in nervous tissue and it is suggested that their interactions may be critical in certain stages during central nervous system histogenesis (Liang, Y. et al., (1999) J. Biol. Chem. 274:17885-17892).

Neuropeptides and vasomediators (NP/VM) comprise a large family of endogenous signaling molecules. Included in this family are neuropeptides and neuropeptide hormones such as bombesin, neuropeptide Y, neurotensin, neuromedin N, melanocortins, opioids, galanin, somatostatin, tachykinins, urotensin II and related peptides involved in smooth muscle stimulation, vasopressin, vasoactive intestinal peptide, and circulatory system-borne signaling molecules such as angiotensin, complement, calcitonin, endothelins, formyl-methionyl peptides, glucagon, cholecystokinin and gastrin. NP/VMs can transduce signals directly, modulate the activity or release of other neurotransmitters and hormones, and act as catalytic enzymes in cascades. The effects of NP/VMs range from extremely brief to long-lasting. (Reviewed in Martin, C. R. et al. (1985) *Endocrine Physiology*, Oxford University Press, New York, N.Y., pp. 57-62.)

NP/VMs are involved in numerous neurological and cardiovascular disorders. For example, neuropeptide Y is involved in hypertension, congestive heart failure, affective disorders, and appetite regulation. Somatostatin inhibits secretion of growth hormone and prolactin in the anterior pituitary, as well as inhibiting secretion in intestine, pancreatic acinar cells, and pancreatic beta-cells. A reduction in somatostatin levels has been reported in Alzheimer's disease and Parkinson's disease. Vasopressin acts in the kidney to increase water and sodium absorption, and in higher concentrations stimulates contraction of vascular smooth muscle, platelet activation, and glycogen breakdown in the liver. Vasopressin and its analogues are used clinically to treat diabetes insipidus. Endothelin and angiotensin are involved in hypertension, and drugs, such as captopril, which reduce plasma levels of angiotensin, are used to reduce blood pressure (Watson, S. and S. Arkinstall (1994) *The G-protein Linked Receptor Facts Book*. Academic Press, San Diego Calif., pp. 194; 252; 284; 55; 111).

Neuropeptides have also been shown to have roles in nociception (pain). Vasoactive intestinal peptide appears to play an important role in chronic neuropathic pain. Nociceptin, an endogenous ligand for for the opioid receptor-like 1 receptor, is thought to have a predominantly anti-nociceptive effect, and has been shown to have analgesic properties in different animal models of tonic or chronic pain (Dickinson, T. and Fleetwood-Walker, S. M. (1998) Trends Pharmacol. Sci. 19:346-348).

Other proteins that contain signal peptides include secreted proteins with enzymatic activity. Such activity includes, for example, oxidoreductase/dehydrogenase activity, transferase activity, hydrolase activity, lyase activity, isomerase activity, or ligase activity. For example, matrix metalloproteinases are secreted hydrolytic enzymes that degrade the extracellular matrix and thus play an important role in tumor metastasis, tissue morphogenesis, and arthritis (Reponen, P. et al. (1995) Dev. Dyn. 202:388-396; Firestein, G. S. (1992) Curr. Opin. Rheumatol. 4:348-354; Ray, J. M. and Stetler-Stevenson, W. G. (1994) Eur. Respir. J. 7:2062-2072; and Mignatti, P. and Rifkin, D. B. (1993) Physiol. Rev. 73:161-195). Additional examples are the acetyl-CoA synthetases which activate acetate for use in lipid synthesis or energy generation (Luong, A. et al. (2000) J. Biol. Chem. 275:26458-26466). The result of acetyl-CoA synthetase activity is the formation of acetyl-CoA from acetate and CoA. Acetyl-CoA sythetases share a region of sequence similarity identified as the AMP-binding domain signature. Acetyl-CoA synthetase has been shown to be associated with hypertension (H. Toh (1991) Protein Seq. Data Anal. 4:111-117; and Iwai, N. et al., (1994) Hypertension 23:375-380).

A number of isomerases catalyze steps in protein folding, phototransduction, and various anabolic and catabolic pathways. One class of isomerases is known as peptidyl-prolyl cis-trans isomerases (PPIases). PPIases catalyze the cis to trans isomerization of certain proline imidic bonds in proteins. Two families of PPIases are the FK506 binding proteins (FKBPs), and cyclophilins (CyPs). FKBPs bind the potent immunosuppressants FK506 and rapamycin, thereby inhibiting signaling pathways in T-cells. Specifically, the PPIase activity of FKBPs is inhibited by binding of FK506 or rapamycin. There are five members of the FKBP family which are named according to their calculated molecular masses (FKBP12, FKBP13, FKBP25, FKBP52, and FKBP65), and localized to different regions of the cell where they associate with different protein complexes (Coss, M. et al. (1995) J. Biol. Chem. 270:29336-29341; Schreiber, S. L. (1991) Science 251:283-287).

The peptidyl-prolyl isomerase activity of CyP may be part of the signaling pathway that leads to T-cell activation. CyP isomerase activity is associated with protein folding and protein trafficking, and may also be involved in assembly/disassembly of protein complexes and regulation of protein activity. For example, in *Drosophila*, the CyP NinaA is required for correct localization of rhodopsins, while a mammalian CyP (Cyp40) is part of the Hsp90/Hsc70 complex that binds steroid receptors. The mammalian CypA has been shown to bind the gag protein from human immunodeficiency virus 1 (HIV-1), an interaction that can be inhibited by cyclosporin. Since cyclosporin has potent anti-HIV-1 activity, CypA may play an essential function in HIV-1 replication. Finally, Cyp40 has been shown to bind and inactivate the transcription factor c-Myb, an effect that is reversed by cyclosporin. This effect implicates CyPs in the regulation of transcription, transformation, and differentiation (Bergsma, D. J. et al (1991) J. Biol. Chem. 266:23204-23214; Hunter, T. (1998) Cell 92: 141-143; and Leverson, J. D. and Ness, S. A. (1998) Mol. Cell. 1:203-211).

Gamma-carboxyglutamic acid (Gla) proteins rich in proline (PRGPs) are members of a family of vitamin K-dependent single-pass integral membrane proteins. These proteins are characterized by an extracellular amino terminal domain of approximately 45 amino acids rich in Gla. The intracellular carboxyl terminal region contains one or two copies of the sequence PPXY, a motif present in a variety of proteins involved in such diverse cellular functions as signal transduction, cell cycle progression, and protein turnover (Kulman, J. D. et al., (2001) Proc. Natl. Acad. Sci. U.S.A. 98:1370-1375). The process of post-translational modification of glutamic residues to form Gla is Vitamin K-dependent carboxylation. Proteins which contain Gla include plasma proteins involved in blood coagulation. These proteins are prothrombin, proteins C, S, and Z, and coagulation factors VII, IX, and X. Osteocalcin (bone-Gla protein, BGP) and matrix Gla-protein (MGP) also contain Gla (Friedman, P. A., and C. T. Przysiecki (1987) Int. J. Biochem. 19:1-7; C. Vermeer (1990) Biochem. J. 266:625-636).

The *Drosophila* sp. gene crossveinless 2 is characterized as having a putative signal or transmembrane sequence, and a partial Von Willebrand Factor D domain similar to those domains known to regulate the formation of intramolecular and intermolecular bonds and five cysteine-rich domains, known to bind BMP-like (bone morphogenetic proteins) ligands. These features suggest that crossveinless 2 may act extracelluarly or in the secretory pathway to directly potentiate ligand signaling and hence, involvement in the BMP-like signaling pathway known to play a role in vein specification (Conley, C. A. et al., (2000) Development 127:3947-3959). The dorsal-ventral patterning in both vertebrate and *Drosophila* embryos requires a conserved system of extracellular proteins to generate a positional informational gradient.

The discovery of new secreted proteins, and the polynucleotides encoding them, satisfies a need in the art by providing new compositions which are useful in the diagnosis, prevention, and treatment of cell proliferative, autoimmune/inflammatory, cardiovascular, neurological, and developmental disorders, and in the assessment of the effects of exogenous compounds on the expression of nucleic acid and amino acid sequences of secreted proteins.

SUMMARY OF THE INVENTION

The invention features purified polypeptides, secreted proteins, referred to collectively as "SECP" and individually as "SECP-1," "SECP-2," "SECP-3," "SECP-4," "SECP-5," "SECP-6," "SECP-7," "SECP-8," "SECP-9," "SECP-10," "SECP-11," "SECP-12," "SECP-13," "SECP-14 "SECP-15," "SECP-16," "SECP-17," "SECP-18," "SECP-19," "SECP-20," "SECP-21," "SECP-22," "SECP-23," "SECP-24," "SECP-25," "SECP-26," "SECP-27," "SECP-28,", "SECP-29," "SECP-30," "SECP-31," "SECP-32." "SECP-33," "SECP-34," "SECP-35," "SECP-36," "SECP-37," "SECP-38," "SECP-39," "SECP-40," "SECP41," "SECP42," "SECP-43 "SECP-44," "SECP-45," "SECP-46," "SECP-47," "SECP-48," "SECP-49," "SECP-50," "SECP-51," "SECP-52," "SECP-53," "SECP-54," "SECP-55," "SECP-56," "SECP-57," "SECP-58," "SECP-59," "SECP-60," "SECP-61," "SECP-62," and "SECP-63." In one aspect, the invention provides an isolated polypeptide selected from the group consisting of a) a polypeptide comprising an amino acid sequence selected from the group consisting of SEQ ID NO:1-63, b) a polypeptide comprising a naturally occurring amino acid sequence at least 90% identical to an amino acid sequence selected from the group consisting of SEQ ID NO: 1-63, c) a biologically active fragment of a polypeptide having an amino acid sequence selected from the group consisting of SEQ ID NO: 1-63, and d) an immunogenic fragment of a polypeptide having an amino acid sequence selected from the group consisting of SEQ ID NO: 1-63. In one alternative, the invention provides an isolated polypeptide comprising the amino acid sequence of SEQ ID NO: 1-63.

The invention further provides an isolated polynucleotide encoding a polypeptide selected from the group consisting of a) a polypeptide comprising an amino acid sequence selected from the group consisting of SEQ ID NO: 1-63, b) a polypeptide comprising a naturally occurring amino acid sequence at least 90% identical to an amino acid sequence selected from the group consisting of SEQ ID NO: 1-63, c) a biologically active fragment of a polypeptide having an amino acid sequence selected from the group consisting of SEQ ID NO: 1-63, and d) an immunogenic fragment of a polypeptide having an amino acid sequence selected from the group consisting of SEQ ID NO: 1-63. In one alternative, the polynucleotide encodes a polypeptide selected from the group consisting of SEQ ID NO: 1-63. In another alternative, the polynucleotide is selected from the group consisting of SEQ ID NO:64-126.

Additionally, the invention provides a recombinant polynucleotide comprising a promoter sequence operably linked to a polynucleotide encoding a polypeptide selected from the group consisting of a) a polypeptide comprising an amino acid sequence selected from the group consisting of SEQ ID NO: 1-63, b) a polypeptide comprising a naturally occurring amino acid sequence at least 90% identical to an amino acid sequence selected from the group consisting of SEQ ID NO: 1-63, c) a biologically active fragment of a polypeptide having an amino acid sequence selected from the group consisting of SEQ ID NO: 1-63, and d) an immunogenic fragment of a polypeptide having an amino acid sequence selected from the group consisting of SEQ ID NO: 1-63. In one alternative, the invention provides a cell transformed with the recombinant polynucleotide. In another alternative, the invention provides a transgenic organism comprising the recombinant polynucleotide.

The invention also provides a method for producing a polypeptide selected from the group consisting of a) a polypeptide comprising an amino acid sequence selected from the group consisting of SEQ ID NO: 1-63, b) a polypeptide comprising a naturally occurring amino acid sequence at least 90% identical to an amino acid sequence selected from the group consisting of SEQ ID NO: 1-63, c) a biologically active fragment of a polypeptide having an amino acid sequence selected from the group consisting of SEQ ID NO: 1-63, and d) an immunogenic fragment of a polypeptide having an amino acid sequence selected from the group consisting of SEQ ID NO: 1-63. The method comprises a) culturing a cell under conditions suitable for expression of the polypeptide, wherein said cell is transformed with a recombinant polynucleotide comprising a promoter sequence operably linked to a polynucleotide encoding the polypeptide, and b) recovering the polypeptide so expressed.

Additionally, the invention provides an isolated antibody which specifically binds to a polypeptide selected from the group consisting of a) a polypeptide comprising an amino acid sequence selected from the group consisting of SEQ ID NO: 1-63, b) a polypeptide comprising a naturally occurring amino acid sequence at least 90% identical to an amino acid sequence selected from the group consisting of SEQ ID NO: 1-63, c) a biologically active fragment of a polypeptide having an amino acid sequence selected from the group consisting of SEQ ID NO: 1-63, and d) an immunogenic fragment of a polypeptide having an amino acid sequence selected from the group consisting of SEQ ID NO: 1-63.

The invention further provides an isolated polynucleotide selected from the group consisting of a) a polynucleotide comprising a polynucleotide sequence selected from the group consisting of SEQ ID NO:64-126, b) a polynucleotide comprising a naturally occurring polynucleotide sequence at least 90% identical to a polynucleotide sequence selected from the group consisting of SEQ ID NO:64-126, c) a polynucleotide complementary to the polynucleotide of a), d) a polynucleotide complementary to the polynucleotide of b), and e) an RNA equivalent of a)-d). In one alternative, the polynucleotide comprises at least 60 contiguous nucleotides.

Additionally, the invention provides a method for detecting a target polynucleotide in a sample, said target polynucleotide having a sequence of a polynucleotide selected from the group consisting of a) a polynucleotide comprising a polynucleotide sequence selected from the group consisting of SEQ ID NO:64-126, b) a polynucleotide comprising a naturally occurring polynucleotide sequence at least 90% identical to a polynucleotide sequence selected from the group consisting of SEQ ID NO:64-126, c) a polynucleotide complementary to the polynucleotide of a), d) a polynucleotide complementary to the polynucleotide of b), and e) an RNA equivalent of a)-d). The method comprises a) hybridizing the sample with a probe comprising at least 20 contiguous nucleotides comprising a sequence complementary to said target polynucleotide in the sample, and which probe specifically hybridizes to said target polynucleotide, under conditions whereby a hybridization complex is formed between said probe and said target polynucleotide or fragments thereof, and b) detecting the presence or absence of said hybridization complex, and optionally, if present, the amount thereof. In one alternative, the probe comprises at least 60 contiguous nucleotides.

The invention further provides a method for detecting a target polynucleotide in a sample, said target polynucleotide having a sequence of a polynucleotide selected from the group consisting of a) a polynucleotide comprising a polynucleotide sequence selected from the group consisting of SEQ ID NO:64-126, b) a polynucleotide comprising a naturally occurring polynucleotide sequence at least 90% identical to a polynucleotide sequence selected from the group consisting of SEQ ID NO:64-126, c) a polynucleotide complementary to the polynucleotide of a), d) a polynucleotide complementary to the polynucleotide of b), and e) an RNA equivalent of a)-d). The method comprises a) amplifying said target polynucleotide or fragment thereof using polymerase chain reaction amplification, and b) detecting the presence or absence of said amplified target polynucleotide or fragment thereof, and, optionally, if present, the amount thereof.

The invention further provides a composition comprising an effective amount of a polypeptide selected from the group consisting of a) a polypeptide comprising an amino acid sequence selected from the group consisting of SEQ ID NO: 1-63, b) a polypeptide comprising a naturally occurring amino acid sequence at least 90% identical to an amino acid sequence selected from the group consisting of SEQ ID NO: 1-63, c) a biologically active fragment of a polypeptide having an amino acid sequence selected from the group consisting of SEQ ID NO: 1-63, and d) an immunogenic fragment of a polypeptide having an amino acid sequence selected from the group consisting of SEQ ID NO: 1-63, and a pharmaceutically acceptable excipient. In one embodiment, the composition comprises an amino acid sequence selected from the group consisting of SEQ ID NO: 1-63. The invention additionally provides a method of treating a disease or condition associated with decreased expression of functional SECP, comprising administering to a patient in need of such treatment the composition.

The invention also provides a method for screening a compound for effectiveness as an agonist of a polypeptide selected from the group consisting of a) a polypeptide comprising an amino acid sequence selected from the group consisting of SEQ ID NO: 1-63, b) a polypeptide comprising a naturally occurring amino acid sequence at least 90% identical to an amino acid sequence selected from the group consisting of SEQ ID NO: 1-63, c) a biologically active fragment of a polypeptide having an amino acid sequence selected from the group consisting of SEQ ID NO: 1-63, and d) an immunogenic fragment of a polypeptide having an amino acid sequence selected from the group consisting of SEQ ID NO: 1-63. The method comprises a) exposing a sample comprising the polypeptide to a compound, and b) detecting agonist activity in the sample. In one alternative, the invention provides a composition comprising an agonist compound identified by the method and a pharmaceutically acceptable excipient. In another alternative, the invention provides a method of treating a disease or condition associated with decreased expression of functional SECP, comprising administering to a patient in need of such treatment the composition.

Additionally, the invention provides a method for screening a compound for effectiveness as an antagonist of a polypeptide selected from the group consisting of a) a polypeptide comprising an amino acid sequence selected from the group consisting of SEQ ID NO: 1-63, b) a polypeptide comprising a naturally occurring amino acid sequence at least 90% identical to an amino acid sequence selected from the group consisting of SEQ ID NO: 1-63, c) a biologically active fragment of a polypeptide having an amino acid sequence selected from the group consisting of SEQ ID NO:1-63, and d) an immunogenic fragment of a polypeptide having an amino acid sequence selected from the group consisting of SEQ ID NO: 1-63. The method comprises a) exposing a sample comprising the polypeptide to a compound, and b) detecting antagonist activity in the sample. In one alternative, the invention provides a composition comprising an antagonist compound identified by the method and a pharmaceutically acceptable excipient. In another alternative, the invention provides a method of treating a disease or condition associated with overexpression of functional SECP, comprising administering to a patient in need of such treatment the composition.

The invention further provides a method of screening for a compound that specifically binds to a polypeptide selected from the group consisting of a) a polypeptide comprising an amino acid sequence selected from the group consisting of SEQ ID NO: 1-63, b) a polypeptide comprising a naturally occurring amino acid sequence at least 90% identical to an amino acid sequence selected from the group consisting of SEQ ID NO: 1-63, c) a biologically active fragment of a polypeptide having an amino acid sequence selected from the group consisting of SEQ ID NO: 1-63, and d) an immunogenic fragment of a polypeptide having an amino acid sequence selected from the group consisting of SEQ ID NO: 1-63. The method comprises a) combining the polypeptide with at least one test compound under suitable conditions, and b) detecting binding of the polypeptide to the test compound, thereby identifying a compound that specifically binds to the polypeptide.

The invention further provides a method of screening for a compound that modulates the activity of a polypeptide selected from the group consisting of a) a polypeptide comprising an amino acid sequence selected from the group consisting of SEQ ID NO: 1-63, b) a polypeptide comprising a naturally occurring amino acid sequence at least 90% identical to an amino acid sequence selected from the group consisting of SEQ ID NO: 1-63, c) a biologically active fragment of a polypeptide having an amino acid sequence selected from the group consisting of SEQ ID NO: 1-63, and d) an immunogenic fragment of a polypeptide having an amino acid sequence selected from the group consisting of SEQ ID NO: 1-63. The method comprises a) combining the polypeptide with at least one test compound under conditions permissive for the activity of the polypeptide, b) assessing the activity of the polypeptide in the presence of the test compound, and c) comparing the activity of the polypeptide in the presence of the test compound with the activity of the polypeptide in the absence of the test compound, wherein a change in the activity of the polypeptide in the presence of the test compound is indicative of a compound that modulates the activity of the polypeptide.

The invention further provides a method for screening a compound for effectiveness in altering expression of a target polynucleotide, wherein said target polynucleotide comprises a polynucleotide sequence selected from the group consisting of SEQ ID NO:64-126, the method comprising a) exposing a sample comprising the target polynucleotide to a compound, and b) detecting altered expression of the target polynucleotide.

The invention further provides a method for assessing toxicity of a test compound, said method comprising a) treating a biological sample containing nucleic acids with the test compound; b) hybridizing the nucleic acids of the treated biological sample with a probe comprising at least 20 contiguous nucleotides of a polynucleotide selected from the group consisting of i) a polynucleotide comprising a polynucleotide sequence selected from the group consisting of SEQ ID NO:64-126, ii) a polynucleotide comprising a naturally occurring polynucleotide sequence at least 90% identical to a polynucleotide sequence selected from the group consisting of SEQ ID NO:64-126, iii) a polynucleotide having a sequence complementary to i), iv) a polynucleotide complementary to the polynucleotide of ii), and v) an RNA equivalent of i)-iv). Hybridization occurs under conditions whereby a specific hybridization complex is formed between said probe and a target polynucleotide in the biological sample, said target polynucleotide selected from the group consisting of i) a polynucleotide comprising a polynucleotide sequence selected from the group consisting of SEQ ID NO:64-126, ii) a polynucleotide comprising a naturally occurring polynucleotide sequence at least 90% identical to a polynucleotide sequence selected from the group consisting of SEQ ID NO:64-126, iii) a polynucleotide complementary to the polynucleotide of i), iv) a polynucleotide complementary to the polynucleotide of ii), and v) an RNA equivalent of i)-iv). Alternatively, the target polynucleotide comprises a fragment of a polynucleotide sequence selected from the group consisting of i)-v) above; c) quantifying the amount of hybridization complex; and d) comparing the amount of hybridization complex in the treated biological sample with the amount of hybridization complex in an untreated biological sample, wherein a difference in the amount of hybridization complex in the treated biological sample is indicative of toxicity of the test compound.

BRIEF DESCRIPTION OF THE TABLES

Table 1 summarizes the nomenclature for the full length polynucleotide and polypeptide sequences of the present invention.

Table 2 shows the GenBank identification number and annotation of the nearest GenBank homolog, for polypeptides of the invention. The probability scores for the matches between each polypeptide and its homolog(s) are also shown.

Table 3 shows structural features of polypeptide sequences of the invention, including predicted motifs and domains, along with the methods, algorithms, and searchable databases used for analysis of the polypeptides.

Table 4 lists the cDNA and/or genomic DNA fragments which were used to assemble polynucleotide sequences of the invention, along with selected fragments of the polynucleotide sequences.

Table 5 shows the representative cDNA library for polynucleotides of the invention.

Table 6 provides an appendix which describes the tissues and vectors used for construction of the cDNA libraries shown in Table 5.

Table 7 shows the tools, programs, and algorithms used to analyze the polynucleotides and polypeptides of the invention, along with applicable descriptions, references, and threshold parameters.

DESCRIPTION OF THE INVENTION

Before the present proteins, nucleotide sequences, and methods are described, it is understood that this invention is not limited to the particular machines, materials and methods described, as these may vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a," "an," and "the" include plural reference unless the context clearly dictates otherwise. Thus, for example, a reference to "a host cell" includes a plurality of such host cells, and a reference to "an antibody" is a reference to one or more antibodies and equivalents thereof known to those skilled in the art, and so forth.

Unless defined otherwise, all technical and scientific terms used herein have the same meanings as commonly understood by one of ordinary skill in the art to which this invention belongs. Although any machines, materials, and methods similar or equivalent to those described herein can be used to practice or test the present invention, the preferred machines, materials and methods are now described. All publications mentioned herein are cited for the purpose of describing and disclosing the cell lines, protocols, reagents and vectors which are reported in the publications and which might be used in connection with the invention. Nothing herein is to be construed as an admission that the invention is not entitled to antedate such disclosure by virtue of prior invention.

Definitions

"SECP" refers to the amino acid sequences of substantially purified SECP obtained from any species, particularly a mammalian species, including bovine, ovine, porcine, murine, equine, and human, and from any source, whether natural, synthetic, semi-synthetic, or recombinant.

The term "agonist" refers to a molecule which intensifies or mimics the biological activity of SECP. Agonists may include proteins, nucleic acids, carbohydrates, small molecules, or any other compound or composition which modulates the activity of SECP either by directly interacting with SECP or by acting on components of the biological pathway in which SECP participates.

An "allelic variant" is an alternative form of the gene encoding SECP. Allelic variants may result from at least one mutation in the nucleic acid sequence and may result in altered mRNAs or in polypeptides whose structure or function may or may not be altered. A gene may have none, one, or many allelic variants of its naturally occurring form. Common mutational changes which give rise to allelic variants are generally ascribed to natural deletions, additions, or substitutions of nucleotides. Each of these types of changes may occur alone, or in combination with the others, one or more times in a given sequence.

"Altered" nucleic acid sequences encoding SECP include those sequences with deletions, insertions, or substitutions of different nucleotides, resulting in a polypeptide the same as SECP or a polypeptide with at least one functional characteristic of SECP. Included within this definition are polymorphisms which may or may not be readily detectable using a particular oligonucleotide probe of the polynucleotide encoding SECP, and improper or unexpected hybridization to allelic variants, with a locus other than the normal chromosomal locus for the polynucleotide sequence encoding SECP. The encoded protein may also be "altered," and may contain deletions, insertions, or substitutions of amino acid residues which produce a silent change and result in a functionally equivalent SECP. Deliberate amino acid substitutions may be made on the basis of similarity in polarity, charge, solubility, hydrophobicity, hydrophilicity, and/or the amphipathic nature of the residues, as long as the biological or immunological activity of SECP is retained. For example, negatively charged amino acids may include aspartic acid and glutamic acid, and positively charged amino acids may include lysine and arginine. Amino acids with uncharged polar side chains having similar hydrophilicity values may include: asparagine and glutamine; and serine and threonine. Amino acids with uncharged side chains having similar hydrophilicity values may include: leucine, isoleucine, and valine; glycine and alanine; and phenylalanine and tyrosine.

The terms "amino acid" and "amino acid sequence" refer to an oligopeptide, peptide, polypeptide, or protein sequence, or a fragment of any of these, and to naturally occurring or synthetic molecules. Where "amino acid sequence" is recited to refer to a sequence of a naturally occurring protein molecule, "amino acid sequence" and like terms are not meant to limit the amino acid sequence to the complete native amino acid sequence associated with the recited protein molecule.

"Amplification" relates to the production of additional copies of a nucleic acid sequence. Amplification is generally carried out using polymerase chain reaction (PCR) technologies well known in the art.

The term "antagonist" refers to a molecule which inhibits or attenuates the biological activity of SECP. Antagonists may include proteins such as antibodies, nucleic acids, carbohydrates, small molecules, or any other compound or composition which modulates the activity of SECP either by directly interacting with SECP or by acting on components of the biological pathway in which SECP participates.

The term "antibody" refers to intact immunoglobulin molecules as well as to fragments thereof, such as Fab, F(ab')$_2$, and Fv fragments, which are capable of binding an epitopic determinant. Antibodies that bind SECP polypeptides can be prepared using intact polypeptides or using fragments containing small peptides of interest as the immunizing antigen. The polypeptide or oligopeptide used to immunize an animal (e.g., a mouse, a rat, or a rabbit) can be derived from the translation of RNA, or synthesized chemically, and can be conjugated to a carrier protein if desired. Commonly used carriers that are chemically coupled to peptides include bovine serum albumin, thyroglobulin, and keyhole limpet hemocyanin (KLH). The coupled peptide is then used to immunize the animal.

The term "antigenic determinant" refers to that region of a molecule (i.e., an epitope) that makes contact with a particular antibody. When a protein or a fragment of a protein is used to immunize a host animal, numerous regions of the protein may induce the production of antibodies which bind specifically to antigenic determinants (particular regions or three-dimensional structures on the protein). An antigenic determinant may compete with the intact antigen (i.e., the immunogen used to elicit the immune response) for binding to an antibody.

The term "aptamer" refers to a nucleic acid or oligonucleotide molecule that binds to a specific molecular target. Aptamers are derived from an in vitro evolutionary process (e.g., SELEX (Systematic Evolution of Ligands by EXponential Enrichment), described in U.S. Pat. No. 5,270,163), which selects for target-specific aptamer sequences from large combinatorial libraries. Aptamer compositions may be double-stranded or single-stranded, and may include deoxyribonucleotides, ribonucleotides, nucleotide derivatives, or other nucleotide-like molecules. The nucleotide components of an aptamer may have modified sugar groups (e.g., the 2'-OH group of a ribonucleotide may be replaced by 2'-F or 2'-NH$_2$), which may improve a desired property, e.g., resistance to nucleases or longer lifetime in blood. Aptamers may be conjugated to other molecules, e.g., a high molecular weight carrier to slow clearance of the aptamer from the circulatory system. Aptamers may be specifically cross-linked to their cognate ligands, e.g., by photo-activation of a cross-linker. (See, e.g., Brody, E. N. and L. Gold (2000) J. Biotechnol. 74:5-13.)

The term "intramer" refers to an aptamer which is expressed in vivo. For example, a vaccinia virus-based RNA expression system has been used to express specific RNA aptamers at high levels in the cytoplasm of leukocytes (Blind, M. et al. (1999) Proc. Natl Acad. Sci. USA 96:3606-3610).

The term "spiegelmer" refers to an aptamer which includes L-DNA, L-RNA, or other left-handed nucleotide derivatives or nucleotide-like molecules. Aptamers containing left-handed nucleotides are resistant to degradation by naturally occurring enzymes, which normally act on substrates containing right-handed nucleotides.

The term "antisense" refers to any composition capable of base-pairing with the "sense" (coding) strand of a specific nucleic acid sequence. Antisense compositions may include DNA; RNA; peptide nucleic acid (PNA); oligonucleotides having modified backbone linkages such as phosphorothioates, methylphosphonates, or benzylphosphonates; oligonucleotides having modified sugar groups such as 2'-methoxyethyl sugars or 2'-methoxyethoxy sugars; or oligonucleotides having modified bases such as 5-methyl cytosine, 2'-deoxyuracil, or 7-deaza-2'-deoxyguanosine. Antisense molecules may be produced by any method including chemical synthesis or transcription. Once introduced into a cell, the complementary antisense molecule base-pairs with a naturally occurring nucleic acid sequence produced by the cell to form duplexes which block either transcription or translation. The designation "negative" or "minus" can refer to the antisense strand, and the designation "positive" or "plus" can refer to the sense strand of a reference DNA molecule.

The term "biologically active" refers to a protein having structural, regulatory, or biochemical functions of a naturally occurring molecule. Likewise, "immunologically active" or "immunogenic" refers to the capability of the natural, recombinant, or synthetic SECP, or of any oligopeptide thereof, to induce a specific immune response in appropriate animals or cells and to bind with specific antibodies.

"Complementary" describes the relationship between two single-stranded nucleic acid sequences that anneal by base-pairing. For example, 5'-AGT-3' pairs with its complement, 3'-TCA-5'.

A "composition comprising a given polynucleotide sequence" and a "composition comprising a given amino acid sequence" refer broadly to any composition containing the given polynucleotide or amino acid sequence. The composition may comprise a dry formulation or an aqueous solution. Compositions comprising polynucleotide sequences encoding SECP or fragments of SECP may be employed as hybridization probes. The probes may be stored in freeze-dried form and may be associated with a stabilizing agent such as a carbohydrate. In hybridizations, the probe may be deployed in an aqueous solution containing salts (e.g., NaCl), detergents (e.g., sodium dodecyl sulfate; SDS), and other components (e.g., Denhardt's solution, dry milk, salmon sperm DNA, etc.).

"Consensus sequence" refers to a nucleic acid sequence which has been subjected to repeated DNA sequence analysis to resolve uncalled bases, extended using the XL-PCR kit (Applied Biosystems, Foster City Calif.) in the 5' and/or the 3' direction, and resequenced, or which has been assembled from one or more overlapping cDNA, EST, or genomic DNA fragments using a computer program for fragment assembly, such as the GELVIEW fragment assembly system (GCG, Madison Wis.) or Phrap (University of Washington, Seattle Wash.). Some sequences have been both extended and assembled to produce the consensus sequence.

"Conservative amino acid substitutions" are those substitutions that are predicted to least interfere with the properties of the original protein, i.e., the structure and especially the function of the protein is conserved and not significantly changed by such substitutions. The table below shows amino acids which may be substituted for an original amino acid in a protein and which are regarded as conservative amino acid substitutions.

| Original Residue | Conservative Substitution |
| --- | --- |
| Ala | Gly, Ser |
| Arg | His, Lys |
| Asn | Asp, Gln, His |
| Asp | Asn, Glu |
| Cys | Ala, Ser |
| Gln | Asn, Glu, His |
| Glu | Asp, Gln, His |
| Gly | Ala |
| His | Asn, Arg, Gln, Glu |
| Ile | Leu, Val |
| Leu | Ile, Val |
| Lys | Arg, Gln, Glu |
| Met | Leu, Ile |
| Phe | His, Met, Leu, Trp, Tyr |
| Ser | Cys, Thr |
| Thr | Ser, Val |
| Trp | Phe, Tyr |
| Tyr | His, Phe, Trp |
| Val | Ile, Leu, Thr |

Conservative amino acid substitutions generally maintain (a) the structure of the polypeptide backbone in the area of the substitution, for example, as a beta sheet or alpha helical conformation, (b) the charge or hydrophobicity of the molecule at the site of the substitution, and/or (c) the bulk of the side chain.

A "deletion" refers to a change in the amino acid or nucleotide sequence that results in the absence of one or more amino acid residues or nucleotides.

The term "derivative" refers to a chemically modified polynucleotide or polypeptide. Chemical modifications of a polynucleotide can include, for example, replacement of hydrogen by an alkyl, acyl, hydroxyl, or amino group. A derivative polynucleotide encodes a polypeptide which retains at least one biological or immunological function of the natural molecule. A derivative polypeptide is one modified by glycosylation, pegylation, or any similar process that retains at least one biological or immunological function of the polypeptide from which it was derived.

A "detectable label" refers to a reporter molecule or enzyme that is capable of generating a measurable signal and is covalently or noncovalently joined to a polynucleotide or polypeptide.

"Differential expression" refers to increased or upregulated; or decreased, downregulated, or absent gene or protein expression, determined by comparing at least two different samples. Such comparisons may be carried out between, for example, a treated and an untreated sample, or a diseased and a normal sample.

"Exon shuffling" refers to the recombination of different coding regions (exons). Since an exon may represent a structural or functional domain of the encoded protein, new proteins may be assembled through the novel reassortment of stable substructures, thus allowing acceleration of the evolution of new protein functions.

A "fragment" is a unique portion of SECP or the polynucleotide encoding SECP which is identical in sequence to but shorter in length than the parent sequence. A fragment may comprise up to the entire length of the defined sequence, minus one nucleotide/amino acid residue. For example, a fragment may comprise from 5 to 1000 contiguous nucleotides or amino acid residues. A fragment used as a probe, primer, antigen, therapeutic molecule, or for other purposes, may be at least 5, 10, 15, 16, 20, 25, 30, 40, 50, 60, 75, 100, 150, 250 or at least 500 contiguous nucleotides or amino acid residues in length. Fragments may be preferentially selected from certain regions of a molecule. For example, a polypeptide fragment may comprise a certain length of contiguous amino acids selected from the first 250 or 500 amino acids (or first 25% or 50%) of a polypeptide as shown in a certain defined sequence. Clearly these lengths are exemplary, and any length that is supported by the specification, including the Sequence Listing, tables, and FIGURES, may be encompassed by the present embodiments.

A fragment of SEQ ID NO:64-126 comprises a region of unique polynucleotide sequence that specifically identifies SEQ ID NO:64-126, for example, as distinct from any other sequence in the genome from which the fragment was obtained. A fragment of SEQ ID NO:64-126 is useful, for example, in hybridization and amplification technologies and in analogous methods that distinguish SEQ ID NO:64-126 from related polynucleotide sequences. The precise length of a fragment of SEQ ID NO:64-126 and the region of SEQ ID NO:64-126 to which the fragment corresponds are routinely determinable by one of ordinary skill in the art based on the intended purpose for the fragment.

A fragment of SEQ ID NO: 1-63 is encoded by a fragment of SEQ ID NO:64-126. A fragment of SEQ ID NO: 1-63 comprises a region of unique amino acid sequence that specifically identifies SEQ ID NO:1-63. For example, a fragment of SEQ ID NO:1-63 is useful as an immunogenic peptide for the development of antibodies that specifically recognize SEQ ID NO: 1-63. The precise length of a fragment of SEQ ID NO: 1-63 and the region of SEQ ID NO: 1-63 to which the fragment corresponds are routinely determinable by one of ordinary skill in the art based on the intended purpose for the fragment.

A "full length" polynucleotide sequence is one containing at least a translation initiation codon (e.g., methionine) followed by an open reading frame and a translation termination codon. A "full length" polynucleotide sequence encodes a "full length" polypeptide sequence.

"Homology" refers to sequence similarity or, interchangeably, sequence identity, between two or more polynucleotide sequences or two or more polypeptide sequences.

The terms "percent identity" and "% identity," as applied to polynucleotide sequences, refer to the percentage of residue matches between at least two polynucleotide sequences aligned using a standardized algorithm. Such an algorithm may insert, in a standardized and reproducible way, gaps in the sequences being compared in order to optimize alignment between two sequences, and therefore achieve a more meaningful comparison of the two sequences.

Percent identity between polynucleotide sequences may be determined using the default parameters of the CLUSTAL V algorithm as incorporated into the MEGALIGN version 3.12e sequence alignment program. This program is part of the LASERGENE software package, a suite of molecular biological analysis programs (DNASTAR, Madison Wis.). CLUSTAL V is described in Higgins, D. G. and P. M. Sharp (1989) CABIOS 5:151-153 and in Higgins, D. G. et al. (1992) CABIOS 8:189-191. For pairwise alignments of polynucleotide sequences, the default parameters are set as follows: Ktuple=2, gap penalty=5, window=4, and "diagonals saved"-4. The "weighted" residue weight table is selected as the default. Percent identity is reported by CLUSTAL V as the "percent similarity" between aligned polynucleotide sequences.

Alternatively, a suite of commonly used and freely available sequence comparison algorithms is provided by the National Center for Biotechnology Information (NCBI) Basic Local Alignment Search Tool (BLAST) (Altschul, S. F. et al. (1990) J. Mol. Biol. 215:403-410), which is available from several sources, including the NCBI, Bethesda, Md., and on the Internet at http://www.ncbi.nlm.nih.gov-BLAST/. The BLAST software suite includes various sequence analysis programs including "blastn," that is used to align a known polynucleotide sequence with other polynucleotide sequences from a variety of databases. Also available is a tool called "BLAST 2 Sequences" that is used for direct pairwise comparison of two nucleotide sequences. "BLAST 2 Sequences" can be accessed and used interactively at http://www.ncbi.nlm.nih.gov/gorf/bl2.html. The "BLAST 2 Sequences" tool can be used for both blastn and blastp (discussed below). BLAST programs are commonly used with gap and other parameters set to default settings. For example, to compare two nucleotide sequences, one may use blastn with the "BLAST 2 Sequences" tool Version 2.0.12 (Apr. 21, 2000) set at default parameters. Such default parameters may be, for example:

Matrix: BLOSUM62
Reward for match: 1
Penalty for mismatch: −2
Open Gap: 5 and Extension Gap: 2 penalties
Gap x drop-off 50
Expect: 10
Word Size: 11
Filter: on Percent identity may be measured over the length of an entire defined sequence, for example, as defined by a particular SEQ ID number, or may be measured over a shorter length, for example, over the length of a fragment taken from a larger, defined sequence, for instance, a fragment of at least 20, at least 30, at least 40, at least 50, at least 70, at least 100, or at least 200 contiguous nucleotides. Such lengths are exemplary only, and it is understood that any fragment length supported by the sequences shown herein, in the tables, FIGURES, or Sequence Listing, may be used to describe a length over which percentage identity may be measured.

Nucleic acid sequences that do not show a high degree of identity may nevertheless encode similar amino acid sequences due to the degeneracy of the genetic code. It is understood that changes in a nucleic acid sequence can be made using this degeneracy to produce multiple nucleic acid sequences that all encode substantially the same protein.

The phrases "percent identity" and "% identity," as applied to polypeptide sequences, refer to the percentage of residue matches between at least two polypeptide sequences aligned using a standardized algorithm. Methods of polypeptide sequence alignment are well-known. Some alignment methods take into account conservative amino acid substitutions. Such conservative substitutions, explained in more detail above, generally preserve the charge and hydrophobicity at the site of substitution, thus preserving the structure (and therefore function) of the polypeptide.

Percent identity between polypeptide sequences may be determined using the default parameters of the CLUSTAL V algorithm as incorporated into the MEGALIGN version 3.12e sequence alignment program (described and referenced above). For pairwise alignments of polypeptide sequences using CLUSTAL V, the default parameters are set as follows: Ktuple=1, gap penalty=3, window=5, and "diagonals saved"=5. The PAM250 matrix is selected as the default residue weight table. As with polynucleotide alignments, the percent identity is reported by CLUSTAL V as the "percent similarity" between aligned polypeptide sequence pairs.

Alternatively the NCBI BLAST software suite may be used. For example, for a pairwise comparison of two polypeptide sequences, one may use the "BLAST 2 Sequences" tool Version 2.0.12 (Apr. 21, 2000) with blastp set at default parameters. Such default parameters may be, for example:

Matrix: BLOSUM62
Open Gap: 11 and Extension Gap: 1 penalties
Gap x drop-off: 50
Expect: 10
Word Size: 3
Filter: on Percent identity may be measured over the length of an entire defined polypeptide sequence, for example, as defined by a particular SEQ ID number, or may be measured over a shorter length, for example, over the length of a fragment taken from a larger, defined polypeptide sequence, for instance, a fragment of at least 15, at least 20, at least 30, at least 40, at least 50, at least 70 or at least 150 contiguous residues. Such lengths are exemplary only, and it is understood that any fragment length supported by the sequences shown herein, in the tables, FIGURES or Sequence Listing, may be used to describe a length over which percentage identity may be measured.

"Human artificial chromosomes" (HACs) are linear microchromosomes which may contain DNA sequences of about 6 kb to 10 Mb in size and which contain all of the elements required for chromosome replication, segregation and maintenance.

The term "humanized antibody" refers to an antibody molecule in which the amino acid sequence in the non-antigen binding regions has been altered so that the antibody more closely resembles a human antibody, and still retains its original binding ability.

"Hybridization" refers to the process by which a polynucleotide strand anneals with a complementary strand through base pairing under defined hybridization conditions. Specific hybridization is an indication that two nucleic acid sequences share a high degree of complementarity. Specific hybridization complexes form under permissive annealing conditions and remain hybridized after the "washing" step(s). The washing step(s) is particularly important in determining the stringency of the hybridization process, with more stringent conditions allowing less non-specific binding, i.e., binding between pairs of nucleic acid strands that are not perfectly matched. Permissive conditions for annealing of nucleic acid sequences are routinely determinable by one of ordinary skill in the art and may be consistent among hybridization experiments, whereas wash conditions may be varied among experiments to achieve the desired stringency, and therefore hybridization specificity. Permissive annealing conditions occur, for example, at 68° C. in the presence of about 6×SSC, about 1% (w/v) SDS, and about 100 µg/ml sheared, denatured salmon sperm DNA.

Generally, stringency of hybridization is expressed, in part, with reference to the temperature under which the wash step is carried out. Such wash temperatures are typically selected to be about 5° C. to 20° C. lower than the thermal melting point ($T_m$) for the specific sequence at a defined ionic strength and pH. The $T_m$ is the temperature (under defined ionic strength and pH) at which 50% of the target sequence hybridizes to a perfectly matched probe. An equation for calculating $T_m$ and conditions for nucleic acid hybridization are well known and can be found in Sambrook, J. et al. (1989) *Molecular Cloning: A Laboratory Manual*, 2$^{nd}$ ed., vol. 1-3, Cold Spring Harbor Press, Plainview N.Y.; specifically see volume 2, chapter 9.

High stringency conditions for hybridization between polynucleotides of the present invention include wash conditions of 68° C. in the presence of about 0.2×SSC and about 0.1% SDS, for 1 hour. Alternatively, temperatures of about 65° C., 60° C., 55° C., or 42° C. may be used. SSC concentration may be varied from about 0.1 to 2×SSC, with SDS being present at about 0.1%. Typically, blocking reagents are used to block non-specific hybridization. Such blocking reagents include, for instance, sheared and denatured salmon sperm DNA at about 100-200 µg/ml. Organic solvent, such as formamide at a concentration of about 35-50% v/v, may also be used under particular circumstances, such as for RNA:DNA hybridizations. Useful variations on these wash conditions will be readily apparent to those of ordinary skill in the art. Hybridization, particularly under high stringency conditions, may be suggestive of evolutionary similarity between the nucleotides. Such similarity is strongly indicative of a similar role for the nucleotides and their encoded polypeptides.

The term "hybridization complex" refers to a complex formed between two nucleic acid sequences by virtue of the formation of hydrogen bonds between complementary bases. A hybridization complex may be formed in solution (e.g., $C_0 t$ or $R_0 t$ analysis) or formed between one nucleic acid sequence present in solution and another nucleic acid sequence immobilized on a solid support (e.g., paper, membranes, filters, chips, pins or glass slides, or any other appropriate substrate to which cells or their nucleic acids have been fixed).

The words "insertion" and "addition" refer to changes in an amino acid or nucleotide sequence resulting in the addition of one or more amino acid residues or nucleotides, respectively.

"Immune response" can refer to conditions associated with inflammation, trauma, immune disorders, or infectious or genetic disease, etc. These conditions can be characterized by expression of various factors, e.g., cytokines, chemokines, and other signaling molecules, which may affect cellular and systemic defense systems.

An "immunogenic fragment" is a polypeptide or oligopeptide fragment of SECP which is capable of eliciting an immune response when introduced into a living organism, for example, a mammal. The term "immunogenic fragment" also includes any polypeptide or oligopeptide fragment of SECP which is useful in any of the antibody production methods disclosed herein or known in the art.

The term "microarray" refers to an arrangement of a plurality of polynucleotides, polypeptides, or other chemical compounds on a substrate.

The terms "element" and "array element" refer to a polynucleotide, polypeptide, or other chemical compound having a unique and defined position on a microarray.

The term "modulate" refers to a change in the activity of SECP. For example, modulation may cause an increase or a decrease in protein activity, binding characteristics, or any other biological, functional, or immunological properties of SECP.

The phrases "nucleic acid" and "nucleic acid sequence" refer to a nucleotide, oligonucleotide, polynucleotide, or any fragment thereof. These phrases also refer to DNA or RNA of genomic or synthetic origin which may be single-stranded or double-stranded and may represent the sense or the antisense strand, to peptide nucleic acid (PNA), or to any DNA-like or RNA-like material.

"Operably linked" refers to the situation in which a first nucleic acid sequence is placed in a functional relationship with a second nucleic acid sequence. For instance, a promoter is operably linked to a coding sequence if the promoter affects the transcription or expression of the coding sequence. Operably linked DNA sequences may be in close proximity or contiguous and, where necessary to join two protein coding regions, in the same reading frame.

"Peptide nucleic acid" (PNA) refers to an antisense molecule or anti-gene agent which comprises an oligonucleotide of at least about 5 nucleotides in length linked to a peptide backbone of amino acid residues ending in lysine. The terminal lysine confers solubility to the composition. PNAs preferentially bind complementary single stranded DNA or RNA and stop transcript elongation, and may be pegylated to extend their lifespan in the cell.

"Post-translational modification" of an SECP may involve lipidation, glycosylation, phosphorylation, acetylation, racemization, proteolytic cleavage, and other modifications known in the art. These processes may occur synthetically or biochemically. Biochemical modifications will vary by cell type depending on the enzymatic milieu of SECP.

"Probe" refers to nucleic acid sequences encoding SECP, their complements, or fragments thereof, which are used to detect identical, allelic or related nucleic acid sequences. Probes are isolated oligonucleotides or polynucleotides attached to a detectable label or reporter molecule. Typical labels include radioactive isotopes, ligands, chemiluminescent agents, and enzymes. "Primers" are short nucleic acids, usually DNA oligonucleotides, which may be annealed to a target polynucleotide by complementary base-pairing. The primer may then be extended along the target DNA strand by a DNA polymerase enzyme. Primer pairs can be used for amplification (and identification) of a nucleic acid sequence, e.g., by the polymerase chain reaction (PCR).

Probes and primers as used in the present invention typically comprise at least 15 contiguous nucleotides of a known sequence. In order to enhance specificity, longer probes and primers may also be employed, such as probes and primers that comprise at least 20, 25, 30, 40, 50, 60, 70, 80, 90, 100, or at least 150 consecutive nucleotides of the disclosed nucleic acid sequences. Probes and primers may be considerably longer than these examples, and it is understood that any length supported by the specification, including the tables, FIGURES, and Sequence Listing, may be used.

Methods for preparing and using probes and primers are described in the references, for example Sambrook, J. et al. (1989) *Molecular Cloning: A Laboratory Manual*, $2^{nd}$ ed., vol. 1-3, Cold Spring Harbor Press, Plainview N.Y.; Ausubel, F. M. et al. (1987) *Current Protocols in Molecular Biology*, Greene Publ. Assoc. & Wiley-Intersciences, New York N.Y.; Innis, M. et al. (1990) *PCR Protocols, A Guide to Methods and Applications*, Academic Press, San Diego Calif. PCR primer pairs can be derived from a known sequence, for example, by using computer programs intended for that purpose such as Primer (Version 0.5, 1991, Whitehead Institute for Biomedical Research, Cambridge Mass.).

Oligonucleotides for use as primers are selected using software known in the art for such purpose. For example, OLIGO 4.06 software is useful for the selection of PCR primer pairs of up to 100 nucleotides each, and for the analysis of oligonucleotides and larger polynucleotides of up to 5,000 nucleotides from an input polynucleotide sequence of up to 32 kilobases. Similar primer selection programs have incorporated additional features for expanded capabilities. For example, the PrimOU primer selection program (available to the public from the Genome Center at University of Texas South West Medical Center, Dallas Tex.) is capable of choosing specific primers from megabase sequences and is thus useful for designing primers on a genome-wide scope. The Primer3 primer selection program (available to the public from the Whitehead Institute/MIT Center for Genome Research, Cambridge Mass.) allows the user to input a "mispriming library," in which sequences to avoid as primer binding sites are user-specified. Primer3 is useful, in particular, for the selection of oligonucleotides for microarrays. (The source code for the latter two primer selection programs may also be obtained from their respective sources and modified to meet the user's specific needs.) The PrimeGen program (available to the public from the UK Human Genome Mapping Project Resource Centre, Cambridge UK) designs primers based on multiple sequence alignments, thereby allowing selection of primers that hybridize to either the most conserved or least conserved regions of aligned nucleic acid sequences. Hence, this program is useful for identification of both unique and conserved oligonucleotides and polynucleotide fragments. The oligonucleotides and polynucleotide fragments identified by any of the above selection methods are useful in hybridization technologies, for example, as PCR or sequencing primers, microarray elements, or specific probes to identify fully or partially complementary polynucleotides in a sample of nucleic acids. Methods of oligonucleotide selection are not limited to those described above.

A "recombinant nucleic acid" is a sequence that is not naturally occurring or has a sequence that is made by an artificial combination of two or more otherwise separated segments of sequence. This artificial combination is often accomplished by chemical synthesis or, more commonly, by the artificial manipulation of isolated segments of nucleic acids, e.g., by genetic engineering techniques such as those described in Sambrook, sura. The term recombinant includes nucleic acids that have been altered solely by addition, substitution, or deletion of a portion of the nucleic acid. Frequently, a recombinant nucleic acid may include a nucleic acid sequence operably linked to a promoter sequence. Such a recombinant nucleic acid may be part of a vector that is used, for example, to transform a cell.

Alternatively, such recombinant nucleic acids may be part of a viral vector, e.g., based on a vaccinia virus, that could be use to vaccinate a mammal wherein the recombinant nucleic acid is expressed, inducing a protective immunological response in the mammal.

A "regulatory element" refers to a nucleic acid sequence usually derived from untranslated regions of a gene and includes enhancers, promoters, introns, and 5' and 3' untranslated regions (UTRs). Regulatory elements interact with host or viral proteins which control transcription, translation, or RNA stability.

"Reporter molecules" are chemical or biochemical moieties used for labeling a nucleic acid, amino acid, or antibody. Reporter molecules include radionuclides; enzymes; fluorescent, chemiluminescent, or chromogenic agents; substrates; cofactors; inhibitors; magnetic particles; and other moieties known in the art.

An "RNA equivalent," in reference to a DNA sequence, is composed of the same linear sequence of nucleotides as the reference DNA sequence with the exception that all occurrences of the nitrogenous base thymine are replaced with uracil, and the sugar backbone is composed of ribose instead of deoxyribose.

The term "sample" is used in its broadest sense. A sample suspected of containing SECP, nucleic acids encoding SECP, or fragments thereof may comprise a bodily fluid; an extract from a cell, chromosome, organelle, or membrane isolated from a cell; a cell; genomic DNA, RNA, or cDNA, in solution or bound to a substrate; a tissue; a tissue print; etc.

The terms "specific binding" and "specifically binding" refer to that interaction between a protein or peptide and an agonist, an antibody, an antagonist, a small molecule, or any natural or synthetic binding composition. The interaction is dependent upon the presence of a particular structure of the protein, e.g., the antigenic determinant or epitope, recognized by the binding molecule. For example, if an antibody is specific for epitope "A," the presence of a polypeptide comprising the epitope A, or the presence of free unlabeled A, in a reaction containing free labeled A and the antibody will reduce the amount of labeled A that binds to the antibody.

The term "substantially purified" refers to nucleic acid or amino acid sequences that are removed from their natural environment and are isolated or separated, and are at least 60% free, preferably at least 75% free, and most preferably at least 90% free from other components with which they are naturally associated.

A "substitution" refers to the replacement of one or more amino acid residues or nucleotides by different amino acid residues or nucleotides, respectively.

"Substrate" refers to any suitable rigid or semi-rigid support including membranes, filters, chips, slides, wafers, fibers, magnetic or nonmagnetic beads, gels, tubing, plates, polymers, microparticles and capillaries. The substrate can have a variety of surface forms, such as wells, trenches, pins, channels and pores, to which polynucleotides or polypeptides are bound.

A "transcript image" or "expression profile" refers to the collective pattern of gene expression by a particular cell type or tissue under given conditions at a given time.

"Transformation" describes a process by which exogenous DNA is introduced into a recipient cell. Transformation may occur under natural or artificial conditions according to various methods well known in the art, and may rely on any known method for the insertion of foreign nucleic acid sequences into a prokaryotic or eukaryotic host cell. The method for transformation is selected based on the type of host cell being transformed and may include, but is not limited to, bacteriophage or viral infection, electroporation, heat shock, lipofection, and particle bombardment. The term "transformed cells" includes stably transformed cells in which the inserted DNA is capable of replication either as an autonomously replicating plasmid or as part of the host chromosome, as well as transiently transformed cells which express the inserted DNA or RNA for limited periods of time.

A "transgenic organism," as used herein, is any organism, including but not limited to animals and plants, in which one or more of the cells of the organism contains heterologous nucleic acid introduced by way of human intervention, such as by transgenic techniques well known in the art. The nucleic acid is introduced into the cell, directly or indirectly by introduction into a precursor of the cell, by way of deliberate genetic manipulation, such as by microinjection or by infection with a recombinant virus. The term genetic manipulation does not include classical cross-breeding, or in vitro fertilization, but rather is directed to the introduction of a recombinant DNA molecule. The transgenic organisms contemplated in accordance with the present invention include bacteria, cyanobacteria, fungi, plants and animals. The isolated DNA of the present invention can be introduced into the host by methods known in the art, for example infection, transfection, transformation or transconjugation. Techniques for transferring the DNA of the present invention into such organisms are widely known and provided in references such as Sambrook et al. (1989), supra.

A "variant" of a particular nucleic acid sequence is defined as a nucleic acid sequence having at least 40% sequence identity to the particular nucleic acid sequence over a certain length of one of the nucleic acid sequences using blastn with the "BLAST 2 Sequences" tool Version 2.0.9 (May 7-1999) set at default parameters. Such a pair of nucleic acids may show, for example, at least 50%, at least 60%, at least 70%, at least 80%, at least 85%, at least 90%, at least 91%, at least 92%, at least 93%, at least 94%, at least 95%, at least 96%, at least 97%, at least 98%, or at least 99% or greater sequence identity over a certain defined length. A variant may be described as, for example, an "allelic" (as defined above), "splice," "species," or "polymorphic" variant. A splice variant may have significant identity to a reference molecule, but will generally have a greater or lesser number of polynucleotides due to alternate splicing of exons during mRNA processing. The corresponding polypeptide may possess additional functional domains or lack domains that are present in the reference molecule. Species variants are polynucleotide sequences that vary from one species to another. The resulting polypeptides will generally have significant amino acid identity relative to each other. A polymorphic variant is a variation in the polynucleotide sequence of a particular gene between individuals of a given species. Polymorphic variants also may encompass "single nucleotide polymorphisms" (SNPs) in which the polynucleotide sequence varies by one nucleotide base. The presence of SNPs may be indicative of, for example, a certain population, a disease state, or a propensity for a disease state.

A "variant" of a particular polypeptide sequence is defined as a polypeptide sequence having at least 40% sequence identity to the particular polypeptide sequence over a certain length of one of the polypeptide sequences using blastp with the "BLAST 2 Sequences" tool Version 2.0.9 (May 7-1999) set at default parameters. Such a pair of polypeptides may show, for example, at least 50%, at least 60%, at least 70%, at least 80%, at least 90%, at least 91%, at least 92%, at least 93%, at least 94%, at least 95%, at least 96%, at least 97%, at least 98%, or at least 99% or greater sequence identity over a certain defined length of one of the polypeptides.

THE INVENTION

The invention is based on the discovery of new human secreted proteins (SECP), the polynucleotides encoding SECP, and the use of these compositions for the diagnosis, treatment, or prevention of cell proliferative, autoimmune/ inflammatory, cardiovascular, neurological, and developmental disorders.

Table 1 summarizes the nomenclature for the full length polynucleotide and polypeptide sequences of the invention. Each polynucleotide and its corresponding polypeptide are correlated to a single Incyte project identification number (Incyte Project ID). Each polypeptide sequence is denoted by both a polypeptide sequence identification number (Polypeptide SEQ ID NO:) and an Incyte polypeptide sequence number (Incyte Polypeptide ID) as shown. Each polynucleotide sequence is denoted by both a polynucleotide sequence identification number (Polynucleotide SEQ ID NO:) and an Incyte polynucleotide consensus sequence number (Incyte Polynucleotide ID) as shown.

Table 2 shows sequences with homology to the polypeptides of the invention as identified by BLAST analysis against the GenBank protein (genpept) database. Columns 1 and 2 show the polypeptide sequence identification number (Polypeptide SEQ ID NO:) and the corresponding Incyte polypeptide sequence number (Incyte Polypeptide ID) for polypeptides of the invention. Column 3 shows the GenBank identification number (GenBank ID NO:) of the nearest GenBank homolog. Column 4 shows the probability scores for the matches between each polypeptide and its homolog(s). Column 5 shows the annotation of the GenBank homolog(s) along with relevant citations where applicable, all of which are expressly incorporated by reference herein.

Table 3 shows various structural features of the polypeptides of the invention. Columns 1 and 2 show the polypeptide sequence identification number (SEQ ID NO:) and the corresponding Incyte polypeptide sequence number (Incyte Polypeptide ID) for each polypeptide of the invention. Column 3 shows the number of amino acid residues in each polypeptide. Column 4 shows potential phosphorylation sites, and column 5 shows potential glycosylation sites, as determined by the MOTIFS program of the GCG sequence analysis software package (Genetics Computer Group, Madison Wis.). Column 6 shows amino acid residues comprising signature sequences, domains, and motifs. Column 7 shows analytical methods for protein structure/function analysis and in some cases, searchable databases to which the analytical methods were applied.

Together, Tables 2 and 3 summarize the properties of polypeptides of the invention, and these properties establish that the claimed polypeptides are secreted proteins. For example, SEQ ID NO:1 is 34% identical to human seizure related gene 6 (mouse)-like protein, isoform 1 (GenBank ID g6941612) as determined by the Basic Local Alignment Search Tool (BLAST). The BLAST probability score is 8.5e-34, which indicates the probability of obtaining the observed polypeptide sequence alignment by chance. SEQ ID NO:1 also contains two CUB domains and a sushi domain (SCR repeat) as determined by searching for statistically significant matches in the hidden Markov model (HMM)-based PFAM database of conserved protein family domains. (See Table 3.). In an alternative example, SEQ ID NO:2 is 40% identical to Drosophila melanoraster peroxidasin precursor (GenBank ID g531385) as determined by the Basic Local Alignment Search Tool (BLAST). (See Table 2.) The BLAST probability score is 7.8e-266, which indicates the probability of obtaining the observed polypeptide sequence alignment by chance. SEQ ID NO:2 also contains a peroxidase domain, four immunoglobulin domains, six leucine-rich repeats, a leucine-rich repeat C-terminal domain, and a von Willebrand factor type C domain as determined by searching for statistically significant matches in the hidden Markov model (HMM)-based PFAM database of conserved protein family domains. (See Table 3.) Data from BLIMPS and MOTIFS analyses provide further corroborative evidence that SEQ ID NO:2 is a peroxidasin homolog. In an alternative example, SEQ ID NO:4 is 98% identical to Rattus norvegicus neurexophilin (GenBank ID g508574) as determined by the Basic Local Alignment Search Tool (BLAST). (See Table 2.) The BLAST probability score is 4.7e-148, which indicates the probability of obtaining the observed polypeptide sequence alignment by chance. Data from SPSCAN and BLAST_PRODOM analyses provide further corroborative evidence that SEQ ID NO:4 is a secreted neurexophilin. In an alternative example, SEQ ID NO:6 is 68% identical to pig preprosecretin (GenBank ID g164671) as determined by the Basic Local Alignment Search Tool (BLAST). (See Table 2.) The BLAST probability score is 2.3e-36, which indicates the probability of obtaining the observed polypeptide sequence alignment by chance. SEQ ID NO:6 has a signal peptide, as predicted by HMMER and SPSCAN. SEQ ID NO:6 also contains a polypeptide hormone domain as determined by searching for statistically significant matches in the hidden Markov model (HMM)-based PFAM database of conserved protein family domains. (See Table 3.) The presence of this domain is confirmed by BLIMPS and MOTIFS analyses, providing further corroborative evidence that SEQ ID NO:6 is a secreted hormone. In an alternative example, SEQ ID NO:28 is 78% identical to Mus musculus nodal, a TGF-β like gene (GenBank ID g296605) as determined by the Basic Local Alignment Search Tool (BLAST). (See Table 2.) The BLAST probability score is 7.5e-148, which indicates the probability of obtaining the observed polypeptide sequence alignment by chance. SEQ ID NO:28 also contains a TGF-β like domain as determined by searching for statistically significant matches in the hidden Markov model (HMM)-based PFAM database of conserved protein family domains. (See Table 3.) Data from BLIMPS, MOTIFS, and PROFILESCAN analyses provide further corroborative evidence that SEQ ID NO:28 is a TGF-β like protein. In an alternative example, SEQ ID NO:63 is 86% identical to rat late gestation lung protein 1 (GenBank ID g4324682) as determined by the Basic Local Alignment Search Tool (BLAST). (See Table 2.) The BLAST probability score is 3.4e-97, which indicates the probability of obtaining the observed polypeptide sequence alignment by chance. SEQ ID NO:63 also contains an SCP (sperm-coating glycoprotein)-like extracellular protein domain as determined by searching for statistically significant matches in the hidden Markov model (HMM)-based PFAM database of conserved protein family domains. (See Table 3.) Data from BLIMPS and MOTIFS analyses provide further corroborative evidence that SEQ ID NO:63 is a protease inhibitor-like protein. SEQ ID NO:3, SEQ ID NO:5, SEQ ID NO:7-27, and SEQ ID NO:29-62 were analyzed and annotated in a similar manner. The algorithms and parameters for the analysis of SEQ ID NO: 1-63 are described in Table 7.

As shown in Table 4, the full length polynucleotide sequences of the present invention were assembled using cDNA sequences or coding (exon) sequences derived from genomic DNA, or any combination of these two types of sequences. Columns 1 and 2 list the polynucleotide sequence identification number (Polynucleotide SEQ ID NO:) and the corresponding Incyte polynucleotide consensus sequence number (Incyte Polynucleotide ID) for each polynucleotide of the invention. Column 3 shows the length of each polynucleotide sequence in basepairs. Column 4 lists fragments of the polynucleotide sequences which are useful, for example, in hybridization or amplification technologies that identify SEQ ID NO:64-126 or that distinguish between SEQ ID NO:64-126 and related polynucleotide sequences. Column 5 shows identification numbers corresponding to cDNA sequences, coding sequences (exons) predicted from genomic DNA, and/or sequence assemblages comprised of both cDNA and genomic DNA. These sequences were used to assemble the full length polynucleotide sequences of the invention. Columns 6 and 7 of Table 4 show the nucleotide start (5') and stop (3') positions of the cDNA and/or genomic sequences in column 5 relative to their respective full length sequences.

The identification numbers in Column 5 of Table 4 may refer specifically, for example, to Incyte cDNAs along with their corresponding cDNA libraries. For example, 2719959T6 is the identification number of an Incyte cDNA sequence, and LUNGTUTI0 is the cDNA library from which it is derived. Incyte cDNAs for which cDNA libraries are not indicated were derived from pooled cDNA libraries (e.g., 56002879J1). Alternatively, the identification numbers in column 5 may refer to GenBank cDNAs or ESTs (e.g., g1547765) which contributed to the assembly of the full length polynucleotide sequences. In addition, the identification numbers in column 5 may identify sequences derived from the ENSEMBL (The Sanger Centre, Cambridge, UK) database (i.e., those sequences including the designation "ENST"). Alternatively, the identification numbers in column 5 may be derived from the NCBI RefSeq Nucleotide Sequence Records Database (i.e., those sequences including the designation "NM" or "NT") or the NCBI RefSeq Protein Sequence Records (i.e., those sequences including the designation "NP"). Alternatively, the identification numbers in column 5 may refer to assemblages of both cDNA and Genscan-predicted exons brought together by an "exon stitching" algorithm. For example, FL_XXXXXX_$N_1$_$N_2$_YYYYYY_$N_3$_$N_4$ represents a "stitched" sequence in which XXXXXX is the identification number of the cluster of sequences to which the algorithm was applied, and YYYYY is the number of the prediction generated by the algorithm, and $N_{1, 2, 3 \ldots}$, if present, represent specific exons that may have been manually edited during analysis (See Example V). Alternatively, the identification numbers in column 5 may refer to assemblages of exons brought together by an "exon-stretching" algorithm. For example, FLXXXXXX_gAAAAA_gBBBBB_1_N is the identification number of a "stretched" sequence, with XXXXXX being the Incyte project identification number, gAAAAA being the GenBank identification number of the human genomic sequence to which the "exon-stretching" algorithm was applied, gBBBBB being the GenBank identification number or NCBI RefSeq identification number of the nearest GenBank protein homolog, and N referring to specific exons (See Example V). In instances where a RefSeq sequence was used as a protein homolog for the "exon-stretching" algorithm, a RefSeq identifier (denoted by "NM," "NP," or "NT") may be used in place of the GenBank identifier (i.e., gBBBBB).

Alternatively, a prefix identifies component sequences that were hand-edited, predicted from genomic DNA sequences, or derived from a combination of sequence analysis methods. The following Table lists examples of component sequence prefixes and corresponding sequence analysis methods associated with the prefixes (see Example IV and Example V).

| Prefix | Type of analysis and/or examples of programs |
|---|---|
| GNN, GFG, ENST | Exon prediction from genomic sequences using, for example, GENSCAN (Stanford University, CA, USA) or FGENES (Computer Genomics Group, The Sanger Centre, Cambridge, UK). |
| GBI | Hand-edited analysis of genomic sequences. |
| FL | Stitched or stretched genomic sequences (see Example V). |
| INCY | Full length transcript and exon prediction from mapping of EST sequences to the genome. Genomic location and EST composition data are combined to predict the exons and resulting transcript. |

In some cases, Incyte cDNA coverage redundant with the sequence coverage shown in column 5 was obtained to confirm the final consensus polynucleotide sequence, but the relevant Incyte cDNA identification numbers are not shown.

Table 5 shows the representative cDNA libraries for those full length polynucleotide sequences which were assembled using Incyte cDNA sequences. The representative cDNA library is the Incyte cDNA library which is most frequently represented by the Incyte cDNA sequences which were used to assemble and confirm the above polynucleotide sequences. The tissues and vectors which were used to construct the cDNA libraries shown in Table 5 are described in Table 6.

The invention also encompasses SECP variants. A preferred SECP variant is one which has at least about 80%, or alternatively at least about 90%, or even at least about 95% amino acid sequence identity to the SECP amino acid sequence, and which contains at least one functional or structural characteristic of SECP.

The invention also encompasses polynucleotides which encode SECP. In a particular embodiment, the invention encompasses a polynucleotide sequence comprising a sequence selected from the group consisting of SEQ ID NO:64-126, which encodes SECP. The polynucleotide sequences of SEQ ID NO:64-126, as presented in the Sequence Listing, embrace the equivalent RNA sequences, wherein occurrences of the nitrogenous base thymine are replaced with uracil, and the sugar backbone is composed of ribose instead of deoxyribose.

The invention also encompasses a variant of a polynucleotide sequence encoding SECP. In particular, such a variant polynucleotide sequence will have at least about 70%, or alternatively at least about 85%, or even at least about 95% polynucleotide sequence identity to the polynucleotide sequence encoding SECP. A particular aspect of the invention encompasses a variant of a polynucleotide sequence comprising a sequence selected from the group consisting of SEQ ID NO:64-126 which has at least about 70%, or alternatively at least about 85%, or even at least about 95% polynucleotide sequence identity to a nucleic acid sequence selected from the group consisting of SEQ ID NO:64-126. Any one of the polynucleotide variants described above can encode an amino acid sequence which contains at least one functional or structural characteristic of SECP.

In addition, or in the alternative, a polynucleotide variant of the invention is a splice variant of a polynucleotide sequence encoding SECP. A splice variant may have portions which have significant sequence identity to the polynucleotide sequence encoding SECP, but will generally have a greater or lesser number of polynucleotides due to additions or deletions of blocks of sequence arising from alternate splicing of exons during mRNA processing. A splice variant may have less than about 70%, or alternatively less than about 60%, or alternatively less than about 50% polynucleotide sequence identity to the polynucleotide sequence encoding SECP over its entire length; however, portions of the splice variant will have at least about 70%, or alternatively at least about 85%, or alternatively at least about 95%, or alternatively 100% polynucleotide sequence identity to portions of the polynucleotide sequence encoding SECP. Any one of the splice variants described above can encode an amino acid sequence which contains at least one functional or structural characteristic of SECP.

It will be appreciated by those skilled in the art that as a result of the degeneracy of the genetic code, a multitude of polynucleotide sequences encoding SECP, some bearing minimal similarity to the polynucleotide sequences of any known and naturally occurring gene, may be produced. Thus, the invention contemplates each and every possible variation of polynucleotide sequence that could be made by selecting combinations based on possible codon choices. These combinations are made in accordance with the standard triplet genetic code as applied to the polynucleotide sequence of naturally occurring SECP, and all such variations are to be considered as being specifically disclosed.

Although nucleotide sequences which encode SECP and its variants are generally capable of hybridizing to the nucleotide sequence of the naturally occurring SECP under appropriately selected conditions of stringency, it may be advantageous to produce nucleotide sequences encoding SECP or its derivatives possessing a substantially different codon usage, e.g., inclusion of non-naturally occurring codons. Codons may be selected to increase the rate at which expression of the peptide occurs in a particular prokaryotic or eukaryotic host in accordance with the frequency with which particular codons are utilized by the host. Other reasons for substantially altering the nucleotide sequence encoding SECP and its derivatives without altering the encoded amino acid sequences include the production of RNA transcripts having more desirable properties, such as a greater half-life, than transcripts produced from the naturally occurring sequence.

The invention also encompasses production of DNA sequences which encode SECP and SECP derivatives, or fragments thereof, entirely by synthetic chemistry. After production, the synthetic sequence may be inserted into any of the many available expression vectors and cell systems using reagents well known in the art. Moreover, synthetic chemistry may be used to introduce mutations into a sequence encoding SECP or any fragment thereof.

Also encompassed by the invention are polynucleotide sequences that are capable of hybridizing to the claimed polynucleotide sequences, and, in particular, to those shown in SEQ ID NO:64-126 and fragments thereof under various conditions of stringency. (See, e.g., Wahl, G. M. and S. L. Berger (1987) Methods Enzymol. 152:399-407; Kimmel, A. R. (1987) Methods Enzymol. 152:507-511.) Hybridization conditions, including annealing and wash conditions, are described in "Definitions."

Methods for DNA sequencing are well known in the art and may be used to practice any of the embodiments of the invention. The methods may employ such enzymes as the Klenow fragment of DNA polymerase I, SEQUENASE (US Biochemical, Cleveland Ohio), Taq polymerase (Applied Biosystems), thermostable T7 polymerase (Amersham Pharmacia Biotech, Piscataway N.J.), or combinations of polymerases and proofreading exonucleases such as those found in the ELONGASE amplification system (Life Technologies, Gaithersburg Md.). Preferably, sequence preparation is automated with machines such as the MICROLAB 2200 liquid transfer system (Hamilton, Reno Nev.), PTC200 thermal cycler (MJ Research, Watertown Mass.) and ABI CATALYST 800 thermal cycler (Applied Biosystems). Sequencing is then carried out using either the ABI 373 or 377 DNA sequencing system (Applied Biosystems), the MEGABACE 1000 DNA sequencing system (Molecular Dynamics, Sunnyvale Calif.), or other systems known in the art. The resulting sequences are analyzed using a variety of algorithms which are well known in the art. (See, e.g., Ausubel, F. M. (1997) Short Protocols in Molecular Biology, John Wiley & Sons, New York N.Y., unit 7.7; Meyers, R. A. (1995) Molecular Biology and Biotechnology, Wiley VCH, New York N.Y., pp. 856-853.)

The nucleic acid sequences encoding SECP may be extended utilizing a partial nucleotide sequence and employing various PCR-based methods known in the art to detect upstream sequences, such as promoters and regulatory elements. For example, one method which may be employed, restriction-site PCR, uses universal and nested primers to amplify unknown sequence from genomic DNA within a cloning vector. (See, e.g., Sarkar, G. (1993) PCR Methods Applic. 2:318-322.) Another method, inverse PCR, uses primers that extend in divergent directions to amplify unknown sequence from a circularized template. The template is derived from restriction fragments comprising a known genomic locus and surrounding sequences. (See, e.g., Triglia, T. et al. (1988) Nucleic Acids Res. 16:8186.) A third method, capture PCR, involves PCR amplification of DNA fragments adjacent to known sequences in human and yeast artificial chromosome DNA. (See, e.g., Lagerstrom, M. et al. (1991) PCR Methods Applic. 1:111-119.) In this method, multiple restriction enzyme digestions and ligations may be used to insert an engineered double-stranded sequence into a region of unknown sequence before performing PCR. Other methods which may be used to retrieve unknown sequences are known in the art. (See, e.g., Parker, J. D. et al. (1991) Nucleic Acids Res. 19:3055-3060). Additionally, one may use PCR, nested primers, and PROMOTERFINDER libraries (Clontech, Palo Alto Calif.) to walk genomic DNA. This procedure avoids the need to screen libraries and is useful in finding intron/exon junctions. For all PCR-based methods, primers may be designed using commercially available software, such as OLIGO 4.06 primer analysis software (National Biosciences, Plymouth Minn.) or another appropriate program, to be about 22 to 30 nucleotides in length, to have a GC content of about 50% or more, and to anneal to the template at temperatures of about 68° C. to 72° C.

When screening for full length cDNAs, it is preferable to use libraries that have been size-selected to include larger cDNAs. In addition, random-primed libraries, which often include sequences containing the 5' regions of genes, are preferable for situations in which an oligo d(T) library does not yield a full-length cDNA. Genomic libraries may be useful for extension of sequence into 5' non-transcribed regulatory regions.

Capillary electrophoresis systems which are commercially available may be used to analyze the size or confirm the nucleotide sequence of sequencing or PCR products. In particular, capillary sequencing may employ flowable polymers for electrophoretic separation, four different nucleotide-specific, laser-stimulated fluorescent dyes, and a charge coupled device camera for detection of the emitted wavelengths. Output/light intensity may be converted to electrical signal using appropriate software (e.g., GENOTYPER and SEQUENCE NAVIGATOR, Applied Biosystems), and the entire process from loading of samples to computer analysis and electronic data display may be computer controlled.

Capillary electrophoresis is especially preferable for sequencing small DNA fragments which may be present in limited amounts in a particular sample.

In another embodiment of the invention, polynucleotide sequences or fragments thereof which encode SECP may be cloned in recombinant DNA molecules that direct expression of SECP, or fragments or functional equivalents thereof, in appropriate host cells. Due to the inherent degeneracy of the genetic code, other DNA sequences which encode substantially the same or a functionally equivalent amino acid sequence may be produced and used to express SECP.

The nucleotide sequences of the present invention can be engineered using methods generally known in the art in order to alter SECP-encoding sequences for a variety of purposes including, but not limited to, modification of the cloning, processing, and/or expression of the gene product. DNA shuffling by random fragmentation and PCR reassembly of gene fragments and synthetic oligonucleotides may be used to engineer the nucleotide sequences. For example, oligonucleotide-mediated site-directed mutagenesis may be used to introduce mutations that create new restriction sites, alter glycosylation patterns, change codon preference, produce splice variants, and so forth.

The nucleotides of the present invention may be subjected to DNA shuffling techniques such as MOLECULAR-BREEDING (Maxygen Inc., Santa Clara Calif.; described in U.S. Pat. No. 5,837,458; Chang, C.-C. et al. (1999) Nat. Biotechnol. 17:793-797; Christians, F. C. et al. (1999) Nat. Biotechnol. 17:259-264; and Crameri, A. et al. (1996) Nat. Biotechnol. 14:315-319) to alter or improve the biological properties of SECP, such as its biological or enzymatic activity or its ability to bind to other molecules or compounds. DNA shuffling is a process by which a library of gene variants is produced using PCR-mediated recombination of gene fragments. The library is then subjected to selection or screening procedures that identify those gene variants with the desired properties. These preferred variants may then be pooled and further subjected to recursive rounds of DNA shuffling and selection/screening. Thus, genetic diversity is created through "artificial" breeding and rapid molecular evolution. For example, fragments of a single gene containing random point mutations may be recombined, screened, and then reshuffled until the desired properties are optimized. Alternatively, fragments of a given gene may be recombined with fragments of homologous genes in the same gene family, either from the same or different species, thereby maximizing the genetic diversity of multiple naturally occurring genes in a directed and controllable manner.

In another embodiment, sequences encoding SECP may be synthesized, in whole or in part, using chemical methods well known in the art. (See, e.g., Caruthers, M. H. et al. (1980) Nucleic Acids Symp. Ser. 7:215-223; and Horn, T. et al. (1980) Nucleic Acids Symp. Ser. 7:225-232.) Alternatively, SECP itself or a fragment thereof may be synthesized using chemical methods. For example, peptide synthesis can be performed using various solution-phase or solid-phase techniques. (See, e.g., Creighton, T. (1984) *Proteins, Structures and Molecular Properties*, WH Freeman, New York N.Y., pp. 55-60; and Roberge, J. Y. et al. (1995) Science 269:202-204.) Automated synthesis may be achieved using the ABI 431A peptide synthesizer (Applied Biosystems). Additionally, the amino acid sequence of SECP, or any part thereof, may be altered during direct synthesis and/or combined with sequences from other proteins, or any part thereof, to produce a variant polypeptide or a polypeptide having a sequence of a naturally occurring polypeptide.

The peptide may be substantially purified by preparative high performance liquid chromatography. (See, e.g., Chiez, R. M. and F. Z. Regnier (1990) Methods Enzymol. 182:392-421.) The composition of the synthetic peptides may be confirmed by amino acid analysis or by sequencing. (See, e.g., Creighton, supra, pp. 28-53.)

In order to express a biologically active SECP, the nucleotide sequences encoding SECP or derivatives thereof may be inserted into an appropriate expression vector, i.e., a vector which contains the necessary elements for transcriptional and translational control of the inserted coding sequence in a suitable host. These elements include regulatory sequences, such as enhancers, constitutive and inducible promoters, and 5' and 3' untranslated regions in the vector and in polynucleotide sequences encoding SECP. Such elements may vary in their strength and specificity. Specific initiation signals may also be used to achieve more efficient translation of sequences encoding SECP. Such signals include the ATG initiation codon and adjacent sequences, e.g. the Kozak sequence. In cases where sequences encoding SECP and its initiation codon and upstream regulatory sequences are inserted into the appropriate expression vector, no additional transcriptional or translational control signals may be needed. However, in cases where only coding sequence, or a fragment thereof, is inserted, exogenous translational control signals including an in-frame ATG initiation codon should be provided by the vector. Exogenous translational elements and initiation codons may be of various origins, both natural and synthetic. The efficiency of expression may be enhanced by the inclusion of enhancers appropriate for the particular host cell system used. (See, e.g., Scharf, D. et al. (1994) Results Probl. Cell Differ. 20:125-162.)

Methods which are well known to those skilled in the art may be used to construct expression vectors containing sequences encoding SECP and appropriate transcriptional and translational control elements. These methods include in vitro recombinant DNA techniques, synthetic techniques, and in vivo genetic recombination. (See, e.g., Sambrook, J. et al. (1989) *Molecular Cloning, A Laboratory Manual*, Cold Spring Harbor Press, Plainview N.Y., ch. 4, 8, and 16-17; Ausubel, F. M. et al. (1995) *Current Protocols in Molecular Biology*, John Wiley & Sons, New York N.Y., ch. 9, 13, and 16.)

A variety of expression vector/host systems may be utilized to contain and express sequences encoding SECP. These include, but are not limited to, microorganisms such as bacteria transformed with recombinant bacteriophage, plasmid, or cosmid DNA expression vectors; yeast transformed with yeast expression vectors; insect cell systems infected with viral expression vectors (e.g., baculovirus); plant cell systems transformed with viral expression vectors (e.g., cauliflower mosaic virus, CaMV, or tobacco mosaic virus, TMV) or with bacterial expression vectors (e.g., Ti or pBR322 plasmids); or animal cell systems. (See, e.g., Sambrook, pr; Ausubel, supra; Van Heeke, G. and S. M. Schuster (1989) J. Biol. Chem. 264:5503-5509; Engelhard, E. K. et al. (1994) Proc. Natl. Acad. Sci. USA 91:3224-3227; Sandig, V. et al. (1996) Hum. Gene Ther. 7:1937-1945; Takamatsu, N. (1987) EMBO J. 6:307-311; *The McGraw Hill Yearbook of Science and Technology* (1992) McGraw Hill, New York N.Y., pp. 191-196; Logan, J. and T. Shenk (1984) Proc. Natl. Acad. Sci. USA 81:3655-3659; and Harrington, J. J. et al. (1997) Nat. Genet. 15:345-355.) Expression vectors derived from retroviruses, adenoviruses, or herpes or vaccinia viruses, or from various bacterial plasmids, may be used for delivery of nucleotide sequences to the targeted organ, tissue, or cell population. (See, e.g., Di Nicola, M. et al. (1998) Cancer Gen. Ther. 5(6):350-356; Yu, M. et al. (1993) Proc. Natl. Acad. Sci. USA 90(13):6340-6344; Buller, R. M. et al. (1985) Nature 317(6040):813-815; McGregor, D. P. et al. (1994) Mol. Immunol. 31(3):219-226; and Verma, I. M. and N. Somia (1997) Nature 389:239-242.) The invention is not limited by the host cell employed.

In bacterial systems, a number of cloning and expression vectors may be selected depending upon the use intended for polynucleotide sequences encoding SECP. For example, routine cloning, subcloning, and propagation of polynucleotide sequences encoding SECP can be achieved using a multifunctional *E. coli* vector such as PBLUESCRIPT (Stratagene, La Jolla Calif.) or PSPORT1 plasmid (Life Technologies). Ligation of sequences encoding SECP into the vector's multiple cloning site disrupts the lacZ gene, allowing a colorimetric screening procedure for identification of transformed bacteria containing recombinant molecules. In addition, these vectors may be useful for in vitro transcription, dideoxy sequencing, single strand rescue with helper phage, and creation of nested deletions in the cloned sequence. (See, e.g., Van Heeke, G. and S. M. Schuster (1989) J. Biol. Chem. 264:5503-5509.) When large quantities of SECP are needed, e.g. for the production of antibodies, vectors which direct high level expression of SECP may be used. For example, vectors containing the strong, inducible SP6 or T7 bacteriophage promoter may be used.

Yeast expression systems may be used for production of SECP. A number of vectors containing constitutive or inducible promoters, such as alpha factor, alcohol oxidase, and PGH promoters, may be used in the yeast *Saccharomyces cerevisiae* or *Pichia pastoris*. In addition, such vectors direct either the secretion or intracellular retention of expressed proteins and enable integration of foreign sequences into the host genome for stable propagation. (See, e.g., Ausubel, 1995, supra; Bitter. G. A. et al. (1987) Methods Enzymol. 153:516-544; and Scorer, C. A. et al. (1994) Bio/Technology 12:181-184.)

Plant systems may also be used for expression of SECP. Transcription of sequences encoding SECP may be driven by viral promoters, e.g., the 35S and 19S promoters of CaMV used alone or in combination with the omega leader sequence from TMV (Takamatsu, N. (1987) EMBO J. 6:307-311). Alternatively, plant promoters such as the small subunit of RUBISCO or heat shock promoters may be used. (See, e.g., Coruzzi, G. et al. (1984) EMBO J. 3:1671-1680; Broglie, R. et al. (1984) Science 224:838-843; and Winter, J. et al. (1991) Results Probl. Cell Differ. 17:85-105.) These constructs can be introduced into plant cells by direct DNA transformation or pathogen-mediated transfection. (See, e.g., *The McGraw Hill Yearbook of Science and Technology* (1992) McGraw Hill, New York N.Y., pp. 191-196.)

In mammalian cells, a number of viral-based expression systems may be utilized. In cases where an adenovirus is used as an expression vector, sequences encoding SECP may be ligated into an adenovirus transcription/translation complex consisting of the late promoter and tripartite leader sequence. Insertion in a non-essential E1 or E3 region of the viral genome may be used to obtain infective virus which expresses SECP in host cells. (See, e.g., Logan, J. and T. Shenk (1984) Proc. Natl. Acad. Sci. USA 81:3655-3659.) In addition, transcription enhancers, such as the Rous sarcoma virus (RSV) enhancer, may be used to increase expression in mammalian host cells. SV40 or EBV-based vectors may also be used for high-level protein expression.

Human artificial chromosomes (HACs) may also be employed to deliver larger fragments of DNA than can be contained in and expressed from a plasmid. HACs of about 6 kb to 10 Mb are constructed and delivered via conventional delivery methods (liposomes, polycationic amino polymers, or vesicles) for therapeutic purposes. (See, e.g., Harrington, J. J. et al. (1997) Nat. Genet. 15:345-355.)

For long term production of recombinant proteins in mammalian systems, stable expression of SECP in cell lines is preferred. For example, sequences encoding SECP can be transformed into cell lines using expression vectors which may contain viral origins of replication and/or endogenous expression elements and a selectable marker gene on the same or on a separate vector. Following the introduction of the vector, cells may be allowed to grow for about 1 to 2 days in enriched media before being switched to selective media. The purpose of the selectable marker is to confer resistance to a selective agent, and its presence allows growth and recovery of cells which successfully express the introduced sequences. Resistant clones of stably transformed cells may be propagated using tissue culture techniques appropriate to the cell type.

Any number of selection systems may be used to recover transformed cell lines. These include, but are not limited to, the herpes simplex virus thymidine kinase and adenine phosphoribosyltransferase genes, for use in tk$^-$ and apr$^-$ cells, respectively. (See, e.g., Wigler, M. et al. (1977) Cell 11:223-232; Lowy, I. et al. (1980) Cell 22:817-823.) Also, antimetabolite, antibiotic, or herbicide resistance can be used as the basis for selection. For example, dhfr confers resistance to methotrexate; neo confers resistance to the aminoglycosides neomycin and G-418: and als and pat confer resistance to chlorsulfuron and phosphinotricin acetyltransferase, respectively. (See, e.g., Wigler, M. et al. (1980) Proc. Natl. Acad. Sci. USA 77:3567-3570; Colbere-Garapin, F. et al. (1981) J. Mol. Biol. 150:1-14.) Additional selectable genes have been described, e.g., trpB and hisD, which alter cellular requirements for metabolites. (See, e.g., Hartman, S. C. and R. C. Mulligan (1988) Proc. Natl. Acad. Sci. USA 85:8047-8051.) Visible markers, e.g., anthocyanins, green fluorescent proteins (GFP; Clontech), β glucuronidase and its substrate β-glucuronide, or luciferase and its substrate luciferin may be used. These markers can be used not only to identify transformants, but also to quantify the amount of transient or stable protein expression attributable to a specific vector system. (See, e.g., Rhodes, C. A. (1995) Methods Mol. Biol. 55:121-131.)

Although the presence/absence of marker gene expression suggests that the gene of interest is also present, the presence and expression of the gene may need to be confirmed. For example, if the sequence encoding SECP is inserted within a marker gene sequence, transformed cells containing sequences encoding SECP can be identified by the absence of marker gene function. Alternatively, a marker gene can be placed in tandem with a sequence encoding SECP under the control of a single promoter. Expression of the marker gene in response to induction or selection usually indicates expression of the tandem gene as well.

In general, host cells that contain the nucleic acid sequence encoding SECP and that express SECP may be identified by a variety of procedures known to those of skill in the art. These procedures include, but are not limited to, DNA-DNA or DNA-RNA hybridizations, PCR amplification, and protein bioassay or immunoassay techniques which include membrane, solution, or chip based technologies for the detection and/or quantification of nucleic acid or protein sequences.

Immunological methods for detecting and measuring the expression of SECP using either specific polyclonal or monoclonal antibodies are known in the art. Examples of such techniques include enzyme-linked immunosorbent assays (ELISAs), radioimmunoassays (RIAs), and fluorescence activated cell sorting (FACS). A two-site, monoclonal-based immunoassay utilizing monoclonal antibodies reactive to two non-interfering epitopes on SECP is preferred, but a competitive binding assay may be employed. These and other assays are well known in the art. (See, e.g., Hampton, R. et al. (1990) *Serological Methods, a Laboratory Manual*, APS Press, St. Paul Minn., Sect. IV; Coligan, J. E. et al. (1997) *Current Protocols in Immunology*, Greene Pub. Associates and Wiley-Interscience, New York N.Y.; and Pound, J. D. (1998) *Immunochemical Protocols*, Humana Press, Totowa N.J.)

A wide variety of labels and conjugation techniques are known by those skilled in the art and may be used in various nucleic acid and amino acid assays. Means for producing labeled hybridization or PCR probes for detecting sequences related to polynucleotides encoding SECP include oligolabeling, nick translation, end-labeling, or PCR amplification using a labeled nucleotide. Alternatively, the sequences encoding SECP, or any fragments thereof, may be cloned into a vector for the production of an mRNA probe. Such vectors are known in the art, are commercially available, and may be used to synthesize RNA probes in vitro by addition of an appropriate RNA polymerase such as T7, T3, or SP6 and labeled nucleotides. These procedures may be conducted using a variety of commercially available kits, such as those provided by Amersham Pharmacia Biotech, Promega (Madison Wis.), and US Biochemical. Suitable reporter molecules or labels which may be used for ease of detection include radionuclides, enzymes, fluorescent, chemiluminescent, or chromogenic agents, as well as substrates, cofactors, inhibitors, magnetic particles, and the like.

Host cells transformed with nucleotide sequences encoding SECP may be cultured under conditions suitable for the expression and recovery of the protein from cell culture. The protein produced by a transformed cell may be secreted or retained intracellularly depending on the sequence and/or the vector used. As will be understood by those of skill in the art, expression vectors containing polynucleotides which encode SECP may be designed to contain signal sequences which direct secretion of SECP through a prokaryotic or eukaryotic cell membrane.

In addition, a host cell strain may be chosen for its ability to modulate expression of the inserted sequences or to process the expressed protein in the desired fashion. Such modifications of the polypeptide include, but are not limited to, acetylation, carboxylation, glycosylation, phosphorylation, lipidation, and acylation. Post-translational processing which cleaves a "prepro" or "pro" form of the protein may also be used to specify protein targeting, folding, and/or activity. Different host cells which have specific cellular machinery and characteristic mechanisms for post-translational activities (e.g., CHO, HeLa, MDCK, HEK293, and WI38) are available from the American Type Culture Collection (ATCC, Manassas Va.) and may be chosen to ensure the correct modification and processing of the foreign protein.

In another embodiment of the invention, natural, modified, or recombinant nucleic acid sequences encoding SECP may be ligated to a heterologous sequence resulting in translation of a fusion protein in any of the aforementioned host systems. For example, a chimeric SECP protein containing a heterologous moiety that can be recognized by a commercially available antibody may facilitate the screening of peptide libraries for inhibitors of SECP activity. Heterologous protein and peptide moieties may also facilitate purification of fusion proteins using commercially available affinity matrices. Such moieties include, but are not limited to, glutathione S-transferase (GST), maltose binding protein (MBP), thioredoxin (Trx), calmodulin binding peptide (CBP), 6-His, FLAG, c-myc, and hemagglutinin (HA). GST, MBP, Trx, CBP, and 6-His enable purification of their cognate fusion proteins on immobilized glutathione, maltose, phenylarsine oxide, calmodulin, and metal-chelate resins, respectively. FLAG, c-myc, and hemagglutinin (HA) enable immunoaffinity purification of fusion proteins using commercially available monoclonal and polyclonal antibodies that specifically recognize these epitope tags. A fusion protein may also be engineered to contain a proteolytic cleavage site located between the SECP encoding sequence and the heterologous protein sequence, so that SECP may be cleaved away from the heterologous moiety following purification. Methods for fusion protein expression and purification are discussed in Ausubel (1995, supra, ch. 10). A variety of commercially available kits may also be used to facilitate expression and purification of fusion proteins.

In a further embodiment of the invention, synthesis of radiolabeled SECP may be achieved in vitro using the TNT rabbit reticulocyte lysate or wheat germ extract system (Promega). These systems couple transcription and translation of protein-coding sequences operably associated with the T7, T3, or SP6 promoters. Translation takes place in the presence of a radiolabeled amino acid precursor, for example, $^{35}$S-methionine.

SECP of the present invention or fragments thereof may be used to screen for compounds that specifically bind to SECP. At least one and up to a plurality of test compounds may be screened for specific binding to SECP. Examples of test compounds include antibodies, oligonucleotides, proteins (e.g., receptors), or small molecules.

In one embodiment, the compound thus identified is closely related to the natural ligand of SECP, e.g., a ligand or fragment thereof, a natural substrate, a structural or functional mimetic, or a natural binding partner. (See, e.g., Coligan, J. E. et al. (1991) *Current Protocols in Immunology* 1(2): Chapter 5.) Similarly, the compound can be closely related to the natural receptor to which SECP binds, or to at least a fragment of the receptor, e.g., the ligand binding site. In either case, the compound can be rationally designed using known techniques. In one embodiment, screening for these compounds involves producing appropriate cells which express SECP, either as a secreted protein or on the cell membrane. Preferred cells include cells from mammals, yeast, *Drosophila*, or *E. coli*. Cells expressing SECP or cell membrane fractions which contain SECP are then contacted with a test compound and binding, stimulation, or inhibition of activity of either SECP or the compound is analyzed.

An assay may simply test binding of a test compound to the polypeptide, wherein binding is detected by a fluorophore, radioisotope, enzyme conjugate, or other detectable label. For example, the assay may comprise the steps of combining at least one test compound with SECP, either in solution or affixed to a solid support, and detecting the binding of SECP to the compound. Alternatively, the assay may detect or measure binding of a test compound in the presence of a labeled competitor. Additionally, the assay may be carried out using cell-free preparations, chemical libraries, or natural product mixtures, and the test compound(s) may be free in solution or affixed to a solid support.

SECP of the present invention or fragments thereof may be used to screen for compounds that modulate the activity of SECP. Such compounds may include agonists, antagonists, or partial or inverse agonists. In one embodiment, an assay is performed under conditions permissive for SECP activity, wherein SECP is combined with at least one test compound, and the activity of SECP in the presence of a test compound is compared with the activity of SECP in the absence of the test compound. A change in the activity of SECP in the presence of the test compound is indicative of a compound that modulates the activity of SECP. Alternatively, a test compound is combined with an in vitro or cell-free system comprising SECP under conditions suitable for SECP activity, and the assay is performed. In either of these assays, a test compound which modulates the activity of SECP may do so indirectly and need not come in direct contact with the test compound. At least one and up to a plurality of test compounds may be screened.

In another embodiment, polynucleotides encoding SECP or their mammalian homologs may be "knocked out" in an animal model system using homologous recombination in embryonic stem (ES) cells. Such techniques are well known in the art and are useful for the generation of animal models of human disease. (See, e.g., U.S. Pat. No. 5,175,383 and U.S. Pat. No. 5,767,337.) For example, mouse ES cells, such as the mouse 129/SvJ cell line, are derived from the early mouse embryo and grown in culture. The ES cells are transformed with a vector containing the gene of interest disrupted by a marker gene, e.g., the neomycin phosphotransferase gene (neo; Capecchi, M. R. (1989) Science 244:1288-1292). The vector integrates into the corresponding region of the host genome by homologous recombination. Alternatively, homologous recombination takes place using the Cre-loxP system to knockout a gene of interest in a tissue- or developmental stage-specific manner (Marth, J. D. (1996) Clin. Invest. 97:1999-2002; Wagner, K. U. et al. (1997) Nucleic Acids Res. 25:43234330). Transformed ES cells are identified and microinjected into mouse cell blastocysts such as those from the C57BL/6 mouse strain. The blastocysts are surgically transferred to pseudopregnant dams, and the resulting chimeric progeny are genotyped and bred to produce heterozygous or homozygous strains. Transgenic animals thus generated may be tested with potential therapeutic or toxic agents.

Polynucleotides encoding SECP may also be manipulated in vitr in ES cells derived from human blastocysts. Human ES cells have the potential to differentiate into at least eight separate cell lineages including endoderm, mesoderm, and ectodermal cell types. These cell lineages differentiate into, for example, neural cells, hematopoietic lineages, and cardiomyocytes (Thomson, J. A. et al. (1998) Science 282: 1145-1147).

Polynucleotides encoding SECP can also be used to create "knockin" humanized animals (pigs) or transgenic animals (mice or rats) to model human disease. With knockin technology, a region of a polynucleotide encoding SECP is injected into animal ES cells, and the injected sequence integrates into the animal cell genome. Transformed cells are injected into blastulae, and the blastulae are implanted as described above. Transgenic progeny or inbred lines are studied and treated with potential pharmaceutical agents to obtain information on treatment of a human disease. Alternatively, a mammal inbred to overexpress SECP, e.g., by secreting SECP in its milk, may also serve as a convenient source of that protein (Janne, J. et al. (1998) Biotechnol. Annu. Rev. 4:55-74).

Therapeutics

Chemical and structural similarity, e.g., in the context of sequences and motifs, exists between regions of SECP and secreted proteins. In addition, the expression of SECP is closely associated with normal and tumorous lung, heart, brain, skin, colon epithelium, and cardiovascular tissues, as well as, neurological, urinary, reproductive, digestive, immunological, diseased, and tumorous tissues. Therefore, SECP appears to play a role in cell proliferative, autoimmune/inflammatory, cardiovascular, neurological, and developmental disorders. In the treatment of disorders associated with increased SECP expression or activity, it is desirable to decrease the expression or activity of SECP. In the treatment of disorders associated with decreased SECP expression or activity, it is desirable to increase the expression or activity of SECP.

Therefore, in one embodiment, SECP or a fragment or derivative thereof may be administered to a subject to treat or prevent a disorder associated with decreased expression or activity of SECP. Examples of such disorders include, but are not limited to, a cell proliferative disorder such as actinic keratosis, arteriosclerosis, atherosclerosis, bursitis, cirrhosis, hepatitis, mixed connective tissue disease (MCTD), myelofibrosis, paroxysmal nocturnal hemoglobinuria, polycythemia vera, psoriasis, primary thrombocythemia, and cancers including adenocarcinoma, leukemia, lymphoma, melanoma, myeloma, sarcoma, teratocarcinoma, and, in particular, a cancer of the adrenal gland, bladder, bone, bone marrow, brain, breast, cervix, gall bladder, ganglia, gastrointestinal tract, heart, kidney, liver, lung, muscle, ovary, pancreas, parathyroid, penis, prostate, salivary glands, skin, spleen, testis, thymus, thyroid, and uterus; an autoimmune/inflammatory disorder such as acquired immunodeficiency syndrome (AIDS), Addison's disease, adult respiratory distress syndrome, allergies, ankylosing spondylitis, amyloidosis, anemia, asthma, atherosclerosis, autoimmune hemolytic anemia, autoimmune thyroiditis, autoimmune polyendocrinopathy-candidiasis-ectodermal dystrophy (APECED), bronchitis, cholecystitis, contact dermatitis, Crohn's disease, atopic dermatitis, dermatomyositis, diabetes mellitus, emphysema, episodic lymphopenia with lymphocytotoxins, erythroblastosis fetalis, erythema nodosum, atrophic gastritis, glomerulonephritis, Goodpasture's syndrome, gout, Graves' disease, Hashimoto's thyroiditis, hypereosinophilia, irritable bowel syndrome, multiple sclerosis, myasthenia gravis, myocardial or pericardial inflammation, osteoarthritis, osteoporosis, pancreatitis, polymyositis, psoriasis, Reiter's syndrome, rheumatoid arthritis, scleroderma, Sjögren's syndrome, systemic anaphylaxis, systemic lupus erythematosus, systemic sclerosis, thrombocytopenic purpura, ulcerative colitis, uveitis, Werner syndrome, complications of cancer, hemodialysis, and extracorporeal circulation, viral, bacterial, fungal, parasitic, protozoal, and helminthic infections, and trauma; a cardiovascular disorder such as congestive heart failure, ischemic heart disease, angina pectoris, myocardial infarction, hypertensive heart disease, degenerative valvular heart disease, calcific aortic valve stenosis, congenitally bicuspid aortic valve, mitral annular calcification, mitral valve prolapse, rheumatic fever and rheumatic heart disease, infective endocarditis, nonbacterial thrombotic endocarditis, endocarditis of systemic lupus erythematosus, carcinoid heart disease, cardiomyopathy, myocarditis, pericarditis, neoplastic heart disease, congenital heart disease, complications of cardiac transplantation, arteriovenous fistula, atherosclerosis, hypertension, vasculitis, Raynaud's disease, aneurysms, arterial dissections, varicose veins, thrombophlebitis and phlebothrombosis, vascular tumors, and complications of thrombolysis, balloon angioplasty, vascular replacement, and coronary artery bypass graft surgery; a neurological disorder such as epilepsy, ischemic cerebrovascular disease, stroke, cerebral neoplasms, Alzheimer's disease, Pick's disease, Huntington's disease, dementia, Parkinson's disease and other extrapyramidal disorders, amyotrophic lateral sclerosis and other motor neuron disorders, progressive neural muscular atrophy, retinitis pigmentosa, hereditary ataxias, multiple sclerosis and other demyelinating diseases, bacterial and viral meningitis, brain abscess, subdural empyema, epidural abscess, suppurative intracranial thrombophlebitis, myelitis and radiculitis, viral central nervous system disease, prion diseases including kuru, Creutzfeldt-Jakob disease, and Gerstmann-Straussler-Scheinker syndrome, fatal familial insomnia, nutritional and metabolic diseases of the nervous system, neurofibromatosis, tuberous sclerosis, cerebelloretinal hemangioblastomatosis, encephalotrigeminal syndrome, mental retardation and other developmental disorders of the central nervous system including Down syndrome, cerebral palsy, neuroskeletal disorders, autonomic nervous system disorders, cranial nerve disorders, spinal cord diseases, muscular dystrophy and other neuromuscular disorders, peripheral nervous system disorders, dermatomyositis and polymyositis, inherited, metabolic, endocrine, and toxic myopathies, myasthenia gravis, periodic paralysis, mental disorders including mood, anxiety, and schizophrenic disorders, seasonal affective disorder (SAD), akathesia, amnesia, catatonia, diabetic neuropathy, tardive dyskinesia, dystonias, paranoid psychoses, postherpetic neuralgia, Tourette's disorder, progressive supranuclear palsy, corticobasal degeneration, and familial frontotemporal dementia; and a developmental disorder such as renal tubular acidosis, anemia, Cushing's syndrome, achondroplastic dwarfism, Duchenne and Becker muscular dystrophy, epilepsy, gonadal dysgenesis, WAGR syndrome (Wilms' tumor, aniridia, genitourinary abnormalities, and mental retardation), Smith-Magenis syndrome, myelodysplastic syndrome, hereditary mucoepithelial dysplasia, hereditary keratodermas, hereditary neuropathies such as Charcot-Marie-Tooth disease and neurofibromatosis, hypothyroidism, hydrocephalus, seizure disorders such as Syndenham's chorea and cerebral palsy, spina bifida, anencephaly, craniorachischisis, congenital glaucoma, cataract, and sensorineural hearing loss.

In another embodiment, a vector capable of expressing SECP or a fragment or derivative thereof may be administered to a subject to treat or prevent a disorder associated with decreased expression or activity of SECP including, but not limited to, those described above.

In a further embodiment, a composition comprising a substantially purified SECP in conjunction with a suitable pharmaceutical carrier may be administered to a subject to treat or prevent a disorder associated with decreased expression or activity of SECP including, but not limited to, those provided above.

In still another embodiment, an agonist which modulates the activity of SECP may be administered to a subject to treat or prevent a disorder associated with decreased expression or activity of SECP including, but not limited to, those listed above.

In a further embodiment, an antagonist of SECP may be administered to a subject to treat or prevent a disorder associated with increased expression or activity of SECP. Examples of such disorders include, but are not limited to, those cell proliferative, autoimmune/inflammatory, cardiovascular, neurological, and developmental disorders described above. In one aspect, an antibody which specifically binds SECP may be used directly as an antagonist or indirectly as a targeting or delivery mechanism for bringing a pharmaceutical agent to cells or tissues which express SECP.

In an additional embodiment, a vector expressing the complement of the polynucleotide encoding SECP may be administered to a subject to treat or prevent a disorder associated with increased expression or activity of SECP including, but not limited to, those described above.

In other embodiments, any of the proteins, antagonists, antibodies, agonists, complementary sequences, or vectors of the invention may be administered in combination with other appropriate therapeutic agents. Selection of the appropriate agents for use in combination therapy may be made by one of ordinary skill in the art, according to conventional pharmaceutical principles. The combination of therapeutic agents may act synergistically to effect the treatment or prevention of the various disorders described above. Using this approach, one may be able to achieve therapeutic efficacy with lower dosages of each agent, thus reducing the potential for adverse side effects.

An antagonist of SECP may be produced using methods which are generally known in the art. In particular, purified SECP may be used to produce antibodies or to screen libraries of pharmaceutical agents to identify those which specifically bind SECP. Antibodies to SECP may also be generated using methods that are well known in the art. Such antibodies may include, but are not limited to, polyclonal, monoclonal, chimeric, and single chain antibodies, Fab fragments, and fragments produced by a Fab expression library. Neutralizing antibodies (i.e., those which inhibit dimer formation) are generally preferred for therapeutic use.

For the production of antibodies, various hosts including goats, rabbits, rats, mice, humans, and others may be immunized by injection with SECP or with any fragment or oligopeptide thereof which has immunogenic properties. Depending on the host species, various adjuvants may be used to increase immunological response. Such adjuvants include, but are not limited to, Freund's, mineral gels such as aluminum hydroxide, and surface active substances such as lysolecithin, pluronic polyols, polyanions, peptides, oil emulsions, KLH, and dinitrophenol. Among adjuvants used in humans, BCG (bacilli Calmette-Guerin) and *Corynebacterium parvum* are especially preferable.

It is preferred that the oligopeptides, peptides, or fragments used to induce antibodies to SECP have an amino acid sequence consisting of at least about 5 amino acids, and generally will consist of at least about 10 amino acids. It is also preferable that these oligopeptides, peptides, or fragments are identical to a portion of the amino acid sequence of the natural protein. Short stretches of SECP amino acids may be fused with those of another protein, such as KLH, and antibodies to the chimeric molecule may be produced.

Monoclonal antibodies to SECP may be prepared using any technique which provides for the production of antibody molecules by continuous cell lines in culture. These include, but are not limited to, the hybridoma technique, the human B-cell hybridoma technique, and the EBV-hybridoma technique. (See, e.g., Kohler, G. et al. (1975) Nature 256:495-497; Kozbor, D. et al. (1985) J. Immunol. Methods 81:31-42; Cote, R. J. et al. (1983) Proc. Natl. Acad. Sci. USA 80:2026-2030; and Cole, S. P. et al. (1984) Mol. Cell Biol. 62:109-120.)

In addition, techniques developed for the production of "chimeric antibodies," such as the splicing of mouse antibody genes to human antibody genes to obtain a molecule with appropriate antigen specificity and biological activity, can be used. (See, e.g., Morrison, S. L. et al. (1984) Proc. Natl. Acad. Sci. USA 81:6851-6855; Neuberger, M. S. et al. (1984) Nature 312:604-608; and Takeda, S. et al. (1985) Nature 314:452-454.) Alternatively, techniques described for the production of single chain antibodies may be adapted, using methods known in the art, to produce SECP-specific single chain antibodies. Antibodies with related specificity, but of distinct idiotypic composition, may be generated by chain shuffling from random combinatorial immunoglobulin libraries. (See, e.g., Burton, D. R. (1991) Proc. Natl. Acad. Sci. USA 88:10134-10137.)

Antibodies may also be produced by inducing in vivo production in the lymphocyte population or by screening immunoglobulin libraries or panels of highly specific binding reagents as disclosed in the literature. (See, e.g., Orlandi, R. et al. (1989) Proc. Natl. Acad. Sci. USA 86:3833-3837; Winter, G. et al. (1991) Nature 349:293-299.)

Antibody fragments which contain specific binding sites for SECP may also be generated. For example, such fragments include, but are not limited to, F(ab')$_2$ fragments produced by pepsin digestion of the antibody molecule and Fab fragments generated by reducing the disulfide bridges of the F(ab')2 fragments. Alternatively, Fab expression libraries may be constructed to allow rapid and easy identification of monoclonal Fab fragments with the desired specificity. (See, e.g., Huse, W. D. et al. (1989) Science 246:1275-1281.)

Various immunoassays may be used for screening to identify antibodies having the desired specificity. Numerous protocols for competitive binding or immunoradiometric assays using either polyclonal or monoclonal antibodies with established specificities are well known in the art. Such immunoassays typically involve the measurement of complex formation between SECP and its specific antibody. A two-site, monoclonal-based immunoassay utilizing monoclonal antibodies reactive to two non-interfering SECP epitopes is generally used, but a competitive binding assay may also be employed (Pound, supra).

Various methods such as Scatchard analysis in conjunction with radioimmunoassay techniques may be used to assess the affinity of antibodies for SECP. Affinity is expressed as an association constant, $K_a$, which is defined as the molar concentration of SECP-antibody complex divided by the molar concentrations of free antigen and free antibody under equilibrium conditions. The $K_a$ determined for a preparation of polyclonal antibodies, which are heterogeneous in their affinities for multiple SECP epitopes, represents the average affinity, or avidity, of the antibodies for SECP. The $K_a$ determined for a preparation of monoclonal antibodies, which are monospecific for a particular SECP epitope, represents a true measure of affinity. High-affinity antibody preparations with $K_a$ ranging from about $10^9$ to $10^{12}$ L/mole are preferred for use in immunoassays in which the SECP-antibody complex must withstand rigorous manipulations. Low-affinity antibody preparations with $K_a$ ranging from about $10^6$ to $10^7$ L/mole are preferred for use in immunopurification and similar procedures which ultimately require dissociation of SECP, preferably in active form, from the antibody (Catty, D. (1988) *Antibodies, Volume I: A Practical Approach*, IRL Press, Washington D.C.; Liddell, J. E. and A. Cryer (1991) *A Practical Guide to Monoclonal Antibodies*, John Wiley & Sons, New York N.Y.).

The titer and avidity of polyclonal antibody preparations may be further evaluated to determine the quality and suitability of such preparations for certain downstream applications. For example, a polyclonal antibody preparation containing at least 1-2 mg specific antibody/ml, preferably 5-10 mg specific antibody/ml, is generally employed in procedures requiring precipitation of SECP-antibody complexes. Procedures for evaluating antibody specificity, titer, and avidity, and guidelines for antibody quality and usage in various applications, are generally available. (See, e.g., Catty, supra, and Coligan et al. supra.)

In another embodiment of the invention, the polynucleotides encoding SECP, or any fragment or complement thereof, may be used for therapeutic purposes. In one aspect, modifications of gene expression can be achieved by designing complementary sequences or antisense molecules (DNA, RNA, PNA, or modified oligonucleotides) to the coding or regulatory regions of the gene encoding SECP. Such technology is well known in the art, and antisense oligonucleotides or larger fragments can be designed from various locations along the coding or control regions of sequences encoding SECP. (See, e.g., Agrawal, S., ed. (1996) *Antisense Therapeutics*, Humana Press Inc., Totawa N.J.)

In therapeutic use, any gene delivery system suitable for introduction of the antisense sequences into appropriate target cells can be used. Antisense sequences can be delivered intracellularly in the form of an expression plasmid which, upon transcription, produces a sequence complementary to at least a portion of the cellular sequence encoding the target protein. (See, e.g., Slater, J. E. et al. (1998) J. Allergy Clin. Immunol. 102(3):469-475; and Scanlon, K. J. et al. (1995) 9(13): 1288-1296.) Antisense sequences can also be introduced intracellularly through the use of viral vectors, such as retrovirus and adeno-associated virus vectors. (See, e.g., Miller, A. D. (1990) Blood 76:271; Ausubel, supra; Uckert, W. and W. Walther (1994) Pharmacol. Ther. 63(3):323-347.) Other gene delivery mechanisms include liposome-derived systems, artificial viral envelopes, and other systems known in the art. (See, e.g., Rossi, J. J. (1995) Br. Med. Bull. 51(1):217-225; Boado, R. J. et al. (1998) J. Pharm. Sci. 87(11): 1308-1315; and Morris, M. C. et al. (1997) Nucleic Acids Res. 25(14):2730-2736.)

In another embodiment of the invention, polynucleotides encoding SECP may be used for somatic or germline gene therapy. Gene therapy may be performed to (i) correct a genetic deficiency (e.g., in the cases of severe combined immunodeficiency (SCID)-X1 disease characterized by X-linked inheritance (Cavazzana-Calvo, M. et al. (2000) Science 288:669-672), severe combined immunodeficiency syndrome associated with an inherited adenosine deaminase (ADA) deficiency (Blaese, R. M. et al. (1995) Science 270:475-480; Bordignon, C. et al. (1995) Science 270:470-475), cystic fibrosis (Zabner, J. et al. (1993) Cell 75:207-216; Crystal. R. G. et al. (1995) Hum. Gene Therapy 6:643-666; Crystal, R. G. et al. (1995) Hum. Gene Therapy 6:667-703), thalassamias, familial hypercholesterolemia, and hemophilia resulting from Factor VIII or Factor IX deficiencies (Crystal, R. G. (1995) Science 270:404-410; Verma, I. M. and N. Somia (1997) Nature 389:239-242)), (ii) express a conditionally lethal gene product (e.g., in the case of cancers which result from unregulated cell proliferation), or (iii) express a protein which affords protection against intracellular parasites (e.g., against human retroviruses, such as human immunodeficiency virus (HIV) (Baltimore, D. (1988) Nature 335:395-396; Poeschla, E. et al. (1996) Proc. Natl. Acad. Sci. USA. 93:11395-11399), hepatitis B or C virus (HBV, HCV); fungal parasites, such as *Candida albicans* and *Paracoccidioides brasiliensis*; and protozoan parasites such as *Plasmodium falciparum* and *Trypanosoma cruzi*). In the case where a genetic deficiency in SECP expression or regulation causes disease, the expression of SECP from an appropriate population of transduced cells may alleviate the clinical manifestations caused by the genetic deficiency.

In a further embodiment of the invention, diseases or disorders caused by deficiencies in SECP are treated by constructing mammalian expression vectors encoding SECP and introducing these vectors by mechanical means into SECP-deficient cells. Mechanical transfer technologies for use with cells in vivo or ex vitro include (i) direct DNA microinjection into individual cells, (ii) ballistic gold particle delivery, (iii) liposome-mediated transfection, (iv) receptor-mediated gene transfer, and (v) the use of DNA transposons (Morgan, R. A. and W. F. Anderson (1993) Annu. Rev. Biochem. 62:191-217; Ivics, Z. (1997) Cell 91:501-510; Boulay, J-L. and H. Récipon (1998) Curr. Opin. Biotechnol. 9:445-450).

Expression vectors that may be effective for the expression of SECP include, but are not limited to, the PCDNA 3.1, EPITAG, PRCCMV2, PREP, PVAX, PCR2-TOPOTA vectors (Invitrogen, Carlsbad Calif.), PCMV-SCRIPT, PCMV-TAG, PEGSH/PERV (Stratagene, La Jolla Calif.), and PTET-OFF, PTET-ON, PTRE2, PTRE2-LUC, PTK-HYG (Clontech, Palo Alto Calif.). SECP may be expressed using (i) a constitutively active promoter, (e.g., from cytomegalovirus (CMV), Rous sarcoma virus (RSV), SV40 virus, thymidine kinase (TK), or O-actin genes), (ii) an inducible promoter (e.g., the tetracycline-regulated promoter (Gossen, M. and H. Bujard (1992) Proc. Natl. Acad. Sci. USA 89:5547-5551; Gossen, M. et al. (1995) Science 268:1766-1769; Rossi, F. M. V. and H. M. Blau (1998) Curr. Opin. Biotechnol. 9:451-456), commercially available in the T-REX plasmid (Invitrogen)); the ecdysone-inducible promoter (available in the plasmids PVGRXR and PIND; Invitrogen); the FK506/rapamycin inducible promoter; or the RU486/mifepristone inducible promoter (Rossi, F. M. V. and H. M. Blau, supra)), or (iii) a tissue-specific promoter or the native promoter of the endogenous gene encoding SECP from a normal individual.

Commercially available liposome transformation kits (e.g., the PERFECT LIPID TRANSFECTION KIT, available from Invitrogen) allow one with ordinary skill in the art to deliver polynucleotides to target cells in culture and require minimal effort to optimize experimental parameters. In the alternative, transformation is performed using the calcium phosphate method (Graham, F. L. and A. J. Eb (1973) Virology 52:456-467), or by electroporation (Neumann, E. et al. (1982) EMBO J. 1:841-845). The introduction of DNA to primary cells requires modification of these standardized mammalian transfection protocols.

In another embodiment of the invention, diseases or disorders caused by genetic defects with respect to SECP expression are treated by constructing a retrovirus vector consisting of (i) the polynucleotide encoding SECP under the control of an independent promoter or the retrovirus long terminal repeat (LTR) promoter, (ii) appropriate RNA packaging signals, and (iii) a Rev-responsive element (RRE) along with additional retrovirus cis-acting RNA sequences and coding sequences required for efficient vector propagation. Retrovirus vectors (e.g., PFB and PFBNEO) are commercially available (Stratagene) and are based on published data (Riviere, I. et al. (1995) Proc. Natl. Acad. Sci. USA 92:6733-6737), incorporated by reference herein. The vector is propagated in an appropriate vector producing cell line (VPCL) that expresses an envelope gene with a tropism for receptors on the target cells or a promiscuous envelope protein such as VSVg (Armentano, D. et al. (1987) J. Virol. 61:1647-1650; Bender, M. A. et al. (1987) J. Virol. 61:1639-1646; Adam, M. A. and A. D. Miller (1988) J. Virol. 62:3802-3806; Dull, T. et al. (1998) J. Virol. 72:8463-8471; Zufferey, R. et al. (1998) J. Virol. 72:9873-9880). U.S. Pat. No. 5,910,434 to Rigg ("Method for obtaining retrovirus packaging cell lines producing high transducing efficiency retroviral supernatant") discloses a method for obtaining retrovirus packaging cell lines and is hereby incorporated by reference. Propagation of retrovirus vectors, transduction of a population of cells (e.g., $CD4^+$ T-cells), and the return of transduced cells to a patient are procedures well known to persons skilled in the art of gene therapy and have been well documented (Ranga, U. et al. (1997) J. Virol. 71:7020-7029; Bauer, G. et al. (1997) Blood 89:2259-2267; Bonyhadi, M. L. (1997) J. Virol. 71:4707-4716; Ranga, U. et al. (1998) Proc. Natl. Acad. Sci. USA 95:1201-1206; Su, L. (1997) Blood 89:2283-2290).

In the alternative, an adenovirus-based gene therapy delivery system is used to deliver polynucleotides encoding SECP to cells which have one or more genetic abnormalities with respect to the expression of SECP. The construction and packaging of adenovirus-based vectors are well known to those with ordinary skill in the art. Replication defective adenovirus vectors have proven to be versatile for importing genes encoding immunoregulatory proteins into intact islets in the pancreas (Csete, M. E. et al. (1995) Transplantation 27:263-268). Potentially useful adenoviral vectors are described in U.S. Pat. No. 5,707,618 to Armentano ("Adenovirus vectors for gene therapy"), hereby incorporated by reference. For adenoviral vectors, see also Antinozzi, P. A. et al. (1999) Annu. Rev. Nutr. 19:511-544 and Verma, I. M. and N. Somia (1997) Nature 18:389:239-242, both incorporated by reference herein.

In another alternative, a herpes-based, gene therapy delivery system is used to deliver polynucleotides encoding SECP to target cells which have one or more genetic abnormalities with respect to the expression of SECP. The use of herpes simplex virus (HSV)-based vectors may be especially valuable for introducing SECP to cells of the central nervous system, for which HSV has a tropism. The construction and packaging of herpes-based vectors are well known to those with ordinary skill in the art. A replication-competent herpes simplex virus (HSV) type 1-based vector has been used to deliver a reporter gene to the eyes of primates (Liu, X. et al. (1999) Exp. Eye Res. 169:385-395). The construction of a HSV-1 virus vector has also been disclosed in detail in U.S. Pat. No. 5,804,413 to DeLuca ("Herpes simplex virus strains for gene transfer"), which is hereby incorporated by reference. U.S. Pat. No. 5,804,413 teaches the use of recombinant HSV d92 which consists of a genome containing at least one exogenous gene to be transferred to a cell under the control of the appropriate promoter for purposes including human gene therapy. Also taught by this patent are the construction and use of recombinant HSV strains deleted for ICP4, ICP27 and ICP22. For HSV vectors, see also Goins, W. F. et al. (1999) J. Virol. 73:519-532 and Xu, H. et al. (1994) Dev. Biol. 163:152-161, hereby incorporated by reference. The manipulation of cloned herpesvirus sequences, the generation of recombinant virus following the transfection of multiple plasmids containing different segments of the large herpesvirus genomes, the growth and propagation of herpesvirus, and the infection of cells with herpesvirus are techniques well known to those of ordinary skill in the art.

In another alternative, an alphavirus (positive, single-stranded RNA virus) vector is used to deliver polynucleotides encoding SECP to target cells. The biology of the prototypic alphavirus, Semliki Forest Virus (SFV), has been studied extensively and gene transfer vectors have been based on the SFV genome (Garoff, H. and K.-J. Li (1998) Curr. Opin. Biotechnol. 9:464-469). During alphavirus RNA replication, a subgenomic RNA is generated that normally encodes the viral capsid proteins. This subgenomic RNA replicates to higher levels than the full length genomic RNA, resulting in the overproduction of capsid proteins relative to the viral proteins with enzymatic activity (e.g., protease and polymerase). Similarly, inserting the coding sequence for SECP into the alphavirus genome in place of the capsid-coding region results in the production of a large number of SECP-coding RNAs and the synthesis of high levels of SECP in vector transduced cells. While alphavirus infection is typically associated with cell lysis within a few days, the ability to establish a persistent infection in hamster normal kidney cells (BHK-21) with a variant of Sindbis virus (SIN) indicates that the lytic replication of alphaviruses can be altered to suit the needs of the gene therapy application (Dryga, S. A. et al. (1997) Virology 228:74-83). The wide host range of alphaviruses will allow the introduction of SECP into a variety of cell types. The specific transduction of a subset of cells in a population may require the sorting of cells prior to transduction. The methods of manipulating infectious cDNA clones of alphaviruses, performing alphavirus cDNA and RNA transfections, and performing alphavirus infections, are well known to those with ordinary skill in the art.

Oligonucleotides derived from the transcription initiation site. e.g., between about positions −10 and +10 from the start site, may also be employed to inhibit gene expression. Similarly, inhibition can be achieved using triple helix base-pairing methodology. Triple helix pairing is useful because it causes inhibition of the ability of the double helix to open sufficiently for the binding of polymerases, transcription factors, or regulatory molecules. Recent therapeutic advances using triplex DNA have been described in the literature. (See, e.g., Gee, J. E. et al. (1994) in Huber, B. E. and B. I. Carr, *Molecular and Immunologic Approaches*, Futura Publishing, Mt. Kisco N.Y., pp. 163-177.) A complementary sequence or antisense molecule may also be designed to block translation of mRNA by preventing the transcript from binding to ribosomes.

Ribozymes, enzymatic RNA molecules, may also be used to catalyze the specific cleavage of RNA. The mechanism of ribozyme action involves sequence-specific hybridization of the ribozyme molecule to complementary target RNA, followed by endonucleolytic cleavage. For example, engineered hammerhead motif ribozyme molecules may specifically and efficiently catalyze endonucleolytic cleavage of sequences encoding SECP.

Specific ribozyme cleavage sites within any potential RNA target are initially identified by scanning the target molecule for ribozyme cleavage sites, including the following sequences: GUA, GUU, and GUC. Once identified, short RNA sequences of between 15 and 20 ribonucleotides, corresponding to the region of the target gene containing the cleavage site, may be evaluated for secondary structural features which may render the oligonucleotide inoperable. The suitability of candidate targets may also be evaluated by testing accessibility to hybridization with complementary oligonucleotides using ribonuclease protection assays.

Complementary ribonucleic acid molecules and ribozymes of the invention may be prepared by any method known in the art for the synthesis of nucleic acid molecules. These include techniques for chemically synthesizing oligonucleotides such as solid phase phosphoramidite chemical synthesis. Alternatively, RNA molecules may be generated by in vitro and in vivo transcription of DNA sequences encoding SECP. Such DNA sequences may be incorporated into a wide variety of vectors with suitable RNA polymerase promoters such as T7 or SP6. Alternatively, these cDNA constructs that synthesize complementary RNA, constitutively or inducibly, can be introduced into cell lines, cells, or tissues.

RNA molecules may be modified to increase intracellular stability and half-life. Possible modifications include, but are not limited to, the addition of flanking sequences at the 5' and/or 3' ends of the molecule, or the use of phosphorothioate or 2' O-methyl rather than phosphodiesterase linkages within the backbone of the molecule. This concept is inherent in the production of PNAs and can be extended in all of these molecules by the inclusion of nontraditional bases such as inosine, queosine, and wybutosine, as well as acetyl-, methyl-, thio-, and similarly modified forms of adenine, cytidine, guanine, thymine, and uridine which are not as easily recognized by endogenous endonucleases.

An additional embodiment of the invention encompasses a method for screening for a compound which is effective in altering expression of a polynucleotide encoding SECP. Compounds which may be effective in altering expression of a specific polynucleotide may include, but are not limited to, oligonucleotides, antisense oligonucleotides, triple helix-forming oligonucleotides, transcription factors and other polypeptide transcriptional regulators, and non-macromolecular chemical entities which are capable of interacting with specific polynucleotide sequences. Effective compounds may alter polynucleotide expression by acting as either inhibitors or promoters of polynucleotide expression. Thus, in the treatment of disorders associated with increased SECP expression or activity, a compound which specifically inhibits expression of the polynucleotide encoding SECP may be therapeutically useful, and in the treatment of disorders associated with decreased SECP expression or activity, a compound which specifically promotes expression of the polynucleotide encoding SECP may be therapeutically useful.

At least one, and up to a plurality, of test compounds may be screened for effectiveness in altering expression of a specific polynucleotide. A test compound may be obtained by any method commonly known in the art, including chemical modification of a compound known to be effective in altering polynucleotide expression; selection from an existing, commercially-available or proprietary library of naturally-occurring or non-natural chemical compounds; rational design of a compound based on chemical and/or structural properties of the target polynucleotide; and selection from a library of chemical compounds created combinatorially or randomly. A sample comprising a polynucleotide encoding SECP is exposed to at least one test compound thus obtained. The sample may comprise, for example, an intact or permeabilized cell, or an in vitro cell-free or reconstituted biochemical system. Alterations in the expression of a polynucleotide encoding SECP are assayed by any method commonly known in the art. Typically, the expression of a specific nucleotide is detected by hybridization with a probe having a nucleotide sequence complementary to the sequence of the polynucleotide encoding SECP. The amount of hybridization may be quantified, thus forming the basis for a comparison of the expression of the polynucleotide both with and without exposure to one or more test compounds. Detection of a change in the expression of a polynucleotide exposed to a test compound indicates that the test compound is effective in altering the expression of the polynucleotide. A screen for a compound effective in altering expression of a specific polynucleotide can be carried out, for example, using a *Schizosaccharomyces pombe* gene expression system (Atkins, D. et al. (1999)

U.S. Pat. No. 5,932,435; Arndt, G. M. et al. (2000) Nucleic Acids Res. 28:E15) or a human cell line such as HeLa cell (Clarke, M. L. et al. (2000) Biochem. Biophys. Res. Commun. 268:8-13). A particular embodiment of the present invention involves screening a combinatorial library of oligonucleotides (such as deoxyribonucleotides, ribonucleotides, peptide nucleic acids, and modified oligonucleotides) for antisense activity against a specific polynucleotide sequence (Bruice, T. W. et al. (1997) U.S. Pat. No. 5,686,242; Bruice, T. W. et al. (2000) U.S. Pat. No. 6,022,691).

Many methods for introducing vectors into cells or tissues are available and equally suitable for use in vivo, in vitro, and ex vivo. For ex vivo therapy, vectors may be introduced into stem cells taken from the patient and clonally propagated for autologous transplant back into that same patient. Delivery by transfection, by liposome injections, or by polycationic amino polymers may be achieved using methods which are well known in the art. (See, e.g., Goldman, C. K. et al. (1997) Nat. Biotechnol. 15:462-466.)

Any of the therapeutic methods described above may be applied to any subject in need of such therapy, including, for example, mammals such as humans, dogs, cats, cows, horses, rabbits, and monkeys.

An additional embodiment of the invention relates to the administration of a composition which generally comprises an active ingredient formulated with a pharmaceutically acceptable excipient. Excipients may include, for example, sugars, starches, celluloses, gums, and proteins. Various formulations are commonly known and are thoroughly discussed in the latest edition of *Remington's Pharmaceutical Sciences* (Maack Publishing, Easton Pa.). Such compositions may consist of SECP, antibodies to SECP, and mimetics, agonists, antagonists, or inhibitors of SECP.

The compositions utilized in this invention may be administered by any number of routes including, but not limited to, oral, intravenous, intramuscular, intra-arterial, intramedullary, intrathecal, intraventricular, pulmonary, transdermal, subcutaneous, intraperitoneal, intranasal, enteral, topical, sublingual, or rectal means.

Compositions for pulmonary administration may be prepared in liquid or dry powder form. These compositions are generally aerosolized immediately prior to inhalation by the patient. In the case of small molecules (e.g. traditional low molecular weight organic drugs), aerosol delivery of fast-acting formulations is well-known in the art. In the case of macromolecules (e.g. larger peptides and proteins), recent developments in the field of pulmonary delivery via the alveolar region of the lung have enabled the practical delivery of drugs such as insulin to blood circulation (see, e.g., Patton, J. S. et al., U.S. Pat. No. 5,997,848). Pulmonary delivery has the advantage of administration without needle injection, and obviates the need for potentially toxic penetration enhancers.

Compositions suitable for use in the invention include compositions wherein the active ingredients are contained in an effective amount to achieve the intended purpose. The determination of an effective dose is well within the capability of those skilled in the art.

Specialized forms of compositions may be prepared for direct intracellular delivery of macromolecules comprising SECP or fragments thereof. For example, liposome preparations containing a cell-impermeable macromolecule may promote cell fusion and intracellular delivery of the macromolecule. Alternatively, SECP or a fragment thereof may be joined to a short cationic N-terminal portion from the HIV Tat-1 protein. Fusion proteins thus generated have been found to transduce into the cells of all tissues, including the brain, in a mouse model system (Schwarze, S. R. et al. (1999) Science 285:1569-1572).

For any compound, the therapeutically effective dose can be estimated initially either in cell culture assays, e.g., of neoplastic cells, or in animal models such as mice, rats, rabbits, dogs, monkeys, or pigs. An animal model may also be used to determine the appropriate concentration range and route of administration. Such information can then be used to determine useful doses and routes for administration in humans.

A therapeutically effective dose refers to that amount of active ingredient, for example SECP or fragments thereof, antibodies of SECP, and agonists, antagonists or inhibitors of SECP, which ameliorates the symptoms or condition. Therapeutic efficacy and toxicity may be determined by standard pharmaceutical procedures in cell cultures or with experimental animals, such as by calculating the $ED_{50}$ (the dose therapeutically effective in 50% of the population) or $LD_{50}$ (the dose lethal to 50% of the population) statistics. The dose ratio of toxic to therapeutic effects is the therapeutic index, which can be expressed as the $LD_{50}/ED_{50}$ ratio. Compositions which exhibit large therapeutic indices are preferred. The data obtained from cell culture assays and animal studies are used to formulate a range of dosage for human use. The dosage contained in such compositions is preferably within a range of circulating concentrations that includes the $ED_{50}$ with little or no toxicity. The dosage varies within this range depending upon the dosage form employed, the sensitivity of the patient, and the route of administration.

The exact dosage will be determined by the practitioner, in light of factors related to the subject requiring treatment. Dosage and administration are adjusted to provide sufficient levels of the active moiety or to maintain the desired effect. Factors which may be taken into account include the severity of the disease state, the general health of the subject, the age, weight, and gender of the subject, time and frequency of administration, drug combination(s), reaction sensitivities, and response to therapy. Long-acting compositions may be administered every 3 to 4 days, every week, or biweekly depending on the half-life and clearance rate of the particular formulation.

Normal dosage amounts may vary from about 0.1 µg to 100.000 µg, up to a total dose of about 1 gram, depending upon the route of administration. Guidance as to particular dosages and methods of delivery is provided in the literature and generally available to practitioners in the art. Those skilled in the art will employ different formulations for nucleotides than for proteins or their inhibitors. Similarly, delivery of polynucleotides or polypeptides will be specific to particular cells, conditions, locations, etc.

Diagnostics

In another embodiment, antibodies which specifically bind SECP may be used for the diagnosis of disorders characterized by expression of SECP, or in assays to monitor patients being treated with SECP or agonists, antagonists, or inhibitors of SECP. Antibodies useful for diagnostic purposes may be prepared in the same manner as described above for therapeutics. Diagnostic assays for SECP include methods which utilize the antibody and a label to detect SECP in human body fluids or in extracts of cells or tissues. The antibodies may be used with or without modification, and may be labeled by covalent or non-covalent attachment of a reporter molecule. A wide variety of reporter molecules, several of which are described above, are known in the art and may be used.

A variety of protocols for measuring SECP, including ELISAs, RIAs, and FACS, are known in the art and provide a basis for diagnosing altered or abnormal levels of SECP expression. Normal or standard values for SECP expression are established by combining body fluids or cell extracts taken from normal mammalian subjects, for example, human subjects, with antibodies to SECP under conditions suitable for complex formation. The amount of standard complex formation may be quantitated by various methods, such as photometric means. Quantities of SECP expressed in subject, control, and disease samples from biopsied tissues are compared with the standard values. Deviation between standard and subject values establishes the parameters for diagnosing disease.

In another embodiment of the invention, the polynucleotides encoding SECP may be used for diagnostic purposes. The polynucleotides which may be used include oligonucleotide sequences, complementary RNA and DNA molecules, and PNAs. The polynucleotides may be used to detect and quantify gene expression in biopsied tissues in which expression of SECP may be correlated with disease. The diagnostic assay may be used to determine absence, presence, and excess expression of SECP, and to monitor regulation of SECP levels during therapeutic intervention.

In one aspect, hybridization with PCR probes which are capable of detecting polynucleotide sequences, including genomic sequences, encoding SECP or closely related molecules may be used to identify nucleic acid sequences which encode SECP. The specificity of the probe, whether it is made from a highly specific region, e.g., the 5' regulatory region, or from a less specific region, e.g., a conserved motif, and the stringency of the hybridization or amplification will determine whether the probe identifies only naturally occurring sequences encoding SECP, allelic variants, or related sequences.

Probes may also be used for the detection of related sequences, and may have at least 50% sequence identity to any of the SECP encoding sequences. The hybridization probes of the subject invention may be DNA or RNA and may be derived from the sequence of SEQ ID NO:64-126 or from genomic sequences including promoters, enhancers, and introns of the SECP gene.

Means for producing specific hybridization probes for DNAs encoding SECP include the cloning of polynucleotide sequences encoding SECP or SECP derivatives into vectors for the production of mRNA probes. Such vectors are known in the art, are commercially available, and may be used to synthesize RNA probes in vitro by means of the addition of the appropriate RNA polymerases and the appropriate labeled nucleotides. Hybridization probes may be labeled by a variety of reporter groups, for example, by radionuclides such as $^{32}P$ or $^{35}S$, or by enzymatic labels, such as alkaline phosphatase coupled to the probe via avidin/biotin coupling systems, and the like.

Polynucleotide sequences encoding SECP may be used for the diagnosis of disorders associated with expression of SECP. Examples of such disorders include, but are not limited to, a cell proliferative disorder such as actinic keratosis, arteriosclerosis, atherosclerosis, bursitis, cirrhosis, hepatitis, mixed connective tissue disease (MCTD), myelofibrosis, paroxysmal nocturnal hemoglobinuria, polycythemia vera, psoriasis, primary thrombocythemia, and cancers including adenocarcinoma, leukemia, lymphoma, melanoma, myeloma, sarcoma, teratocarcinoma, and, in particular, a cancer of the adrenal gland, bladder, bone, bone marrow, brain, breast, cervix, gall bladder, ganglia, gastrointestinal tract, heart, kidney, liver, lung, muscle, ovary, pancreas, parathyroid, penis, prostate, salivary glands, skin, spleen, testis, thymus, thyroid, and uterus; an autoimmune/inflammatory disorder such as acquired immunodeficiency syndrome (AIDS), Addison's disease, adult respiratory distress syndrome, allergies, ankylosing spondylitis, amyloidosis, anemia, asthma, atherosclerosis, autoimmune hemolytic anemia, autoimmune thyroiditis, autoimmune polyendocrinopathy-candidiasis-ectodermal dystrophy (APECED), bronchitis, cholecystitis, contact dermatitis, Crohn's disease, atopic dermatitis, dermatomyositis, diabetes mellitus, emphysema, episodic lymphopenia with lymphocytotoxins, erythroblastosis fetalis, erythema nodosum, atrophic gastritis, glomerulonephritis, Goodpasture's syndrome, gout, Graves' disease, Hashimoto's thyroiditis, hypereosinophilia, irritable bowel syndrome, multiple sclerosis, myasthenia gravis, myocardial or pericardial inflammation, osteoarthritis, osteoporosis, pancreatitis, polymyositis, psoriasis, Reiter's syndrome, rheumatoid arthritis, scleroderma, Sjögren's syndrome, systemic anaphylaxis, systemic lupus erythematosus, systemic sclerosis, thrombocytopenic purpura, ulcerative colitis, uveitis, Werner syndrome, complications of cancer, hemodialysis, and extracorporeal circulation, viral, bacterial, fungal, parasitic, protozoal, and helminthic infections, and trauma; a cardiovascular disorder such as congestive heart failure, ischemic heart disease, angina pectoris, myocardial infarction, hypertensive heart disease, degenerative valvular heart disease, calcific aortic valve stenosis, congenitally bicuspid aortic valve, mitral annular calcification, mitral valve prolapse, rheumatic fever and rheumatic heart disease, infective endocarditis, nonbacterial thrombotic endocarditis, endocarditis of systemic lupus erythematosus, carcinoid heart disease, cardiomyopathy, myocarditis, pericarditis, neoplastic heart disease, congenital heart disease, complications of cardiac transplantation, arteriovenous fistula, atherosclerosis, hypertension, vasculitis, Raynaud's disease, aneurysms, arterial dissections, varicose veins, thrombophlebitis and phlebothrombosis, vascular tumors, and complications of thrombolysis, balloon angioplasty, vascular replacement, and coronary artery bypass graft surgery; a neurological disorder such as epilepsy, ischemic cerebrovascular disease, stroke, cerebral neoplasms, Alzheimer's disease, Pick's disease, Huntington's disease, dementia, Parkinson's disease and other extrapyramidal disorders, amyotrophic lateral sclerosis and other motor neuron disorders, progressive neural muscular atrophy, retinitis pigmentosa, hereditary ataxias, multiple sclerosis and other demyelinating diseases, bacterial and viral meningitis, brain abscess, subdural empyema, epidural abscess, suppurative intracranial thrombophlebitis, myelitis and radiculitis, viral central nervous system disease, prion diseases including kuru, Creutzfeldt-Jakob disease, and Gerstmann-Straussler-Scheinker syndrome, fatal familial insomnia, nutritional and metabolic diseases of the nervous system, neurofibromatosis, tuberous sclerosis, cerebelloretinal hemangioblastomatosis, encephalotrigeminal syndrome, mental retardation and other developmental disorders of the central nervous system including Down syndrome, cerebral palsy, neuroskeletal disorders, autonomic nervous system disorders, cranial nerve disorders, spinal cord diseases, muscular dystrophy and other neuromuscular disorders, peripheral nervous system disorders, dermatomyositis and polymyositis, inherited, metabolic, endocrine, and toxic myopathies, myasthenia gravis, periodic paralysis, mental disorders including mood, anxiety, and schizophrenic disorders, seasonal affective disorder (SAD), akathesia, amnesia, catatonia, diabetic neuropathy, tardive dyskinesia, dystonias, paranoid psychoses, postherpetic neuralgia, Tourette's disorder, progressive supranuclear palsy, corticobasal degeneration, and familial frontotemporal dementia; and a developmental disorder such as renal tubular acidosis, anemia, Cushing's syndrome, achondroplastic dwarfism, Duchenne and Becker muscular dystrophy, epilepsy, gonadal dysgenesis, WAGR syndrome (Wilms' tumor, aniridia, genitourinary abnormalities, and mental retardation), Smith-Magenis syndrome, myelodysplastic syndrome, hereditary mucoepithelial dysplasia, hereditary keratodermas, hereditary neuropathies such as Charcot-Marie-Tooth disease and neurofibromatosis, hypothyroidism, hydrocephalus, seizure disorders such as Syndenham's chorea and cerebral palsy, spina bifida, anencephaly, craniorachischisis, congenital glaucoma, cataract, and sensorineural hearing loss. The polynucleotide sequences encoding SECP may be used in Southern or northern analysis, dot blot, or other membrane-based technologies; in PCR technologies; in dipstick, pin, and multiformat ELISA-like assays; and in microarrays utilizing fluids or tissues from patients to detect altered SECP expression. Such qualitative or quantitative methods are well known in the art.

In a particular aspect, the nucleotide sequences encoding SECP may be useful in assays that detect the presence of associated disorders, particularly those mentioned above. The nucleotide sequences encoding SECP may be labeled by standard methods and added to a fluid or tissue sample from a patient under conditions suitable for the formation of hybridization complexes. After a suitable incubation period, the sample is washed and the signal is quantified and compared with a standard value. If the amount of signal in the patient sample is significantly altered in comparison to a control sample then the presence of altered levels of nucleotide sequences encoding SECP in the sample indicates the presence of the associated disorder. Such assays may also be used to evaluate the efficacy of a particular therapeutic treatment regimen in animal studies, in clinical trials, or to monitor the treatment of an individual patient.

In order to provide a basis for the diagnosis of a disorder associated with expression of SECP, a normal or standard profile for expression is established. This may be accomplished by combining body fluids or cell extracts taken from normal subjects, either animal or human, with a sequence, or a fragment thereof, encoding SECP, under conditions suitable for hybridization or amplification. Standard hybridization may be quantified by comparing the values obtained from normal subjects with values from an experiment in which a known amount of a substantially purified polynucleotide is used. Standard values obtained in this manner may be compared with values obtained from samples from patients who are symptomatic for a disorder. Deviation from standard values is used to establish the presence of a disorder.

Once the presence of a disorder is established and a treatment protocol is initiated, hybridization assays may be repeated on a regular basis to determine if the level of expression in the patient begins to approximate that which is observed in the normal subject. The results obtained from successive assays may be used to show the efficacy of treatment over a period ranging from several days to months.

With respect to cancer, the presence of an abnormal amount of transcript (either under- or overexpressed) in biopsied tissue from an individual may indicate a predisposition for the development of the disease, or may provide a means for detecting the disease prior to the appearance of actual clinical symptoms. A more definitive diagnosis of this type may allow health professionals to employ preventative measures or aggressive treatment earlier thereby preventing the development or further progression of the cancer.

Additional diagnostic uses for oligonucleotides designed from the sequences encoding SECP may involve the use of PCR. These oligomers may be chemically synthesized, generated enzymatically, or produced in vitro. Oligomers will preferably contain a fragment of a polynucleotide encoding SECP, or a fragment of a polynucleotide complementary to the polynucleotide encoding SECP, and will be employed under optimized conditions for identification of a specific gene or condition. Oligomers may also be employed under less stringent conditions for detection or quantification of closely related DNA or RNA sequences.

In a particular aspect, oligonucleotide primers derived from the polynucleotide sequences encoding SECP may be used to detect single nucleotide polymorphisms (SNPs). SNPs are substitutions, insertions and deletions that are a frequent cause of inherited or acquired genetic disease in humans. Methods of SNP detection include, but are not limited to, single-stranded conformation polymorphism (SSCP) and fluorescent SSCP (fSSCP) methods. In SSCP, oligonucleotide primers derived from the polynucleotide sequences encoding SECP are used to amplify DNA using the polymerase chain reaction (PCR). The DNA may be derived, for example, from diseased or normal tissue, biopsy samples, bodily fluids, and the like. SNPs in the DNA cause differences in the secondary and tertiary structures of PCR products in single-stranded form, and these differences are detectable using gel electrophoresis in non-denaturing gels. In fSCCP, the oligonucleotide primers are fluorescently labeled, which allows detection of the amplimers in high-throughput equipment such as DNA sequencing machines. Additionally, sequence database analysis methods, termed in silico SNP (isSNP), are capable of identifying polymorphisms by comparing the sequence of individual overlapping DNA fragments which assemble into a common consensus sequence. These computer-based methods filter out sequence variations due to laboratory preparation of DNA and sequencing errors using statistical models and automated analyses of DNA sequence chromatograms. In the alternative, SNPs may be detected and characterized by mass spectrometry using, for example, the high throughput MASSARRAY system (Sequenom, Inc., San Diego Calif.).

Methods which may also be used to quantify the expression of SECP include radiolabeling or biotinylating nucleotides, coamplification of a control nucleic acid, and interpolating results from standard curves. (See, e.g., Melby, P. C. et al. (1993) J. Immunol. Methods 159:235-244; Duplaa, C. et al. (1993) Anal. Biochem. 212:229-236.) The speed of quantitation of multiple samples may be accelerated by running the assay in a high-throughput format where the oligomer or polynucleotide of interest is presented in various dilutions and a spectrophotometric or colorimetric response gives rapid quantitation.

In further embodiments, oligonucleotides or longer fragments derived from any of the polynucleotide sequences described herein may be used as elements on a microarray. The microarray can be used in transcript imaging techniques which monitor the relative expression levels of large numbers of genes simultaneously as described below. The microarray may also be used to identify genetic variants, mutations, and polymorphisms. This information may be used to determine gene function, to understand the genetic basis of a disorder, to diagnose a disorder, to monitor progression/regression of disease as a function of gene expression, and to develop and monitor the activities of therapeutic agents in the treatment of disease. In particular, this information may be used to develop a pharmacogenomic profile of a patient in order to select the most appropriate and effective treatment regimen for that patient. For example, therapeutic agents which are highly effective and display the fewest side effects may be selected for a patient based on his/her pharmacogenomic profile.

In another embodiment, SECP, fragments of SECP, or antibodies specific for SECP may be used as elements on a microarray. The microarray may be used to monitor or measure protein-protein interactions, drug-target interactions, and gene expression profiles, as described above.

A particular embodiment relates to the use of the polynucleotides of the present invention to generate a transcript image of a tissue or cell type. A transcript image represents the global pattern of gene expression by a particular tissue or cell type. Global gene expression patterns are analyzed by quantifying the number of expressed genes and their relative abundance under given conditions and at a given time. (See Seilhamer et al., "Comparative Gene Transcript Analysis," U.S. Pat. No. 5,840,484, expressly incorporated by reference herein.) Thus a transcript image may be generated by hybridizing the polynucleotides of the present invention or their complements to the totality of transcripts or reverse transcripts of a particular tissue or cell type. In one embodiment, the hybridization takes place in high-throughput format, wherein the polynucleotides of the present invention or their complements comprise a subset of a plurality of elements on a microarray. The resultant transcript image would provide a profile of gene activity.

Transcript images may be generated using transcripts isolated from tissues, cell lines, biopsies, or other biological samples. The transcript image may thus reflect gene expression in vive, as in the case of a tissue or biopsy sample, or in vitro, as in the case of a cell line.

Transcript images which profile the expression of the polynucleotides of the present invention may also be used in conjunction with in vitro model systems and preclinical evaluation of pharmaceuticals, as well as toxicological testing of industrial and naturally-occurring environmental compounds. All compounds induce characteristic gene expression patterns, frequently termed molecular fingerprints or toxicant signatures, which are indicative of mechanisms of action and toxicity (Nuwaysir, E. F. et al. (1999) Mol. Carcinog. 24:153-159; Steiner, S. and N. L. Anderson (2000) Toxicol. Lett. 112-113:467471, expressly incorporated by reference herein). If a test compound has a signature similar to that of a compound with known toxicity, it is likely to share those toxic properties. These fingerprints or signatures are most useful and refined when they contain expression information from a large number of genes and gene families. Ideally, a genome-wide measurement of expression provides the highest quality signature. Even genes whose expression is not altered by any tested compounds are important as well, as the levels of expression of these genes are used to normalize the rest of the expression data. The normalization procedure is useful for comparison of expression data after treatment with different compounds. While the assignment of gene function to elements of a toxicant signature aids in interpretation of toxicity mechanisms, knowledge of gene function is not necessary for the statistical matching of signatures which leads to prediction of toxicity. (See, for example, Press Release 00-02 from the National Institute of Environmental Health Sciences, released Feb. 29, 2000, available at http://www.niehs.nih.gov/oc/news/toxchip.htm.) Therefore, it is important and desirable in toxicological screening using toxicant signatures to include all expressed gene sequences.

In one embodiment, the toxicity of a test compound is assessed by treating a biological sample containing nucleic acids with the test compound. Nucleic acids that are expressed in the treated biological sample are hybridized with one or more probes specific to the polynucleotides of the present invention, so that transcript levels corresponding to the polynucleotides of the present invention may be quantified. The transcript levels in the treated biological sample are compared with levels in an untreated biological sample. Differences in the transcript levels between the two samples are indicative of a toxic response caused by the test compound in the treated sample.

Another particular embodiment relates to the use of the polypeptide sequences of the present invention to analyze the proteome of a tissue or cell type. The term proteome refers to the global pattern of protein expression in a particular tissue or cell type. Each protein component of a proteome can be subjected individually to further analysis. Proteome expression patterns, or profiles, are analyzed by quantifying the number of expressed proteins and their relative abundance under given conditions and at a given time. A profile of a cell's proteome may thus be generated by separating and analyzing the polypeptides of a particular tissue or cell type. In one embodiment, the separation is achieved using two-dimensional gel electrophoresis, in which proteins from a sample are separated by isoelectric focusing in the first dimension, and then according to molecular weight by sodium dodecyl sulfate slab gel electrophoresis in the second dimension (Steiner and Anderson, supra). The proteins are visualized in the gel as discrete and uniquely positioned spots, typically by staining the gel with an agent such as Coomassie Blue or silver or fluorescent stains. The optical density of each protein spot is generally proportional to the level of the protein in the sample. The optical densities of equivalently positioned protein spots from different samples, for example, from biological samples either treated or untreated with a test compound or therapeutic agent, are compared to identify any changes in protein spot density related to the treatment. The proteins in the spots are partially sequenced using, for example, standard methods employing chemical or enzymatic cleavage followed by mass spectrometry. The identity of the protein in a spot may be determined by comparing its partial sequence, preferably of at least 5 contiguous amino acid residues, to the polypeptide sequences of the present invention. In some cases, further sequence data may be obtained for definitive protein identification.

A proteomic profile may also be generated using antibodies specific for SECP to quantify the levels of SECP expression. In one embodiment, the antibodies are used as elements on a microarray, and protein expression levels are quantified by exposing the microarray to the sample and detecting the levels of protein bound to each array element (Lueking, A. et al. (1999) Anal. Biochem. 270:103-111; Mendoze, L. G. et al. (1999) Biotechniques 27:778-788). Detection may be performed by a variety of methods known in the art, for example, by reacting the proteins in the sample with a thiol- or amino-reactive fluorescent compound and detecting the amount of fluorescence bound at each array element.

Toxicant signatures at the proteome level are also useful for toxicological screening, and should be analyzed in parallel with toxicant signatures at the transcript level. There is a poor correlation between transcript and protein abundances for some proteins in some tissues (Anderson, N. L. and J. Seilhamer (1997) Electrophoresis 18:533-537), so proteome toxicant signatures may be useful in the analysis of compounds which do not significantly affect the transcript image, but which alter the proteomic profile. In addition, the analysis of transcripts in body fluids is difficult, due to rapid degradation of mRNA, so proteomic profiling may be more reliable and informative in such cases.

In another embodiment, the toxicity of a test compound is assessed by treating a biological sample containing proteins with the test compound. Proteins that are expressed in the treated biological sample are separated so that the amount of each protein can be quantified. The amount of each protein is compared to the amount of the corresponding protein in an untreated biological sample. A difference in the amount of protein between the two samples is indicative of a toxic response to the test compound in the treated sample. Individual proteins are identified by sequencing the amino acid residues of the individual proteins and comparing these partial sequences to the polypeptides of the present invention.

In another embodiment, the toxicity of a test compound is assessed by treating a biological sample containing proteins with the test compound. Proteins from the biological sample are incubated with antibodies specific to the polypeptides of the present invention. The amount of protein recognized by the antibodies is quantified. The amount of protein in the treated biological sample is compared with the amount in an untreated biological sample. A difference in the amount of protein between the two samples is indicative of a toxic response to the test compound in the treated sample.

Microarrays may be prepared, used, and analyzed using methods known in the art. (See, e.g., Brennan, T. M. et al. (1995) U.S. Pat. No. 5,474,796; Schena, M. et al. (1996) Proc. Natl. Acad. Sci. USA 93:10614-10619; Baldeschweiler et al. (1995) PCT application WO95/251116; Shalon, D. et al. (1995) PCT application WO95/35505; Heller, R. A. et al. (1997) Proc. Natl. Acad. Sci. USA 94:2150-2155; and Heller, M. J. et al. (1997) U.S. Pat. No. 5,605,662.) Various types of microarrays are well known and thoroughly described in *DNA Microarrays: A Practical Approach*, M. Schena, ed. (1999) Oxford University Press, London, hereby expressly incorporated by reference.

In another embodiment of the invention, nucleic acid sequences encoding SECP may be used to generate hybridization probes useful in mapping the naturally occurring genomic sequence. Either coding or noncoding sequences may be used, and in some instances, noncoding sequences may be preferable over coding sequences. For example, conservation of a coding sequence among members of a multi-gene family may potentially cause undesired cross hybridization during chromosomal mapping. The sequences may be mapped to a particular chromosome, to a specific region of a chromosome, or to artificial chromosome constructions, e.g., human artificial chromosomes (HACs), yeast artificial chromosomes (YACs), bacterial artificial chromosomes (BACs), bacterial PI constructions, or single chromosome cDNA libraries. (See, e.g., Harrington, J. J. et al. (1997) Nat. Genet. 15:345-355; Price, C. M. (1993) Blood Rev. 7:127-134; and Trask, B. J. (1991) Trends Genet. 7:149-154.) Once mapped, the nucleic acid sequences of the invention may be used to develop genetic linkage maps, for example, which correlate the inheritance of a disease state with the inheritance of a particular chromosome region or restriction fragment length polymorphism (RFLP). (See, for example, Lander, E. S. and D. Botstein (1986) Proc. Natl. Acad. Sci. USA 83:7353-7357.)

Fluorescent in situ hybridization (FISH) may be correlated with other physical and genetic map data. (See, e.g., Heinz-Ulrich, et al. (1995) in Meyers, supra, pp. 965-968.) Examples of genetic map data can be found in various scientific journals or at the Online Mendelian Inheritance in Man (OMIM) World Wide Web site. Correlation between the location of the gene encoding SECP on a physical map and a specific disorder, or a predisposition to a specific disorder, may help define the region of DNA associated with that disorder and thus may further positional cloning efforts.

In situ hybridization of chromosomal preparations and physical mapping techniques, such as linkage analysis using established chromosomal markers, may be used for extending genetic maps. Often the placement of a gene on the chromosome of another mammalian species, such as mouse, may reveal associated markers even if the exact chromosomal locus is not known. This information is valuable to investigators searching for disease genes using positional cloning or other gene discovery techniques. Once the gene or genes responsible for a disease or syndrome have been crudely localized by genetic linkage to a particular genomic region, e.g., ataxia-telangiectasia to 11q22-23, any sequences mapping to that area may represent associated or regulatory genes for further investigation. (See, e.g., Gatti, R. A. et al. (1988) Nature 336:577-580.) The nucleotide sequence of the instant invention may also be used to detect differences in the chromosomal location due to translocation, inversion, etc., among normal, carrier, or affected individuals.

In another embodiment of the invention. SECP, its catalytic or immunogenic fragments, or oligopeptides thereof can be used for screening libraries of compounds in any of a variety of drug screening techniques. The fragment employed in such screening may be free in solution, affixed to a solid support, borne on a cell surface, or located intracellularly. The formation of binding complexes between SECP and the agent being tested may be measured.

Another technique for drug screening provides for high throughput screening of compounds having suitable binding affinity to the protein of interest. (See, e.g., Geysen, et al. (1984) PCT application WO84/03564.) In this method, large numbers of different small test compounds are synthesized on a solid substrate. The test compounds are reacted with SECP, or fragments thereof, and washed. Bound SECP is then detected by methods well known in the art. Purified SECP can also be coated directly onto plates for use in the aforementioned drug screening techniques. Alternatively, non-neutralizing antibodies can be used to capture the peptide and immobilize it on a solid support.

In another embodiment, one may use competitive drug screening assays in which neutralizing antibodies capable of binding SECP specifically compete with a test compound for binding SECP. In this manner, antibodies can be used to detect the presence of any peptide which shares one or more antigenic determinants with SECP.

In additional embodiments, the nucleotide sequences which encode SECP may be used in any molecular biology techniques that have yet to be developed, provided the new techniques rely on properties of nucleotide sequences that are currently known, including, but not limited to, such properties as the triplet genetic code and specific base pair interactions.

Without further elaboration, it is believed that one skilled in the art can, using the preceding description, utilize the present invention to its fullest extent. The following embodiments are, therefore, to be construed as merely illustrative, and not limitative of the remainder of the disclosure in any way whatsoever.

The disclosures of all patents, applications and publications, mentioned above and below and including U.S. Ser.

No. 60/247,642, U.S. Ser. No. 60/249,824, U.S. Ser. No. 60/252,824, U.S. Ser. No. 60/247,505, U.S. Ser. No. 60/254,305, and U.S. Ser. No. 60/256,448, are expressly incorporated by reference herein.

EXAMPLES

I. Construction of cDNA Libraries

Incyte cDNAs were derived from cDNA libraries described in the LIFESEQ GOLD database (Incyte Genomics, Palo Alto Calif.) and shown in Table 4, column 5. Some tissues were homogenized and lysed in guanidinium isothiocyanate, while others were homogenized and lysed in phenol or in a suitable mixture of denaturants, such as TRIZOL (Life Technologies), a monophasic solution of phenol and guanidine isothiocyanate. The resulting lysates were centrifuged over CsCl cushions or extracted with chloroform. RNA was precipitated from the lysates with either isopropanol or sodium acetate and ethanol, or by other routine methods.

Phenol extraction and precipitation of RNA were repeated as necessary to increase RNA purity. In some cases, RNA was treated with DNase. For most libraries, poly(A)+RNA was isolated using oligo d(T)-coupled paramagnetic particles (Promega), OLIGOTEX latex particles (QIAGEN, Chatsworth Calif.), or an OLIGOTEX mRNA purification kit (QIAGEN). Alternatively, RNA was isolated directly from tissue lysates using other RNA isolation kits, e.g., the POLY(A)PURE mRNA purification kit (Ambion, Austin Tex.).

In some cases, Stratagene was provided with RNA and constructed the corresponding cDNA libraries. Otherwise, cDNA was synthesized and cDNA libraries were constructed with the UNIZAP vector system (Stratagene) or SUPERSCRIPT plasmid system (Life Technologies), using the recommended procedures or similar methods known in the art. (See, e.g., Ausubel, 1997, supra, units 5.1-6.6.) Reverse transcription was initiated using oligo d(T) or random primers. Synthetic oligonucleotide adapters were ligated to double stranded cDNA, and the cDNA was digested with the appropriate restriction enzyme or enzymes. For most libraries, the cDNA was size-selected (300-1000 bp) using SEPHACRYL S1000, SEPHAROSE CL2B, or SEPHAROSE CL4B column chromatography (Amersham Pharmacia Biotech) or preparative agarose gel electrophoresis. cDNAs were ligated into compatible restriction enzyme sites of the polylinker of a suitable plasmid, e.g., PBLUESCRIPT plasmid (Stratagene), PSPORT1 plasmid (Life Technologies), PCDNA2.1 plasmid (Invitrogen, Carlsbad Calif.), PBK-CMV plasmid (Stratagene), PCR2-TOPOTA plasmid (Invitrogen), PCMV-ICIS plasmid (Stratagene), pIGEN (Incyte Genomics, Palo Alto Calif.), or pINCY (Incyte Genomics), or derivatives thereof. Recombinant plasmids were transformed into competent *E. coli* cells including XLL-Blue, XL1-BlueMRF, or SOLR from Stratagene or DH5α, DH10B, or ElectroMAX DH10B from Life Technologies.

II. Isolation of cDNA Clones

Plasmids obtained as described in Example I were recovered from host cells by in vivo excision using the UNIZAP vector system (Stratagene) or by cell lysis. Plasmids were purified using at least one of the following: a Magic or WIZARD Minipreps DNA purification system (Promega); an AGTC Miniprep purification kit (Edge Biosystems, Gaithersburg Md.); and QIAWELL 8 Plasmid, QIAWELL 8 Plus Plasmid, QIAWELL 8 Ultra Plasmid purification systems or the R.E.A.L. PREP 96 plasmid purification kit from QIAGEN. Following precipitation, plasmids were resuspended in 0.1 ml of distilled water and stored, with or without lyophilization, at 4° C.

Alternatively, plasmid DNA was amplified from host cell lysates using direct link PCR in a high-throughput format (Rao, V. B. (1994) Anal. Biochem. 216:1-14). Host cell lysis and thermal cycling steps were carried out in a single reaction mixture. Samples were processed and stored in 384-well plates, and the concentration of amplified plasmid DNA was quantified fluorometrically using PICOGREEN dye (Molecular Probes, Eugene Oreg.) and a FLUOROSKAN II fluorescence scanner (Labsystems Oy, Helsinki, Finland).

III. Sequencing and Analysis

Incyte cDNA recovered in plasmids as described in Example II were sequenced as follows. Sequencing reactions were processed using standard methods or high-throughput instrumentation such as the ABI CATALYST 800 (Applied Biosystems) thermal cycler or the PTC-200 thermal cycler (MJ Research) in conjunction with the HYDRA microdispenser (Robbins Scientific) or the MICROLAB 2200 (Hamilton) liquid transfer system. cDNA sequencing reactions were prepared using reagents provided by Amersham Pharmacia Biotech or supplied in ABI sequencing kits such as the ABI PRISM BIGDYE Terminator cycle sequencing ready reaction kit (Applied Biosystems). Electrophoretic separation of cDNA sequencing reactions and detection of labeled polynucleotides were carried out using the MEGABACE 1000 DNA sequencing system (Molecular Dynamics); the ABI PRISM 373 or 377 sequencing system (Applied Biosystems) in conjunction with standard ABI protocols and base calling software; or other sequence analysis systems known in the art. Reading frames within the cDNA sequences were identified using standard methods (reviewed in Ausubel, 1997, sugpa, unit 7.7). Some of the cDNA sequences were selected for extension using the techniques disclosed in Example VIII.

The polynucleotide sequences derived from Incyte cDNAs were validated by removing vector, linker, and poly(A) sequences and by masking ambiguous bases, using algorithms and programs based on BLAST, dynamic programming, and dinucleotide nearest neighbor analysis. The Incyte cDNA sequences or translations thereof were then queried against a selection of public databases such as the GenBank primate, rodent, mammalian, vertebrate, and eukaryote databases, and BLOCKS, PRINTS, DOMO, PRODOM; PROTEOME databases with sequences from *Homo sapiens, Rattus norvegicus, Mus musculus, Caenorhabditis elegans, Saccharomyces cerevisiae, Schizosaccharomvces pombe,* and *Candida albicans* (Incyte Genomics, Palo Alto Calif.); and hidden Markov model (HMM)-based protein family databases such as PFAM. (HMM is a probabilistic approach which analyzes consensus primary structures of gene families. See, for example, Eddy, S. R. (1996) Curr. Opin. Struct. Biol. 6:361-365.) The queries were performed using programs based on BLAST, FASTA, BLIMPS, and HMMER. The Incyte cDNA sequences were assembled to produce full length polynucleotide sequences. Alternatively, GenBank cDNAs, GenBank ESTs, stitched sequences, stretched sequences, or Genscan-predicted coding sequences (see Examples IV and V) were used to extend Incyte cDNA assemblages to full length. Assembly was performed using programs based on Phred, Phrap, and Consed, and cDNA assemblages were screened for open reading frames using programs based on GeneMark, BLAST, and FASTA. The full length polynucleotide sequences were translated to derive the corresponding full length polypeptide sequences. Alternatively, a polypeptide of the invention may begin at any of the methionine residues of the full length translated polypeptide. Full length polypeptide sequences were subsequently analyzed by querying against databases such as the GenBank protein databases (genpept), SwissProt, the PROTEOME databases, BLOCKS, PRINTS, DOMO, PRODOM, Prosite, and hidden Markov model (HMM)-based protein family databases such as PFAM. Full length polynucleotide sequences are also analyzed using MACDNASIS PRO software (Hitachi Software Engineering, South San Francisco Calif.) and LASERGENE software (DNASTAR). Polynucleotide and polypeptide sequence alignments are generated using default parameters specified by the CLUSTAL algorithm as incorporated into the MEGALIGN multisequence alignment program (DNASTAR), which also calculates the percent identity between aligned sequences.

Table 7 summarizes the tools, programs, and algorithms used for the analysis and assembly of Incyte cDNA and full length sequences and provides applicable descriptions, references, and threshold parameters. The first column of Table 7 shows the tools, programs, and algorithms used, the second column provides brief descriptions thereof, the third column presents appropriate references, all of which are incorporated by reference herein in their entirety, and the fourth column presents, where applicable, the scores, probability values, and other parameters used to evaluate the strength of a match between two sequences (the higher the score or the lower the probability value, the greater the identity between two sequences).

The programs described above for the assembly and analysis of full length polynucleotide and polypeptide sequences were also used to identify polynucleotide sequence fragments from SEQ ID NO:64-126. Fragments from about 20 to about 4000 nucleotides which are useful in hybridization and amplification technologies are described in Table 4, column 4.

IV. Identification and Editing of Coding Sequences from Genomic DNA

Putative secreted proteins were initially identified by running the Genscan gene identification program against public genomic sequence databases (e.g., gbpri and gbhtg). Genscan is a general-purpose gene identification program which analyzes genomic DNA sequences from a variety of organisms (See Burge, C. and S. Karlin (1997) J. Mol. Biol. 268:78-94, and Burge, C. and S. Karlin (1998) Curr. Opin. Struct. Biol. 8:346-354). The program concatenates predicted exons to form an assembled cDNA sequence extending from a methionine to a stop codon. The output of Genscan is a FASTA database of polynucleotide and polypeptide sequences. The maximum range of sequence for Genscan to analyze at once was set to 30 kb. To determine which of these Genscan predicted cDNA sequences encode secreted proteins, the encoded polypeptides were analyzed by querying against PFAM models for secreted proteins. Potential secreted proteins were also identified by homology to Incyte cDNA sequences that had been annotated as secreted proteins. These selected Genscan-predicted sequences were then compared by BLAST analysis to the genpept and gbpri public databases. Where necessary, the Genscan-predicted sequences were then edited by comparison to the top BLAST hit from genpept to correct errors in the sequence predicted by Genscan, such as extra or omitted exons. BLAST analysis was also used to find any Incyte cDNA or public cDNA coverage of the Genscan-predicted sequences, thus providing evidence for transcription. When Incyte cDNA coverage was available, this information was used to correct or confirm the Genscan predicted sequence.

Full length polynucleotide sequences were obtained by assembling Genscan-predicted coding sequences with Incyte cDNA sequences and/or public cDNA sequences using the assembly process described in Example m. Alternatively, full length polynucleotide sequences were derived entirely from edited or unedited Genscan-predicted coding sequences.

V. Assembly of Genomic Sequence Data with cDNA Sequence Data

"Stitched" Sequences

Partial cDNA sequences were extended with exons predicted by the Genscan gene identification program described in Example IV. Partial cDNAs assembled as described in Example III were mapped to genomic DNA and parsed into clusters containing related cDNAs and Genscan exon predictions from one or more genomic sequences. Each cluster was analyzed using an algorithm based on graph theory and dynamic programming to integrate cDNA and genomic information, generating possible splice variants that were subsequently confirmed, edited, or extended to create a full length sequence. Sequence intervals in which the entire length of the interval was present on more than one sequence in the cluster were identified, and intervals thus identified were considered to be equivalent by transitivity. For example, if an interval was present on a cDNA and two genomic sequences, then all three intervals were considered to be equivalent. This process allows unrelated but consecutive genomic sequences to be brought together, bridged by cDNA sequence. Intervals thus identified were then "stitched" together by the stitching algorithm in the order that they appear along their parent sequences to generate the longest possible sequence, as well as sequence variants. Linkages between intervals which proceed along one type of parent sequence (cDNA to cDNA or genomic sequence to genomic sequence) were given preference over linkages which change parent type (cDNA to genomic sequence). The resultant stitched sequences were translated and compared by BLAST analysis to the genpept and gbpri public databases. Incorrect exons predicted by Genscan were corrected by comparison to the top BLAST hit from genpept. Sequences were further extended with additional cDNA sequences, or by inspection of genomic DNA, when necessary.

"Stretched" Sequences

Partial DNA sequences were extended to full length with an algorithm based on BLAST analysis. First, partial cDNAs assembled as described in Example [ ] were queried against public databases such as the GenBank primate, rodent, mammalian, vertebrate, and eukaryote databases using the BLAST program. The nearest GenBank protein homolog was then compared by BLAST analysis to either Incyte cDNA sequences or GenScan exon predicted sequences described in Example IV. A chimeric protein was generated by using the resultant high-scoring segment pairs (HSPs) to map the translated sequences onto the GenBank protein homolog. Insertions or deletions may occur in the chimeric protein with respect to the original GenBank protein homolog. The GenBank protein homolog, the chimeric protein, or both were used as probes to search for homologous genomic sequences from the public human genome databases. Partial DNA sequences were therefore "stretched" or extended by the addition of homologous genomic sequences. The resultant stretched sequences were examined to determine whether it contained a complete gene.

VI. Chromosomal Mapping of SECP Encoding Polynucleotides

The sequences which were used to assemble SEQ ID NO:64-126 were compared with sequences from the Incyte LIFESEQ database and public domain databases using BLAST and other implementations of the Smith-Waterman algorithm. Sequences from these databases that matched SEQ ID NO:64-126 were assembled into clusters of contiguous and overlapping sequences using assembly algorithms such as Phrap (Table 7). Radiation hybrid and genetic mapping data available from public resources such as the Stanford Human Genome Center (SHGC), Whitehead Institute for Genome Research (WIGR), and Généthon were used to determine if any of the clustered sequences had been previously mapped. Inclusion of a mapped sequence in a cluster resulted in the assignment of all sequences of that cluster, including its particular SEQ ID NO:, to that map location.

Map locations are represented by ranges, or intervals, of human chromosomes. The map position of an interval, in centiMorgans, is measured relative to the terminus of the chromosome's p-arm. (The centiMorgan (cM) is a unit of measurement based on recombination frequencies between chromosomal markers. On average, 1 cM is roughly equivalent to 1 megabase (Mb) of DNA in humans, although this can vary widely due to hot and cold spots of recombination.) The cM distances are based on genetic markers mapped by Généthon which provide boundaries for radiation hybrid markers whose sequences were included in each of the clusters. Human genome maps and other resources available to the public, such as the NCBI "GeneMap'99" World Wide Web site (http://www.ncbi.nlm.nih.gov/genemap/), can be employed to determine if previously identified disease genes map within or in proximity to the intervals indicated above.

VII. Analysis of Polynucleotide Expression

Northern analysis is a laboratory technique used to detect the presence of a transcript of a gene and involves the hybridization of a labeled nucleotide sequence to a membrane on which RNAs from a particular cell type or tissue have been bound. (See, e.g., Sambrook, sugra, ch. 7; Ausubel (1995) supra, ch. 4 and 16.)

Analogous computer techniques applying BLAST were used to search for identical or related molecules in cDNA databases such as GenBank or LIFESEQ (Incyte Genomics). This analysis is much faster than multiple membrane-based hybridizations. In addition, the sensitivity of the computer search can be modified to determine whether any particular match is categorized as exact or similar. The basis of the search is the product score, which is defined as:

$$\frac{\text{BLAST Score} \times \text{Percent Identity}}{5 \times \text{minimum}\{\text{length}(Seq. 1), \text{length}(Seq. 2)\}}$$

The product score takes into account both the degree of similarity between two sequences and the length of the sequence match. The product score is a normalized value between 0 and 100, and is calculated as follows: the BLAST score is multiplied by the percent nucleotide identity and the product is divided by (5 times the length of the shorter of the two sequences). The BLAST score is calculated by assigning a score of +5 for every base that matches in a high-scoring segment pair (HSP), and −4 for every mismatch. Two sequences may share more than one HSP (separated by gaps). If there is more than one HSP, then the pair with the highest BLAST score is used to calculate the product score.

The product score represents a balance between fractional overlap and quality in a BLAST alignment. For example, a product score of 100 is produced only for 100% identity over the entire length of the shorter of the two sequences being compared. A product score of 70 is produced either by 100% identity and 70% overlap at one end, or by 88% identity and 100% overlap at the other. A product score of 50 is produced either by 100% identity and 50% overlap at one end, or 79% identity and 100% overlap.

Alternatively, polynucleotide sequences encoding SECP are analyzed with respect to the tissue sources from which they were derived. For example, some full length sequences are assembled, at least in part, with overlapping Incyte cDNA sequences (see Example III). Each cDNA sequence is derived from a cDNA library constructed from a human tissue. Each human tissue is classified into one of the following organ/tissue categories: cardiovascular system; connective tissue; digestive system; embryonic structures; endocrine system; exocrine glands; genitalia, female; genitalia, male; germ cells; hemic and immune system; liver; musculoskeletal system; nervous system; pancreas; respiratory system; sense organs; skin; stomatognathic system; unclassified/mixed; or urinary tract. The number of libraries in each category is counted and divided by the total number of libraries across all categories. Similarly, each human tissue is classified into one of the following disease/condition categories: cancer, cell line, developmental, inflammation, neurological, trauma, cardiovascular, pooled, and other, and the number of libraries in each category is counted and divided by the total number of libraries across all categories. The resulting percentages reflect the tissue- and disease-specific expression of cDNA encoding SECP. cDNA sequences and cDNA library/tissue information are found in the LIFESEQ GOLD database (Incyte Genomics, Palo Alto Calif.).

VIII. Extension of SECP Encoding Polynucleotides

Full length polynucleotide sequences were also produced by extension of an appropriate fragment of the full length molecule using oligonucleotide primers designed from this fragment. One primer was synthesized to initiate 5' extension of the known fragment, and the other primer was synthesized to initiate 3' extension of the known fragment. The initial primers were designed using OLIGO 4.06 software (National Biosciences), or another appropriate program, to be about 22 to 30 nucleotides in length, to have a GC content of about 50% or more, and to anneal to the target sequence at temperatures of about 68° C. to about 72° C. Any stretch of nucleotides which would result in hairpin structures and primer-primer dimerizations was avoided.

Selected human cDNA libraries were used to extend the sequence. If more than one extension was necessary or desired, additional or nested sets of primers were designed.

High fidelity amplification was obtained by PCR using methods well known in the art. PCR was performed in 96-well plates using the PTC-200 thermal cycler (MJ Research, Inc.). The reaction mix contained DNA template, 200 nmol of each primer, reaction buffer containing $Mg^{2+}$, $(NH_4)_2SO_4$, and 2-mercaptoethanol, Taq DNA polymerase (Amersham Pharmacia Biotech), ELONGASE enzyme (Life Technologies), and Pfu DNA polymerase (Stratagene), with the following parameters for primer pair PCI A and PCI B: Step 1: 94° C., 3 min; Step 2: 94° C., 15 sec; Step 3: 60° C., 1 min; Step 4: 68° C., 2 min; Step 5: Steps 2, 3, and 4 repeated 20 times; Step 6: 68° C., 5 min; Step 7: storage at 4° C. In the alternative, the parameters for primer pair T7 and SK+ were as follows: Step 1: 94° C., 3 min; Step 2: 94°

C., 15 sec; Step 3: 57° C., 1 min; Step 4: 68° C., 2 min; Step 5: Steps 2, 3, and 4 repeated 20 times; Step 6: 68° C., 5 min; Step 7: storage at 4° C.

The concentration of DNA in each well was determined by dispensing 100 µl PICOGREEN quantitation reagent (0.25% (v/v) PICOGREEN; Molecular Probes, Eugene Oreg.) dissolved in IX TE and 0.5 µl of undiluted PCR product into each well of an opaque fluorimeter plate (Corning Costar, Acton Mass.), allowing the DNA to bind to the reagent. The plate was scanned in a Fluoroskan II (Labsystems Oy, Helsinki, Finland) to measure the fluorescence of the sample and to quantify the concentration of DNA. A 5 µl to 10 µl aliquot of the reaction mixture was analyzed by electrophoresis on a 1% agarose gel to determine which reactions were successful in extending the sequence.

The extended nucleotides were desalted and concentrated, transferred to 384-well plates, digested with CviJI cholera virus endonuclease (Molecular Biology Research, Madison Wis.), and sonicated or sheared prior to religation into pUC 18 vector (Amersham Pharmacia Biotech). For shotgun sequencing, the digested nucleotides were separated on low concentration (0.6 to 0.8%) agarose gels, fragments were excised, and agar digested with Agar ACE (Promega). Extended clones were religated using T4 ligase (New England Biolabs, Beverly Mass.) into pUC 18 vector (Amersham Pharmacia Biotech), treated with Pfu DNA polymerase (Stratagene) to fill-in restriction site overhangs, and transfected into competent *E. coli* cells. Transformed cells were selected on antibiotic-containing media, and individual colonies were picked and cultured overnight at 37° C. in 384-well plates in LB/2x carb liquid media.

The cells were lysed, and DNA was amplified by PCR using Taq DNA polymerase (Amersham Pharmacia Biotech) and Pfu DNA polymerase (Stratagene) with the following parameters: Step 1: 94° C., 3 min; Step 2: 94° C., 15 sec; Step 3: 60° C., 1 min; Step 4: 72° C., 2 min; Step 5: steps 2, 3, and 4 repeated 29 times; Step 6: 72° C., 5 min; Step 7: storage at 4° C. DNA was quantified by PICOGREEN reagent (Molecular Probes) as described above. Samples with low DNA recoveries were reamplified using the same conditions as described above. Samples were diluted with 20% dimethysulfoxide (1:2, v/v), and sequenced using DYENAMIC energy transfer sequencing primers and the DYENAMIC DIRECT kit (Amersham Pharmacia Biotech) or the ABI PRISM BIGDYE Terminator cycle sequencing ready reaction kit (Applied Biosystems).

In like manner, full length polynucleotide sequences are verified using the above procedure or are used to obtain 5' regulatory sequences using the above procedure along with oligonucleotides designed for such extension, and an appropriate genomic library.

IX. Labeling and Use of Individual Hybridization Probes

Hybridization probes derived from SEQ ID NO:64-126 are employed to screen cDNAs, genomic DNAs, or mRNAs. Although the labeling of oligonucleotides, consisting of about 20 base pairs, is specifically described, essentially the same procedure is used with larger nucleotide fragments. Oligonucleotides are designed using state-of-the-art software such as OLIGO 4.06 software (National Biosciences) and labeled by combining 50 pmol of each oligomer, 250 µCi of [γ-$^{32}$P] adenosine triphosphate (Amersham Pharmacia Biotech), and T4 polynucleotide kinase (DuPont NEN, Boston Mass.). The labeled oligonucleotides are substantially purified using a SEPHADEX G-25 superfine size exclusion dextran bead column (Amersham Pharmacia Biotech). An aliquot containing $10^7$ counts per minute of the labeled probe is used in a typical membrane-based hybridization analysis of human genomic DNA digested with one of the following endonucleases: Ase I, Bgl II, Eco RI, Pst I, Xba I, or Pvu II (DuPont NEN).

The DNA from each digest is fractionated on a 0.7% agarose gel and transferred to nylon membranes (Nytran Plus. Schleicher & Schuell, Durham N. H.). Hybridization is carried out for 16 hours at 40° C. To remove nonspecific signals, blots are sequentially washed at room temperature under conditions of up to, for example, 0.1x saline sodium citrate and 0.5% sodium dodecyl sulfate. Hybridization patterns are visualized using autoradiography or an alternative imaging means and compared.

X. Microarrays

The linkage or synthesis of array elements upon a microarray can be achieved utilizing photolithography, piezoelectric printing (ink-jet printing, See, e.g., Baldeschweiler, sura.), mechanical microspotting technologies, and derivatives thereof. The substrate in each of the aforementioned technologies should be uniform and solid with a non-porous surface (Schena (1999), supra). Suggested substrates include silicon, silica, glass slides, glass chips, and silicon wafers. Alternatively, a procedure analogous to a dot or slot blot may also be used to arrange and link elements to the surface of a substrate using thermal, UV, chemical, or mechanical bonding procedures. A typical array may be produced using available methods and machines well known to those of ordinary skill in the art and may contain any appropriate number of elements. (See, e.g., Schena, M. et al. (1995) Science 270:467-470; Shalon, D. et al. (1996) Genome Res. 6:639-645; Marshall, A. and J. Hodgson (1998) Nat. Biotechnol. 16:27-31.)

Full length cDNAs, Expressed Sequence Tags (ESTs), or fragments or oligomers thereof may comprise the elements of the microarray. Fragments or oligomers suitable for hybridization can be selected using software well known in the art such as LASERGENE software (DNASTAR). The array elements are hybridized with polynucleotides in a biological sample. The polynucleotides in the biological sample are conjugated to a fluorescent label or other molecular tag for ease of detection. After hybridization, nonhybridized nucleotides from the biological sample are removed, and a fluorescence scanner is used to detect hybridization at each array element. Alternatively, laser desorbtion and mass spectrometry may be used for detection of hybridization. The degree of complementarity and the relative abundance of each polynucleotide which hybridizes to an element on the microarray may be assessed. In one embodiment, microarray preparation and usage is described in detail below.

Tissue or Cell Sample Preparation

Total RNA is isolated from tissue samples using the guanidinium thiocyanate method and poly(A)$^+$ RNA is purified using the oligo-(dT) cellulose method. Each poly (A)$^+$ RNA sample is reverse transcribed using MMLV reverse-transcriptase, 0.05 pg/µl oligo-(dT) primer (21mer), IX first strand buffer, 0.03 units/µl RNase inhibitor, 500 µM dATP, 500 µM dGTP, 500 µM dTTP, 40 µM dCTP, 40 µM dCTP-Cy3 (BDS) or dCTP-Cy5 (Amersham Pharmacia Biotech). The reverse transcription reaction is performed in a 25 ml volume containing 200 ng poly(A)$^+$ RNA with GEMBRIGHT kits (Incyte). Specific control poly(A)$^+$ RNAs are synthesized by in vitro transcription from non-coding yeast genomic DNA. After incubation at 37° C. for 2 hr, each reaction sample (one with Cy3 and another with Cy5 labeling) is treated with 2.5 ml of 0.5M sodium hydroxide and incubated for 20 minutes at 85° C. to the stop the reaction and degrade the RNA. Samples are purified using two successive CHROMA SPIN 30 gel filtration spin columns (CLONTECH Laboratories, Inc. (CLONTECH), Palo Alto Calif.) and after combining, both reaction samples are ethanol precipitated using 1 ml of glycogen (1 mg/ml), 60 ml sodium acetate, and 300 ml of 100% ethanol. The sample is then dried to completion using a SpeedVAC (Savant Instruments Inc., Holbrook N.Y.) and resuspended in 14 µl 5×SSC/0.2% SDS.

Microarray Preparation

Sequences of the present invention are used to generate array elements. Each array element is amplified from bacterial cells containing vectors with cloned cDNA inserts. PCR amplification uses primers complementary to the vector sequences flanking the cDNA insert. Array elements are amplified in thirty cycles of PCR from an initial quantity of 1-2 ng to a final quantity greater than 5 µg. Amplified array elements are then purified using SEPHACRYL-400 (Amersham Pharmacia Biotech).

Purified array elements are immobilized on polymer-coated glass slides. Glass microscope slides (Corning) are cleaned by ultrasound in 0.1% SDS and acetone, with extensive distilled water washes between and after treatments. Glass slides are etched in 4% hydrofluoric acid (VWR Scientific Products Corporation (VWR), West Chester Pa.), washed extensively in distilled water, and coated with 0.05% aminopropyl silane (Sigma) in 95% ethanol. Coated slides are cured in a 110° C. oven.

Array elements are applied to the coated glass substrate using a procedure described in U.S. Pat. No. 5,807,522, incorporated herein by reference. 1 µl of the array element DNA, at an average concentration of 100 ng/µl, is loaded into the open capillary printing element by a high-speed robotic apparatus. The apparatus then deposits about 5 nl of array element sample per slide.

Microarrays are UV-crosslinked using a STRATA-LINKER UV-crosslinker (Stratagene). Microarrays are washed at room temperature once in 0.2% SDS and three times in distilled water. Non-specific binding sites are blocked by incubation of microarrays in 0.2% casein in phosphate buffered saline (PBS) (Tropix, Inc., Bedford Mass.) for 30 minutes at 60° C. followed by washes in 0.2% SDS and distilled water as before.

Hybridization

Hybridization reactions contain 9 µl of sample mixture consisting of 0.2 g each of Cy3 and Cy5 labeled cDNA synthesis products in 5×SSC, 0.2% SDS hybridization buffer. The sample mixture is heated to 65° C. for 5 minutes and is aliquoted onto the microarray surface and covered with an 1.8 cm$^2$ coverslip. The arrays are transferred to a waterproof chamber having a cavity just slightly larger than a microscope slide. The chamber is kept at 100% humidity internally by the addition of 140 µl of 5×SSC in a corner of the chamber. The chamber containing the arrays is incubated for about 6.5 hours at 60° C. The arrays are washed for 10 min at 45° C. in a first wash buffer (1X SSC, 0.1% SDS), three times for 10 minutes each at 45° C. in a second wash buffer (0.1×SSC), and dried.

Detection

Reporter-labeled hybridization complexes are detected with a microscope equipped with an Innova 70 mixed gas 10 W laser (Coherent, Inc., Santa Clara Calif.) capable of generating spectral lines at 488 nm for excitation of Cy3 and at 632 nm for excitation of Cy5. The excitation laser light is focused on the array using a 20× microscope objective (Nikon, Inc., Melville N.Y.). The slide containing the array is placed on a computer-controlled X-Y stage on the microscope and raster-scanned past the objective. The 1.8 cm×1.8 cm array used in the present example is scanned with a resolution of 20 micrometers.

In two separate scans, a mixed gas multiline laser excites the two fluorophores sequentially. Emitted light is split, based on wavelength, into two photomultiplier tube detectors (PMT R1477, Hamamatsu Photonics Systems, Bridgewater N.J.) corresponding to the two fluorophores. Appropriate filters positioned between the array and the photomultiplier tubes are used to filter the signals. The emission maxima of the fluorophores used are 565 nm for Cy3 and 650 nm for Cy5. Each array is typically scanned twice, one scan per fluorophore using the appropriate filters at the laser source, although the apparatus is capable of recording the spectra from both fluorophores simultaneously.

The sensitivity of the scans is typically calibrated using the signal intensity generated by a cDNA control species added to the sample mixture at a known concentration. A specific location on the array contains a complementary DNA sequence, allowing the intensity of the signal at that location to be correlated with a weight ratio of hybridizing species of 1:100,000. When two samples from different sources (e.g., representing test and control cells), each labeled with a different fluorophore, are hybridized to a single array for the purpose of identifying genes that are differentially expressed, the calibration is done by labeling samples of the calibrating cDNA with the two fluorophores and adding identical amounts of each to the hybridization mixture.

The output of the photomultiplier tube is digitized using a 12-bit RTI-835H analog-to-digital (A/D) conversion board (Analog Devices, Inc., Norwood Mass.) installed in an IBM-compatible PC computer. The digitized data are displayed as an image where the signal intensity is mapped using a linear 20-color transformation to a pseudocolor scale ranging from blue (low signal) to red (high signal). The data is also analyzed quantitatively. Where two different fluorophores are excited and measured simultaneously, the data are first corrected for optical crosstalk (due to overlapping emission spectra) between the fluorophores using each fluorophore's emission spectrum.

A grid is superimposed over the fluorescence signal image such that the signal from each spot is centered in each element of the grid. The fluorescence signal within each element is then integrated to obtain a numerical value corresponding to the average intensity of the signal. The software used for signal analysis is the GEMTOOLS gene expression analysis program (Incyte).

XI. Complementary Polynucleotides

Sequences complementary to the SECP-encoding sequences, or any parts thereof, are used to detect, decrease, or inhibit expression of naturally occurring SECP. Although use of oligonucleotides comprising from about 15 to 30 base pairs is described, essentially the same procedure is used with smaller or with larger sequence fragments. Appropriate oligonucleotides are designed using OLIGO 4.06 software (National Biosciences) and the coding sequence of SECP. To inhibit transcription, a complementary oligonucleotide is designed from the most unique 5' sequence and used to prevent promoter binding to the coding sequence. To inhibit translation, a complementary oligonucleotide is designed to prevent ribosomal binding to the SECP-encoding transcript.

XII. Expression of SECP

Expression and purification of SECP is achieved using bacterial or virus-based expression systems. For expression of SECP in bacteria, cDNA is subcloned into an appropriate vector containing an antibiotic resistance gene and an inducible promoter that directs high levels of cDNA transcription. Examples of such promoters include, but are not limited to, the trp-lac (tac) hybrid promoter and the T5 or T7 bacteriophage promoter in conjunction with the lac operator regulatory element. Recombinant vectors are transformed into suitable bacterial hosts, e.g., BL21(DE3). Antibiotic resistant bacteria express SECP upon induction with isopropyl beta-D-thiogalactopyranoside (IPTG). Expression of SECP in eukaryotic cells is achieved by infecting insect or mammalian cell lines with recombinant *Autographica californica* nuclear polyhedrosis virus (AcMNPV), commonly known as baculovirus. The nonessential polyhedrin gene of baculovirus is replaced with cDNA encoding SECP by either homologous recombination or bacterial-mediated transposition involving transfer plasmid intermediates. Viral infectivity is maintained and the strong polyhedrin promoter drives high levels of cDNA transcription. Recombinant baculovirus is used to infect *Spodoptera frugiperda* (Sf9) insect cells in most cases, or human hepatocytes, in some cases. Infection of the latter requires additional genetic modifications to baculovirus. (See Engelhard, E. K. et al. (1994) Proc. Natl. Acad. Sci. USA 91:3224-3227; Sandig, V. et al. (1996) Hum. Gene Ther. 7:1937-1945.)

In most expression systems, SECP is synthesized as a fusion protein with, e.g., glutathione S-transferase (GST) or a peptide epitope tag, such as FLAG or 6-His, permitting rapid, single-step, affinity-based purification of recombinant fusion protein from crude cell lysates. GST, a 26-kilodalton enzyme from *Schistosoma japonicum*, enables the purification of fusion proteins on immobilized glutathione under conditions that maintain protein activity and antigenicity (Amersham Pharmacia Biotech). Following purification, the GST moiety can be proteolytically cleaved from SECP at specifically engineered sites. FLAG, an 8-amino acid peptide, enables immunoaffinity purification using commercially available monoclonal and polyclonal anti-FLAG antibodies (Eastman Kodak). 6-His, a stretch of six consecutive histidine residues, enables purification on metal-chelate resins (QIAGEN). Methods for protein expression and purification are discussed in Ausubel (1995, supra, ch. 10 and 16). Purified SECP obtained by these methods can be used directly in the assays shown in Examples XVI, XVII, and XVIII where applicable.

XIII. Functional Assays

SECP function is assessed by expressing the sequences encoding SECP at physiologically elevated levels in mammalian cell culture systems. cDNA is subcloned into a mammalian expression vector containing a strong promoter that drives high levels of cDNA expression. Vectors of choice include PCMV SPORT (Life Technologies) and PCR3.1 (Invitrogen, Carlsbad Calif.), both of which contain the cytomegalovirus promoter. 5-10 g of recombinant vector are transiently transfected into a human cell line, for example, an endothelial or hematopoietic cell line, using either liposome formulations or electroporation. 1-2 g of an additional plasmid containing sequences encoding a marker protein are co-transfected. Expression of a marker protein provides a means to distinguish transfected cells from non-transfected cells and is a reliable predictor of cDNA expression from the recombinant vector. Marker proteins of choice include, e.g., Green Fluorescent Protein (GFP; Clontech), CD64, or a CD64-GFP fusion protein. Flow cytometry (FCM), an automated, laser optics-based technique, is used to identify transfected cells expressing GFP or CD64-GFP and to evaluate the apoptotic state of the cells and other cellular properties. FCM detects and quantifies the uptake of fluorescent molecules that diagnose events preceding or coincident with cell death. These events include changes in nuclear DNA content as measured by staining of DNA with propidium iodide; changes in cell size and granularity as measured by forward light scatter and 90 degree side light scatter; down-regulation of DNA synthesis as measured by decrease in bromodeoxyuridine uptake; alterations in expression of cell surface and intracellular proteins as measured by reactivity with specific antibodies; and alterations in plasma membrane composition as measured by the binding of fluorescein-conjugated Annexin V protein to the cell surface. Methods in flow cytometry are discussed in Ormerod, M. G. (1994) *Flow Cytometry*, Oxford, New York N.Y.

The influence of SECP on gene expression can be assessed using highly purified populations of cells transfected with sequences encoding SECP and either CD64 or CD64-GFP. CD64 and CD64-GFP are expressed on the surface of transfected cells and bind to conserved regions of human immunoglobulin G (IgG). Transfected cells are efficiently separated from nontransfected cells using magnetic beads coated with either human IgG or antibody against CD64 (DYNAL, Lake Success N.Y.). mRNA can be purified from the cells using methods well known by those of skill in the art. Expression of mRNA encoding SECP and other genes of interest can be analyzed by northern analysis or microarray techniques.

XIV. Production of SECP Specific Antibodies

SECP substantially purified using polyacrylamide gel electrophoresis (PAGE; see, e.g., Harrington, M. G. (1990) Methods Enzymol. 182:488-495), or other purification techniques, is used to immunize rabbits and to produce antibodies using standard protocols.

Alternatively, the SECP amino acid sequence is analyzed using LASERGENE software (DNASTAR) to determine regions of high immunogenicity, and a corresponding oligopeptide is synthesized and used to raise antibodies by means known to those of skill in the art. Methods for selection of appropriate epitopes, such as those near the C-terminus or in hydrophilic regions are well described in the art. (See, e.g., Ausubel, 1995, supra, ch. 11.)

Typically, oligopeptides of about 15 residues in length are synthesized using an ABI 431A peptide synthesizer (Applied Biosystems) using FMOC chemistry and coupled to KLH (Sigma-Aldrich, St. Louis Mo.) by reaction with N-maleimidobenzoyl-N-hydroxysuccinimide ester (MBS) to increase immunogenicity. (See, e.g., Ausubel, 1995, supra.) Rabbits are immunized with the oligopeptide-KLH complex in complete Freund's adjuvant. Resulting antisera are tested for antipeptide and anti-SECP activity by, for example, binding the peptide or SECP to a substrate, blocking with 1% BSA, reacting with rabbit antisera, washing, and reacting with radio-iodinated goat anti-rabbit IgG.

XV. Purification of Naturally Occurring SECP Using Specific Antibodies

Naturally occurring or recombinant SECP is substantially purified by immunoaffinity chromatography using antibodies specific for SECP. An immunoaffinity column is constructed by covalently coupling anti-SECP antibody to an activated chromatographic resin, such as CNBr-activated SEPHAROSE (Amershant Pharmacia Biotech). After the coupling, the resin is blocked and washed according to the manufacturer's instructions.

Media containing SECP are passed over the immunoaffinity column, and the column is washed under conditions that allow the preferential absorbance of SECP (e.g., high ionic strength buffers in the presence of detergent). The column is eluted under conditions that disrupt antibody/SECP binding (e.g., a buffer of pH 2 to pH 3, or a high concentration of a chaotrope, such as urea or thiocyanate ion), and SECP is collected.

XVI. Identification of Molecules which Interact with SECP

SECP, or biologically active fragments thereof, are labeled with $^{125}$I Bolton-Hunter reagent. (See, e.g., Bolton, A. E. and W. M. Hunter (1973) Biochem. J. 133:529-539.) Candidate molecules previously arrayed in the wells of a multi-well plate are incubated with the labeled SECP, washed, and any wells with labeled SECP complex are assayed. Data obtained using different concentrations of SECP are used to calculate values for the number, affinity, and association of SECP with the candidate molecules.

Alternatively, molecules interacting with SECP are analyzed using the yeast two-hybrid system as described in Fields, S. and O. Song (1989) Nature 340:245-246, or using commercially available kits based on the two-hybrid system, such as the MATCHMAKER system (Clontech).

SECP may also be used in the PATHCALLING process (CuraGen Corp., New Haven Conn.) which employs the yeast two-hybrid system in a high-throughput manner to determine all interactions between the proteins encoded by two large libraries of genes (Nandabalan, K. et al. (2000) U.S. Pat. No. 6,057,101).

XVII. Demonstration of SECP Activity

Peroxidase activity of SECP is measured using a spectrophotometric assay (see, for example, Jeong, M. et al. (2000) J. Biol. Chem. 275:2924-2930), or using an assay kit such as, for example, the AMPLEX Red Peroxidase Assay Kit from Molecular Probes together with a fluorescence microplate reader or fluorometer.

An assay for growth stimulating or inhibiting activity of SECP measures the amount of DNA synthesis in Swiss mouse 3T3 cells (McKay, I. and Leigh, I., eds. (1993) *Growth Factors: A Practical Approach*, Oxford University Press, New York, N.Y.). In this assay, varying amounts of SECP are added to quiescent 3T3 cultured cells in the presence of [$^3$H]thymidine, a radioactive DNA precursor. SECP for this assay can be obtained by recombinant means or from biochemical preparations. Incorporation of [$^3$H]thymidine into acid-precipitable DNA is measured over an appropriate time interval, and the amount incorporated is directly proportional to the amount of newly synthesized DNA. A linear dose-response curve over at least a hundred-fold SECP concentration range is indicative of growth modulating activity. One unit of activity per milliliter is defined as the concentration of SECP producing a 50% response level, where 100% represents maximal incorporation of [$^3$H]thymidine into acid-precipitable DNA.

Alternatively, TGF-β activity is measured by induction of non-neoplastic normal rat kidney fibroblasts to undergo anchorage-independent growth in the presence of epidermal growth factor (2.5 ng/ml) as described by Assoian, R. K. et al. (1983) J. Biol. Chem. 258:7155-7160.

Alternatively, an assay for SECP activity measures the stimulation or inhibition of neurotransmission in cultured cells. Cultured CHO fibroblasts are exposed to SECP. Following endocytic uptake of SECP, the cells are washed with fresh culture medium, and a whole cell voltage-clamped *Xenopus* myocyte is manipulated into contact with one of the fibroblasts in SECP-free medium. Membrane currents are recorded from the myocyte. Increased or decreased current relative to control values are indicative of neuromodulatory effects of SECP (Morimoto, T. et al. (1995) Neuron 15:689-696).

Alternatively, an assay for SECP activity measures the amount of SECP in secretory, membrane-bound organelles. Transfected cells as described above are harvested and lysed. The lysate is fractionated using methods known to those of skill in the art, for example, sucrose gradient ultracentrifugation. Such methods allow the isolation of subcellular components such as the Golgi apparatus, ER, small membrane-bound vesicles, and other secretory organelles. Immunoprecipitations from fractionated and total cell lysates are performed using SECP-specific antibodies, and immunoprecipitated samples are analyzed using SDS-PAGE and immunoblotting techniques. The concentration of SECP in secretory organelles relative to SECP in total cell lysate is proportional to the amount of SECP in transit through the secretory pathway.

Alternatively, an assay for measuring protein kinase activity of SECP is performed by quantifying the phosphorylation of a protein substrate by SECP in the presence of gamma-labeled $^{32}$P-ATP. SECP is incubated with the protein substrate, $^{32}$P-ATP, and an appropriate kinase buffer. The $^{32}$P incorporated into the substrate is separated from free $^{32}$P-ATP by electrophoresis and the incorporated $^{32}$P is counted using a radioisotope counter. The amount of incorporated $^{32}$P is proportional to the activity of SCEP. A determination of the specific amino acid residue phosphorylated is made by phosphoamino acid analysis of the hydrolyzed protein.

Alternatively, AMP binding activity is measured by combining SECP with $^{32}$P-labeled AMP. The reaction is incubated at 37° C. and terminated by addition of trichloroacetic acid. The acid extract is neutralized and subjected to gel electrophoresis to remove unbound label. The radioactivity retained in the gel is proportional to SECP activity.

XVIII. Demonstration of Immunoglobulin Activity

An assay for SECP activity measures the ability of SECP to recognize and precipitate antigens from serum. This activity can be measured by the quantitative precipitin reaction. (Golub, E. S. et al. (1987) *Immunology: A Synthesis*, Sinauer Associates, Sunderland, Mass., pages 113-115.) SECP is isotopically labeled using methods known in the art. Various serum concentrations are added to constant amounts of labeled SECP. SECP-antigen complexes precipitate out of solution and are collected by centrifugation. The amount of precipitable SECP-antigen complex is proportional to the amount of radioisotope detected in the precipitate. The amount of precipitable SECP-antigen complex is plotted against the serum concentration. For various serum concentrations, a characteristic precipitin curve is obtained, in which the amount of precipitable SECP-antigen complex initially increases proportionately with increasing serum concentration, peaks at the equivalence point, and then decreases proportionately with further increases in serum concentration. Thus, the amount of precipitable SECP-antigen complex is a measure of SECP activity which is characterized by sensitivity to both limiting and excess quantities of antigen.

Alternatively, an assay for SECP activity measures the expression of SECP on the cell surface. cDNA encoding SECP is transfected into a non-leukocytic cell line. Cell surface proteins are labeled with biotin (de la Fuente, M. A. et. al. (1997) Blood 90:2398-2405). Immunoprecipitations are performed using SECP-specific antibodies, and immunoprecipitated samples are analyzed using SDS-PAGE and immunoblotting techniques. The ratio of labeled immunoprecipitant to unlabeled immunoprecipitant is proportional to the amount of SECP expressed on the cell surface.

Alternatively, an assay for SECP activity measures the amount of cell aggregation induced by overexpression of SECP. In this assay, cultured cells such as NIH3T3 are transfected with cDNA encoding SECP contained within a suitable mammalian expression vector under control of a strong promoter. Cotransfection with cDNA encoding a fluorescent marker protein, such as Green Fluorescent Protein (CLONTECH), is useful for identifying stable transfectants. The amount of cell agglutination, or clumping, associated with transfected cells is compared with that associated with untransfected cells. The amount of cell agglutination is a direct measure of SECP activity.

Various modifications and variations of the described methods and systems of the invention will be apparent to those skilled in the art without departing from the scope and spirit of the invention. Although the invention has been described in connection with certain embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

TABLE 1

| Incyte Project ID | Polypeptide SEQ ID NO: | Incyte Polypeptide ID | Polynucleotide SEQ ID NO: | Incyte Polynucleotide ID |
|---|---|---|---|---|
| 2719959 | 1 | 2719959CD1 | 64 | 2719959CB1 |
| 7473618 | 2 | 7473618CD1 | 65 | 7473618CB1 |
| 3564136 | 3 | 3564136CD1 | 66 | 3564136CB1 |
| 624334 | 4 | 624334CD1 | 67 | 624334CB1 |
| 7483393 | 5 | 7483393CD1 | 68 | 7483393CB1 |
| 1799943 | 6 | 1799943CD1 | 69 | 1799943CB1 |
| 2013095 | 7 | 2013095CD1 | 70 | 2013095CB1 |
| 4674740 | 8 | 4674740CD1 | 71 | 4674740CB1 |
| 146907 | 9 | 146907CD1 | 72 | 146907CB1 |
| 1513563 | 10 | 1513563CD1 | 73 | 1513563CB1 |
| 3144709 | 11 | 3144709CD1 | 74 | 3144709CB1 |
| 4775686 | 12 | 4775686CD1 | 75 | 4775686CB1 |
| 5851038 | 13 | 5851038CD1 | 76 | 5851038CB1 |
| 71850066 | 14 | 71850066CD1 | 77 | 71850066CB1 |
| 2488934 | 15 | 2488934CD1 | 78 | 2488934CB1 |
| 2667946 | 16 | 2667946CD1 | 79 | 2667946CB1 |
| 2834555 | 17 | 2834555CD1 | 80 | 2834555CB1 |
| 5544174 | 18 | 5544174CD1 | 81 | 5544174CB1 |
| 1728049 | 19 | 1728049CD1 | 82 | 1728049CB1 |
| 2425121 | 20 | 2425121CD1 | 83 | 2425121CB1 |
| 2817925 | 21 | 2817925CD1 | 84 | 2817925CB1 |
| 4000264 | 22 | 4000264CD1 | 85 | 4000264CB1 |
| 4304004 | 23 | 4304004CD1 | 86 | 4304004CB1 |
| 4945912 | 24 | 4945912CD1 | 87 | 4945912CB1 |
| 7230481 | 25 | 7230481CD1 | 88 | 7230481CB1 |
| 71947526 | 26 | 71947526CD1 | 89 | 71947526CB1 |
| 6843919 | 27 | 6843919CD1 | 90 | 6843919CB1 |
| 5866451 | 28 | 5866451CD1 | 91 | 5866451CB1 |
| 1310222 | 29 | 1310222CD1 | 92 | 1310222CB1 |
| 1432223 | 30 | 1432223CD1 | 93 | 1432223CB1 |
| 1537636 | 31 | 1537636CD1 | 94 | 1537636CB1 |
| 1871333 | 32 | 1871333CD1 | 95 | 1871333CB1 |
| 7153010 | 33 | 7153010CD1 | 96 | 7153010CB1 |
| 7996779 | 34 | 7996779CD1 | 97 | 7996779CB1 |
| 640025 | 35 | 640025CD1 | 98 | 640025CB1 |
| 1545079 | 36 | 1545079CD1 | 99 | 1545079CB1 |
| 2668150 | 37 | 2668150CD1 | 100 | 2668150CB1 |
| 2804787 | 38 | 2804787CD1 | 101 | 2804787CB1 |
| 4003882 | 39 | 4003882CD1 | 102 | 4003882CB1 |
| 4737462 | 40 | 4737462CD1 | 103 | 4737462CB1 |
| 4921634 | 41 | 4921634CD1 | 104 | 4921634CB1 |
| 6254942 | 42 | 6254942CD1 | 105 | 6254942CB1 |
| 6747838 | 43 | 6747838CD1 | 106 | 6747838CB1 |
| 7050585 | 44 | 7050585CD1 | 107 | 7050585CB1 |
| 3880321 | 45 | 3880321CD1 | 108 | 3880321CB1 |
| 3950005 | 46 | 3950005CD1 | 109 | 3950005CB1 |
| 3043830 | 47 | 3043830CD1 | 110 | 3043830CB1 |
| 002479 | 48 | 002479CD1 | 111 | 002479CB1 |
| 1395420 | 49 | 1395420CD1 | 112 | 1395420CB1 |
| 1634103 | 50 | 1634103CD1 | 113 | 1634103CB1 |
| 2422023 | 51 | 2422023CD1 | 114 | 2422023CB1 |
| 4241771 | 52 | 4241771CD1 | 115 | 4241771CB1 |
| 5046408 | 53 | 5046408CD1 | 116 | 5046408CB1 |
| 6271376 | 54 | 6271376CD1 | 117 | 6271376CB1 |
| 7032326 | 55 | 7032326CD1 | 118 | 7032326CB1 |
| 7078691 | 56 | 7078691CD1 | 119 | 7078691CB1 |
| 7089352 | 57 | 7089352CD1 | 120 | 7089352CB1 |
| 7284533 | 58 | 7284533CD1 | 121 | 7284533CB1 |
| 7482209 | 59 | 7482209CD1 | 122 | 7482209CB1 |
| 7482314 | 60 | 7482314CD1 | 123 | 7482314CB1 |
| 7482339 | 61 | 7482339CD1 | 124 | 7482339CB1 |
| 7949557 | 62 | 7949557CD1 | 125 | 7949557CB1 |
| 1555909 | 63 | 1555909CD1 | 126 | 1555909CB1 |

TABLE 2

| Polypeptide SEQ ID NO: | Incyte Polypeptide ID | GenBank ID NO: or PROTEOME ID NO: | Probability Score | Annotation |
|---|---|---|---|---|
| 1 | 2719959CD1 | g14794726 | 1.00E−176 | [fl][Homo sapiens] CUB and sushi multiple domains 1 protein (Sun, P. C. et al. (2001) Genomics. 75 (1-3), 17-25) |
| 2 | 7473618CD1 | g531385 | 7.80E−266 | [Drosophila melanogaster] peroxidasin precursor (Nelson, R. E. et al. (1994) EMBO J. 13, 3438-3447) |
| 3 | 3564136CD1 | g537514 | 1.20E−110 | [Homo sapiens] arylacetamide deacetylase (Probst, M. R. et al. (1994) J. Biol. Chem. 34: 21650-21656) |
| 4 | 624334CD1 | g508574 | 4.70E−148 | [Rattus norvegicus] neurexophilin (Petrenko, A. G. et al. (1996) J. Neurosci. 16 (14), 4360-4369) |
| 5 | 7483393CD1 | g13274528 | 1.00E−112 | [fl][Homo sapiens] complement-c1q tumor necrosis factor-related protein |
| 6 | 1799943CD1 | g164671 | 2.30E−36 | [Sus scrofa] preprosecretin precursor (Kopin, A. S. et al. (1990) Proc. Natl. Acad. Sci. U.S.A. 87, 2299-2303) |
| 7 | 2013095CD1 | g3978238 | 2.40E−57 | [Homo sapiens] TNF-induced protein GG2-1 (Horrevoets, A. J. et al. (1999) Blood 93 (10), 3418-3431) |
| 8 | 4674740CD1 | g7271867 | 7.70E−26 | [Homo sapiens] golgi membrane protein GP73 (Kladney, R. D. et al. (2000) Gene 249 (1-2), 53-65) |
| 26 | 71947526CD1 | g387048 | 1.00E−52 | [Cricetus cricetus] DHFR-coamplified protein (Foreman, P. K. et al. (1989) Mol. Cell. Biol. 9, 1137-1147) |
| 27 | 6843919CD1 | g57736 | 4.50E−31 | [Rattus rattus] potential ligand-binding protein (Dear, T. N. et al. (1991) EMBO J. 10 (10), 2813-2819) |

TABLE 2-continued

| Polypeptide SEQ ID NO: | Incyte Polypeptide ID | GenBank ID NO: or PROTEOME ID NO: | Probability Score | Annotation |
|---|---|---|---|---|
| 28 | 5866451CD1 | g296605 | 7.50E−148 | [*Mus musculus*] nodal TGF-beta like gene (Zhou, X. et al. (1993) Nature 361 (6412), 543-547) |
| 45 | 3880321CD1 | g8572229 | 5.80E−22 | [*Homo sapiens*] ubiquitous TPR-motif protein Y isoform (Shen, P. et al. (2000) Proc. Natl. Acad. Sci. U.S.A. 97 (13), 7354-7359) |
| 46 | 3950005CD1 | g2988399 | 1.50E−188 | [*Homo sapiens*] SA gene (Loftus, B. J. et al. (1999) Genomics 60 (3), 295-308) |
| 47 | 3043830CD1 | g3236368 | 0 | [*Mus musculus*] S3-12 (Scherer P. E. et al. (1998) Nature Biotechnol. 16: 581-586) |
| 63 | 1555909CD1 | g4324682 | 3.40E−97 | [*Rattus norvegicus*] late gestation lung protein 1 (Kaplan, F. et al. (1999) Am. J. Physiol. 276 (6), L1027-L1036) |

TABLE 3

| SEQ ID NO: | Incyte Polypeptide ID | Amino Acid Residues | Potential Phosphorylation Sites | Potential Glycosylation Sites | Signature Sequences, Domains and Motifs | Analytical Methods and Databases |
|---|---|---|---|---|---|---|
| 1 | 2719959CD1 | 351 | S145 S151 5172 T236 T241 T4 T59 | N2 N221 N234 N311 N73 | CUB domains: C54-Y159, C231-Y336 | HMMER_PFAM |
| | | | | | Sushi domain (SCR repeat): C170-C227 | HMMER_PFAM |
| | | | | | GLYCOPROTEIN DOMAIN EGFLIKE PROTEIN PRECURSOR SIGNAL RECEPTOR INTRINSIC FACTORB12 REPEAT PD000165: C231-Y336 | BLAST_PRODOM |
| | | | | | C1R/C1S REPEAT DM00162 | I49540 | 748-862: C231-Y336 DM00162 | I49540 | 592-708: C227-S338 DM00162 | I49540 | 438-552: C231-V340 DM00162 | P98063 | 755-862: T236-Y336 | BLAST_DOMO |
| 2 | 7473618CD1 | 1463 | S1164 S1190 S131S S1320 S167 S171 S233 S310 S500 S554 S613 S627 S634 S696 S719 S871 S90 S903 S929 T1070 T1123 T117 T141 T225 T254 T34 T347 T389 T424 T472 T504 T520 T53 T566 T628 T639 T710 T823 Y1234 Y1345 Y303 | N1068 N1161 N1283 N1352 N271 N387 N401 N529 N626 N705 N717 | Signal _cleavage: M1-P23 | SPSCAN |
| | | | | | Signal peptide: M1-C28 | HMMER |
| | | | | | Peroxidase domain: K726-S1164 | HMMER_PFAM |
| | | | | | Immunoglobulin domain: G248-A307, G344-A400, C440-A490, G525-A582 | HMMER_PFAM |
| | | | | | Leucine Rich Repeat: Q51-K74, N75-E98, N99-I122, S123-L146, R147-D170, S171-L195 | HMMER_PFAM |
| | | | | | Leucine rich repeat C-terminal domain LRRCT: N180-Q232 | HMMER_PFAM |
| | | | | | von Willebrand factor type C domain: C1395-C1450 | HMMER PFAM |
| | | | | | Animal haem peroxidase signature PR00457: R751-R762, M802-T817, F954-T972, T972-W992, V997-G1023, T1050-I1060, D1177-W1197, L1248-D1262 | BLIMPS_PRINTS |
| 2 | | | | | PEROXIDASE OXIDOREDUCTASE PRECURSOR SIGNAL HEME GLYCOPROTEIN PROTEIN SIMILAR MYELOPEROXIDASE EOSINOPHIL PD001354: K1166-F1272 | BLAST_PRODOM |
| | | | | | PROTEIN ZK994.3 K09C8.5 PEROXIDASIN PRECURSOR SIGNAL PD144227: N584-K726 | BLAST_PRODOM |
| | | | | | PEROXIDASE OXIDOREDUCTASE PRECURSOR SIGNAL MYELOPEROXIDASE HEME GLYCOPROTEIN ASCORBATE CATALASE LASCORBATE P0000217: Y727-A784; R825-K931; F1086-T1163 | BLAST_PRODOM |
| | | | | | HEMICENTIN PRECURSOR SIGNAL GLYCOPROTEIN EGFLIKE DOMAIN HIM4 PROTEIN ALTERNATIVE SPLICING PD066634: P234-C398 | BLAST_PRODOM |
| | | | | | MYELOPEROXIDASE DM01034 | S46224 | 911-1352: C859-C1298 DM01034 | P09933 | 284-735: A857-D1297 DM01034 | P35419 | 276-725: C859-D1297 DM01034 | P11678 | 282-714: F862-Q1296 | BLAST_DOMO |
| | | | | | VWFC domain signature: C1414-C1450 | MOTIFS |

TABLE 3-continued

| SEQ ID NO: | Incyte Polypeptide ID | Amino Acid Residues | Potential Phosphorylation Sites | Potential Glycosylation Sites | Signature Sequences, Domains and Motifs | Analytical Methods and Databases |
|---|---|---|---|---|---|---|
| 3 | 3564136CD1 | 401 | S100 S119 S231 S30 S395 T102 T255 T80 T85 Y297 | N282 N323 | ARYLACETAMIDE DEACETYLASE EC 3.1.1. AADAC HYDROLASE TRANSMEMBRANE MICROSOME SIGNAL ANCHOR PD087155: E207-D314 PD087138: G2-R105 | BLAST_PRODOM |
|  |  |  |  |  | PROTEIN HYDROLASE PUTATIVE ESTERASE C4A8.06C CHROMOSOME I N-ACETYL PHOSPHINO THRICIN TRIPEPTIDE DEACETYLASE COSMID B1740 PD150195: T102-L194 | LAST_PRODOM |
| 3 |  |  |  |  | Lipolytic enzymes "G-D-X-G" family, histidine BL01173: V107-S119, V140-F166, R182-A195 | BLIMPS_BLOCKS |
|  |  |  |  |  | signal peptide signal_peptide: M1-T21 | HMMER |
|  |  |  |  |  | Spscan signal cleavage: M1-F19 | SPSCAN |
| 4 | 624334CD1 | 271 | S37 S49 S83 T112 T130 T138 T182 T41 T62 T70 Y261 | N146 N156 N162 N23 N68 N93 | NEUREXOPHILIN NEUROPHILIN PD039440: S83-G271 PD123274: M1-Y82 | BLAST_PRODOM |
|  |  |  |  |  | Spscan signal_cleavage: M1-G27 | SPSCAN |
| 5 | 7483393CD1 | 201 | S178 S65 T98 |  | signal_peptide: M1-P18 | HMMER |
|  |  |  |  |  | signal_cleavage: M1-G15 | SPSCAN |
|  |  |  |  |  | Complement protein C1q domain C1q: A63-V190 | HMMER_PFAM |
|  |  |  |  |  | C1q domain proteins. BL01113: G30-C56, P80-A115, A147-Q166, S183-S192 | BLIMPS_BLOCKS |
|  |  |  |  |  | Complement C1Q domain signature PR00007: F101-A120, A147-G168, T181-Y191, P74-K100 | BLIMPS_PRINTS |
|  |  |  |  |  | C1Q DOMAIN DM00777 | Q02105 | 71-245: P29-D193 DM00777 | P98085 | 222-418: G30-D193 DM00777 | P23206 | 477-673: P29-V190 DM00777 | S23297 | 465-674: P29-L189 | BLAST_DOMO |
|  |  |  |  |  | C1QB PRECURSOR SIGNAL COLLAGEN REPEAT HYDROXYLATION GLYCOPROTEIN CHAIN PLASMA EXTRACELLULAR MATRIX PD002992: A63-V190 | LAST_PRODOM |
| 6 | 1799943CD1 | 121 | S29 S58 T117 |  | signal_peptide: M1-A18 | HMMER |
|  |  |  |  |  | signal_cleavage: M1-A18 | SPSCAN |
|  |  |  |  |  | Peptide hormone hormone2: H28-G55 | HMMER_PFAM |
|  |  |  |  |  | Glucagon/GIP/secretin/VIP family BL00260: H28-V54 | BLIMPS_BLOCKS |
|  |  |  |  |  | GLUCAGON POLYPEPTIDE HORMONE PR00275: H28-S38, R39-L50 | BLIMPS_PRINTS |
|  |  |  |  |  | BRAIN NATRIURETIC PEPTIDE PR00712C: L46-N64 | BLIMPS_PRINTS |
|  |  |  |  |  | Glucagon/GIP/secretin/VIP family signature: H28-L50 | MOTIFS |
| 7 | 2013095CD1 | 186 | S5 S52 T136 T34 |  | signal_cleavage: M1-S36 | SPSCAN |
| 8 | 4674740CD1 | 436 | S277 S328 S36 S366 S68 S92 T195 T312 T76 Y399 | N115 N150 | signal_peptide: M1-A29 | HMMER |
|  |  |  |  |  | signal_cleavage: M1-A29 | SPSCAN |
|  |  |  |  |  | transmembrane_domain: G11-N31 | HMMER |
| 9 | 146907CD1 | 134 | T49 S50 S55 |  | signal_peptide: M101-L129 | HMMER |
| 10 | 1513563CD1 | 172 | T142 S3 S50 |  | signal_peptide: M7-G36 | HMMER |
| 11 | 3144709CD1 | 80 |  |  | signal_peptide: M1-S19 | HMMER |
| 12 | 4775686CD1 | 92 | T29 T36 |  | signal_peptide: M1-S21 | HMMER |

TABLE 3-continued

| SEQ ID NO: | Incyte Polypeptide ID | Amino Acid Residues | Potential Phosphorylation Sites | Potential Glycosylation Sites | Signature Sequences, Domains and Motifs | Analytical Methods and Databases |
|---|---|---|---|---|---|---|
| 13 | 5851038CD1 | 90 | S37 | | signal_peptide: M1-G21 | HMMER |
| 14 | 71850066CD1 | 354 | S12 S133 S15 S192 S195 S52 S71 T213 T314 | N129 N163 | signal_cleavage: M1-S15 | SPSCAN |
| | | | | | KTI12 PROTEIN ATPBINDING PD040436: M1-P110 | BLAST_PRODOM |
| | | | | | ATP/GTP-binding site motif A (P-loop): G8-S15 | MOTIFS |
| 15 | 2488934CD1 | 101 | S20 | | signal_peptide: M1-S21 | HMMER |
| | | | | | signal_cleavage: M1-M22 | SPSCAN |
| 16 | 2667946CD1 | 74 | S11 T4 | N14 | signal_peptide: M1-A31 | HMMER |
| | | | | | signal_cleavage: M1-T40 | SPSCAN |
| | | | | | Sodium: solute symporter family signature sodium_symporters_1.prf: P9-F52 | PROFILESCAN |
| 17 | 2834555CD1 | 100 | S47 T50 | | signal_peptide: M1-G21 | HMMER |
| 18 | 5544174CD1 | 94 | S2 S59 | | signal_peptide: M1-S22 | HMMER |
| | | | | | signal_cleavage: M1-A65 | SPSCAN |
| 19 | 1728049CD1 | 143 | S128 S90 T83 | N81 | signal_peptide: M1-A27 | HMMER |
| | | | | | signal_cleavage: M1-O35 | SPSCAN |
| 20 | 2425121CD1 | 116 | S2 S48 S97 | | signal_peptide: M1-A25 | HMMER |
| | | | | | signal_cleavage: M1-R28 | SPSCAN |
| 21 | 2817925CD1 | 76 | S15 T18 T37 | | signal_peptide: M1-R20 | HMMER |
| | | | | | signal_cleavage: M1-C39 | SPSCAN |
| 22 | 4000264CD1 | 116 | S61 T111 | | signal_peptide: M1-G27 | HMMER |
| | | | | | signal_cleavage: M1-G29 | SPSCAN |
| 23 | 4304004CD1 | 210 | S116 S120 S39 S88 T123 T131 T15 T205 Y132 | | signal_cleavage: M1-G41 | SPSCAN |
| | | | | | transmembrane_domain: Y18-W38 | HMMER |
| 24 | 4945912CD1 | 195 | S128 T131 T181 | | signal_cleavage: M1-A58 | SPSCAN |
| 25 | 7230481CD1 | 140 | S103 S3 | | signal_peptide: M1-A19 | HMMER |
| | | | | | Actinin-type actin-binding domain signatures actinin_2.prf: N48-Q94 | PROFILESCAN |
| 26 | 71947526CD1 | 585 | S136 S263 Y73 S265 S281 T91 S352 S532 S63 S550 S78 T104 T317 T35 T359 T371 T376 | N106 N189 N220 N315 N89 | signal_cleavage: M1-R37 | SPSCAN |
| | | | | | transmembrane_domain: K13-A33 | HMMER |
| | | | | | Aminotransferases class-V pyridoxal-phosphate attachment site: L312-I329 | MOTIFS |
| 27 | 6843919CD1 | 95 | S68 T22 T41 | | signal_peptide: M1-G23 | HMMER |
| | | | | | signal_cleavage: M1-G23 | SPSCAN |
| | | | | | UTEROGLOBIN FAMILY DM02636 | S17449 | 1-94: M1-D93 | LAST_DOMO |
| | | | | | POTENTIAL LIGAND BINDING PROTEIN RYD5 PD065166: M1-D93 | BLAST_PRODOM |
| | | | | | UTEROGLOBIN SIGNATURE PR00486A: K2-C16 | BLIMPS_PRINTS |
| 28 | 5866451CD1 | 347 | S127 S219 S83 S99 | N199 N72 | Signal_cleavage: M1-G33 | SPSCAN |
| 28 | | | | | Signal_peptide: M1-A25 | HMMER |
| | | | | | TGF-beta family signature I265-C280 | MOTIFS |

TABLE 3-continued

| SEQ ID NO: | Incyte Polypeptide ID | Amino Acid Residues | Potential Phosphorylation Sites | Potential Glycosylation Sites | Signature Sequences, Domains and Motifs | Analytical Methods and Databases |
|---|---|---|---|---|---|---|
| | | | | | Transforming growth factor beta like TGF-beta: C247-L347 | HMMER_PFAM |
| | | | | | TGF-beta family signature tgf_beta.prf: Q245-K301 | PROFILESCAN |
| | | | | | TGF-beta family proteins BL00250: C247-N282, T311-C346 | BLIMPS_BLOCKS |
| | | | | | GROWTH FACTOR CYSTINE KN PR00438: N272-P281, E342-C346 | BLIMPS_PRINTS |
| | | | | | GLYCOPROTEIN PRECURSOR SIGNAL GROWTH FACTOR PD000357: C247-C346 | BLAST_PRODOM |
| | | | | | NODAL PRECURSOR DEVELOPMENTAL PROTEIN GROWTH FACTOR PD117903: M1-P53 | BLAST_PRODOM |
| | | | | | TGF-BETA FAMILY DM00245 \| P43021 \| 34-354: G33-L347 DM00245 \| P48970 \| 64-383: S244-C346, F77-W162 DM00245 \| I49541 \| 105-420: K233-C346, P51-R157 DM00245 \| P12644 \| 95-408: K233-C346, P51-R157 | BLAST_DOMO |
| 29 | 1310222CD1 | 63 | | | Signal_cleavage: M1-R19 | SPSCAN |
| 30 | 1432223CD1 | 208 | | | Signal_cleavage: M1-N65 | SPSCAN |
| | | | | | PROTEIN COX4AL F25H2.4 PD022799: A8-I195 | BTAST_PRODOM |
| 31 | 1537636CD1 | 256 | S131 S236 S30 S69 S9 T172 T194 T215 | | Signal_cleavage: M1-G54 | SPSCAN |
| 32 | 1871333CD1 | 229 | S172 S225 T23 T26 T85 | N148 | Signal_cleavage: M1-G19 | SPSCAN |
| | | | | | Signal_peptide: M1-A20 | HMMER |
| | | | | | Transmembrane domain: L3-G22, | HMMER |
| | | | | | F55A8.1 PROTEIN PD146797: E33-K214 | BLAST_PRODOM |
| 33 | 7153010CD1 | 327 | S126 S213 S307 T23 | N172 N311 | Signal_cleavage: M1-S19 | SPSCAN |
| | | | | | Signal_peptide: M1-V21 | HMMER |
| | | | | | Immunoglobulin domain ig: G57-V144, C187-A239 | HMMER_PFAM |
| | | | | | CELL PRECURSOR GLYCOPROTEIN TRANSMEMBRANE SIGNAL IMMUNOGLOBULIN FOLD ADHESION ALTERNATIVE SPLICING PD005007: W44-G201 | BLAST_PRODOM |
| | | | | | MYELIN; SCHWANN; SIALOADHESIN; FORM; DM03744 \| P20138 \| 1-142: W44-T165 | BLAST_DOMO |
| 34 | 7995779CD1 | 104 | S45 | | Signal_cleavage: M1-G30 | SPSCAN |
| | | | | | Signal_peptide: M1-G30 | HMMER |
| 35 | 640025CD1 | 82 | S51 | | Signal_cleavage: M1-A35 | SPSCAN |
| | | | | | Signal_peptide: M34-S51 | HMMER |
| 36 | 1545079CD1 | 367 | S117 S21 T327 Y219 | N285 | Signal_cleavage: M1-A63 | SPSCAN |
| | | | | | Leucine zipper pattern L346-L367 | MOTIFS |
| 36 | | | | | SUA5/yciO/yrdC family pr BL01147: V170-V194, L228-M241, L251-P263 | BLIMPS_BLOCKS |
| | | | | | Signal_peptide: M89-S117 HMM_score 17.56 | HMMER |
| | | | | | SUA5/yciO/yrdC family Sua5_yciO_yrd: V162-G343 | HMMER_PFAM |
| | | | | | PROTEIN HYPF TRANSCRIPTIONAL REGULATORY DNABINDING ZINCFINGER CONSERVED INTERGENIC PD002209: A163-S332 | BLAST_PRODOM |
| | | | | | HYPOTHETICAL SUA5/YCIO/YRDC FAMILY DM02523 \| P45831 \| 25-166: A163-E296 DM02523 \| P45103 \| 1-206: L158-G343 DM02523 \| P39153 \| 26-169: A163-E296 DM02523 \| P45847 \| 1-217: L158-S332 | BLAST_DOMO |

TABLE 3-continued

| SEQ ID NO: | Incyte Polypeptide ID | Amino Acid Residues | Potential Phosphorylation Sites | Potential Glycosylation Sites | Signature Sequences, Domains and Motifs | Analytical Methods and Databases |
|---|---|---|---|---|---|---|
| 37 | 2668150CD1 | 70 | S50 S52 T45 | N59 | Signal_cleavage: M1-R25 | SPSCAN |
| | | | | | Signal_peptide: M1-R25 | HMMER |
| | | | | | Transmembran domain: I6-V23, | HMMER |
| 38 | 2804787CD1 | 73 | | N67 | Signal_peptide: M1-G23 | HMMER |
| | | | | | Signal_cleavage: M1-S65 | SPSCAN |
| | | | | | Transmembrane domain: L4-I21, | HMMER |
| 39 | 4003882CD1 | 76 | S64 T67 | | Signal_cleavage: M1-S65 | SPSCAN |
| | | | | | Leucine zipper pattern L26-L47, L30-L51 | MOTIFS |
| 40 | 4737462CD1 | 80 | S36 S50 | | Signal_cleavage: M1-G21 | SPSCAN |
| 40 | | | | | Signal_peptide: M1-G22 | HMMER |
| 41 | 4921634CD1 | 73 | S63 | | Signal_cleavage: M1-S17 | SPSCAN |
| | | | | | Signal_peptide: M1-C22 | HMMER |
| | | | | | Transmembrane domain: M1-F25, | HMMER |
| 42 | 6254942CD1 | 116 | S11 S3 T17 | | Signal_cleavage: M1-A42 | SPSCAN |
| | | | | | Transmembrane domain: I49-A66 | HMMER |
| 43 | 6747838CD1 | 95 | S54 S64 S80 | | Signal_peptide: M1-A18 | HMMER |
| 44 | 7050585CD1 | 138 | S131 T121 T64 T73 | | Sianal_cleavage: M1-L49 | SPSCAN |
| | | | | | Signal_peptide: M1-W18 | HMMER |
| 45 | 3880321CD1 | 134 | S46 S59 S65 | | Signal_cleavage: M1-S32 | SPSCAN |
| 46 | 3950005CD1 | 570 | S195 S254 S339 S479 S504 S525 S64 S91 S99 T150 T262 T345 T362 T544 T84 Y464 | N269 N288 N476 N82 | Putative AMP-binding domain signature I227-K238 | MOTIFS |
| | | | | | Signal_peptide: M1-C20 | HMMER |
| | | | | | AMP-binding enzyme AMP-binding: S91-V502 | HMMER_PFAM |
| | | | | | Putative AMP-binding domain signature amp_binding.prf: E209-V259 | PROFILESCAN |
| | | | | | AMP-BINDING SIGNATURE PR00154: R222-T233, T234-H242 | BLIMPS_PRINTS |
| | | | | | LIGASE SYNTHETASE PROTEIN ENZYME BIOSYNTHESIS MULTIFUNCTIONAL REPEAT ACYLCOA PD000070: T147-V421 | BLAST_PRODOM |
| 46 | | | | | SA PROTEIN GENE SIGNAL KIDNEY SPECIFIC PD151238: V49-W90 | BLAST_PRODOM |
| | | | | | PUTATIVE AMP-BINDING DOMAIN DM00073 \| A61209 \| 65-538: E67-Q402, G417-K561 DM00073 \| P39062 \| 50-555: K89-K561 DM00073 \| P27550 \| 82-615: F203-K561, L66-D170 DM00073 \| P27095 \| 107-644: R197-K561, G70-V276 | BLAST_DOMO |
| 47 | 3043830CD1 | 1325 | | | Signal_cleavage: M1-A32 | SPSCAN |
| | | | | | SUBMAXILLARY APOMUCIN ICE NUCLEATION PROTEIN FILAMENTOUS HEMAGGLUTININ ANTIGEN S312 PD011940: T82-T996 | BLAST_PRODOM |
| | | | | | PROTEIN PERILIPIN ADIPOSE DIFFERENTIATION RELATED ADRP MEMBRANE CARGO SELECTION TIP47 A/B PD018256: P1135-F1318 | BLAST_PRODOM |
| | | | | | S312 PD185810: M1-L112 | BLAST_PRODOM |
| | | | | | PROTEIN F36H.3A F36H2.3B PD004794: L251-T1048 | BLAST_PRODOM |
| | | | | | SURFACE; S-LAYER; ARRAY; SAPA2; | BLAST_DOMO |

TABLE 3-continued

| SEQ ID NO: | Incyte Polypeptide ID | Amino Acid Residues | Potential Phosphorylation Sites | Potential Glycosylation Sites | Signature Sequences, Domains and Motifs | Analytical Methods and Databases |
|---|---|---|---|---|---|---|
| | | | | | DM08156 \| A56143 \| 1-932: G28-V877 ICE NUCLEATION PROTEIN | BLAST_DOMO |
| | | | | | DM00787 \| P18127 \| 603-942: G507-G855 | |
| 48 | 002479CD1 | 228 | S44 S165 S187 S207 T62 T83 T214 | | DM00787 \| P06620 \| 194-533: V481-Q802 signal_cleavage: M1-R46 | SPSCAN |
| 49 | 1395420CD1 | 80 | S74 | N10 | signal_cleavage: M1-S58 | SPSCAN |
| 49 | | | | | GHMP kinases putative ATP-binding domain: R3-N69 | PROFILESCAN |
| 50 | 1634103CD1 | 538 | S220 S489 S522 T105 T464 | | signal_cleavage: M1-A35 | SPSCAN |
| | | | | | transmembrane domain: P127-T150 | HMMER |
| | | | | | NICOTINATE PHOSPHO RIBOSYLTRANSFERASE TRANSFERASE GLYCOSYLTRANSFERASE PD008895: E268-L434, F92-E223 PD011757: L16-L80 | BLAST_PRODOM |
| 51 | 2422023CD1 | 73 | T25 | | signal_cleavage: M1-G19 | SPSCAN |
| | | | | | signal peptide: M1-G19 | HMMER |
| 52 | 4241771CD1 | 108 | S89 S102 | N33 | signal_cleavage: M1-C24 | SPSCAN |
| | | | | | signal peptide: M1-P26 | HMMER |
| 53 | 5046408CD1 | 80 | | N15 | signal_cleavage: M1-G19 | SPSCAN |
| | | | | | signal peptide: M1-G19 | HMMER |
| 54 | 6271376CD1 | 87 | S18 S38 S43 S47 | | signal_cleavage: M1-A15 | SPSCAN |
| | | | | | signal peptide: M1-S18 | HMMER |
| 55 | 7032326CD1 | 78 | S5 S76 | | signal_cleavage: M1-A27 | SPSCAN |
| | | | | | signal peptide: M1-G29 | HMMER |
| 56 | 7078691CD1 | 108 | S60 S75 | | signal_cleavage: M1-C19 | SPSCAN |
| | | | | | signal peptide: M1-G21 | HMMER |
| 57 | 7089352CD1 | 81 | S27 S42 S49 S78 | | signal_cleavage: M1-A26 | SPSCAN |
| | | | | | signal peptide: M1-A26 | HMMER |
| 58 | 7284533CD1 | 146 | S107 T101 T122 T123 | | signal_cleavage: M1-A62 | SPSCAN |
| | | | | | signal peptide: M1-G27 | HMMER |
| 59 | 7482209CD1 | 92 | S17 S59 T21 T81 | N71 | signal_cleavage: M1-A16 | SPSCAN |
| | | | | | signal peptide: M1-S19 | HMMER |
| 60 | 7482314CD1 | 119 | S100 T90 T113 | | signal peptide: M50-R81 | HMMER |
| 61 | 7482339CD1 | 92 | S58 | N41 | signal_cleavage: M1-S24 | SPSCAN |
| | | | | | signal peptide: M1-S24 | HMMER |
| 62 | 7949557CD1 | 107 | S34 S89 S105 | | signal_cleavage: M1-T27 | SPSCAN |
| | | | | | transmembrane domain: I5-L22 | HMMER |
| 63 | 1555909CD1 | 497 | S75 S130 S201 S228 S279 S362 S453 S471 T29 T81 T170 T179 T184 T241 T467 T483 Y392 | N27 N41 N451 | signal_cleavage: M1-G22 | SPSCAN |
| | | | | | signal peptide: M1-G22 | HMMER |
| | | | | | SCP-like extracellular protein: K56-G208 | HMMER_PFAM |
| | | | | | Extracellular proteins SCP/Tpx-1/Ag5/PR-1/Sc7 proteins BL01009: M80-C97, H127-Y140, T160-C180, | BLIMPS_BLOCKS |

TABLE 3-continued

| SEQ ID NO: | Incyte Polypeptide ID | Amino Acid Residues | Potential Phosphorylation Sites | Potential Glycosylation Sites | Signature Sequences, Domains and Motifs | Analytical Methods and Databases |
|---|---|---|---|---|---|---|
| | | | | | V194-E209 | |
| | | | | | Allergen V5/Tpx-1 family signature PR00837: H127-Y140, C159-C175, Y195-G208, M80-I98 | BLIMPS_PRINTS |
| | | | | | Venom allergen 5 signature PR00838: A50-L66, M80-I98, G125-Y140, M158-V177 | BLIMPS_PRINTS |
| | | | | | PROTEIN PRECURSOR SIGNAL PATHOGENESISRELATED ANTIGEN ALLERGEN VENOM MULTIGENE FAMILY AG5 PD000542: R67-G208, R53-G227 | BLAST_PRODOM |
| | | | | | FSG 120K CYSRICH PROTEIN GLYCOPROTEIN EGF LIKE DOMAIN PD128352: I51-G226 | BLAST_PRODOM |
| 63 | | | | | EXTRACELLULAR PROTEINS SCP/TPX-1/AG5/PR-1/SC7 DM00332 | P48060 | 1-175: N41-W206 DM00332 | P35778 | 12-207: D55-P211 DM00332 | Q03401 | 9-181: K56-G208 DM00332 | Q05110 | 34-223: V47-Y212 | BLAST_DOMO |
| | | | | | Extracellular proteins SCP/Tpx-1/Ag5/PR-1/Sc7 signature 2 Y195-W206 | MOTIFS |

TABLE 4

| Polynucleotide SEQ ID NO: | Incyte Polynucleotide ID | Sequence Length | Selected Fragment(s) | Sequence Fragments | 5' Position | 3' Position |
|---|---|---|---|---|---|---|
| 64 | 2719959CB1 | 1338 | 1-363, 1269-1338 | 56002879J1 | 1 | 984 |
| | | | | 2719959T6 (LUNGTUT10) | 724 | 1338 |
| 65 | 7473618CB1 | 5093 | 1-1579, 4240-4299, 2099-3946, 4379-4529 | 6866460E8 (BRAGNON02) | 315 | 550 |
| | | | | 72341159D1 | 4076 | 4718 |
| | | | | GBI.g8152129_000001.edit | 3942 | 4373 |
| | | | | GBI.g8152129_000003.edit | 2447 | 3944 |
| | | | | g1547765 | 3947 | 4380 |
| | | | | 7754154H1 (HEAONOE01) | 331 | 1094 |
| | | | | FL7473618_0096904_000020_g7292259 | 2031 | 3945 |
| | | | | GBI.g8152037_000006.edit2 | 1 | 550 |
| | | | | 7754154J1 (HEAONOE01) | 946 | 1622 |
| | | | | 72342123D1 | 4260 | 5093 |
| | | | | 55081807J1 | 3680 | 4019 |
| | | | | GBI.g8096904_10_14_4_9_20.2.edit | 912 | 2177 |
| 66 | 3564136CB1 | 1392 | 1-242, 478-673 | GBI.g8954235.order_0.edit | 1 | 1041 |
| | | | | 2352447H1 (COLSUCT01) | 784 | 988 |
| | | | | g1525737 | 937 | 1392 |
| | | | | 3564136H1 (SKINNOT05) | 144 | 451 |
| | | | | g1493356 | 224 | 495 |
| | | | | g1678558 | 674 | 1260 |
| 67 | 624334CB1 | 2390 | 710-1069, 2366-2390, 1-245 | 71392568V1 | 302 | 792 |
| | | | | 4338525F6 (BRAUNOT02) | 1 | 453 |
| | | | | 71199569V1 | 1831 | 2380 |
| | | | | g1210731 | 1787 | 2390 |
| | | | | 6273383F8 (BRAIFEN03) | 584 | 1331 |
| | | | | 7130272H1 (BRAHTDK01) | 1423 | 1918 |
| | | | | 6447629H1 (BRAINOC01) | 1186 | 1822 |
| 68 | 7483393CB1 | 3248 | 1-2012 | 71275974V1 | 1 | 638 |
| | | | | 71870255V1 | 1722 | 2386 |
| | | | | 5895459F8 (BRAYDIN03) | 2588 | 3248 |
| | | | | 72032402V1 | 608 | 1438 |
| | | | | 8225765H1 (COLHTUS02) | 2658 | 3248 |
| | | | | 71870671V1 | 1535 | 2084 |
| | | | | 72335020V1 | 2354 | 3247 |
| | | | | 71066648V1 | 1000 | 1634 |
| 69 | 1799943CB1 | 520 | 1-87, 231-520 | GBI.g6715656_000011.edit.3 | 1 | 213 |
| | | | | 1799943T6 (COLNNOT27) | 137 | 520 |
| 70 | 2013095CB1 | 2108 | 134-424, 1-71 | 7724892J1 (THYRDIE01) | 1 | 685 |
| | | | | 8126837H1 (SCOMDIC01) | 562 | 1050 |

TABLE 4-continued

| Polynucleotide SEQ ID NO: | Incyte Polynucleotide ID | Sequence Length | Selected Fragment(s) | Sequence Fragments | 5' Position | 3' Position |
|---|---|---|---|---|---|---|
| | | | | 70284485V1 | 1275 | 1954 |
| | | | | 70285683V1 | 1504 | 2108 |
| 71 | 4674740CB1 | 2219 | 1855-2219 | 2456045F6 (ENDANOT01) | 870 | 1304 |
| | | | | 55048995J1 (ADMEDNV37) | 381 | 1261 |
| | | | | 7468169H1 (LUNGNOE02) | 1 | 496 |
| | | | | 7979128H1 (LSUBDMC01) | 1448 | 2219 |
| | | | | 55048913J1 (ADMEDNV37) | 620 | 1564 |
| 72 | 146907CB1 | 1678 | 270-1678, 1-73 | 71157131V1 | 519 | 1192 |
| | | | | 144826R1 (TLYMNOR01) | 664 | 1259 |
| | | | | 71156479V1 | 1108 | 1678 |
| | | | | 71156776V1 | 1 | 651 |
| 73 | 1513563CB1 | 2374 | 1-1026 | 72106415V1 | 1268 | 2082 |
| | | | | 72106477V1 | 1208 | 1963 |
| | | | | 72106501V1 | 1607 | 2374 |
| | | | | 7463376H1 (LIVRFEE04) | 1 | 557 |
| | | | | 72105630V1 | 570 | 1234 |
| | | | | 72105342V1 | 530 | 1198 |
| 74 | 3144709CB1 | 842 | 38-60, 804-842 | 6728561H1 (COLITUT02) | 1 | 670 |
| | | | | 2837521H2 (DRGLNOT01) | 606 | 842 |
| 75 | 4775686CB1 | 837 | 175-300, 806-837 | 7156574H1 (ESOGTUR02) | 86 | 772 |
| | | | | 805170H1 (BSTMNOT01) | 1 | 208 |
| | | | | 4775686F6 (BRAQNOT01) | 431 | 837 |
| 76 | 5851038CB1 | 828 | 398-762 | 55022063J1 (GPCRDNV87) | 442 | 828 |
| | | | | g2629754 | 1 | 397 |
| | | | | 5851038E7 (FIBAUNT02) | 142 | 661 |
| | | | | 851038H1 (FIBAUNT02) | 141 | 386 |
| 77 | 71850066CB1 | 1696 | 1-653 | 71638522V1 | 396 | 1014 |
| | | | | 5996956H1 (BRAZDIT04) | 1103 | 1696 |
| | | | | 71635790V1 | 851 | 1407 |
| | | | | 2518629F6 (BRAITUT21) | 1 | 478 |
| | | | | 71636467V1 | 473 | 1047 |
| 78 | 2488934CB1 | 841 | 1-218 | 2488934T6 (KIDNTUT13) | 225 | 841 |
| | | | | 2488934F6 (KIDNTUT13) | 1 | 537 |
| 79 | 2667946CB1 | 2752 | 1-566, 2730-2752, 749-909 | 71668418V1 | 895 | 1663 |
| | | | | 8244690H1 (BONEUNR01) | 1 | 666 |
| | | | | 71669177V1 | 1764 | 2417 |
| | | | | 71667244V1 | 2159 | 2752 |
| | | | | 71664085V1 | 1447 | 2225 |
| | | | | 71664868V1 | 646 | 1282 |
| 80 | 2834555CB1 | 934 | 512-934, 1-55, 201-272 | 7002906H1 (COLNFEC01) | 399 | 934 |
| | | | | 3189343R6 (THYMNON04) | 1 | 556 |
| 81 | 5544174CB1 | 815 | 176-481, 61-82 | 5544174F6 (TESTNOC01) | 289 | 815 |
| | | | | 6953446F8 (BRAITDR02) | 1 | 641 |
| 82 | 1728049CB1 | 1242 | 513-962, 1-185 | 724829R6 (SYNOOAT01) | 1 | 673 |
| | | | | 6822418J1 (SINTNOR01) | 502 | 1230 |
| | | | | 1728049F6 (PROSNOT14) | 799 | 1239 |
| | | | | 4803643H1 (MYEPUNT01) | 997 | 1242 |
| 83 | 2425121CB1 | 4217 | 1-1656, 4170-4217 | 1511561F6 (LUNGNOT14) | 1969 | 2533 |
| | | | | 55146378J1 | 1 | 863 |
| | | | | 1293328F1 (PGANNOT03) | 3901 | 4176 |
| | | | | 2291068R6 (BRAINON01) | 3123 | 3718 |
| | | | | 842419R6 (PROSTUT05) | 2707 | 3199 |
| | | | | 3108255F6 (BRSTTUT15) | 903 | 1559 |
| | | | | 7171832H1 (BRSTTMC01) | 1473 | 2025 |
| | | | | 1621469T6 (BRAITUT13) | 3593 | 4169 |
| | | | | 6812454H1 (ADRETUR01) | 2113 | 2680 |
| | | | | 1739860R6 (HIPONON01) | 3416 | 3888 |
| | | | | 3931569H1 (PROSTUT09) | 3982 | 4217 |
| | | | | 6997857R8 (BRAXTDR17) | 573 | 1209 |
| | | | | 7582572H1 (BRAIFEC01) | 1722 | 2108 |
| | | | | 70681972V1 | 2616 | 2968 |
| 84 | 2817925CB1 | 1301 | 1-490, 893-1231 | 7414958T1 (PITUNON01) | 178 | 844 |
| | | | | 1888610F6 (BLADTUT07) | 855 | 1301 |
| | | | | 6305824T6 (NERDTDN03) | 1 | 827 |
| | | | | 8242705J1 (BONEUNR01) | 630 | 1188 |
| 85 | 4000264CB1 | 2148 | 1790-2148, 550-1393 | 7458107H1 (LIVRTUE01) | 1575 | 2148 |
| | | | | 6753255H1 (SINTFER02) | 280 | 780 |
| | | | | 71384040V1 | 1 | 380 |
| | | | | 7071128H1 (BRAUTDR02) | 563 | 1162 |
| | | | | 7022226H1 (PANCNON03) | 1000 | 1640 |
| | | | | 7724208H1 (THYRDIE01) | 1443 | 2045 |
| 86 | 4304004CB1 | 1141 | 961-1141, 376-493, 1-28 | 4304004F8 (BRSTTUT18) | 1 | 553 |
| | | | | 70465082V1 | 497 | 1141 |

TABLE 4-continued

| Polynucleotide SEQ ID NO: | Incyte Polynucleotide ID | Sequence Length | Selected Fragment(s) | Sequence Fragments | 5' Position | 3' Position |
|---|---|---|---|---|---|---|
| 87 | 4945912CB1 | 855 | 80-355, 831-855 | 4945912F8 (SINTNOT25) | 1 | 522 |
| | | | | 71146178V1 | 638 | 852 |
| | | | | 8031651J1 (TESTNOF01) | 397 | 851 |
| | | | | g1941671 | 485 | 855 |
| 88 | 7230481CB1 | 617 | 1-362 | 7230481F8 (BRAXTDR15) | 1 | 617 |
| 89 | 71947526CB1 | 2460 | 1218-1314 | 71265535V1 | 1884 | 2460 |
| | | | | 71947895V1 | 736 | 1561 |
| | | | | 3776352F6 (BRSTNOT27) | 1604 | 2291 |
| | | | | 71682330V1 | 1503 | 2243 |
| | | | | 71947074V1 | 1 | 828 |
| | | | | 72431962D1 | 816 | 1588 |
| 90 | 6843919CB1 | 431 | | 6843919H1 (KIDNTMN03) | 1 | 431 |
| 91 | 5866451CB1 | 1050 | 1-191 | GNN.g7264172_000030_002 | 1 | 1044 |
| | | | | 7317786R8 (BRAWTDK01) | 707 | 1050 |
| 92 | 1310222CB1 | 1822 | 1-221 | 1417610F1 (KIDNNOT09) | 487 | 1141 |
| | | | | SANA03735F1 | 1173 | 1822 |
| | | | | 2383314F6 (ISLTNOT01) | 1 | 562 |
| | | | | 604946H1 (BRSTTUT01) | 1553 | 1822 |
| | | | | 1467420F1 (PANCTUT02) | 606 | 1242 |
| 93 | 1432223CB1 | 855 | | 1432223H1 (BEPINON01) | 1 | 222 |
| | | | | 1476162T6 (LUNGTUT03) | 188 | 849 |
| | | | | 1630467F6 (COLNNOT19) | 373 | 855 |
| 94 | 1537636CB1 | 1440 | 1416-1440 | 801691H1 (BRAVTXT04) | 1 | 264 |
| | | | | 7059329H1 (BRALNON02) | 9 | 730 |
| | | | | g1191911 | 985 | 1440 |
| | | | | 3181951T6 (TLYJNOT01) | 799 | 1326 |
| | | | | 194915T6 (KIDNNOT02) | 416 | 1098 |
| 95 | 1871333CB1 | 1389 | 1-20, 1360-1389, 756-855 | 71129962V1 | 871 | 1389 |
| | | | | 71142771V1 | 600 | 1210 |
| | | | | 71132064V1 | 543 | 1135 |
| | | | | 71179205V1 | 1 | 608 |
| 96 | 17153010CB1 | 1500 | 1-134, 920-971, 1373-1500, 419-753, 1239-1276 | 6934671F6 (SINTTMR02) | 537 | 1273 |
| | | | | 6934671R6 (SINTTMR02) | 775 | 1500 |
| | | | | 7152316F6 (BONEUNR01) | 1 | 668 |
| 97 | 7996779CB1 | 796 | 1-63, 185-196 | 5687774H1 (BRAIUNT01) | 1 | 198 |
| | | | | 7996779H1 (ADRETUC01) | 53 | 796 |
| 98 | 640025CB1 | 2540 | 1-50 | 8077582J1 (ADRETUE02) | 1 | 765 |
| | | | | 7639394H1 (SEMVTDE01) | 1366 | 2059 |
| | | | | 8324134J1 (MIXDUNN04) | 2253 | 2529 |
| | | | | 7440482H1 (ADRETUE02) | 502 | 1123 |
| | | | | g1186398 | 1836 | 2540 |
| | | | | 70673692V1 | 2264 | 2540 |
| | | | | 5506313R6 (BRADDIR01) | 922 | 1412 |
| | | | | 7637348H1 (SINTDIE01) | 1473 | 2075 |
| | | | | 5422789T6 (PROSTMT07) | 1975 | 2524 |
| 99 | 1545079CB1 | 2487 | 1-315 | 6302525H1 (UTREDIT07) | 266 | 596 |
| | | | | 1545079T6 (PROSTUT04) | 1802 | 2471 |
| | | | | 7345625H1 (SYNODIN02) | 649 | 1179 |
| | | | | 4103346F6 (BRSTTUT17) | 450 | 1019 |
| | | | | 2457841F6 (ENDANOT01) | 1754 | 2303 |
| | | | | 066132H1 (HUVESTB01) | 1 | 264 |
| | | | | 1970803H1 (UCMCL5T01) | 206 | 487 |
| | | | | 5599584H1 (UTRENON03) | 2055 | 2487 |
| | | | | 1364772R6 (SCORNON02) | 1249 | 1810 |
| | | | | 6456268H1 (COLNDIC01) | 1138 | 1748 |
| 100 | 2668150CB1 | 701 | 1-110 | 7341082T8 (COLNDIN07) | 1 | 701 |
| 101 | 2804787CB1 | 1956 | 1-39, 507-614, 1014-1454 | 70749428V1 | 791 | 1441 |
| | | | | g2166802 | 1 | 601 |
| | | | | 70749393V1 | 194 | 829 |
| | | | | 70745592V1 | 963 | 1504 |
| | | | | 70054082D1 | 1338 | 1956 |
| 102 | 4003882CB1 | 1063 | 1-1063 | 70788074V1 | 521 | 1063 |
| | | | | 70792833V1 | 1 | 618 |
| 103 | 4737462CB1 | 495 | 1-98, 146-495 | 4737462F6 (THYMNOR02) | 1 | 495 |
| 104 | 4921634CB1 | 880 | 674-880, 450-482 | 4921634F6 (TESTNOT11) | 1 | 588 |
| | | | | 70803614V1 | 322 | 880 |
| 105 | 6254942CB1 | 2666 | 2610-2666, 1-580 | 1943214T6 (HIPONOT01) | 1956 | 2649 |
| | | | | 7744938H1 (ADRETUE04) | 1025 | 1626 |
| | | | | 6476322H1 (PROSTMC01) | 2237 | 2666 |
| | | | | 8133916H1 (SCOMDIC01) | 626 | 1276 |
| | | | | 7991669H2 (UTRSDIC01) | 1 | 510 |
| | | | | 6345860H1 (LUNGDIS03) | 387 | 712 |
| | | | | 1258806F6 (MENITUT03) | 2219 | 2657 |
| | | | | 1271246F1 (TESTTUT02) | 1459 | 2140 |

TABLE 4-continued

| Polynucleotide SEQ ID NO: | Incyte Polynucleotide ID | Sequence Length | Selected Fragment(s) | Sequence Fragments | 5' Position | 3' Position |
|---|---|---|---|---|---|---|
| 106 | 6747838CB1 | 1293 | 1-145, 654-1293 | g4266852 | 258 | 653 |
| | | | | 6747838F8 (BRAXNOT03) | 675 | 1293 |
| | | | | 6919936H1 (BRAITDR03) | 1 | 522 |
| | | | | GBI.g7960452.edit | 1 | 1293 |
| 107 | 7050585CB1 | 693 | 1-693 | 7050539H1 (BRACNOK02) | 1 | 693 |
| | | | | 7050539R8 (BRACNOK02) | 1 | 693 |
| 108 | 3880321CB1 | 860 | 1-509, 787-860 | 71880126V1 | 1 | 600 |
| | | | | 71883910V1 | 280 | 860 |
| 109 | 3950005CB1 | 2738 | 722-1030, 2409-2738 | 70770220V1 | 1321 | 1894 |
| | | | | 4082341F6 (CONFNOT02) | 2266 | 2738 |
| | | | | 4081043F8 (CONFNOT02) | 1167 | 1624 |
| | | | | 70775991V1 | 442 | 1049 |
| | | | | 6837615H1 (BRSTNON02) | 2048 | 2422 |
| | | | | 5276224H1 (MUSLNOT01) | 1662 | 1910 |
| | | | | 4795834F8 (LIVRTUT09) | 1060 | 1602 |
| | | | | 71346657V1 | 1 | 592 |
| | | | | 3175849T6 (UTRSTUT04) | 1820 | 2369 |
| | | | | 70776014V1 | 672 | 1166 |
| 110 | 3043830CB1 | 6108 | 1-3559 | 6902402H1 (MUSLTDR02) | 5094 | 5582 |
| | | | | 7174759H1 (BRSTTMC01) | 3289 | 3958 |
| | | | | 7174777H1 (BRSTTMC01) | 2657 | 3342 |
| | | | | 2775475F6 (PANCNOT15) | 1599 | 2218 |
| | | | | 8225152H1 (COLHTUS02) | 4437 | 5131 |
| | | | | 1964133R6 (BRSTNOT04) | 4379 | 5124 |
| | | | | 55024920H1 (PKINDNV13) | 1 | 693 |
| | | | | 7689084J1 (PROSTME06) | 5474 | 6108 |
| | | | | 55026065J1 (PKINDNV23) | 596 | 1309 |
| | | | | 7173660H2 (BRSTTMC01) | 2466 | 3033 |
| | | | | 2690419F6 (LUNGNOT23) | 3855 | 4423 |
| | | | | 3541678H1 (SEMVNOT04) | 3678 | 4015 |
| | | | | 1961558H1 (BRSTNOT04) | 4066 | 4425 |
| | | | | 55025178J1 (PKINDNV15) | 1033 | 1846 |
| | | | | 3690484F6 (HEAANOT01) | 1908 | 2583 |
| 111 | 002479CB1 | 1110 | 1-836 | 70111790V1 | 560 | 1110 |
| | | | | 70111692V1 | 1 | 613 |
| 112 | 1395420CB1 | 1902 | 1521-1902, 1-27 | 70501084V1 | 1003 | 1462 |
| | | | | 8175577H1 (FETANOA01) | 298 | 828 |
| | | | | 7234467H1 (BRAXTDR15) | 859 | 1429 |
| | | | | 3033671F6 (TLYMNOT05) | 1299 | 1902 |
| | | | | 7730353R6 (UTRCDIE01) | 340 | 997 |
| | | | | 5891913H1 (UTRENOT06) | 1 | 318 |
| 113 | 1634103CB1 | 1960 | 305-324, 1-265 | 6824111H1 (SINTNOR01) | 1 | 499 |
| | | | | 7339828H1 (SINTNON02) | 1408 | 1960 |
| | | | | 6753665J1 (SINTFER02) | 326 | 1069 |
| | | | | 71264720V1 | 1078 | 1752 |
| | | | | 1815281F6 (PROSNOT20) | 1182 | 1774 |
| | | | | 1634103F6 (COLNNOT19) | 586 | 1156 |
| 114 | 2422023CB1 | 540 | 517-540 | 2422023T6 (SCORNON01) | 1 | 50 |
| | | | | 2244504R6 (HIPONON02) | 168 | 540 |
| 115 | 4241771CB1 | 1321 | 1-1023, 1301-1321 | 72582414V1 | 500 | 1321 |
| | | | | 6013180F8 (FIBRUNT02) | 1 | 629 |
| 116 | 5046408CB1 | 536 | 1-536 | 5046408F8 (PLACFER01) | 1 | 535 |
| | | | | 5046408H1 (PLACFER01) | 249 | 536 |
| 117 | 6271376CB1 | 1345 | 1-38, 1238-1345, 933-983 | 4864015F8 (PROSTUT09) | 1 | 660 |
| | | | | 8083757H1 (BRACDIK08) | 621 | 1345 |
| 118 | 7032326CB1 | 1060 | 403-1060 | 6800476R8 (COLENOR03) | 371 | 1060 |
| | | | | 6800476F8 (COLENOR03) | 1 | 653 |
| 119 | 7078691CB1 | 1192 | 113-1192 | 6262640F8 (MCLDTXN03) | 491 | 1192 |
| | | | | 7078691H1 (BRAUTDR04) | 1 | 579 |
| 120 | 7089352CB1 | 693 | 1-554 | 7089352F7 (BRAUTDR03) | 1 | 693 |
| 121 | 7284533CB1 | 888 | 1-340, 761-888 | 7284533H1 (BRAIFEJ01) | 342 | 888 |
| | | | | 7284533R8 (BRAIFEJ01) | 2 | 582 |
| | | | | 7284533F8 (BRAIFEJ01) | 1 | 508 |
| 122 | 7482209CB1 | 618 | 480-618 | 7470241H1 (LUNGNOE02) | 97 | 618 |
| | | | | g6989749 | 1 | 479 |
| 123 | 7482314CB1 | 755 | 1-78, 198-225, 667-755 | g2055889 | 226 | 755 |
| | | | | 6435849F8 (LUNGNON07) | 1 | 420 |
| 124 | 7482339CB1 | 386 | | g1833238 | 1 | 386 |
| 125 | 7949557CB1 | 524 | 1-79, 191-524 | 7949557J1 (BRABNOE02) | 1 | 524 |
| 126 | 1555909CB1 | 3836 | 1-2343, 3746-3836 | 1004107R1 (BRSTNOT03) | 3403 | 3741 |
| | | | | 5000814F8 (PROSTUT21) | 148 | 690 |
| | | | | 7687354H1 (PROSTME06) | 968 | 1595 |
| | | | | 1506470F6 (BRAITUT07) | 2630 | 3218 |
| | | | | 3236711F6 (COLNUCT03) | 1904 | 2434 |

TABLE 4-continued

| Polynucleotide SEQ ID NO: | Incyte Polynucleotide ID | Sequence Length | Selected Fragment(s) | Sequence Fragments | 5' Position | 3' Position |
|---|---|---|---|---|---|---|
| | | | | 7042338H1 (UTRSTMR02) | 1437 | 1953 |
| | | | | 5138056H1 (OVARDIT04) | 3543 | 3791 |
| | | | | 5191912H1 (OVARDIT06) | 3170 | 3432 |
| | | | | 1555909T1 (BLADTUT04) | 2255 | 2788 |
| | | | | 7166118H1 (PLACNOR01) | 1658 | 2199 |
| | | | | 7632327H1 (BLADTUE01) | 629 | 1297 |
| | | | | 3979568H1 (LUNGTUT08) | 3493 | 3753 |
| | | | | 7403782H1 (SINIDME01) | 361 | 817 |
| | | | | g1645738 | 3515 | 3836 |
| | | | | 3675191H1 (PLACNOT07) | 1 | 288 |
| | | | | 4947920H1 (SINTNOT25) | 2222 | 2475 |
| | | | | 1686339H1 (PROSNOT15) | 3239 | 3462 |

TABLE 5

| Polynucleotide SEQ ID NO: | Incyte Project ID: | Representative Library |
|---|---|---|
| 64 | 2719959CB1 | LUNGTUT10 |
| 65 | 7473618CB1 | HEAONOE01 |
| 66 | 3564136CB1 | SKINNOT05 |
| 67 | 624334CB1 | BRAXNOT02 |
| 68 | 7483393CB1 | BRADDIR01 |
| 69 | 1799943CB1 | COLNNOT27 |
| 70 | 2013095CB1 | TESTNOT03 |
| 71 | 4674740CB1 | ADMEDNV37 |
| 72 | 146907CB1 | TLYMNOR01 |
| 73 | 1513563CB1 | BRAINOT11 |
| 74 | 3144709CB1 | DRGLNOT01 |
| 75 | 4775686CB1 | BRAQNOT01 |
| 76 | 5851038CB1 | FIBAUNT02 |
| 77 | 71850066CB1 | URETTUE01 |
| 78 | 2488934CB1 | KIDNTUT13 |
| 79 | 2667946CB1 | UTRENOT09 |
| 80 | 2834555CB1 | THYMNON04 |
| 81 | 5544174CB1 | BRAITDR02 |
| 82 | 1728049CB1 | PROSNOT14 |
| 83 | 2425121CB1 | BLADNOT06 |
| 84 | 2817925CB1 | BRSTNOT14 |
| 85 | 4000264CB1 | HNT2AZS07 |
| 86 | 4304004CB1 | PROSTUT08 |
| 87 | 4945912CB1 | SINTNOT25 |
| 88 | 7230481CB1 | BRAXTDR15 |
| 89 | 71947526CB1 | SINTNOT22 |
| 90 | 6843919CB1 | KIDNTMN03 |
| 91 | 5866451CB1 | BRAWTDK01 |
| 92 | 1310222CB1 | COLNFET02 |
| 93 | 1432223CB1 | COLNNOT19 |
| 94 | 1537636CB1 | BRABDIR01 |
| 95 | 1871333CB1 | LIVRTUT12 |
| 96 | 7153010CB1 | BONEUNR01 |
| 97 | 7996779CB1 | ADRETUC01 |
| 98 | 640025CB1 | BRSTNOT03 |
| 99 | 1545079CB1 | ENDANOT01 |
| 100 | 2668150CB1 | COLNDIN02 |
| 101 | 2804787CB1 | BLADTUT08 |
| 102 | 4003882CB1 | LUNLTUE01 |
| 103 | 4737462CB1 | THYMNOR02 |
| 104 | 4921634CB1 | TESTNOT11 |
| 105 | 6254942CB1 | KIDNNOT05 |
| 106 | 6747838CB1 | BRAXNOT03 |
| 107 | 7050585CB1 | BRACNOK02 |
| 108 | 3880321CB1 | OVARNON03 |
| 109 | 3950005CB1 | CONFNOT02 |
| 110 | 3043830CB1 | BRSTNOT07 |
| 111 | 002479CB1 | U937NOT01 |
| 112 | 1395420CB1 | THYRNOT03 |
| 113 | 1634103CB1 | STOMFET01 |
| 114 | 2422023CB1 | SCORNON02 |
| 115 | 4241771CB1 | LATRTUT02 |
| 116 | 5046408CB1 | PLACFER01 |
| 117 | 6271376CB1 | PROSTUT09 |
| 118 | 7032326CB1 | COLENOR03 |
| 119 | 7078691CB1 | MCLDTXN03 |
| 120 | 7089352CB1 | BRAUTDR03 |
| 121 | 7284533CB1 | BRAIFEJ01 |
| 122 | 7482209CB1 | LUNGNOE02 |
| 123 | 7482314CB1 | LUNGNON07 |
| 125 | 7949557CB1 | BRABNOE02 |
| 126 | 1555909CB1 | PLACFER01 |

TABLE 6

| Library | Vector | Library Description |
|---|---|---|
| ADMEDNV37 | pCR2-TopoTA | Library was constructed using pooled cDNA from 111 different donors. cDNA was generated using mRNA isolated from pooled skeletal muscle tissue removed from 10 Caucasian male and female donors, ages 21-57, who died from sudden death; from pooled thymus tissue removed from 9 Caucasian male and female donors, ages 18-32, who died from sudden death; from pooled fetal liver tissue removed from 32 Caucasian male and female fetuses, ages 18-24 weeks, who died from spontaneous abortions; from pooled fetal kidney tissue removed from 59 Caucasian male and female fetuses, ages 20-33 weeks, who died from spontaneous abortions; and from fetal brain tissue removed from a 23-week-old Caucasian male fetus who died from fetal demise. |
| ADRETUC01 | PSPORT1 | This large size fractionated library was constructed using pooled cDNA from two donors. cDNA was generated using mRNA isolated from adrenal gland tissue removed from an 8-year-old Black male (donor A), who died from anoxia and from adrenal tumor tissue removed from a 52-year-old Caucasian female (donor B) during a unilateral adrenalectomy. For donor A, serologies were negative. Patient medications included DDAVP, Versed, and labetalol. For donor B, pathology indicated a pheochromocytoma. Patient history included benign hypertension, depressive disorder, chronic sinusitis, idiopathic proctocolitis, a cataract, and |

TABLE 6-continued

| Library | Vector | Library Description |
|---|---|---|
| | | urinary tract infection. Previous surgeries included a vaginal hysterectomy. Patient medications included Procardia (one dose only) and Prozac for 5 years. Family history included secondary Parkinsonism in the father; cerebrovascular disease, secondary Parkinsonism and anxiety state in the mother; and benign hypertension, atherosclerotic coronary artery disease, hyperlipidemia, and brain cancer in the sibling(s). |
| BLADNOT06 | pINCY | Library was constructed using RNA isolated from the posterior wall bladder tissue removed from a 66-year-old Caucasian male during a radical prostatectomy, radical cystectomy and urinary diversion. Pathology for the associated tumor tissue indicated grade 3 transitional cell carcinoma on the anterior wall of the bladder and urothelium. Patient history included lung neoplasm, and tobacco abuse in remission. Family history included a malignant breast neoplasm, tuberculosis, cerebrovascular disease, atherosclerotic coronary artery disease, and lung cancer. |
| BLADTUT08 | pINCY | Library was constructed using RNA isolated from bladder tumor tissue removed from a 72-year-old Caucasian male during a radical cystectomy and prostatectomy. Pathology indicated an invasive grade 3 (of 3) transitional cell carcinoma in the right bladder base. Patient history included pure hypercholesterolemia and tobacco abuse. Family history included myocardial infarction, cerebrovascular disease, and brain cancer. |
| BONEUNR01 | PCDNA2.1 | This random primed library was constructed using pooled cDNA from two different donors. cDNA was generated using mRNA isolated from an untreated MG-63 cell line derived from an osteosarcoma tumor removed from a 14-year-old Caucasian male (donor A) and using mRNA isolated from sacral bone tumor tissue removed from an 18-year-old Caucasian female (donor B) during an exploratory laparotomy and soft tissue excision. Pathology indicated giant cell tumor of the sacrum in donor B. Donor B's history included pelvic joint pain, constipation, urinary incontinence, unspecified abdominal/pelvic symptoms, and a pelvic soft tissue malignant neoplasm. Family history included prostate cancer in donor B. |
| BRABDIR01 | pINCY | Library was constructed using RNA isolated from diseased cerebellum tissue removed from the brain of a 57-year-old Caucasian male, who died from a cerebrovascular accident. Patient history included Huntington's disease, emphysema, and tobacco abuse. |
| BRABNOE02 | PBK-CMV | This 5' biased random primed library was constructed using RNA isolated from vermis tissue removed from a 35-year-old Caucasian male who died from cardiac failure. Pathology indicated moderate leptomeningeal fibrosis and multiple microinfarctions of the cerebral neocortex. Patient history included dilated cardiomyopathy, congestive heart failure, cardiomegaly, and an enlarged spleen and liver. Patient medications included simethicone, Lasix, Digoxin, Colace, Zantac, captopril, and Vasotec. |
| BRACNOK02 | PSPORT1 | This amplified and normalized library was constructed using RNA isolated from posterior cingulate tissue removed from an 85-year-old Caucasian female who died from myocardial infarction and retroperitoneal hemorrhage. Pathology indicated atherosclerosis, moderate to severe, involving the circle of Willis, middle cerebral, basilar and vertebral arteries; infarction, remote, left dentate nucleus; and amyloid plaque deposition consistent with age. There was mild to moderate leptomeningeal fibrosis, especially over the convexity of the frontal lobe. There was mild generalized atrophy involving all lobes. The white matter was mildly thinned. Cortical thickness in the temporal lobes, both maximal and minimal, was slightly reduced. The substantia nigra pars compacta appeared mildly depigmented. Patient history included COPD, hypertension, and recurrent deep venous thrombosis. 6.4 million independent clones from this amplified library were normalized in one round using conditions adapted Soares et al., PNAS (1994) 91: 9228-9232 and Bonaldo et al., Genome Research 6 (1996): 791. |
| BRADDIR01 | pINCY | Library was constructed using RNA isolated from diseased choroid plexus tissue of the lateral ventricle, removed from the brain of a 57-year-old Caucasian male, who died from a cerebrovascular accident. |
| BRAIFEJ01 | PRARE | This random primed 5' cap isolated library was constructed using RNA isolated from brain tissue removed from a Caucasian male fetus who died at 23 weeks' gestation from premature birth. Serologies were negative. Family history included diabetes in the mother. |
| BRAINOT11 | pINCY | Library was constructed using RNA isolated from brain tissue removed from the right temporal lobe of a 5-year-old Caucasian male during a hemispherectomy. Pathology indicated extensive polymicrogyria and mild to moderate gliosis (predominantly subpial and subcortical), consistent with chronic seizure disorder. Family history included a cervical neoplasm. |
| BRAITDR02 | PCDNA2.1 | This random primed library was constructed using RNA isolated from allocortex, neocortex, anterior and frontal cingulate tissue removed from a 55-year-old Caucasian female who died from cholangiocarcinoma. Pathology indicated mild meningeal fibrosis predominately over the convexities, scattered axonal spheroids in the white matter of the cingulate cortex and the thalamus, and a few scattered neurofibrillary tangles in the entorhinal cortex and the periaqueductal gray region. Pathology for the associated tumor tissue indicated well-differentiated cholangiocarcinoma of the liver with residual or relapsed tumor. Patient history included cholangiocarcinoma, post-operative Budd-Chiari syndrome, biliary ascites, hydrothorax, dehydration, malnutrition, oliguria and acute renal failure. Previous surgeries included cholecystectomy and resection of 85% of the liver. |

TABLE 6-continued

| Library | Vector | Library Description |
|---|---|---|
| BRAQNOT01 | pINCY | Library was constructed using RNA isolated from midbrain tissue removed from a 35-year-old Caucasian male. No neuropathology was found. Patient history included dilated cardiomyopathy, congestive heart failure, and an enlarged spleen and liver. |
| BRAUTDR03 | PCDNA2.1 | This random primed library was constructed using RNA isolated from pooled globus pallidus and substantia innominata tissue removed from a 55-year-old Caucasian female who died from cholangiocarcinoma. Pathology indicated mild meningeal fibrosis predominately over the convexities, scattered axonal spheroids in the white matter of the cingulate cortex and the thalamus, and a few scattered neurofibrillary tangles in the entorhinal cortex and the periaqueductal gray region. Pathology for the associated tumor tissue indicated well-differentiated cholangiocarcinoma of the liver with residual or relapsed tumor. Patient history included cholangiocarcinoma, post-operative Budd-Chiari syndrome, biliary ascites, hydrothorax, dehydration, malnutrition, oliguria and acute renal failure. Previous surgeries included cholecystectomy and resection of 85% of the liver. |
| BRAWTDK01 | PSPORT1 | This amplified and normalized library was constructed using RNA isolated from dentate nucleus tissue removed from a 55-year-old Caucasian female who died from cholangiocarcinoma. Pathology indicated no diagnostic abnormalities in the brain or intracranial vessels. There was mild meningeal fibrosis predominately over the convexities There were scattered axonal spheroids in the white matter of the cingulate cortex and thalamus. There were a few scattered neurofibrillary tangles in the entorhinal cortex and periaqueductal gray region. Pathology for the associated tumor tissue indicated well-differentiated cholangiocarcinoma of the liver with residual or relapsed tumor, surrounded by foci of bile lakes beneath the hepatic surface scar. The liver had extensive surface scarring, congestion, cholestasis, hemorrhage, necrosis, and chronic inflammation. The patient presented with nausea, vomiting, dehydration, malnutrition, oliguria, and acute renal failure. Patient history included post-operative Budd-Chiari syndrome, biliary ascites, bilateral acute bronchopneumonia with microabscesses, hydrothorax, and bilateral leg pitting edema. Previous surgeries included cholecystectomy, liver resection, hysterectomy, bilateral salpingo-oophorectomy, and portocaval shunt. The patient was treated with a nasogastic feeding tube, biliary drainage stent, paracentesis, pleurodesis and abdominal ultrasound. Patient medications included Ampicillin, niacin, furosemide, Aldactone, Benadryl, and morphine. Independent clones from this amplified library were normalized in one round using conditions adapted from Soares et al., PNAS (1994) 91: 9228-9232 and Bonaldo et al., Genome Research 6 (1996): 791. |
| BRAXNOT02 | pINCY | Library was constructed using RNA isolated from cerebellar tissue removed from a 64-year-old male. Patient history included carcinoma of the left bronchus. |
| BRAXNOT03 | pINCY | Library was constructed using RNA isolated from sensory-motor cortex tissue obtained from the brain of a 35-year-old Caucasian male who died from cardiac failure. Pathology indicated moderate leptomeningeal fibrosis and multiple microinfarctions of the cerebral neocortex. Patient history included dilated cardiomyopathy, congestive heart failure, cardiomegaly and an enlarged spleen and liver. |
| BRAXTDR15 | PCDNA2.1 | This random primed library was constructed using RNA isolated from superior parietal neocortex tissue removed from a 55-year-old Caucasian female who died from cholangiocarcinoma. Pathology indicated mild meningeal fibrosis predominately over the convexities, scattered axonal spheroids in the white matter of the cingulate cortex and the thalamus, and a few scattered neurofibrillary tangles in the entorhinal cortex and the periaqueductal gray region. Pathology for the associated tumor tissue indicated well-differentiated cholangiocarcinoma of the liver with residual or relapsed tumor. Patient history included cholangiocarcinoma, post-operative Budd-Chiari syndrome, biliary ascites, hydrothorax, dehydration, malnutrition, oliguria and acute renal failure. Previous surgeries included cholecystectomy and resection of 85% of the liver. |
| BRSTNOT03 | PSPORT1 | Library was constructed using RNA isolated from diseased breast tissue removed from a 54-year-old Caucasian female during a bilateral radical mastectomy. Pathology for the associated tumor tissue indicated residual invasive grade 3 mammary ductal adenocarcinoma. Patient history included kidney infection and condyloma acuminatum. Family history included benign hypertension, hyperlipidemia and a malignant neoplasm of the colon. |
| BRSTNOT07 | pINCY | Library was constructed using RNA isolated from diseased breast tissue removed from a 43-year-old Caucasian female during a unilateral extended simple mastectomy. Pathology indicated mildly proliferative fibrocystic changes with epithelial hyperplasia, papillomatosis, and duct ectasia. Pathology for the associated tumor tissue indicated invasive grade 4, nuclear grade 3 mammary adenocarcinoma with extensive comedo necrosis. Family history included epilepsy, cardiovascular disease, and type II diabetes. |
| BRSTNOT14 | pINCY | Library was constructed using RNA isolated from breast tissue removed from a 62-year-old Caucasian female during a unilateral extended simple mastectomy. Pathology for the associated tumor tissue indicated an invasive grade 3 (of 4), nuclear grade 3 (of 3) adenocarcinoma, ductal type. Ductal carcinoma in situ, comedo type, comprised 60% of the tumor mass. Metastatic adenocarcinoma was identified in one (of 14) axillary lymph nodes with no perinodal extension. The tumor cells were strongly positive for estrogen receptors and weakly positive for progesterone receptors. Patient history included a benign colon neoplasm, hyperlipidemia, cardiac dysrhythmia, and obesity. Family history included |

TABLE 6-continued

| Library | Vector | Library Description |
|---|---|---|
| | | atherosclerotic coronary artery disease, myocardial infarction, colon cancer, ovarian cancer, lung cancer, and cerebrovascular disease. |
| COLENOR03 | PCDNA2.1 | Library was constructed using RNA isolated from colon epithelium tissue removed from a 13-year-old Caucasian female who died from a motor vehicle accident. |
| COLNDIN02 | pINCY | This normalized library was constructed from 4.72 million independent clones from a diseased colon and colon polyp tissue library. Starting RNA was made from pooled cDNA from two donors. cDNA was generated using mRNA isolated from diseased colon tissue removed from the cecum and descending colon of a 16-year-old Caucasian male (donor A) during partial colectomy, temporary ileostomy, and colonoscopy and from diseased colon polyp tissue removed from the cecum of a 67-year-old female (donor B). Pathology indicated innumerable (greater than 100) adenomatous polyps with low-grade dysplasia involving the entire colonic mucosa in the setting of familial polyposis coli (donor A), and a benign cecum polyp (donor B). Pathology for the associated tumor tissue (B) indicated invasive grade 3 adenocarcinoma that arose in tubulovillous adenoma forming a fungating mass in the cecum. The tumor infiltrated just through the muscularis propria. Multiple (2 of 17) regional lymph nodes were involved by metastatic adenocarcinoma. A tubulovillous adenoma and multiple (6) tubular adenomas with low-grade dysplasia were observed in the cecum and ascending colon. Donor A presented with abdominal pain and flatulence. The patient was not taking any medications. Family history included benign colon neoplasm in the father and sibling(s); benign hypertension, cerebrovascular disease, breast cancer, uterine cancer, and type II diabetes in the grandparent(s). |
| COLNFET02 | pINCY | Library was constructed using RNA isolated from the colon tissue of a Caucasian female fetus, who died at 20 weeks' gestation. |
| COLNNOT19 | pINCY | Library was constructed using RNA isolated from the cecal tissue of an 18-year-old Caucasian female. The cecal tissue, along with the appendix and ileum tissue, were removed during bowel anastomosis. Pathology indicated Crohn's disease of the ileum, involving 15 cm of the small bowel. |
| COLNNOT27 | pINCY | Library was constructed using RNA isolated from diseased cecal tissue removed from 31-year-old Caucasian male during a total intra-abdominal colectomy, appendectomy, and permanent ileostomy. Pathology indicated severe active Crohn's disease involving the colon from the cecum to the rectum. There were deep rake-like ulcerations which spared the intervening mucosa. The ulcers extended into the muscularis, and there was transmural inflammation. Patient history included an irritable colon. Previous surgeries included a colonscopy. |
| CONFNOT02 | pINCY | Library was constructed using RNA isolated from abdominal fat tissue removed from a 52-year-old Caucasian female during an ileum resection and incarcerated ventral hernia repair. Patient history included diverticulitis. Family history included hyperlipidemia. |
| DRGLNOT01 | pINCY | Library was constructed using RNA isolated from dorsal root ganglion tissue removed from the cervical spine of a 32-year-old Caucasian male who died from acute pulmonary edema and bronchopneumonia, bilateral pleural and pericardial effusions, and malignant lymphoma (natural killer cell type). Patient history included probable cytomegalovirus, infection, hepatic congestion and steatosis, splenomegaly, hemorrhagic cystitis, thyroid hemorrhage, and Bell's palsy. Surgeries included colonoscopy, large intestine biopsy, adenotonsillectomy, and nasopharyngeal endoscopy and biopsy; treatment included radiation therapy. |
| ENDANOT01 | PBLUESCRIPT | Library was constructed using RNA isolated from aortic endothelial cell tissue from an explanted heart removed from a male during a heart transplant. |
| FIBAUNT02 | pINCY | Library was constructed using RNA isolated from untreated aortic adventitial fibroblasts obtained from a 65-year-old Caucasian female. |
| HEAONOE01 | PCDNA2.1 | This 5' biased random primed library was constructed using RNA isolated from the aorta of a 39-year-old Caucasian male, who died from a gunshot wound. Serology was positive for cytomegalovirus (CMV). Patient history included tobacco abuse (one pack of cigarettes per day for 25 years), and occasionally cocaine, marijuana, and alcohol use. |
| HNT2AZS07 | PSPORT1 | This subtracted library was constructed from RNA isolated from an hNT2 cell line (derived from a human teratocarcinoma that exhibited properties characteristic of a committed neuronal precursor) treated for three days with 0.35 micromolar AZ. The hybridization probe for subtraction was derived from a similarly constructed library from untreated hNT2 cells. 3.08M clones from the AZ-treated library were subjected to three rounds of subtractive hybridization with 3.04M clones from the untreated library. Subtractive hybridization conditions were based on the methodologies of Swaroop et al. (NAR (1991) 19: 1954) and Bonaldo et al. (Genome Research (1996) 6: 791). |
| KIDNNOT05 | PSPORT1 | Library was constructed using RNA isolated from the kidney tissue of a 2-day-old Hispanic female, who died from cerebral anoxia. Family history included congenital heart disease. |
| KIDNTMN03 | pINCY | This normalized kidney tissue library was constructed from 2.08 million independent clones from a pool of two libraries from two different donors. Starting RNA was made from right kidney tissue removed from an 8-year-old Caucasian female (donor A) who died from a motor vehicle accident and left kidney medulla and cortex tissue removed from a 53-year-old Caucasian female (donor B) during a nephroureterectomy. In donor B, pathology for the matched tumor tissue indicated grade 2 renal cell carcinoma involving the lower pole of the kidney. Medical history included hyperlipidemia, cardiac dysrhythmia, metrorrhagia, normal delivery, cerebrovascular disease, and atherosclerotic coronary artery disease in |

TABLE 6-continued

| Library | Vector | Library Description |
|---|---|---|
| | | donor B. The library was normalized in two rounds using conditions adapted from Soares et al., PNAS (1994) 91: 9228-9232 and Bonaldo et al., Genome Research 6 (1996): 791, except that a significantly longer (48 hours/round) reannealing hybridization was used. |
| KIDNTUT13 | pINCY | Library was constructed using RNA isolated from kidney tumor tissue removed from a 51-year-old Caucasian female during a nephroureterectomy. Pathology indicated a grade 3 renal cell carcinoma. Patient history included depressive disorder, hypoglycemia, and uterine endometriosis. Family history included calculus of the kidney, colon cancer, and type II diabetes. |
| LATRTUT02 | pINCY | Library was constructed using RNA isolated from a myxoma removed from the left atrium of a 43-year-old Caucasian male during annuloplasty. Pathology indicated atrial myxoma. Patient history included pulmonary insufficiency, acute myocardial infarction, atherosclerotic coronary artery disease, hyperlipidemia, and tobacco use. Family history included benign hypertension, acute myocardial infarction, atherosclerotic coronary artery disease, and type II diabetes. |
| LIVRTUT12 | pINCY | Library was constructed using RNA isolated from a treated C3A hepatocyte cell line, which is a derivative of Hep G2, a cell line derived from a hepatoblastoma removed from a 15-year-old Caucasian male. The cells were treated with 3-methylcholanthrene (MCA), 5 mM for 48 hours. |
| LUNGNOE02 | PSPORT | This 5' biased random primed library was constructed using RNA isolated from lung tissue removed from a 35-year-old Caucasian female during who died from a cerebrovascular accident. Serologies were negative. Patient history included mononucleosis, high blood pressure during pregnancies and alcohol use. |
| LUNGNON07 | pINCY | This normalized lung tissue library was constructed from 5.1 million independent clones from a lung tissue library. Starting RNA was made from RNA isolated from lung tissue. The library was normalized in two rounds using conditions adapted from Soares et al., PNAS (1994) 91: 9228-9232 and Bonaldo et al., Genome Research (1996) 6: 791, except that a significantly longer (48 hours/round) reannealing hybridization was used. |
| LUNGTUT10 | pINCY | Library was constructed using RNA isolated from lung tumor tissue removed from the left upper lobe of a 65-year-old Caucasian female during a segmental lung resection. Pathology indicated a metastatic grade 2 myxoid liposarcoma and a metastatic grade 4 liposarcoma. Patient history included soft tissue cancer, breast cancer, and secondary lung cancer. |
| LUNLTUE01 | PCDNA2.1 | This 5' biased random primed library was constructed using RNA isolated from left upper lobe lung tumor tissue removed from a 56-year-old Caucasian male during complete pneumonectomy, pericardectomy and regional lymph node excision. Pathology indicated grade 3 squamous cell carcinoma forming a mass in the left upper lobe centrally. The tumor extended through pleura into adjacent pericardium. Patient history included hemoptysis and tobacco abuse. Family history included benign hypertension, cerebrovascular accident, atherosclerotic coronary artery disease in the mother; prostate cancer in the father; and type II diabetes in the sibling(s). |
| MCLDTXN03 | pINCY | This normalized dendritic cell library was constructed from one million independent clones from a pool of two derived dendritic cell libraries. Starting libraries were constructed using RNA isolated from untreated and treated derived dendritic cells from umbilical cord blood CD34+ precursor cells removed from a male. The cells were derived with granulocyte/macrophage colony stimulating factor (GM-CSF), tumor necrosis factor alpha (TNF alpha), and stem cell factor (SCF). The GM-CSF was added at time 0 at 100 ng/ml, the TNF alpha was added at time 0 at 2.5 ng/ml, and the SCF was added at time 0 at 25 ng/ml. Incubation time was 13 days. The treated cells were then exposed to phorbol myristate acetate (PMA), and Ionomycin. The PMA and Ionomycin were added at 13 days for five hours. The library was normalized in two rounds using conditions adapted from Soares et al., PNAS (1994) 91: 9228-9232 and Bonaldo et al., Genome Research (1996) 6: 791, except that a significantly longer (48 hours/round) reannealing hybridization was used. |
| OVARNON03 | pINCY | This normalized ovarian tissue library was constructed from 5 million independent clones from an ovary library. Starting RNA was made from ovarian tissue removed from a 36-year-old Caucasian female during total abdominal hysterectomy, bilateral salpingo-oophorectomy, soft tissue excision, and an incidental appendectomy. Pathology for the associated tumor tissue indicated one intramural and one subserosal leiomyomata of the myometrium. The endometrium was proliferative phase. Patient history included deficiency anemia, calculus of the kidney, and a kidney anomaly. Family history included hyperlipidemia, acute myocardial infarction, atherosclerotic coronary artery disease, type II diabetes, and chronic liver disease. The library was normalized in two rounds using conditions adapted from Soares et al., PNAS (1994) 91: 9228 and Bonaldo et al., Genome Research (1996) 6: 791, except that a significantly longer (48 hours/round) reannealing hybridization was used. |
| PLACFER01 | pINCY | The library was constructed using RNA isolated from placental tissue removed from a Caucasian fetus, who died after 16 weeks' gestation from fetal demise and hydrocephalus. Patient history included umbilical cord wrapped around the head (3 times) and the shoulders (1 time). Serology was positive for anti-CMV. Family history included multiple pregnancies and live births, and an abortion. |
| PLACFER01 | pINCY | The library was constructed using RNA isolated from placental tissue removed from a Caucasian fetus, who died after 16 weeks' gestation from fetal demise and hydrocephalus. Patient history included umbilical cord wrapped around the head (3 times) and the shoulders (1 time). Serology was positive for anti-CMV. Family history included multiple pregnancies and live births, and an abortion. |

TABLE 6-continued

| Library | Vector | Library Description |
|---|---|---|
| PROSNOT14 | pINCY | Library was constructed using RNA isolated from diseased prostate tissue removed from a 60-year-old Caucasian male during radical prostatectomy and regional lymph node excision. Pathology indicated adenofibromatous hyperplasia. Pathology for the associated tumor tissue indicated an adenocarcinoma (Gleason grade 3 + 4). The patient presented with elevated prostate specific antigen (PSA). Patient history included a kidney cyst and hematuria. Family history included benign hypertension, cerebrovascular disease, and arteriosclerotic coronary artery disease. |
| PROSTUT08 | pINCY | Library was constructed using RNA isolated from prostate tumor tissue removed from a 60-year-old Caucasian male during radical prostatectomy and regional lymph node excision. Pathology indicated an adenocarcinoma (Gleason grade 3 + 4). Adenofibromatous hyperplasia was also present. The patient presented with elevated prostate specific antigen (PSA). Patient history included a kidney cyst, and hematuria. Family history included tuberculosis, cerebrovascular disease, and arteriosclerotic coronary artery disease. |
| PROSTUT09 | pINCY | Library was constructed using RNA isolated from prostate tumor tissue removed from a 66-year-old Caucasian male during a radical prostatectomy, radical cystectomy, and urinary diversion. Pathology indicated grade 3 transitional cell carcinoma. The patient presented with prostatic inflammatory disease. Patient history included lung neoplasm, and benign hypertension. Family history included a malignant breast neoplasm, tuberculosis, cerebrovascular disease, atherosclerotic coronary artery disease and lung cancer. |
| SCORNON02 | PSPORT1 | This normalized spinal cord library was constructed from 3.24M independent clones from the a spinal cord tissue library. RNA was isolated from the spinal cord tissue removed from a 71-year-old Caucasian male who died from respiratory arrest. Patient history included myocardial infarction, gangrene, and end stage renal disease. The normalization and hybridization conditions were adapted from Soares et al. (PNAS (1994) 91: 9228). |
| SINTNOT22 | pINCY | Library was constructed using RNA isolated from small intestine tissue removed from a 15-year-old Caucasian female who died from a closed head injury. Serology was positive for cytomegalovirus. Patient history included seasonal allergies. |
| SINTNOT25 | pINCY | The library was constructed using RNA isolated from smallintestine tissue removed from a 13-year-old Caucasian male, who died from a gunshotwound to the head. Family history included diabetes. |
| SKINNOT05 | pINCY | Library was constructed using RNA isolated from skin tissue removed from a Caucasian male fetus, who died from Patau's syndrome (trisomy 13) at 20-weeks' gestation. |
| STOMFET01 | pINCY | Library was constructed using RNA isolated from the stomach tissue of a Caucasian female fetus, who died at 20 weeks' gestation. |
| TESTNOT03 | PBLUESCRIPT | Library was constructed using RNA isolated from testicular tissue removed from a 37-year-old Caucasian male, who died from liver disease. Patient history included cirrhosis, jaundice, and liver failure. |
| TESTNOT11 | pINCY | Library was constructed using RNA isolated from testicular tissue removed from a 16-year-old Caucasian male who died from hanging. Patient history included drug use (tobacco, marijuana, and cocaine use), and medications included Lithium, Ritalin, and Paxil. |
| THYMNON04 | PSPORT1 | This normalized library was constructed from a thymus tissue library. Starting RNA was made from thymus tissue removed from a 3-year-old Caucasian male, who died from anoxia. Serologies were negative. The patient was not taking any medications. The library was normalized in two rounds using conditions adapted from Soares et al., PNAS (1994) 91: 9228 and Bonaldo et al., Genome Research (1996) 6: 791, except that a significantly longer (48-hours/round) reannealing hybridization was used. |
| THYMNOR02 | pINCY | The library was constructed using RNA isolated from thymus tissue removed from a 2-year-old Caucasian female during a thymectomy and patch closure of left atrioventricular fistula. Pathology indicated there was no gross abnormality of the thymus. The patient presented with congenital heart abnormalities. Patient history included double inlet left ventricle and a rudimentary right ventricle, pulmonary hypertension, cyanosis, subaortic stenosis, seizures, and a fracture of the skull base. Family history included reflux neuropathy. |
| THYRNOT03 | pINCY | Library was constructed using RNA isolated from thyroid tissue removed from the left thyroid of a 28-year-old Caucasian female during a complete thyroidectomy. Pathology indicated a small nodule of adenomatous hyperplasia present in the left thyroid. Pathology for the associated tumor tissue indicated dominant follicular adenoma, forming a well-encapsulated mass in the left thyroid. |
| TLYMNOR01 | PBLUESCRIPT | Library was constructed using RNA isolated from non-adherent peripheral blood mononuclear cells obtained from a 24-year-old Caucasian male. The cells were purified on Ficoll Hypaque, then harvested, lysed in GuSCN, and spun through CsCl to obtain RNA for library construction. |
| U937NOT01 | PBLUESCRIPT | Library was constructed at Stratagene (STR937207), using RNA isolated from the U937 monocyte-like cell line. This line (ATCC CRL1593) was established from malignant cells obtained from the pleural effusion of a 37-year-old Caucasian male with diffuse histiocytic lymphoma. |
| URETTUE01 | PCDNA2.1 | This 5' biased random primed library was constructed using RNA isolated from ureter tumor tissue removed from a 64-year-old Caucasian male during closed bladder biopsy, radical cystectomy, radical prostatectomy, and formation of a cutanious ureterostomy. Pathology indicated in situ and superficially invasive transitional cell carcinoma presenting as 2 separate papillary lesions, one located 7.5 cm from the ureter margin, and the other in the right proximal ureter |

TABLE 6-continued

| Library | Vector | Library Description |
|---|---|---|
| | | extending into the renal pelvis. The tumor invaded just into the submucosal tissue. The ureter margin was involved by focal in situ transitional cell carcinoma. The patient presented with carcinoma in situ of the bladder, malignant neoplasm of the ureter, and secondary malignant kidney neoplasm. Patient history included malignant bladder neoplasm, psoriasis, chronic airway obstruction, testicular hypofunction, and tobacco abuse. Previous surgeries included appendectomy and transurethral destruction of bladder lesion. Patient medications included naproxen, Atrovent, albuterol, and an unspecified psoriasis cream. Family history included malignant stomach neoplasm in the father and malignant bladder neoplasm in the sibling(s). |
| UTRENOT09 | pINCY | Library was constructed using RNA isolated from endometrial tissue removed from a 38-year-old Caucasian female during total abdominal hysterectomy, exploratory laparotomy, cystocele repair, and incidental appendectomy. Patient history included missed abortion, hypertrophy of breast, bronchitis, and an unspecified closed fracture. Previous surgeries included dilation and curettage. Family history included polymyositis and muliple myeloma. |

TABLE 7

| Program | Description | Reference | Parameter Threshold |
|---|---|---|---|
| ABI FACTURA | A program that removes vector sequences and masks ambiguous bases in nucleic acid sequences. | Applied Biosystems, Foster City, CA. | |
| ABI/PARACEL FDF | A Fast Data Finder useful in comparing and annotating amino acid or nucleic acid sequences. | Applied Biosystems, Foster City, CA; Paracel Inc., Pasadena, CA. | Mismatch <50% |
| ABI AutoAssembler | A program that assembles nucleic acid sequences. | Applied Biosystems, Foster City, CA. | |
| BLAST | A Basic Local Alignment Search Tool useful in sequence similarity search for amino acid and nucleic acid sequences. BLAST includes five functions: blastp, blastn, blastx, tblastn, and tblastx. | Altschul, S. F. et al. (1990) J. Mol. Biol. 215: 403-410; Altschul, S. F. et al. (1997) Nucleic Acids Res. 25: 3389-3402. | ESTs: Probability value = 1.0E−8 or less; Full Length sequences: Probability value = 1.0E−10 or less |
| FASTA | A Pearson and Lipman algorithm that searches for similarity between a query sequence and a group of sequences of the same type. FASTA comprises as least five functions: fasta, tfasta, fastx, tfastx, and ssearch. | Pearson, W. R. and D. J. Lipman (1988) Proc. Natl. Acad Sci. USA 85: 2444-2448; Pearson, W. R. (1990) Methods Enzymol. 183: 63-98; and Smith, T. F. and M. S. Waterman (1981) Adv. Appl. Math. 2: 482-489. | ESTs: fasta E value = 1.06E−6; Assembled ESTs: fasta Identity = 95% or greater and Match length = 200 bases or greater; fastx E value = 1.0E−8 or less; Full Length sequences: fastx score = 100 or greater |
| BLIMPS | A BLocks IMProved Searcher that matches a sequence against those in BLOCKS, PRINTS, DOMO, PRODOM, and PFAM databases to search for gene families, sequence homology, and structural fingerprint regions. | Henikoff, S. and J. G. Henikoff (1991) Nucleic Acids Res. 19: 6565-6572; Henikoff, J. G. and S. Henikoff (1996) Methods Enzymol. 266: 88-105; and Attwood, T. K. et al. (1997) J. Chem. Inf. Comput. Sci. 37: 417-424. | Probability value = 1.0E−3 or less |
| HMMER | An algorithm for searching a query sequence against hidden Markov model (HMM)-based databases of protein family consensus sequences, such as PFAM. | Krogh, A. et al. (1994) J. Mol. Biol. 235: 1501-1531; Sonnhammer, E. L. L. et al. (1988) Nucleic Acids Res. 26: 320-322; Durbin, R. et al. (1998) Our World View, in a Nutshell, Cambridge Univ. Press, pp. 1-350. | PFAM hits: Probability value = 1.0E−3 or less; Signal peptide hits: Score = 0 or greater |
| ProfileScan | An algorithm that searches for structural and sequence motifs in protein sequences that match sequence patterns defined in Prosite. | Gribskov, M. et al. (1988) CABIOS 4: 61-66; Gribskov, M. et al. (1989) Methods Enzymol. 183: 146-159; Bairoch, A. et al. (1997) Nucleic Acids Res. 25: 217-221. | Normalized quality score ≥ GCG-specified "HIGH" value for that particular Prosite motif. Generally, score = 1.4-2.1. |
| Phred | A base-calling algorithm that examines automated sequencer traces with high sensitivity and probability. | Ewing, B. et al. (1998) Genome Res. 8: 175-185; Ewing, B. and P. Green (1998) Genome Res. 8: 186-194. | |
| Phrap | A Phils Revised Assembly Program including SWAT and CrossMatch, programs based on efficient implementation of the Smith-Waterman algorithm, useful in searching sequence homology and assembling DNA sequences. | Smith, T. F. and M. S. Waterman (1981) Adv. Appl. Math. 2: 482-489; Smith, T. F. and M. S. Waterman (1981) J. Mol. Biol. 147: 195-197; and Green, P., University of Washington, Seattle, WA. | Score = 120 or greater; Match length = 56 or greater |
| Consed | A graphical tool for viewing and editing Phrap assemblies. | Gordon, D. et al. (1998) Genome Res. 8: 195-202. | |
| SPScan | A weight matrix analysis program that scans protein sequences for the presence of secretory signal peptides. | Nielson, H. et al. (1997) Protein Engineering 10: 1-6; Claverie, J. M. and S. Audic (1997) CABIOS 12: 431-439. | Score = 3.5 or greater |
| TMAP | A program that uses weight matrices to delineate transmembrane segments on protein sequences and determine orientation. | Persson, B. and P. Argos (1994) J. Mol. Biol. 237: 182-192; Persson, B. and P. Argos (1996) Protein Sci. 5: 363-371. | |

TABLE 7-continued

| Program | Description | Reference | Parameter Threshold |
|---|---|---|---|
| TMHMMER | A program that uses a hidden Markov model (HMM) to delineate transmembrane segments on protein sequences and determine orientation. | Sonnhammer, E. L. et al. (1998) Proc. Sixth Intl. Conf. On Intelligent Systems for Mol. Biol., Glasgow et al., eds., The Am. Assoc. for Artificial Intelligence (AAAI) Press, Menlo Park, CA, and MIT Press, Cambridge, MA, pp. 175-182. | |
| Motifs | A program that searches amino acid sequences for patterns that matched those defined in Prosite. | Bairoch, A. et al. (1997) Nucleic Acids Res. 25: 217-221; Wisconsin Package Program Manual, version 9, page M51-59, Genetics Computer Group, Madison, WI. | |

What is claimed is:

1. A method of screening for a compound that specifically binds to a polypeptide, wherein the method comprises: (i) combining at least one test compound under suitable conditions with a polypeptide selected from the group consisting of: SEQ ID NO:6 and H28-G55 of SEQ ID NO:6;
   (ii) detecting binding of the polypeptide to the test compound, thereby identifying a compound that specifically binds to the polypeptide.

2. The method of claim 1, wherein the polypeptide comprises the amino acid sequence of SEQ ID NO:6.

3. The method of claim 1, wherein the polypeptide is encoded by SEQ ID NO:69.

4. The method of claim 1, wherein the test compound is combined with the polypeptide in an in vitro or cell-free system.

5. The method of claim 1, wherein the test compound is a ligand of SECP.

6. The method of claim 1, wherein the test compound is an aptamer.

7. The method of claim 1, wherein the test compound is an antibody.

8. The method of claim 7, wherein the antibody is a humanized antibody.

9. The method of claim 7, wherein the antibody is a single chain antibody, Fab fragment, or a F(ab')$_2$ fragment.

* * * * *